US012746252B2

(12) United States Patent
Kim et al.

(10) Patent No.: US 12,746,252 B2
(45) Date of Patent: Sep. 29, 2026

(54) INTERFERON GENE STIMULATOR COMPOSITION COMPRISING INDOLIZINE DERIVATIVE AS ACTIVE INGREDIENT

(71) Applicants: AJOU UNIVERSITY INDUSTRY-ACADEMIC COOPERATION FOUNDATION, Suwon-si (KR); KOREA INSTITUTE OF SCIENCE AND TECHNOLOGY, Seoul (KR)

(72) Inventors: Eunha Kim, Seoul (KR); Sanghee Lee, Seoul (KR); Sang-Kee Choi, Yongin-si (KR); Hyungi Kim, Seoul (KR); Hee Ra Jung, Seongnam-si (KR)

(73) Assignees: AJOU UNIVERSITY INDUSTRY-ACADEMIC COOPERATION FOUNDATION, Suwon-si (KR); KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 675 days.

(21) Appl. No.: 18/250,002

(22) PCT Filed: Oct. 22, 2021

(86) PCT No.: PCT/KR2021/014889
§ 371 (c)(1),
(2) Date: Apr. 21, 2023

(87) PCT Pub. No.: WO2022/086260
PCT Pub. Date: Apr. 28, 2022

(65) Prior Publication Data

US 2023/0390319 A1 Dec. 7, 2023

(30) Foreign Application Priority Data

Oct. 23, 2020 (KR) ........................ 10-2020-0138399

(51) Int. Cl.

| | |
|---|---|
| *A61K 31/7084* | (2006.01) |
| *A61K 31/437* | (2006.01) |
| *A61K 31/444* | (2006.01) |
| *A61P 35/00* | (2006.01) |
| *A61P 37/04* | (2006.01) |

(52) U.S. Cl.
CPC ........ *A61K 31/7084* (2013.01); *A61K 31/437* (2013.01); *A61K 31/444* (2013.01); *A61P 35/00* (2018.01); *A61P 37/04* (2018.01)

(58) Field of Classification Search
CPC .......... C07H 21/02; A61P 35/00; A61P 37/04; A61P 37/00; A61K 31/437; A61K 31/444; A61K 31/7084
See application file for complete search history.

(56) References Cited

U.S. PATENT DOCUMENTS

| | | | |
|---|---|---|---|
| 2006/0199962 | A1 | 9/2006 | Alcouffe et al. |
| 2017/0319680 | A1 | 11/2017 | Ishii et al. |

FOREIGN PATENT DOCUMENTS

| | | | |
|---|---|---|---|
| CN | 106554416 | A | 4/2017 |
| JP | 2018501319 | A | 1/2018 |
| KR | 20180066241 | A | 6/2018 |
| KR | 20200058411 | A | 5/2020 |
| KR | 20220063600 | A | 5/2022 |
| WO | 2016110821 | A1 | 7/2016 |
| WO | 2017027646 | A1 | 2/2017 |
| WO | 2017093933 | A1 | 6/2017 |
| WO | 2017123669 | A1 | 7/2017 |
| WO | 2020075790 | A1 | 4/2020 |

OTHER PUBLICATIONS

Extended European Search Report corresponding to EP 21883327.5; dated Mar. 21, 2024 (9 pages).
Chen, Peiling, et al., "Discovery and Characterization of GSK2801, a Selective Chemical Probe for the Bromodomains BAZ2A and BAZ2B", Journal of Medicinal Chemistry 59: 1410-1424, 2016.
Dumea, Carmen, et al., "Novel indolizine derivatives with unprecedented inhibitory activity on human farnesyltransferase", Bioorganic & Medicinal Chemistry Letters 24: 5777-5781, 2014.
Moise, Iuliana-Monica, et al., "Indolizine-phenothiazine hybrids as the first dual inhibitors of tubulin polymerization and farnesyltransferase with synergistic antitumor activity", Bioorganic Chemistry 103: 104184, 2020.
Moise, Iuliana-Monica, et al., "New indolizine-chalcones as potent inhibitors of human farnesyltransferase: Design, synthesis and biological evaluation", Bioorganic & Medicinal Chemistry Letters 26: 3730-3734, 2016.
Sandeep, C., et al., "Synthesis and Characterization of Ethyl 7-Acetyl-2-substituted 3-(substituted benzoyl)indolizine-1-carboxylates for in vitro Anticancer Activity", Asian Journal of Chemistry 28(5): 1043-1048, 2016.

(Continued)

*Primary Examiner* — Sahar Javanmard

(74) *Attorney, Agent, or Firm* — Wenderoth, Lind & Ponack, L.L.P.

(57) ABSTRACT

The present invention relates to an interferon gene stimulator composition containing an indolizine derivative as an active ingredient. The composition may overcome the problem of low disease control rate, unlike the use of a cyclic-di-nucleotide alone. Specifically, since the composition contains the cyclic-di-nucleotide together with the compound of Formula 1, it may exhibit high activity even when a low concentration of the cyclic-di-nucleotide is used.

7 Claims, 8 Drawing Sheets

(56) References Cited

OTHER PUBLICATIONS

Terent'Ev, P. B., et al., "Reaction of 2- and 4-vinylpyridines with phenacylpyridinium ylids", Chem Heterocycl Compd 16: 506-511, 1980.

International Search Report corresponding to International Application No. PCT/KR2021/014889, mailed Feb. 14, 2022 (7 pages, including English translation).

Bevill, Samantha M., et al., "GSK2801, a BAZ2/BRD9 bromodomain inhibitor, synergizes with BET inhibitors to induce apoptosis in triple-negative breast cancer", Mol Cancer Res. 17(7): 1503-1518 (2019).

Harabuchi, Shohei, et al., "Intratumoral STING activations overcome negative impact of cisplatin on antitumor immunity by inflaming tumor microenvironment in squamous cell carcinoma", Biochemical and Biophysical Research Communications. 522: 408-414 (2020).

Zhang, Xiao, et al., "Facile Synthesis of Indolizines via 1,3-Dipolar Cycloadditions in [Omim]Br: The Promotion of the Reaction through Noncovalent Interactions", ACS Sustainable Chemistry & Engineering. 5: 9279-9285 (2017).

[Figure 1]
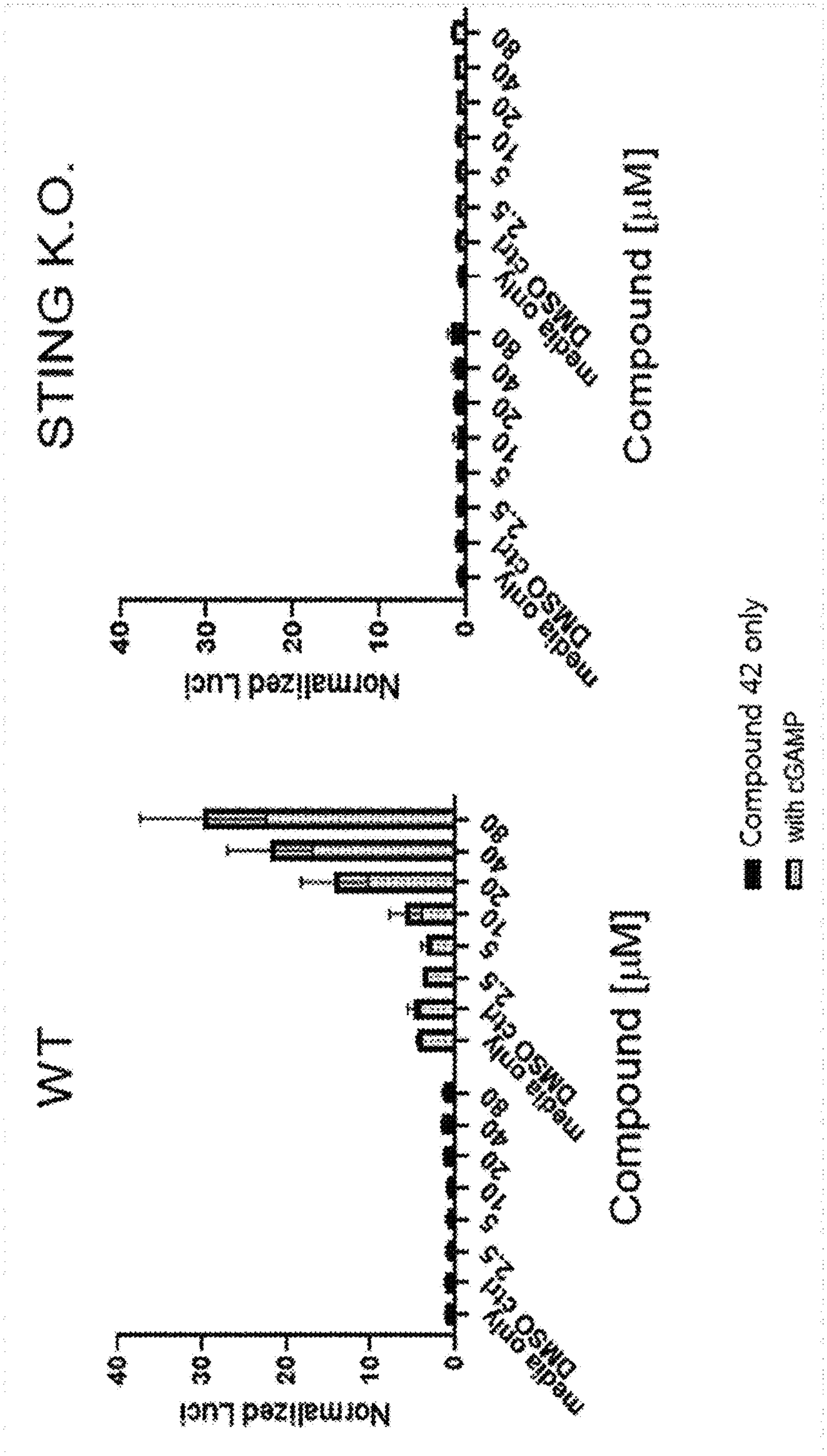

[Figure 2]
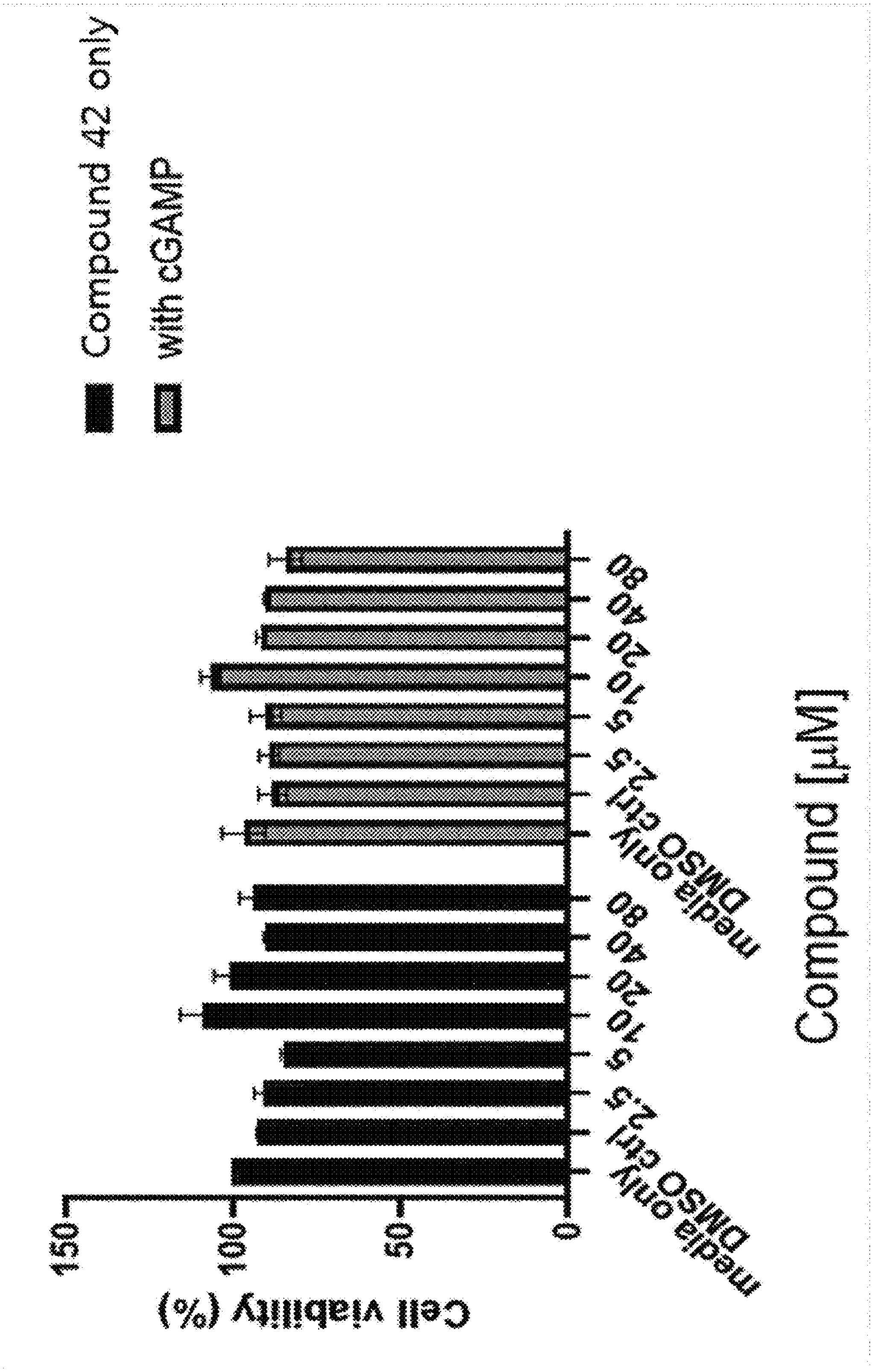

[Figure 3]
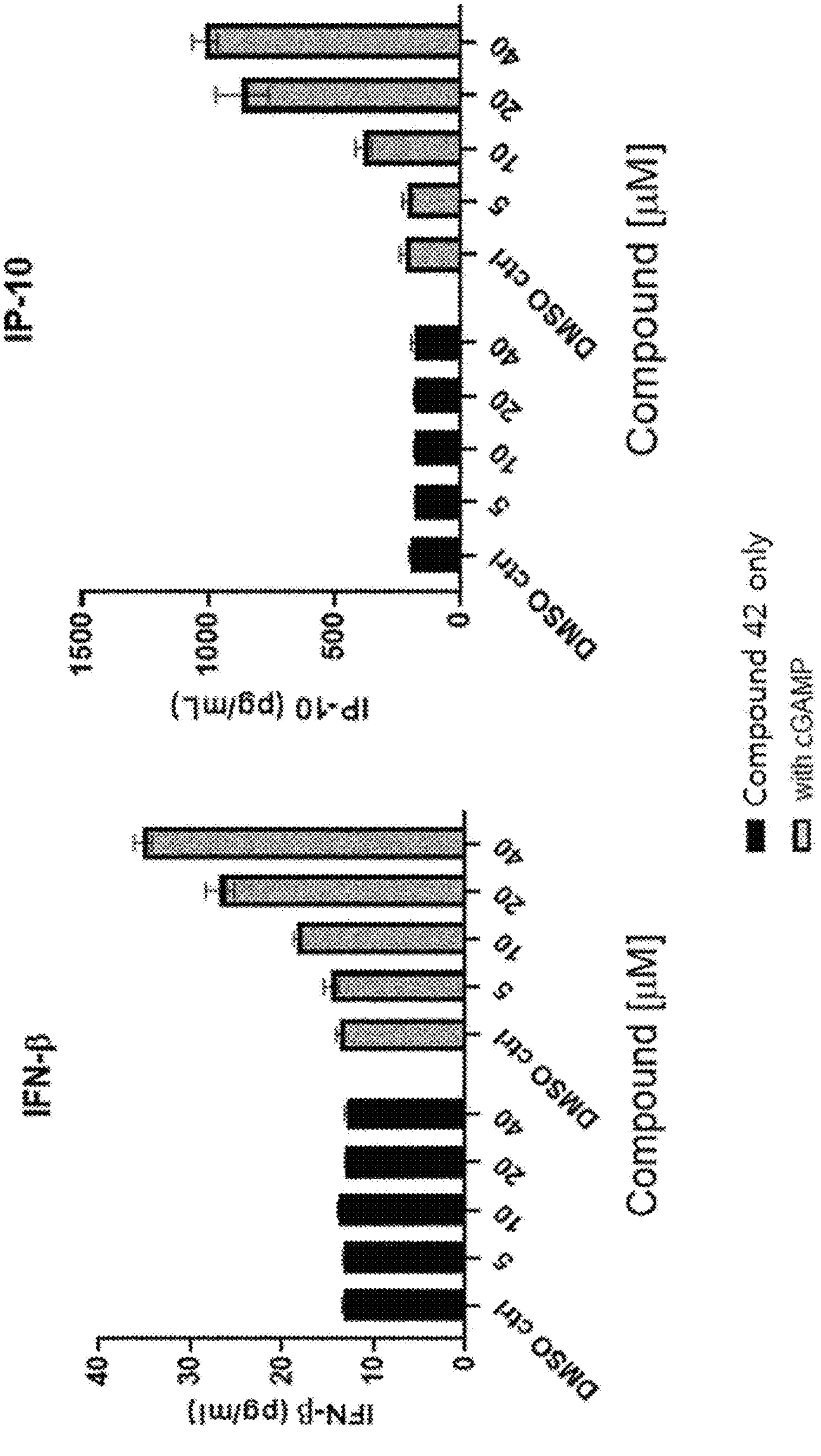

[Figure 4]
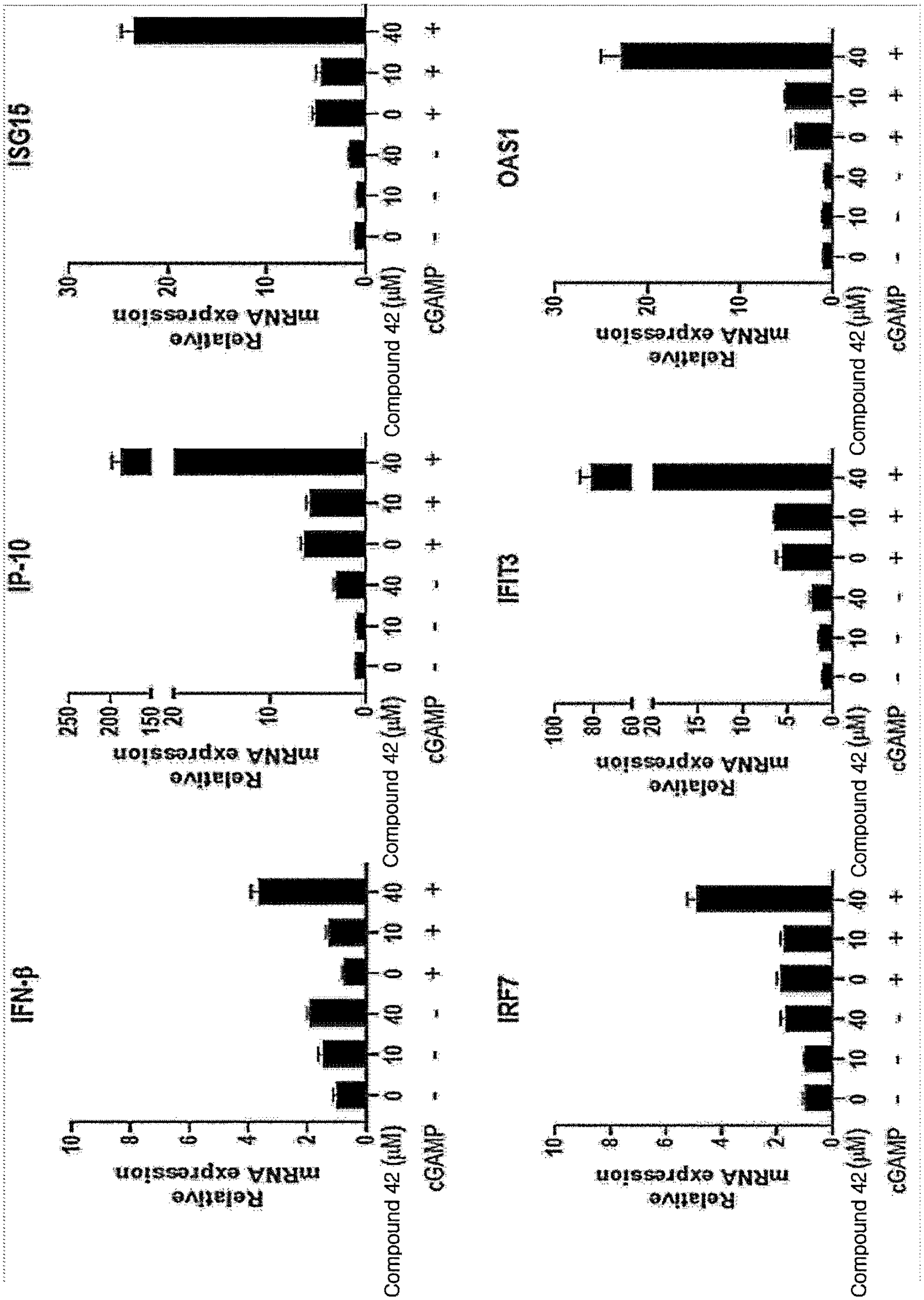

[Figure 5]
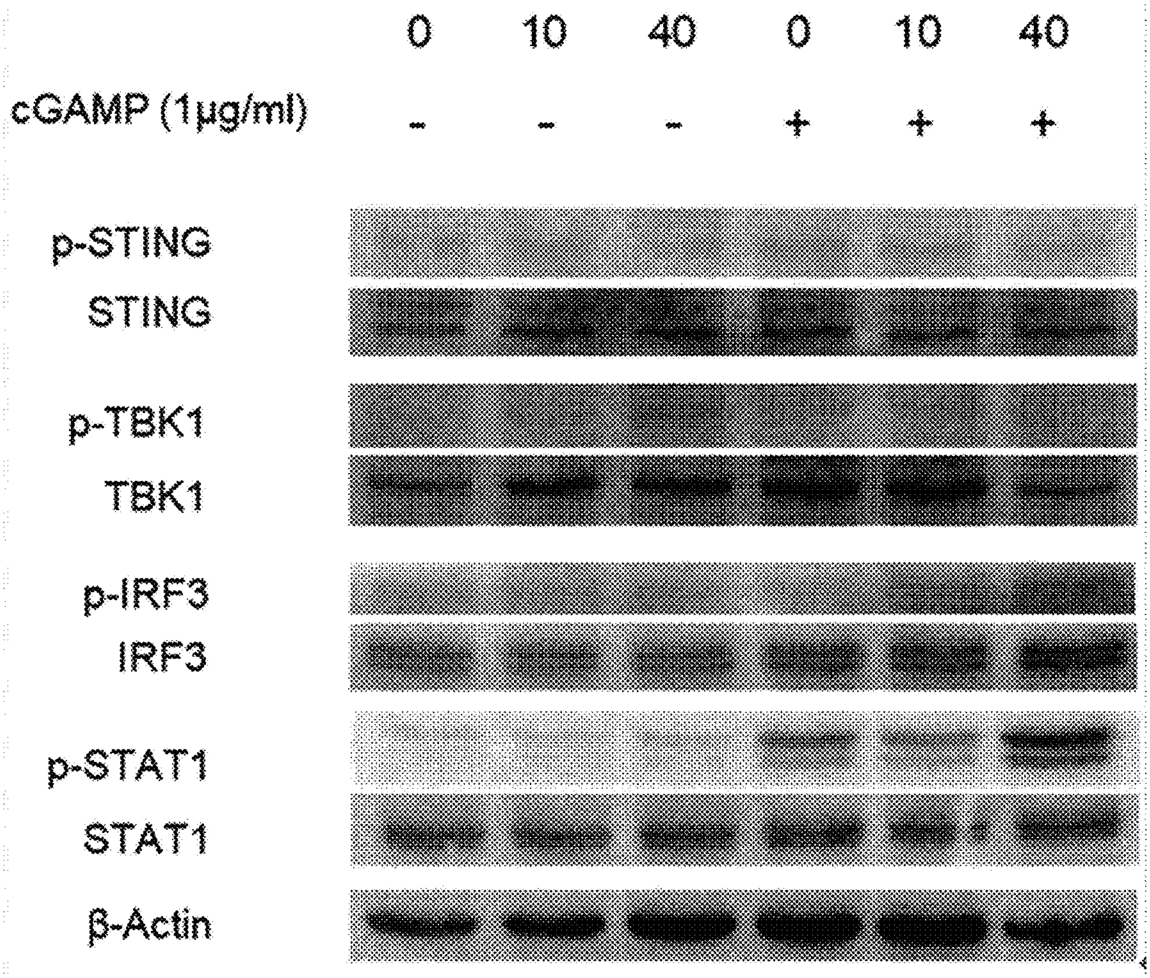

[Figure 6]
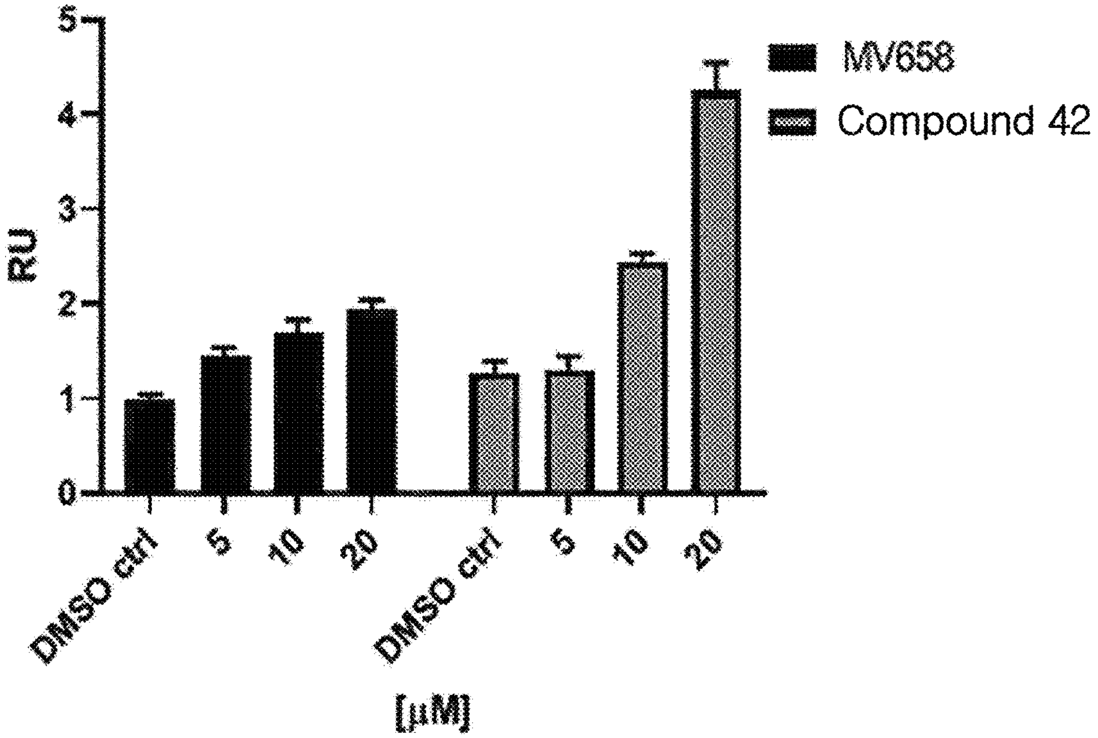

[Figure 7]
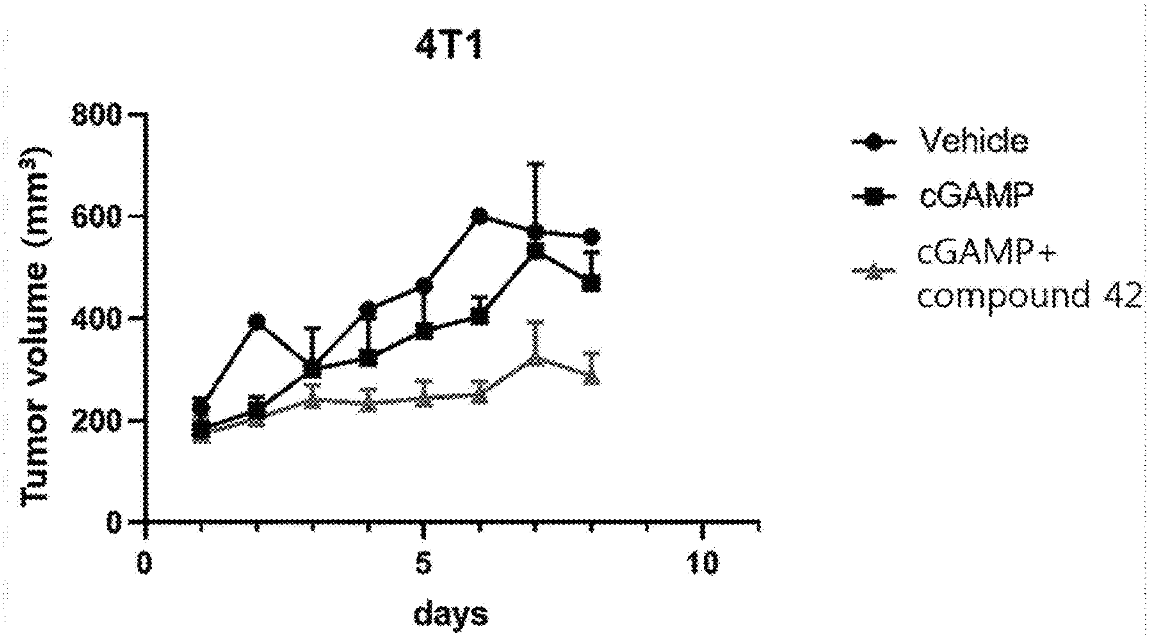

[Figure 8]
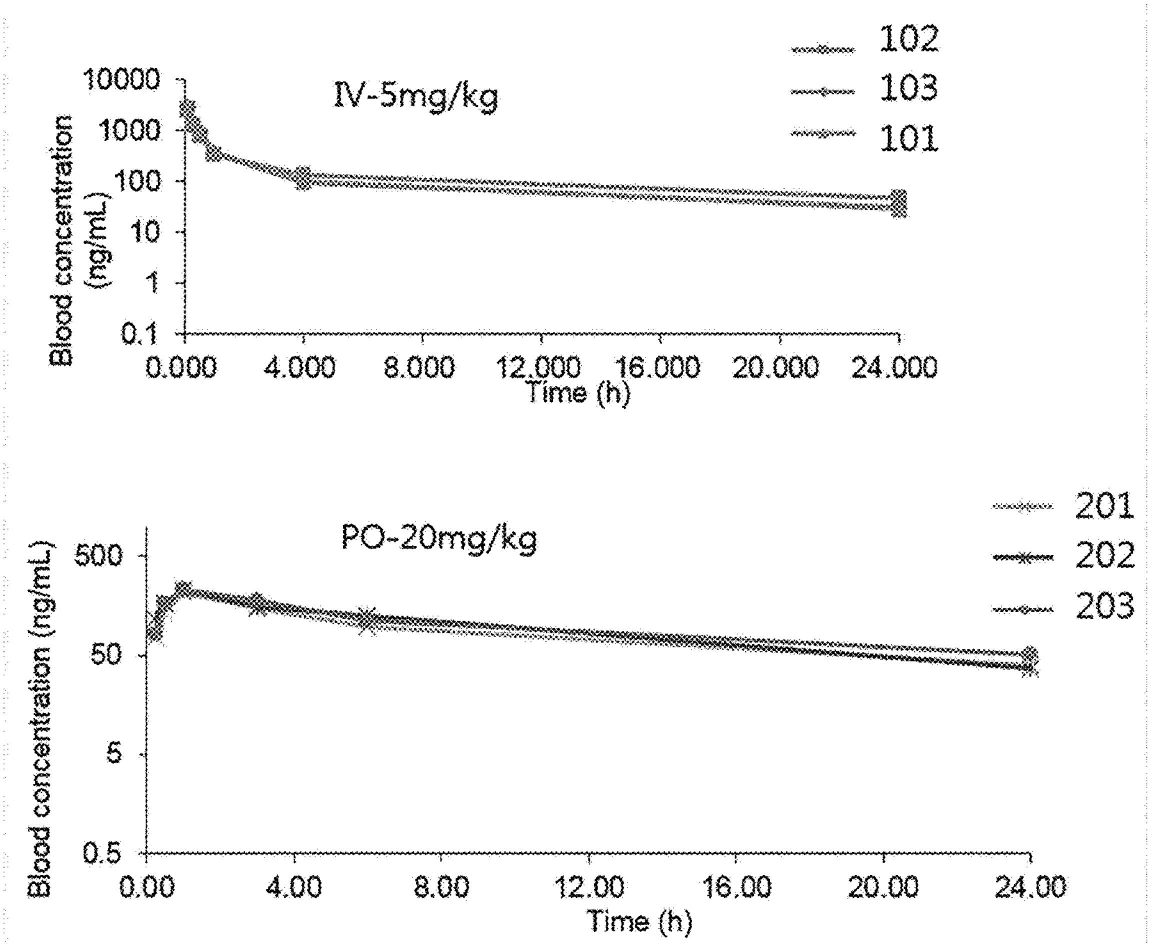

INTERFERON GENE STIMULATOR COMPOSITION COMPRISING INDOLIZINE DERIVATIVE AS ACTIVE INGREDIENT

CROSS-REFERENCE TO RELATED APPLICATIONS

This application is a 35 U.S.C. § 371 national stage application of PCT International Application No. PCT/KR2021/014889, filed Oct. 22, 2021, which claims the benefit of the filing date of Korean Patent Application No. 10-2020-0138399 filed with the Korean Intellectual Property Office on Oct. 23, 2020, the entire content of which is incorporated herein. The above-referenced PCT International Application was published in the Korean language as International Publication No. WO2022/086260 on Apr. 28, 2022.

TECHNICAL FIELD

The present invention relates to an interferon gene stimulator composition containing an indolizine derivative as an active ingredient.

BACKGROUND ART

Recently, the paradigm in the field of cancer treatment has changed from anticancer chemotherapeutic agents and targeted anticancer agents, which attack cancer itself, to immunotherapeutic anticancer agents that activate the body's immune system to induce cancer attacks. Among them, immune checkpoint inhibitors (ICIs) are attracting attention for their excellent and sustained efficacy. However, they still have limitations in that they exhibit efficacy only in some patients or cancer types and in that resistance to the same treatment occurs. Accordingly, active studies have been conducted on tumor microenvironment (TME) factors that affect the efficacy of immunotherapeutic anticancer agents and on the immune evasion mechanisms of cancer.

The degree of infiltration of immune cells into tumor tissue is a very important factor for the success of anticancer immunotherapy. In the evasion mechanism of the cancer-immune cycle in "cold" tumors, there is a defect in the initial stage of the cancer-immune cycle, and most cold tumors do not respond to ICIs. During tumor formation, immunosurveillance removes cancer clones that express strong immunogenic neoantigens. At this point, the tumor evades anticancer immune responses by eliminating immunogenic antigens or maintaining cancer clones without cancer antigens so that they are not recognized by T cells. In other words, cancer clones that evade immunosurveillance have fewer immunogenic antigens. Therefore, there is a need for an innate immunity inducer that increases the immunoreactivity around cancer cells.

Pattern recognition receptors (PRRs) are several different types of receptors that are expressed primarily by innate immune cells, and they can recognize a particular PAMP or DAMP depending on their ligand specificity. Cytoplasmic DNA is a type of molecular pattern recognized by a cytoplasmic DNA sensor (a type of PRR) and triggers an innate immune response. The cGAS-STING pathway (cGAS, cyclic GMP-AMP synthase; STING, stimulator of interferon genes) is involved in both 1) cytoplasmic DNA recognition caused by microbial infection or damage to its own DNA and 2) production of chemical factors, mainly type-1 interferons (IFNs) by activation of the IRE3 transcription factor.

Systemic administration of type-1 IFN showed proven efficacy in the cancer setting because systemic injection of IFN-beta in preclinical mouse models showed tumor regression and improved survival. However, systemic administration of type-1 IFN has a problem in that a high dose is required to reach a therapeutically effective amount necessary for exhibiting therapeutic efficacy. In this case, tolerability problems have been reported.

In recently published reports, clinical results of exogenous STING agonists (modified cyclic dinucleotides) were published, and these agonists showed disease control rates lower than expected, despite an apparent increase in pro-inflammatory cytokine production.

Therefore, there is a need for studies on new therapeutic methods capable of activating the cGAS-STING pathway.

PRIOR ART DOCUMENTS

Patent Documents (Patent Document 1) 1. KR 10-2018-0066241 A1

DISCLOSURE

Technical Problem

One aspect of the present invention is to provide an interferon gene stimulator composition containing an indolizine derivative as an active ingredient.

Technical Solution

One aspect of the present invention provides an interferon gene stimulator composition containing: an indolizine derivative compound represented by the following Formula 1: and a cyclic-di-nucleotide:

[Formula 1]

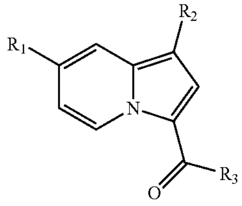

wherein $R_1$ is hydrogen, a $C_1$-$C_8$ straight or branched chain alkyl group, a halogen-substituted $C_1$-$C_8$ straight or branched chain alkyl group, a $C_2$-$C_8$ alkenyl group, a $C_2$-$C_8$ alkynyl group, a halogen group, a nitrile group, a hydroxyl group, a $C_1$-$C_6$ alkoxy group, —$COY_1$ (wherein $Y_1$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), —$CO_2Y_2$ (wherein $Y_2$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), or —$NY_3Y_4$ (wherein $Y_3$ and $Y_4$ are each independently hydrogen, a $C_1$-$C_{10}$ alkyl group, a $C_6$-$C_{20}$ aryl group, or a $C_4$-$C_{20}$ heteroaryl group);

$R_2$ is

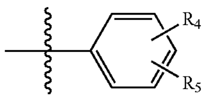

or a pyridinyl group, wherein $R_4$ and $R_5$ are each independently hydrogen, a $C_1$-$C_8$ straight or branched chain alkyl group, a halogen-substituted $C_1$-$C_8$ straight or branched chain alkyl group, a $C_2$-$C_8$ alkenyl group, a $C_2$-$C_8$ alkynyl group, a $C_3$-$C_8$ cycloalkyl group, a $C_5$-$C_{20}$ heterocycloalkyl group, a $C_6$-$C_{20}$ aryl group, a $C_6$-$C_{20}$ heteroaryl group, a halogen group, a nitrile group, a nitro group, a hydroxyl group, a carboxyl group, a $C_1$-$C_6$ alkoxy group, —$COY_3$ (wherein $Y_5$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), —$CO_2Y_6$ (wherein $Y_6$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, a $C_6$-$C_{20}$ aryl group), or —$NY_7Ye$ (wherein $Y_7$ and Ye are each independently hydrogen, a $C_1$-$C_{10}$ alkyl group, a $C_6$-$C_{20}$ aryl group, or a $C_4$-$C_{20}$ heteroaryl group); and $R_3$ is a $C_1$-$C_8$ straight or branched chain alkyl group, or

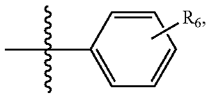

wherein $R_6$ is hydrogen, a $C_1$-$C_8$ straight or branched chain alkyl group, a halogen-substituted $C_1$-$C_8$ straight or branched chain alkyl group, a $C_2$-$C_8$ alkenyl group, a $C_2$-$C_8$ alkynyl group, a $C_3$-$C_8$ cycloalkyl group, a $C_5$-$C_{20}$ heterocycloalkyl group, a $C_6$-$C_{20}$ aryl group, a $C_6$-$C_{20}$ heteroaryl group, a halogen group, a nitrile group, a nitro group, a hydroxyl group, a $C_1$-$C_6$ alkoxy group, —$COY_9$ (wherein $Y_9$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), —$CO_2Y_{10}$ (wherein $Y_{10}$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), or —$NY_{11}Y_{12}$ (wherein $Y_{11}$ and $Y_{12}$ are each independently hydrogen, a $C_1$-$C_{10}$ alkyl group, a $C_6$-$C_{20}$ aryl group, or a $C_4$-$C_{20}$ heteroaryl group).

Advantageous Effects

Since the composition of the present invention contains the indolizine derivative represented by Formula 1 and the cyclic-di-nucleotide, it may overcome the problem of low disease control rate, unlike the use of the cyclic-di-nucleotide alone. Specifically, since the composition contains the cyclic-di-nucleotide together with the compound of Formula I, it may exhibit high activity even when a low concentration of the cyclic-di-nucleotide is used.

BRIEF DESCRIPTION OF DRAWINGS

FIG. 1 shows the results of ISRE reporter assay performed to evaluate the synergistic effect of co-treatment with compound 42 of the present invention and cGAMP and to confirm STING dependence and concentration dependence.

FIG. 2 shows the results of evaluating the cytotoxicity of co-treatment with compound 42 of the present invention and cGAMP.

FIG. 3 shows results indicating that the expression of IFN-beta and IP-10 cytokines was increased, that is, STING (STIMULATOR OF INTERFERON GENE)-dependent signaling was activated, by co-treatment with compound 42 of the present invention and cGAMP.

FIG. 4 shows results indicating that the expression of various Type I IFN signaling-related genes was increased by co-administration of Compound 42 of the present invention and cGAMP.

FIG. 5 shows results indicating that STING (STIMULATOR OF INTERFERON GENE)-dependent signaling was activated by co-treatment with Compound 42 of the present invention and cGAMP.

FIG. 6 shows the results of comparing the effect of activating STING (STIMULATOR OF INTERFERON GENE)-dependent signaling between treatment with a compound (MV658), known as STING pathway therapy, and co-treatment with Compound 42 of the present invention and cGAMP.

FIG. 7 shows the results of evaluating the in vivo anti-cancer activity effect of co-treatment with Compound 42 of the present invention and cGAMP.

FIG. 8 shows the results of measuring the concentration profiles of compound 42 of the present invention in the blood over time after intravenous (IV) and oral administration (PO).

BEST MODE

One aspect of the present invention provides an interferon gene stimulator composition containing: an indolizine derivative compound represented by the following Formula 1: and a cyclic-di-nucleotide:

[Formula 1]

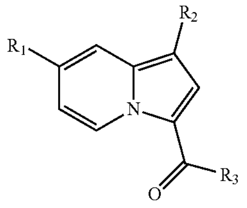

wherein $R_1$ is hydrogen, a $C_1$-$C_8$ straight or branched chain alkyl group, a halogen-substituted $C_1$-$C_8$ straight or branched chain alkyl group, a $C_2$-$C_8$ alkenyl group, a $C_2$-$C_8$ alkynyl group, a halogen group, a nitrile group, a hydroxyl group, a $C_1$-$C_6$ alkoxy group, —$COY_1$ (wherein $Y_1$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), —$CO_2Y_2$ (wherein $Y_2$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), or —$NY_3Y_4$ (wherein $Y_3$ and $Y_4$ are each independently hydrogen, a $C_1$-$C_{10}$ alkyl group, a $C_6$-$C_{20}$ aryl group, or a $C_4$-$C_{20}$ heteroaryl group);

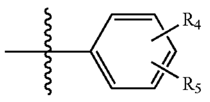

$R_2$ is or a pyridinyl group, wherein $R_4$ and $R_5$ are each independently hydrogen, a $C_1$-$C_8$ straight or branched chain alkyl group, a halogen-substituted $C_1$-$C_8$ straight or branched chain alkyl group, a $C_2$-$C_8$ alkenyl group, a $C_2$-$C_8$ alkynyl group, a $C_3$-$C_8$ cycloalkyl group, a $C_5$-$C_{20}$ heterocycloalkyl group, a $C_6$-$C_{20}$ aryl group, a $C_6$-$C_{20}$ heteroaryl group, a halogen group, a nitrile group, a nitro group, a hydroxyl group, a carboxyl group, a $C_1$-$C_6$ alkoxy group, —$COY_3$ (wherein $Y_5$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), —$CO_2Y_6$ (wherein $Y_6$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, a $C_6$-$C_{20}$ aryl group), or —$NY_7$Ye (wherein $Y_7$ and Ye are each independently hydrogen, a $C_1$-$C_{10}$ alkyl group, a $C_6$-$C_{20}$ aryl group, or a $C_4$-$C_{20}$ heteroaryl group); and $R_3$ is a $C_1$-$C_8$ straight or branched chain alkyl group, or

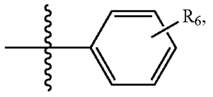

wherein $R_6$ is hydrogen, a $C_1$-$C_8$ straight or branched chain alkyl group, a halogen-substituted $C_1$-$C_8$ straight or branched chain alkyl group, a $C_2$-$C_8$ alkenyl group, a $C_2$-$C_8$ alkynyl group, a $C_3$-$C_8$ cycloalkyl group, a $C_5$-$C_{20}$ heterocycloalkyl group, a $C_6$-$C_{20}$ aryl group, a $C_6$-$C_{20}$ heteroaryl group, a halogen group, a nitrile group, a nitro group, a hydroxyl group, a $C_1$-$C_6$ alkoxy group, —$COY_9$ (wherein $Y_9$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), —$CO_2Y_{10}$ (wherein $Y_{10}$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), or —$NY_{11}Y_{12}$ (wherein $Y_{11}$ and $Y_{12}$ are each independently hydrogen, a $C_1$-$C_{10}$ alkyl group, a $C_6$-$C_{20}$ aryl group, or a $C_4$-$C_{20}$ heteroaryl group).

Specifically, $R_1$ in Formula 1 above may be hydrogen, a $C_1$-$C_8$ straight or branched chain alkyl group, a halogen-substituted $C_1$-$C_8$ straight or branched chain alkyl group, or —$COY_1$ (wherein $Y_1$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group). In this case, $Y_1$ may be more specifically a $C_1$-$C_8$ straight or branched chain alkyl group.

In addition, when $R_2$ in Formula 1 above is

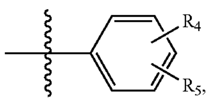

$R_4$ and $R_5$ may be each independently hydrogen, a $C_1$-$C_8$ straight or branched chain alkyl group, a halogen-substituted $C_1$-$C_8$ straight or branched chain alkyl group, a $C_1$-$C_6$ alkoxy group, a carboxyl group, —$COY_5$ (wherein $Y_5$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), or —$NY_7$Ye (wherein $Y_7$ and $Y_8$ may be each independently hydrogen, a $C_1$-$C_{10}$ alkyl group, a $C_6$-$C_{20}$ aryl group, or a $C_4$-$C_{20}$ heteroaryl group). In this case, $Y_5$ may be more specifically a $C_1$-$C_8$ straight or branched chain alkyl group, and $Y_7$ and Ye may be each independently hydrogen or a $C_1$-$C_{10}$ alkyl group.

In addition, $R_3$ in Formula 1 above may be a $C_1$-$C_8$ straight or branched chain alkyl group, specifically a methyl group. In addition, when $R_3$ is

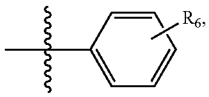

$R_6$ may be hydrogen, a $C_1$-$C_8$ straight or branched chain alkyl group, a halogen-substituted $C_1$-$C_8$ straight or branched chain alkyl group, a $C_1$-$C_6$ alkoxy group, or —$NY_{11}Y_{12}$ (wherein $Y_{11}$ and $Y_{12}$ are each independently hydrogen, a $C_1$-$C_{10}$ alkyl group, a $C_6$-$C_{20}$ aryl group, or a $C_4$-$C_{20}$ heteroaryl group). In this case, $Y_{11}$ and $Y_{12}$ may be each independently hydrogen or a $C_1$-$C_{10}$ alkyl group.

The indolizine derivative compound represented by Formula 1 may be any one of the compounds represented by the following Formulas 1a to 1c:

[Formula 1a]

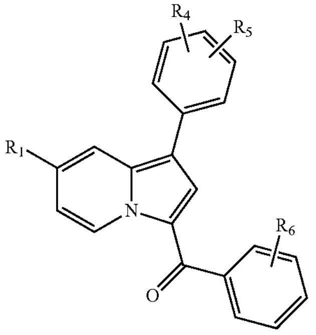

[Formula 1b]

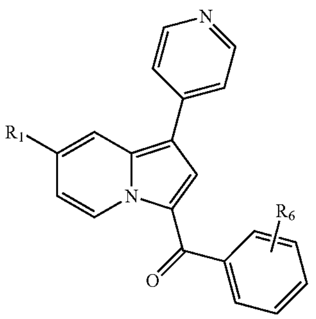

-continued

[Formula 1c]

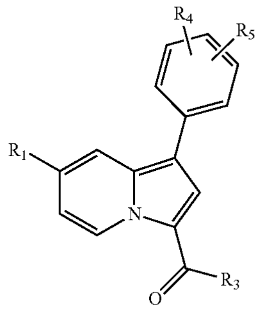

The definition of $R_1$, $R_3$, $R_4$, $R_5$ and $R_6$ in Formulas 1a to 1c above is the same as the definition of $R_1$, $R_3$, $R_4$, $R_5$ and $R_6$ in Formula 1 above.

The indolizine derivative compound represented by Formula 1 may be produced according to the following Reaction Scheme 1:

[Reaction Scheme 1]

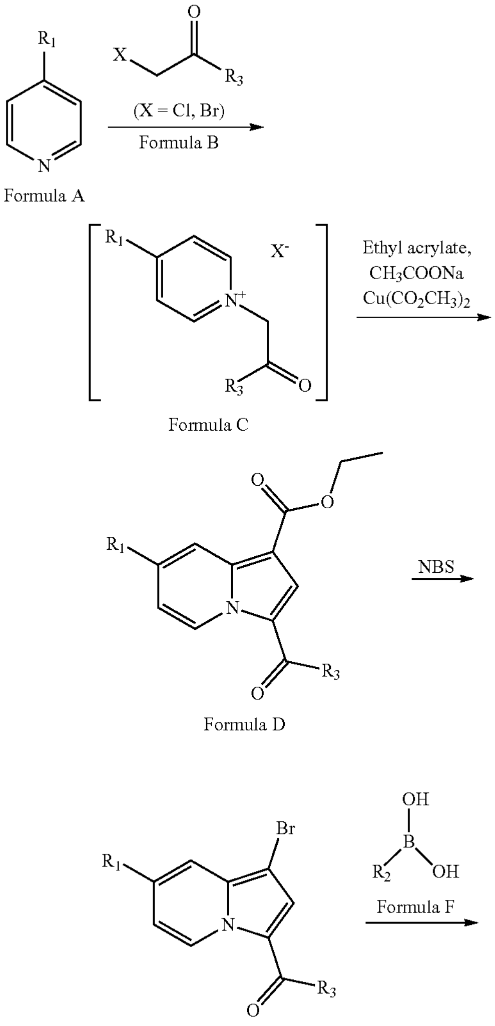

Formula E

-continued

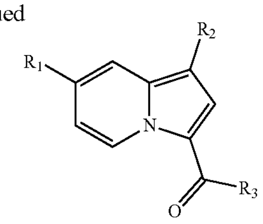

Formula 1

Specifically, the method for producing the indolizine derivative compound represented by Formula 1 may comprise steps of:

(a) reacting a compound of Formula A with a compound of Formula B to produce a compound of Formula C;

(b) reacting the compound of Formula C with ethyl acrylate, sodium acetate and copper(II) acetate monohydrate to produce a compound of Formula D;

(c) reacting the compound of Formula D with N-bromosuccinimide (NBS) to produce a compound of Formula E; and (d) reacting the compound of Formula E with a compound of Formula F to produce the indolizine derivative compound represented by Formula 1.

Details of the method for producing the indolizine derivative compound represented by Formula 1 are as follows.

Step (a): Acylation of Pyridine Compound

In this step, acylation is performed using the compound represented by Formula B as an alkyl halide.

The above acylation may be performed without limitation using a conventional method known in the art. Preferably, the compound represented by Formula B as an alkyl halide is one containing an electrophilic moiety, such as 2-bromo-1-[4-(trifluoromethyl)-phenyl]ethane-1-one, chloroacetone, 2-bromoacetophenone, 2-bromo-4-methoxyacetophenone, 2-bromo-4'-(diethylamino) aceto-phenone, or the like, which contains the substituent $R_3$, and a pyridine having the substituent $R_1$ is used.

Specifically, a solution of an organic mixture of an alkyl halide and pyridine is stirred at an appropriate temperature (20° C. to 100° C.) for 1 hour to 24 hours to produce a pyridine salt compound. At this time, the organic solvent that is used in the reaction may be a conventional organic solvent, and may be appropriately determined by a person skilled in the art depending on the specific type of alkyl halide and pyridine compound.

Step (b): 1,3-Dipolar Cyclization Reaction

In this step, the acylated compound of Formula C obtained in step (a) is reacted with ethyl acrylate, sodium acetate and copper(II) acetate monohydrate to obtain the compound represented by Formula D.

Specifically, an organic mixture solution containing the acylated compound obtained in step (a) is stirred for 1 to 24 hours at an appropriate temperature (50° C. to 120° C.), and then subjected to conventional extraction, drying, filtration, concentration, and purification processes to produce the compound represented by the formula D. At this time, the organic solvent that is used in the reaction may be a conventional organic solvent, and may be appropriately determined by a person skilled in the art depending on the specific type of compound.

Step (c): Br Substituent Introduction Step

In this step, the compound represented by Formula D is subjected to saponification and bromination reactions to obtain the compound represented by Formula E.

The above reactions may be carried out without limitation using conventional methods known in the art. Preferably, the compound represented by Formula D is first dissolved in an organic solvent, and a strong base such as lithium hydroxide, potassium hydroxide, or sodium hydroxide is added thereto. The resulting organic mixture solution is stirred at an appropriate temperature (50° C. to 120° C.) for 1 to 24 hours, and then subjected to conventional extraction, drying, filtration, concentration, and purification processes to obtain an intermediate product. Then, the intermediate product is dissolved in an appropriate organic solvent and then treated with N-bromosuccinimide (NBS), and then the resulting organic mixture solution is stirred at an appropriate temperature (50° C. to 120° C.) for 1 to 24 hours and then subjected to conventional extraction, drying, filtration, concentration and purification processes to obtain the compound represented by Formula E. At this time, the organic solvent that is used in the reaction may be a conventional organic solvent, and may be appropriately determined by a person skilled in the art depending on the specific type of compound.

Step (d): Suzuki Coupling Step

In this step, the compound represented by Formula E is reacted with the compound represented by Formula F in the presence of a Pd catalyst to obtain the indolizine derivative compound represented by Formula 1 according to the present invention.

The above reaction may be performed without limitation using a conventional method known in the art. Specifically, the compound represented by Formula F containing the substituent $R_2$ is not particularly limited and is preferably trifluorophenyl boronic acid, 4-acetylphenyl boronic acid, phenyl boronic acid, 4-methoxyphenyl boronic acid, or 4-(dimethylamino)phenyl boronic acid. In the above reaction, the compound represented by Formula F having the substituent $R_2$ and the compound represented by Formula E obtained in step (c) are mixed with $Pd(PPh_3)_4$ and sodium carbonate in a conventional organic solvent, and the resulting organic mixture solution is stirred at an appropriate temperature (50° C. to 120° C.) for 1 to 24 hours, and then subjected to conventional extraction, drying, filtration, concentration, and purification processes to obtain the indolizine derivative compound of the present invention. At this time, the organic solvent that is used in the reaction may be a conventional organic solvent, and may be appropriately determined by a person skilled in the art depending on the specific type of compound.

The stimulator of interferon genes (STING) according to the present invention is a receptor that recognizes nucleic acids different from TLR (toll-like receptor). Examples of the natural ligands to be recognized include bacterial/protozoan-derived cyclic dinucleotides (CDNs), 2',3'-cGAMPs synthesized by the upstream cGAS (cyclic GMP-AMP synthase), and the like (Trends in Immunology 35:88-93 (2014)). It has been reported that the natural ligand 2',3'-cGAMP is decomposed by ENPP1 (ecto-nucleotide pyrophosphatase/phosphodiesterase), a pyrophosphatase/phosphodiesterase, and that the other CDNs are decomposed by other phosphodiesterases (Nat Chem Biol 10:1043-1048 (2014); Cell Res 25:539-550 (2015); Biochemistry 55:837-849 (2016)). STING activation by these natural ligands induces the phosphorylation of TBK1 (TANK binding kinase 1) in the downstream, and activates IRF3 (interferon regulatory factor 3) signaling and NFkB signaling in the further downstream, leading to the activation of the type-I-interferon (IFN) response (Trends in Immunology 35:88-93 (2014)). The importance of STING signaling in cancer has been indicated by tests using knockout mice. It has been reported that, in tumor-allografted mice using knockout mice for STING and its downstream signal, IRF3, the cancer cells grow by suppression of cancer immune system, compared with in wild-type mouse (Immunity 41: 830-842 (2014)). In addition, it has been reported that cancer cell growth in a tumor-allografted mouse is suppressed by radiation therapy, but in knockout mice for STING and IFNAR1 (interferon (alpha and beta) receptor 1, receptor of type-I IFN produced by the downstream signal), the effect by the radiation therapy is reduced (Immunity 41:843-852 (2014)). For those reasons, it is considered that STING plays an important role on suppression of cancer cell growth, and the activation of immune signaling, which is induced by the activation of STING, leads to anticancer activity. Therefore, a STING agonist may be used as an anticancer agent that targets cancer immunity. In addition, the activation of STING is considered to play an important role on the immune effect of a vaccine, because the activation activates natural immunity (Ther Adv Vaccines 1:131-143 (2013)). Therefore, STING agonists may be used as adjuvants for various vaccines.

The indolizine derivative compound represented by Formula 1 may be a compound represented by the following Formula 1-1 or a compound represented by the following Formula 1-2:

[Formula 1-1]

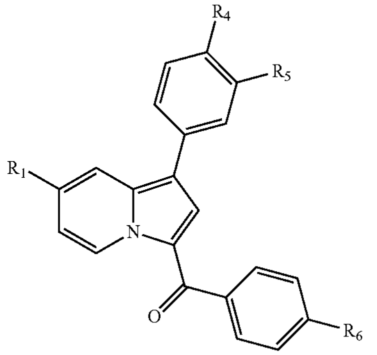

[Formula 1-2]

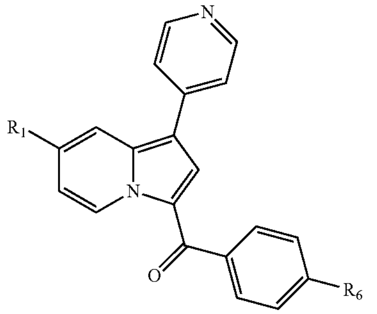

wherein $R_1$ is hydrogen, a $C_1$-$C_8$ straight or branched chain alkyl group, a halogen-substituted $C_1$-$C_8$ straight or branched chain alkyl group, a $C_2$-$C_8$ alkenyl group, a $C_2$-$C_8$ alkynyl group, a halogen group, a nitrile group, a hydroxyl group, a $C_1$-$C_6$ alkoxy group, —$COY_1$ (wherein $Y_1$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), —$CO_2Y_2$ (wherein $Y_2$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), or —$NY_3Y_4$ (wherein $Y_3$ and $Y_4$ are each independently hydrogen, a $C_1$-$C_{10}$ alkyl group, a $C_6$-$C_{20}$ aryl group, or a $C_4$-$C_{20}$ heteroaryl group);

$R_4$ and $R_5$ are each independently hydrogen, a $C_1$-$C_8$ straight or branched chain alkyl group, a halogen-substituted $C_1$-$C_8$ straight or branched chain alkyl group, a $C_2$-$C_8$ alkenyl group, a $C_2$-$C_8$ alkynyl group, a $C_3$-$C_8$ cycloalkyl group, a $C_5$-$C_{20}$ heterocycloalkyl group, a $C_6$-$C_{20}$ aryl group, a $C_6$-$C_{20}$ heteroaryl group, a halogen group, a nitrile group, a nitro group, a hydroxyl group, a carboxyl group, a $C_1$-$C_6$ alkoxy group, —$COY_5$ (wherein $Y_5$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), —$CO_2Y_6$ (wherein $Y_6$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, a $C_6$-$C_{20}$ aryl group), or —$NY_7Ye$ (wherein $Y_7$ and Ye are each independently hydrogen, a $C_1$-$C_{10}$ alkyl group, a $C_6$-$C_{20}$ aryl group, or a $C_4$-$C_{20}$ heteroaryl group); and $R_6$ is hydrogen, a $C_1$-$C_8$ straight or branched chain alkyl group, a halogen-substituted $C_1$-$C_8$ straight or branched chain alkyl group, a $C_2$-$C_8$ alkenyl group, a $C_2$-$C_8$ alkynyl group, a $C_3$-$C_8$ cycloalkyl group, a $C_5$-$C_{20}$ heterocycloalkyl group, a $C_6$-$C_{20}$ aryl group, a $C_6$-$C_{20}$ heteroaryl group, a halogen group, a nitrile group, a nitro group, a hydroxyl group, a $C_1$-$C_6$ alkoxy group, —$COY_9$ (wherein $Y_9$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), —$CO_2Y_{10}$ (wherein $Y_{10}$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), or —$NY_{11}Y_{12}$ (wherein $Y_{11}$ and $Y_{12}$ are each independently hydrogen, a $C_1$-$C_{10}$ alkyl group, a $C_6$-$C_{20}$ aryl group, or a $C_4$-$C_{20}$ heteroaryl group).

Specifically, $R_1$ in Formula 1-1 above may be hydrogen, a $C_1$-$C_8$ straight or branched chain alkyl group, a halogen-substituted $C_1$-$C_8$ straight or branched chain alkyl group, or —$COY_1$ (wherein $Y_1$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group). In this case, $Y_1$ may be more specifically a $C_1$-$C_8$ straight or branched chain alkyl group.

In addition, $R_4$ and $R_5$ in Formula 1-1 above may be each independently hydrogen, a $C_1$-$C_8$ straight or branched chain alkyl group, a halogen-substituted $C_1$-$C_8$ straight or branched chain alkyl group, a $C_1$-$C_6$ alkoxy group, a carboxyl group, —$COY_5$ (wherein $Y_5$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), or —$NY_7Ye$ (wherein $Y_7$ and Ye may be each independently hydrogen, a $C_1$-$C_{10}$ alkyl group, a $C_6$-$C_{20}$ aryl group, or a $C_4$-$C_{20}$ heteroaryl group). In this case, $Y_5$ may be more specifically a $C_1$-$C_8$ straight or branched chain alkyl group, and $Y_7$ and Ye may be each independently hydrogen or a $C_1$-$C_{10}$ alkyl group.

In addition, $R_6$ in Formulas 1-1 and 1-2 above may be hydrogen, a $C_1$-$C_8$ straight or branched chain alkyl group, a halogen-substituted $C_1$-$C_8$ straight or branched chain alkyl group, a $C_1$-$C_6$ alkoxy group, or —$NY_{11}Y_{12}$ (wherein $Y_{11}$ and $Y_{12}$ are each independently hydrogen, a $C_1$-$C_{10}$ alkyl group, a $C_6$-$C_{20}$ aryl group, or a $C_4$-$C_{20}$ heteroaryl group). In this case, $Y_{11}$ and $Y_{12}$ may be each independently hydrogen or a $C_1$-$C_{10}$ alkyl group.

The compound represented by Formula 1a may include the compound represented by Formula 1-1, and the compound represented by Formula 1b may include the compound represented by Formula 1-2. The indolizine derivative compound represented by Formula 1 may be a compound represented by the following Formula 1-3:

[Formula 1-3]

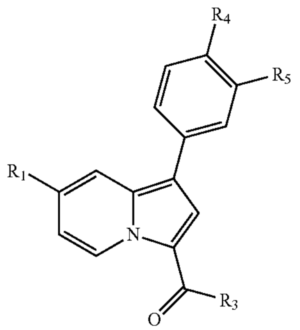

wherein $R_1$ is hydrogen, a $C_1$-$C_8$ straight or branched chain alkyl group, a halogen-substituted $C_1$-$C_8$ straight or branched chain alkyl group, a $C_2$-$C_8$ alkenyl group, a $C_2$-$C_8$ alkynyl group, a halogen group, a nitrile group, a hydroxyl group, a $C_1$-$C_6$ alkoxy group, —$COY_1$ (wherein $Y_1$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), —$CO_2Y_2$ (wherein $Y_2$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), or —$NY_3Y_4$ (wherein $Y_3$ and $Y_4$ are each independently hydrogen, a $C_1$-$C_{10}$ alkyl group, a $C_6$-$C_{20}$ aryl group, or a $C_4$-$C_{20}$ heteroaryl group);

$R_4$ and $R_5$ are each independently hydrogen, a $C_1$-$C_8$ straight or branched chain alkyl group, a halogen-substituted $C_1$-$C_8$ straight or branched chain alkyl group, a $C_2$-$C_8$ alkenyl group, a $C_2$-$C_8$ alkynyl group, a $C_3$-$C_8$ cycloalkyl group, a $C_5$-$C_{20}$ heterocycloalkyl group, a $C_6$-$C_{20}$ aryl group, a $C_6$-$C_{20}$ heteroaryl group, a halogen group, a nitrile group, a nitro group, a hydroxyl group, a carboxyl group, a $C_1$-$C_6$ alkoxy group, —$COY_5$ (wherein $Y_5$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), —$CO_2Y_6$ (wherein $Y_6$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, a $C_6$-$C_{20}$ aryl group), or —$NY_7Ye$ (wherein $Y_7$ and Ye are each independently hydrogen, a $C_1$-$C_{10}$ alkyl group, a $C_6$-$C_{20}$ aryl group, or a $C_4$-$C_{20}$ heteroaryl group); and $R_3$ is a $C_1$-$C_8$ straight or branched chain alkyl group.

Specifically, $R_1$ in Formula 1-3 above may be hydrogen, a $C_1$-$C_8$ straight or branched chain alkyl group, a halogen-substituted $C_1$-$C_8$ straight or branched chain alkyl group, or —$COY_1$ (wherein $Y_1$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group). In this case, $Y_1$ may be more specifically a $C_1$-$C_8$ straight or branched chain alkyl group.

In addition, $R_3$ in Formula 1-3 above may be a $C_1$-$C_8$ straight or branched chain alkyl group, specifically a methyl group.

In addition, $R_4$ and $R_5$ in Formula 1-3 above may be each independently hydrogen, a $C_1$-$C_8$ straight or branched chain alkyl group, a halogen-substituted $C_1$-$C_8$ straight or branched chain alkyl group, a $C_1$-$C_6$ alkoxy group, —$COY_5$ (wherein $Y_5$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), or —$NY_7Ye$ (wherein $Y_7$ and Ye may be each independently hydrogen, a $C_1$-$C_{10}$ alkyl group, a $C_6$-$C_{20}$ aryl group, or a $C_4$-$C_{20}$ heteroaryl group). In this case, $Y_5$ may be more specifically a $C_1$-$C_8$ straight or branched chain alkyl group, and $Y_7$ and $Y_8$ may be each independently hydrogen or a $C_1$-$C_{10}$ alkyl group.

The compound represented by Formula 1c may include the compound represented by Formula 1-3. The indolizine derivative compound represented by Formula 1 may be any one of the following Compounds 1 to 72:

[Compound 1]

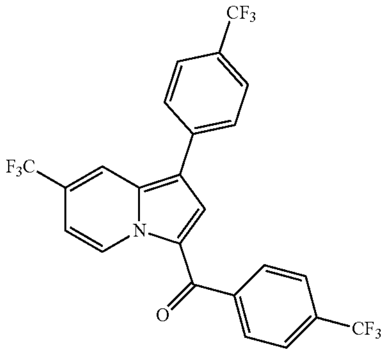

[Compound 2]

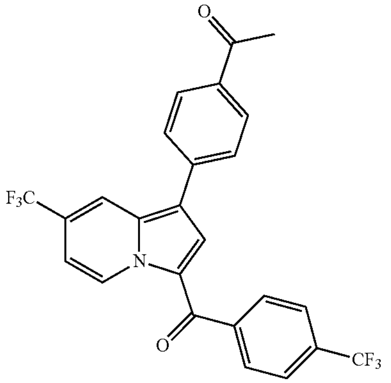

[Compound 3]

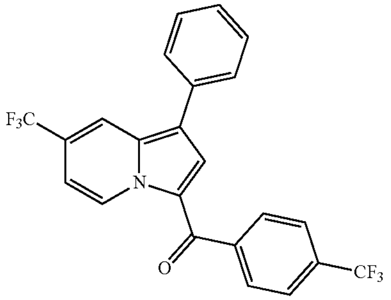

-continued

[Compound 4]

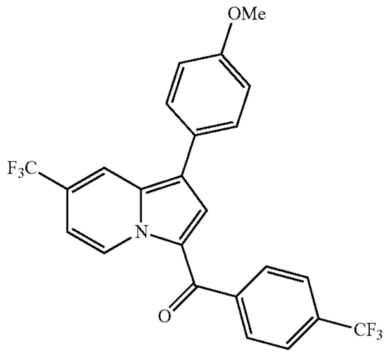

[Formula 5]

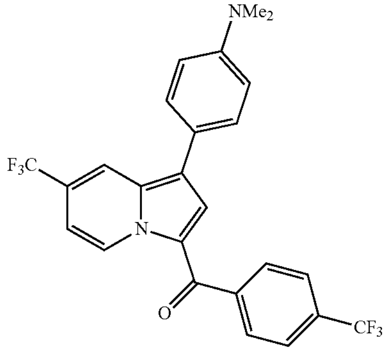

[Formula 6]

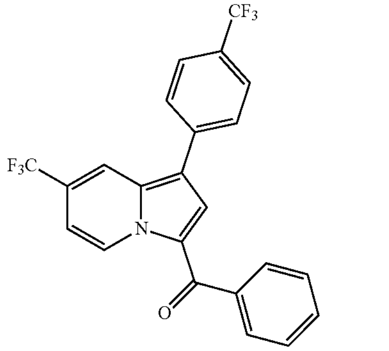

[Compound 7]

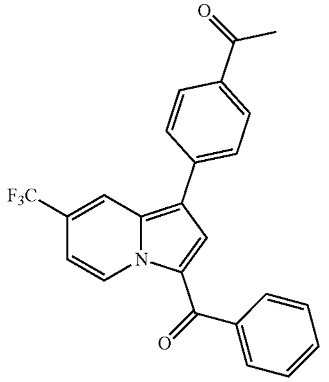

-continued
[Compound 8]
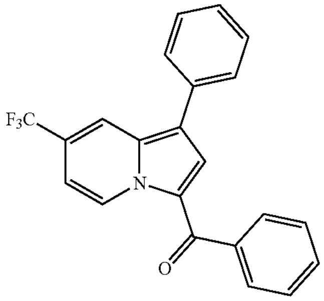
[Compound 9]
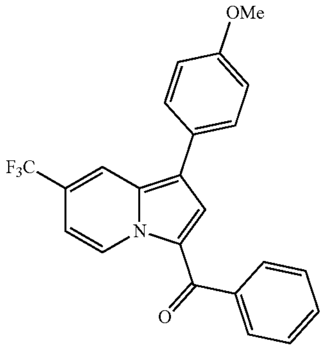
[Compound 10]
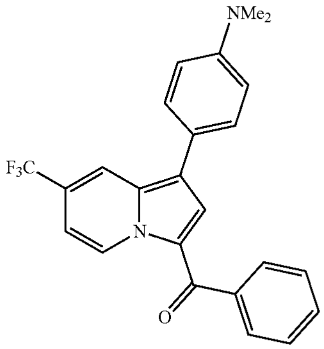
[Compound 11]
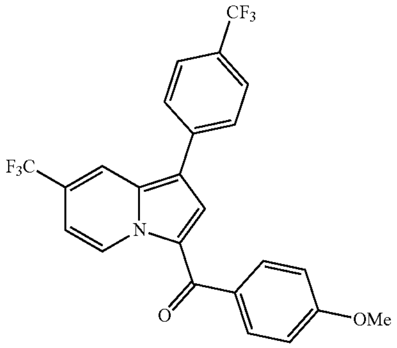
-continued
[Compound 12]
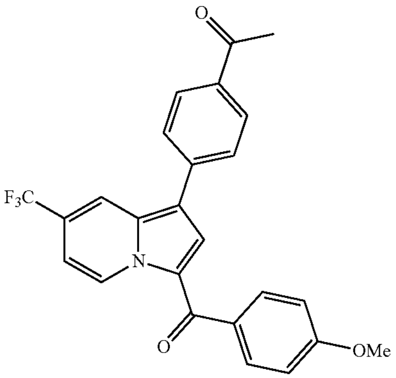
[Compound 13]
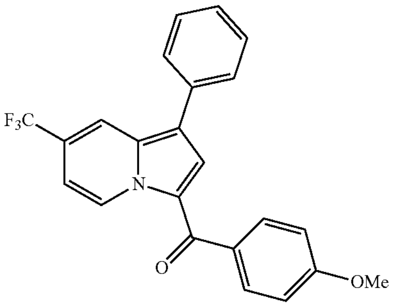
[Compound 14]
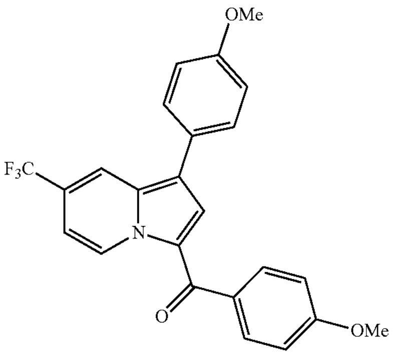
[Compound 15]
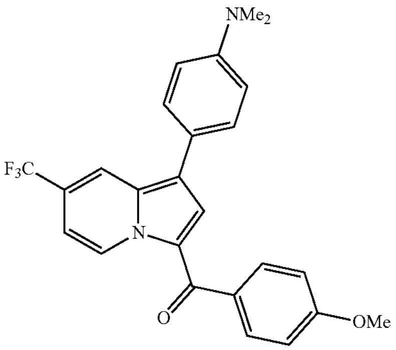

-continued
[Compound 16]
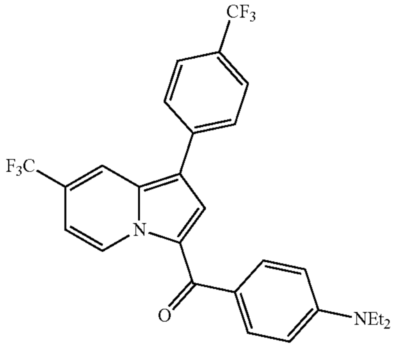
[Compound 17]
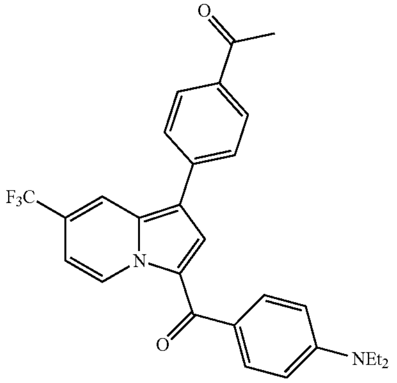
[Compound 18]
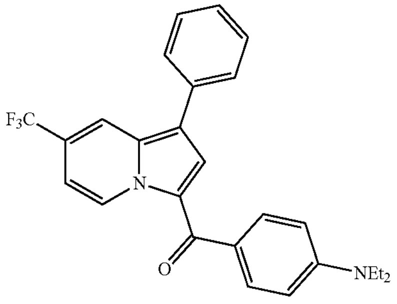
[Compound 19]
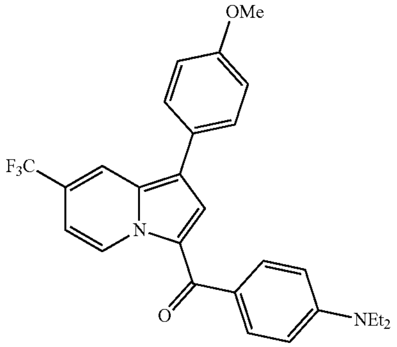
-continued
[Compound 20]
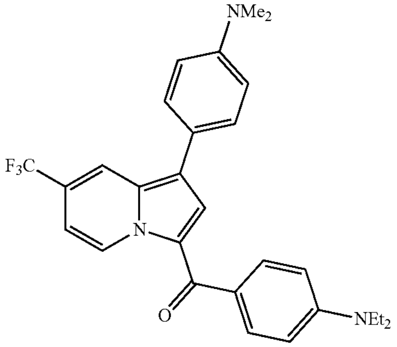
[Compound 21]
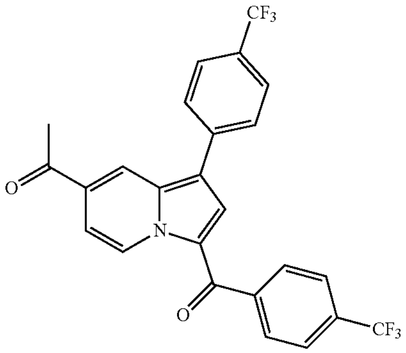
[Compound 22]
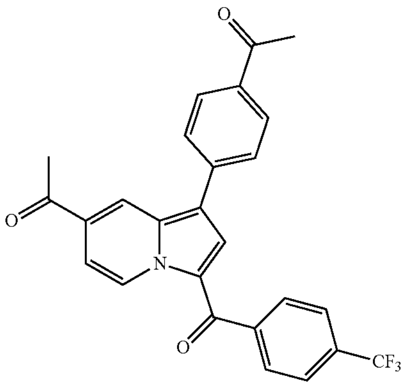
[Compound 23]
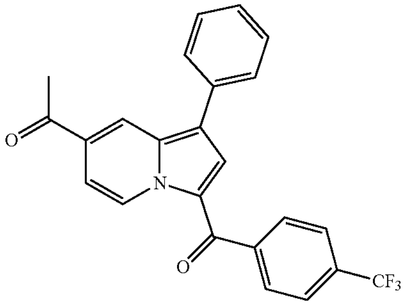

-continued
[Compound 24]
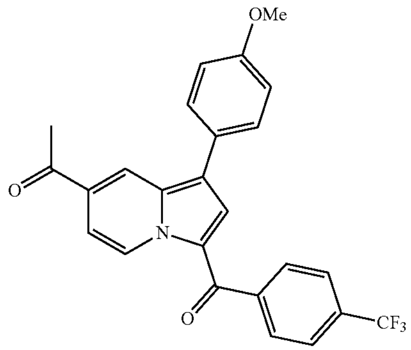
[Compound 25]
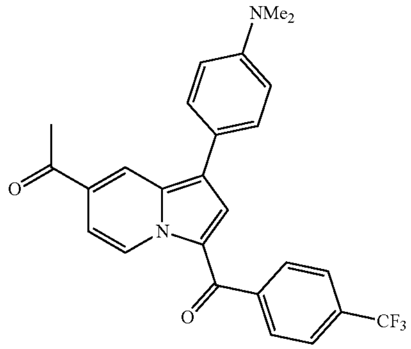
[Compound 26]
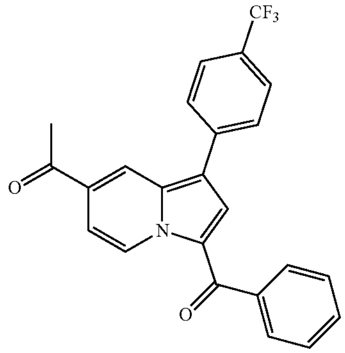
[Compound 27]
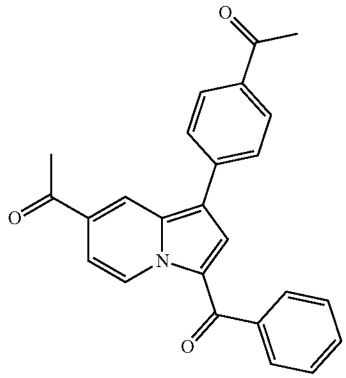
-continued
[Compound 28]
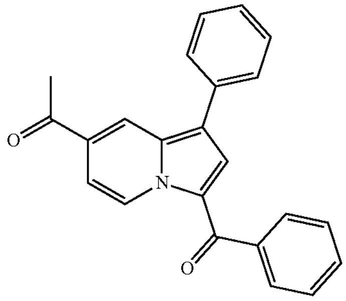
[Compound 29]
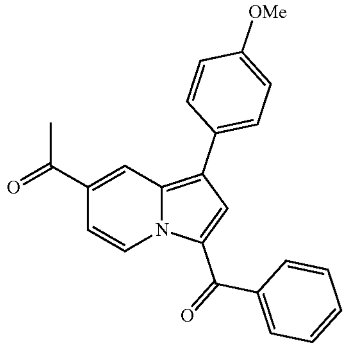
[Compound 30]
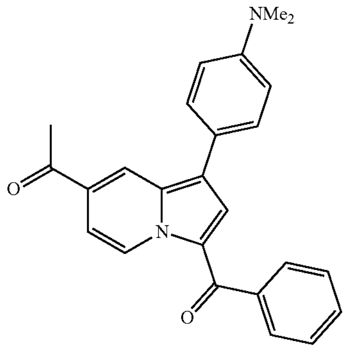
[Compound 31]
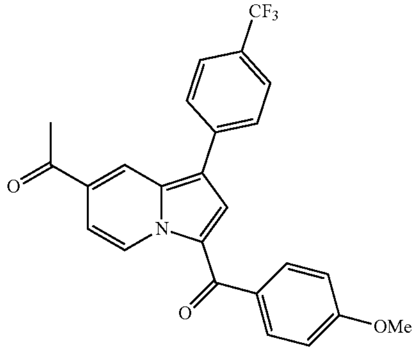

-continued
[Compound 32]
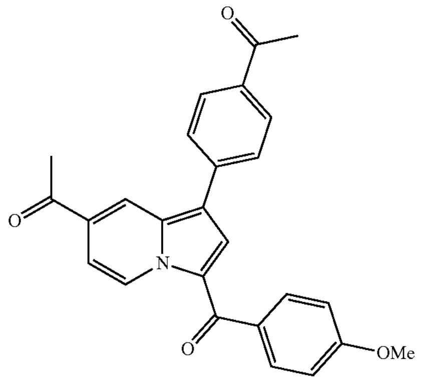
[Compound 33]
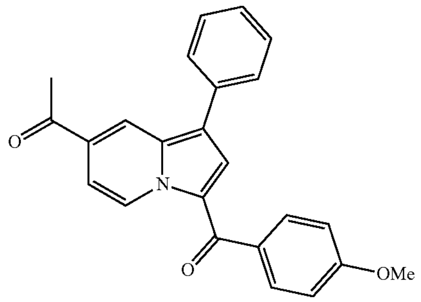
[Compound 34]
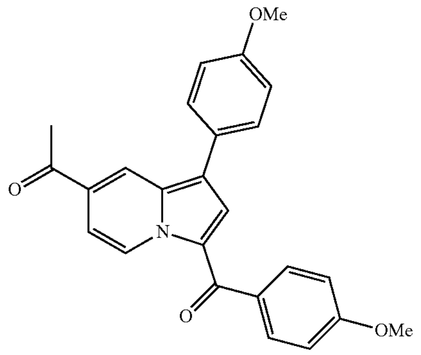
[Compound 35]
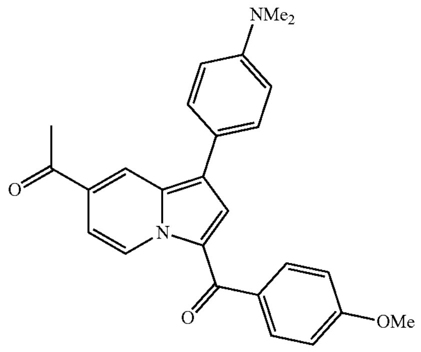
-continued
[Compound 36]
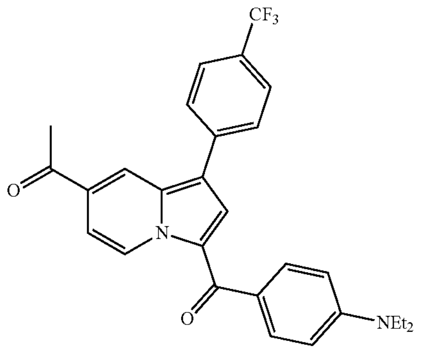
[Compound 37]
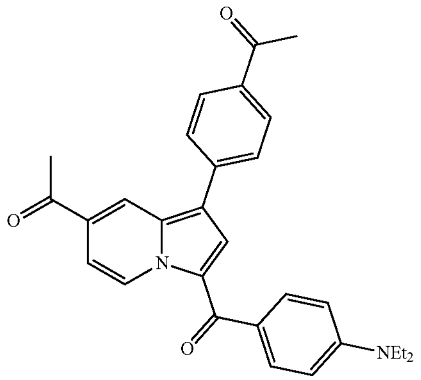
[Compound 38]
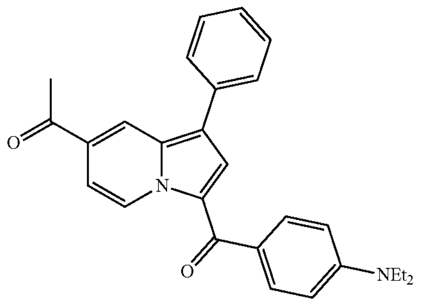
[Compound 39]
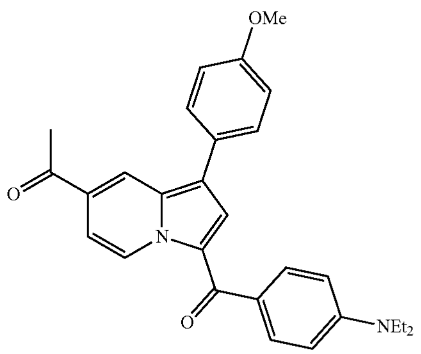

-continued
[Compound 40]
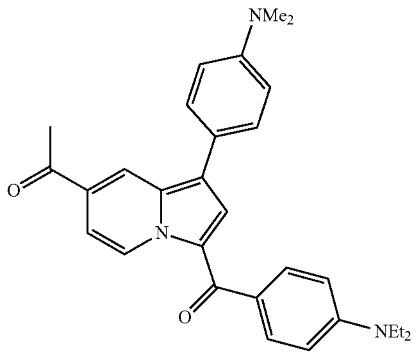
[Compound 41]
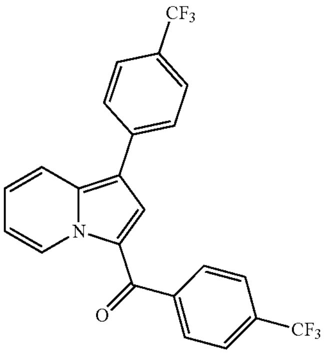
[Compound 42]
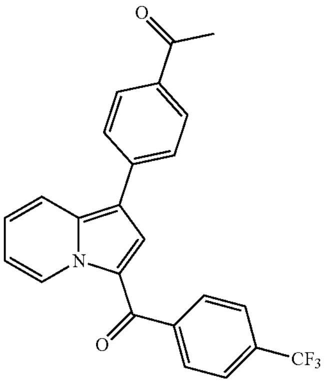
[Compound 43]
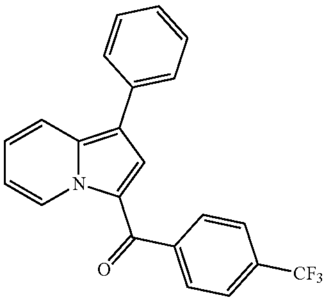
-continued
[Compound 44]
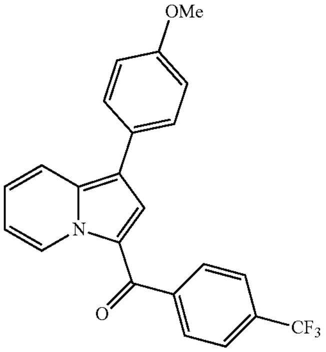
[Compound 45]
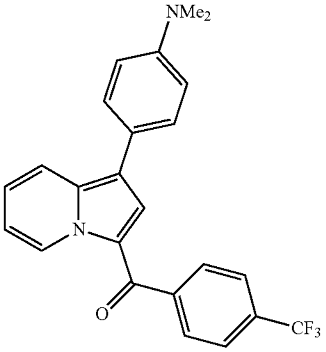
[Compound 46]
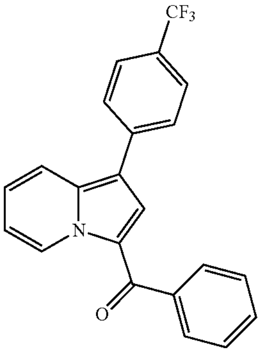
[Compound 47]
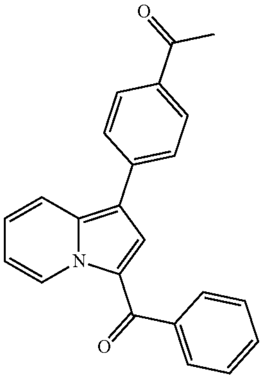

-continued
[Compound 48]
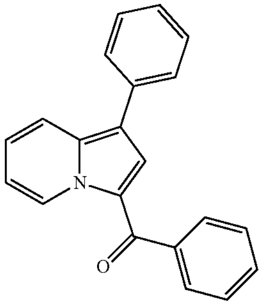
[Compound 49]
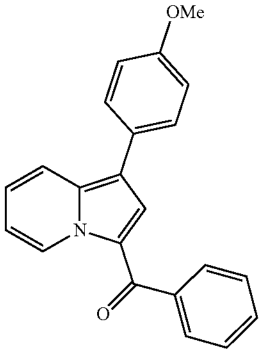
[Compound 50]
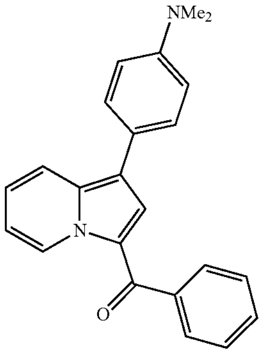
[Compound 51]
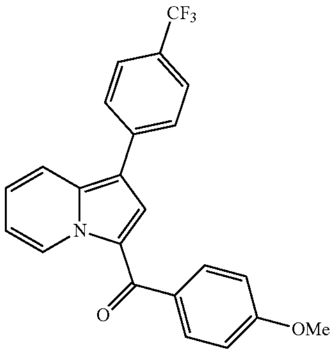
-continued
[Compound 52]
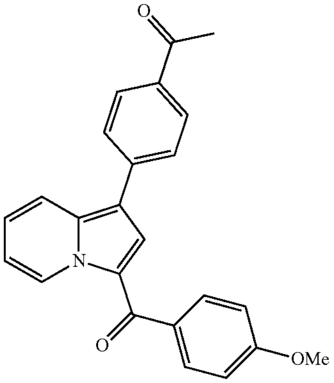
[Compound 53]
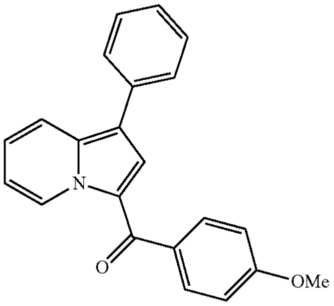
[Compound 54]
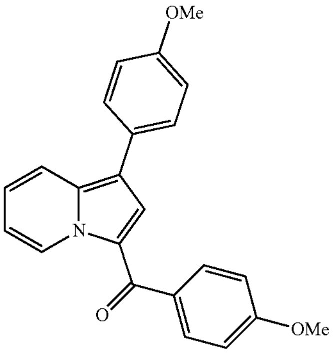
[Compound 55]
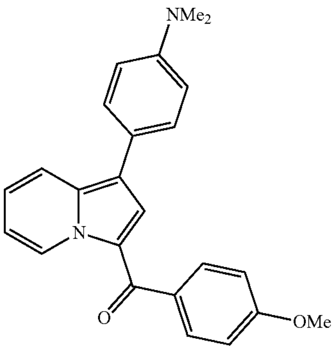

-continued
[Compound 56]
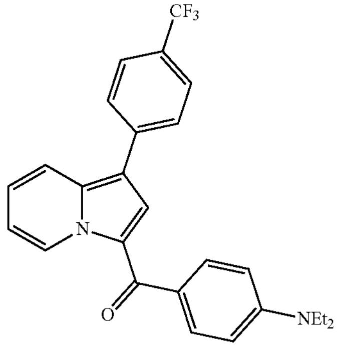
[Compound 57]
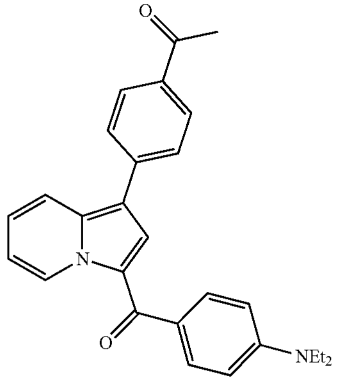
[Compound 58]
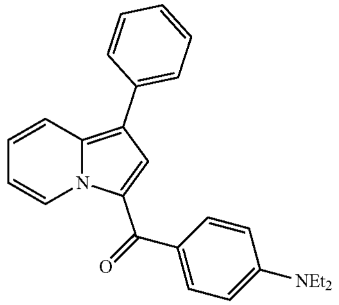
[Compound 59]
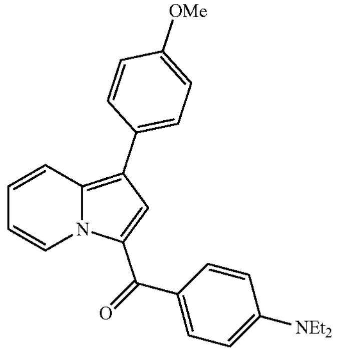
-continued
[Compound 60]
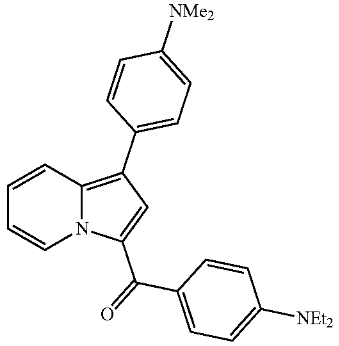
[Compound 61]
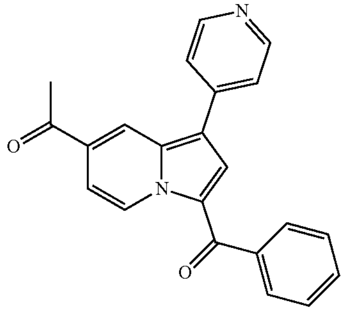
[Compound 62]
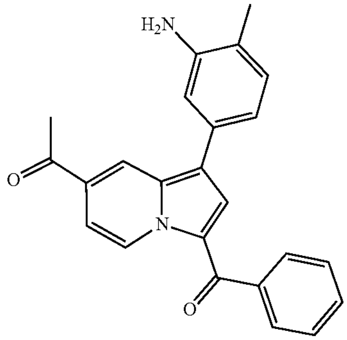
[Compound 63]
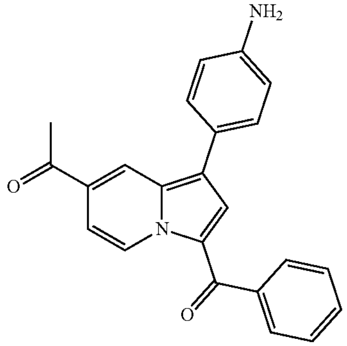

-continued
[Compound 64]
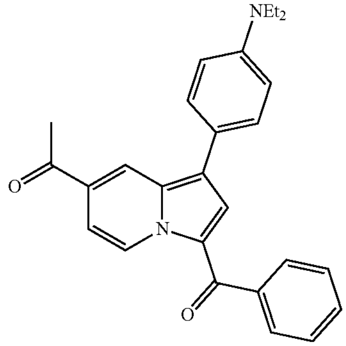
[Compound 65]
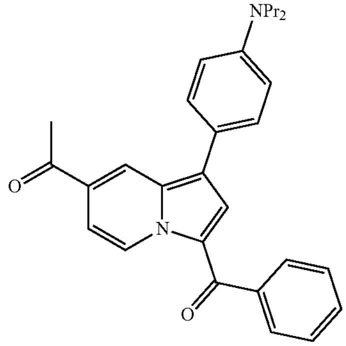
[Compound 66]
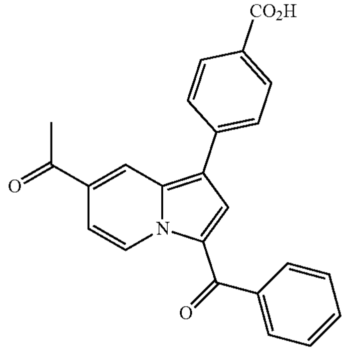
[Compound 67]
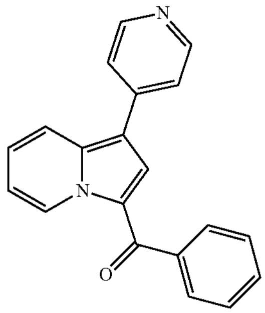
-continued
[Compound 68]
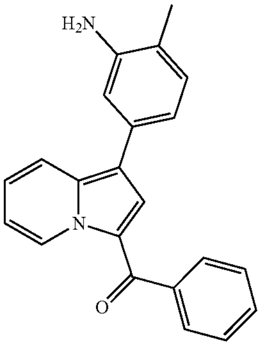
[Compound 69]
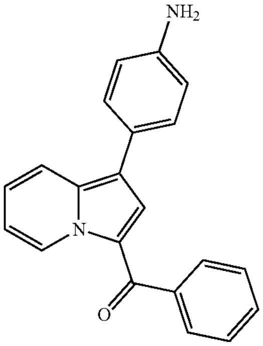
[Compound 70]
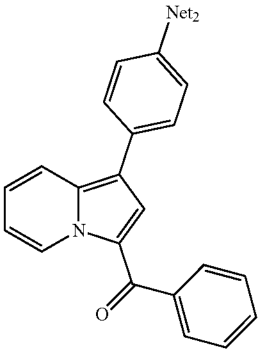
[Compound 71]
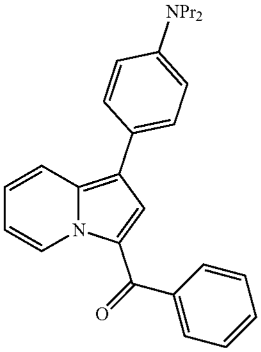

-continued

[Compound 72]

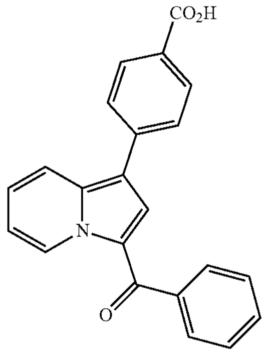

Specifically, the compound represented by Formula 1-1 may be any one of Compound 1 to Compound 60, Compound 62 to Compound 66, and Compound 68 to Compound 72. In addition, the compound represented by Formula 1-2 may be Compound 61 or Compound 67.

The indolizine derivative compound represented by Formula 1 may be any one of Compounds 73 to 87 below.

[Compound 73]

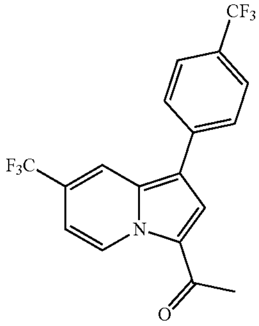

[Compound 74]

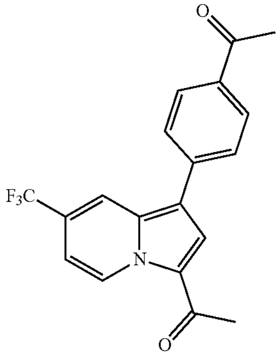

[Compound 75]

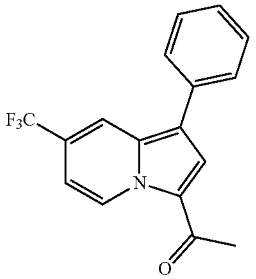

-continued

[Compound 76]

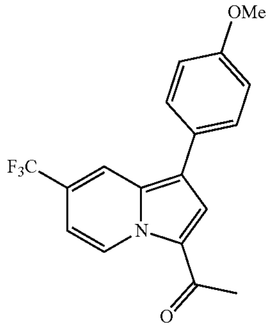

[Compound 77]

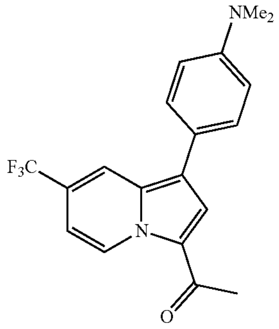

[Compound 78]

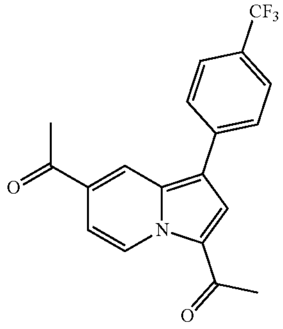

[Compound 79]

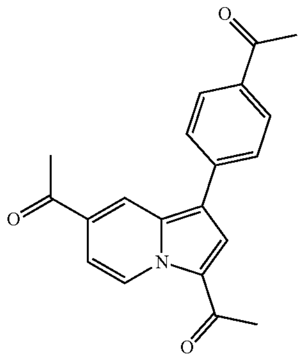

[Compound 80]

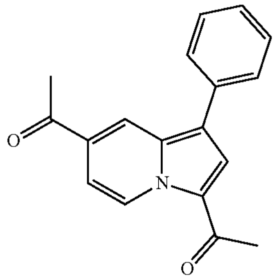

-continued

[Compound 81]

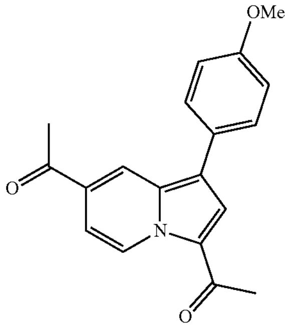

[Compound 82]

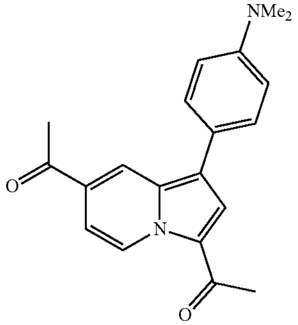

[Compound 83]

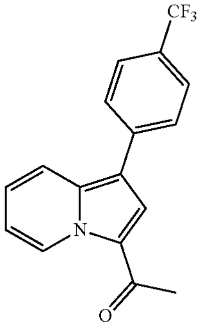

[Compound 84]

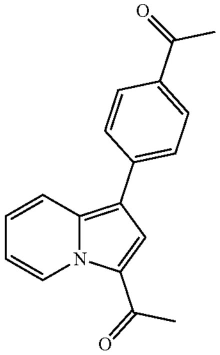

[Compound 85]

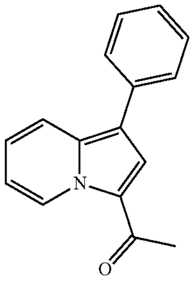

-continued

[Compound 86]

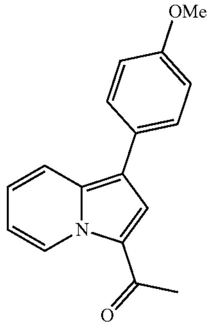

[Compound 87]

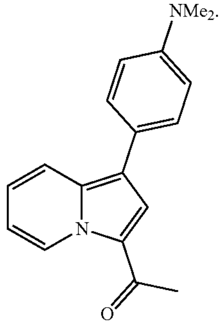

Specifically, the compound represented by Formula 1-3 may be any one of Compound 73 to Compound 87.

The cyclic-di-nucleotide (CDN) is a natural activator of STING described above, is a secondary messenger signaling molecule produced by various bacteria, and is composed of two ribonucleotides connected together via a phosphodiester bond to form a cyclic structure. CDNs Cyclo-di(GMP), cyclo-di(AMP) and hybrid cyclo-(AMP/GMP) derivatives all bind to STING with subsequent activation of the interferon pathway (Gao et al., Cell, 2013, 153, 1094-1107; Zhang et al., Mol. Cell, 2013, 51, 226-235). The canonical 5'-3' phosphodiester linkage is recognized along with various other linkage isomers (notably the 5'-2' linkage, e.g. c[G(2',5')pA(3',5')p]) which all bind to STING with various affinities (Shi et al., PNAS, 2015, 112, 1947-8952). These observations have been corroborated by structural studies (Gao et. al., *Cell,* 2013, 154, 748-762) of various linkage isomers of CDNs bound to the human and mouse STING proteins.

cGAMP, which is an example of the cyclic-di-nucleotide, is a heterodimer linked by one 3'-5' phosphodiester and one 2'-5' phosphodiester (2',3'-cGAMP), while the bacteria CDNs are linked through two 3'-5' phosphodiester linkages (3',3'-CDNs), which can contain two guanosines, two adenosines or one of each (Davies, B. W., 2012). The affinity of 2',3'-cGAMP for human STING is very high, with a dissociation constant of 4.59 nM compared to >1 uM for bacteria 3',3'-CDNs (Zhang, X. et al., 2013; Ablasser, A. et al., 2013; Diner et al., 2013).

However, native CDNs are sensitive to degradation by phosphodiesterases that are present in host cell or in the systemic circulation (Yan et al., 2008). In order to improve hydrolytic stability, synthetic CDN compounds were developed with the substitution of non-bridging oxygen atoms at phosphate bridge with sulfur atoms. It has been found that a bisphosphothionate analogue of endogenous cGAMP (ML cGAMP) is resistant to hydrolysis by ENPP1 phosphodiesterase; therefore, more potent in inducing IFN-β secretion in human THP-1 cells (Li et al., 2014). Similarly, R,R-dithio modified cyclic di-AMP (CDA) (ML RR-S2 CDA and RR-S2 CDA) showed increased type I IFN production over CDA (Leticia C., et al., 2015). In addition, intratumoral injection of ML RR-S2 CDA into B16 melanoma tumors resulted in complete tumor elimination in most of the ML RR-S2 CDA-treated mice and induced lasting systemic antigen-specific CD8+ T-cell immunity. Furthermore, they were completely protected against second tumor rechallenge. Similar results were seen in the 4T-1 breast cancer and MC26 colon cancer models.

This cyclic-di-nucleotides have the problem of low disease control rate despite increased production of pro-inflammatory cytokines. The present inventors have found that, when the cyclic-di-nucleotide having this problem is used together with the compound of Formula 1, the cyclic-di-nucleotide has high activity even when it is used at a low concentration.

In one embodiment of the present invention, the cyclic-di-nucleotide may be substituted with fluorine at any one or more of 2'- and 3'-positions. More specifically, the cyclic-di-nucleotide may be any one of the following compounds.

[Compound 2-1]

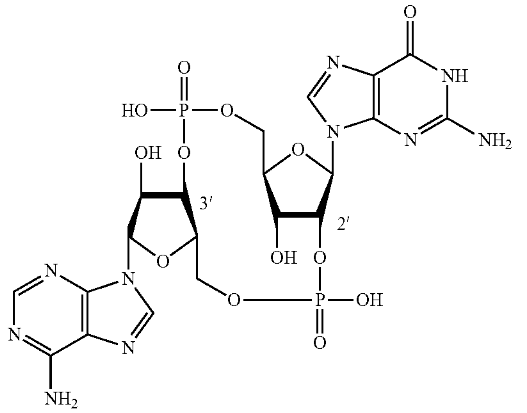

[Compound 2-2]

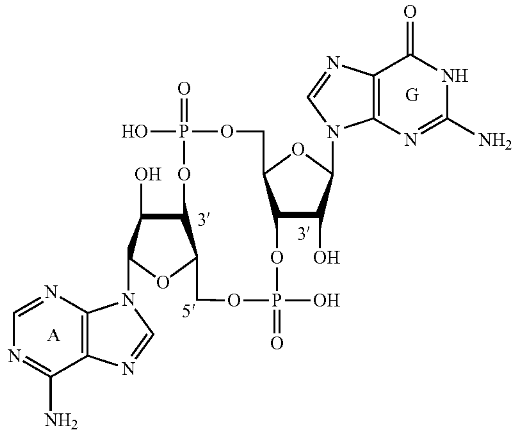

-continued

[Compound 2-3]

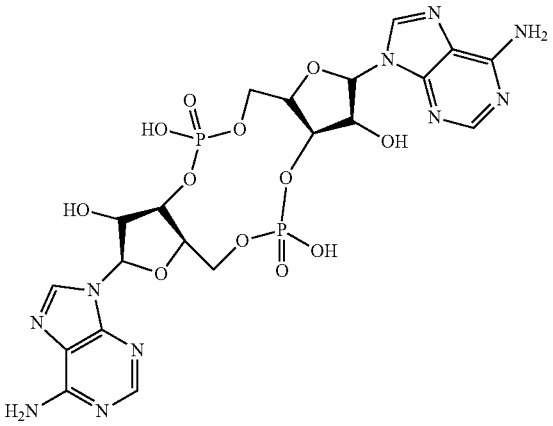

[Compound 2-4]

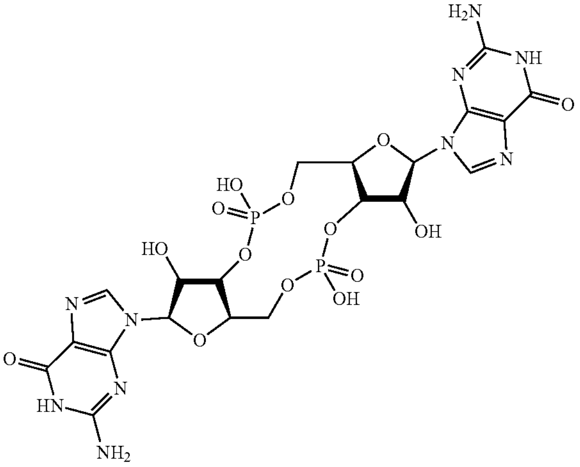

[Compound 2-5]

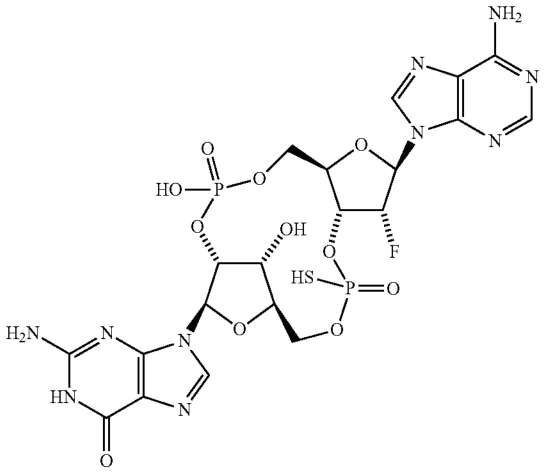

-continued

[Compound 2-6]

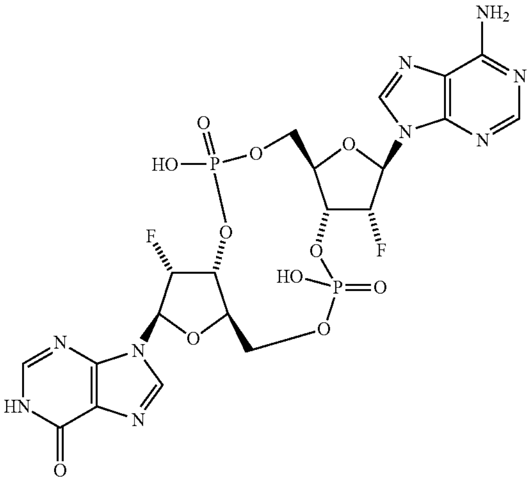

[Compound 2-7]

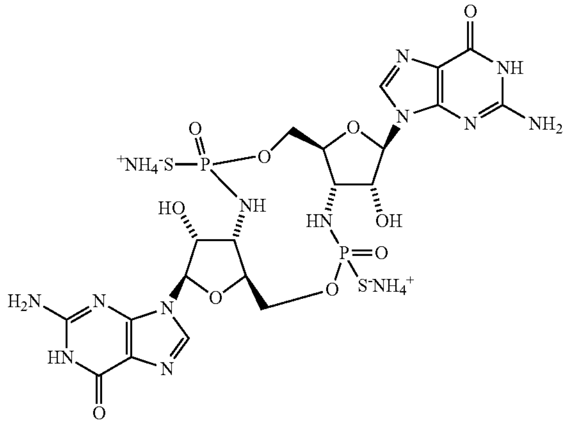

[Compound 2-8]

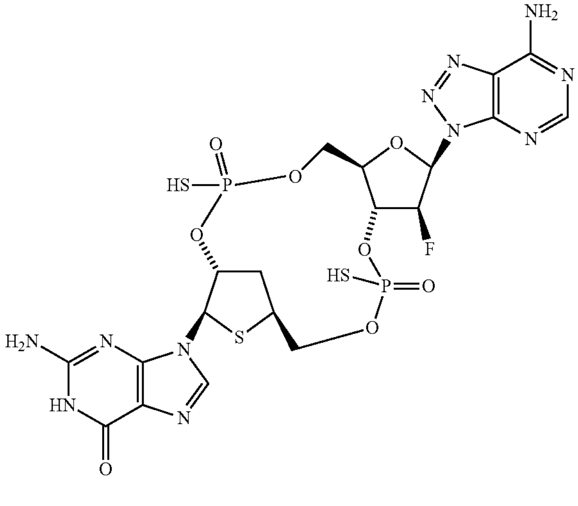

-continued

[Compound 2-9]

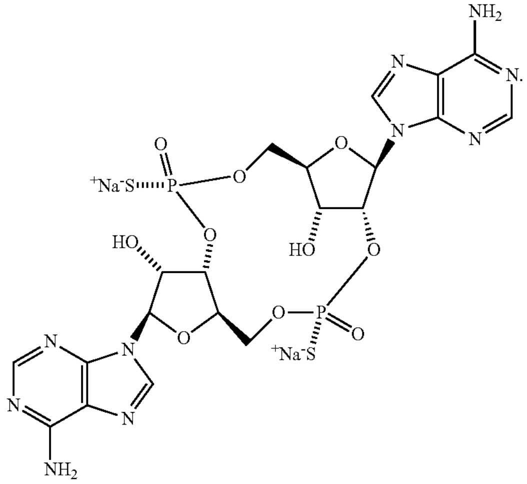

Compound 2-1 is 2,3-cGAMP which is a compound having a chemical name of adenylyl-(3'-5')-2'-guanylic acid, cyclic nucleotide (CAS Number 1441190-66-4), Compound 2-2 is a compound having a chemical name of 3,3-cGAMP adenylyl-(3'-5')-3'-guanylic acid, cyclic nucleotide (CAS Number 849214-0), Compound 2-3 is c-di-AMP which is a compound having a chemical name of adenylyl-(3'-5')-3'-adenylic acid, cyclic nucleotide (CAS Number 54447-84-6), Compound 2-4 is c-di-GMP which is a compound having a chemical name of guanylyl-(3'-5')-3'-guanylic acid, cyclic nucleotide (CAS Number 61093-23-0), Compound 2-5 is Compound 27 disclosed in WO2017093933, which has a chemical name of (1R,6R,8R,9R,10R,15R,17R,18R)-17-(2-amino-6-oxo-6.9-dihydro-1H-purin-9-yl)-8-(6-amino-9H-purin-9-yl)-9-fluoro-18-hydroxy-3,12-disulfanyl-2, 4,7 11,13,16-hexaoxa-3$\lambda^5$, 12$\lambda^5$-diphosphatricyclo[13.2.1.0$^{6,10}$ octadecane-3,12-dione], Compound 2-6 is Compound CL614 disclosed in US20160362441, which has a chemical name of c-(2 FdAMP-2FdIMP), Compound 2-7 is Compound 76 disclosed in WO2017123669, which has a chemical name of [(1S,6S,8R,9R,10S,15S,17R,18R)-8,17-bis(2-amino-6-oxo-6,9-dihydro-1H-purin-9-yl)-9,18-dihydroxy-3,12-dioxo-12-sulfanidyl-4,7,13,16-tetraoxa-2,11-diaza-$3\lambda^5,12\lambda^5$)-diphosphatricyclo[13.3.0.0$^{6,10}$]octadecan-3-yl] sulfanide, Compound 2-8 is Compound 191 disclosed in WO2017027646, which has a chemical name of 2-amino-9-[(5S,7R,8R,12aR,14R,15S,15aR)-14-(7-amino-3H-[1,2,3]triazolo[4,5-d]pyrimidin-3-yl)-15-fluoro-2,10-dihydroxy-2,10-disulfidooctahydro-12H-5,8-methanofuro[3,2-1][1,3,9,1,6,2,0]tetraoxathiadiophosphacyclotetradecin-7-yl]-1,9-dihydro-6H-purin-6-one, and Compound 2-9 is compound ADU-S100 commercially available from Aduro, which has a name of MIW815 (CAS Number 1638750-95-4).

Specifically, the compound cyclic-di-nucleotide may be 2,3-cGAMP.

In one embodiment of the present invention, the composition may be for prevention or treatment of any one autoimmune disease selected from among cancer, solid cancer, non-T cell invasive cancer, cancer having low responsiveness to immune checkpoint inhibitors, and STING-associated vasculopathy with onset in infancy (SAVI).

The composition of the present invention contains both the compound of Formula 1 and the cyclic-di-nucleotide so that they may be co-administered to a subject.

As used herein, the term "co-administration" means that active ingredients are used simultaneously or sequentially.

The present inventors have found that, when the compound of Formula 1 and the cyclic-di-nucleotide are used together, the cyclic-di-nucleotide has high activity even when it is used at a low concentration.

The composition may further contain an acceptable carrier, without being particularly limited thereto.

Examples of the acceptable carrier include, but are not limited to, saline, sterile water, Ringer's solution, buffered saline, cyclodextrin, dextrose solution, maltodextrin solution, glycerol, ethanol, liposome, etc., which are commonly used in formulation. The composition may further contain other conventional additives such as antioxidants and buffers as needed. In addition, the composition may be formulated into an injectable formulation such as an aqueous solution, suspension, or emulsion, pills, capsules, granules, or tablets by additionally adding a diluent, a dispersant, a surfactant, a binder, a lubricant, and the like. Regarding suitable pharmaceutically acceptable carriers and formulations, formulations may be preferably prepared according to each component by using the methods disclosed in Remington's literature. The pharmaceutical composition of the present invention is not particularly limited in formulation, but may be formulated as an injection, an inhalant, or an external preparation for skin.

Another aspect of the present invention is directed to a method for preventing or treating disease, the method comprising a step of administering the composition to a subject in need of treatment or prevention. Specifically, the composition may be used to prevent or treat any one autoimmune disease selected from among cancer, solid cancer, non-T cell invasive cancer, cancer having low responsiveness to immune checkpoint inhibitors, and STING-associated vasculopathy with onset in infancy (SAVI).

In one embodiment of the present invention, the subject in need of treatment or prevention may have or be at high risk of having any one autoimmune disease selected from among cancer, solid cancer, non-T cell invasive cancer, cancer having low responsiveness to immune checkpoint inhibitors, and STING-associated vasculopathy with onset in infancy (SAVI).

The composition may be administered in a pharmaceutically effective amount to the subject in need of treatment or prevention.

The term "pharmaceutically effective amount" refers to an amount sufficient to treat a disease at a reasonable benefit/risk ratio applicable to any medical treatment. The effective dose level of the active ingredient may be determined depending on factors, including the kind and severity of the subject's disease, the subject's age and sex, the activity of the drug, sensitivity to the drug, the time of administration, the route of administration, excretion rate, the duration of treatment, and drugs used in combination with the composition, as well as other factors well known in the medical field.

The composition may be administered as an individual therapeutic agent or in combination with other therapeutic agents, and may be administered sequentially or simultaneously with conventional therapeutic agents. In addition, the composition may be administered in a single or multiple dosage form. It is important to administer the composition in the minimum amount that can exhibit the maximum effect without causing side effects, in view of all the above-described factors, and this amount can be easily determined by a person skilled in the art.

In addition, the composition may be administered orally or parenterally (e.g., intravenously, subcutaneously, intraperitoneally or topically) depending on the desired method, and the dosage of the composition may vary depending on the patient's condition and weight, the severity of the disease, the form of the drug, and the route and duration of administration, but may be selected appropriately by a person skilled in the art.

As a specific example, the composition may generally be administered once or several times a day in an amount of 0.001 to 1000 mg/kg, more specifically 0.05 to 200 mg/kg, most specifically 0.1 to 100 mg/kg, but the preferred dosage of the composition may be appropriately selected by those skilled in the art depending on the subject's condition and weight, the severity of the disease, the form of the drug, and the route and duration of administration.

MODE FOR INVENTION

Hereinafter, one or more embodiments will be described in more detail with reference to examples. However, these examples are intended to illustrate one or more specific examples, and the scope of the present invention is not limited to these examples.

$^1$H and $^{13}$C NMR spectra were recorded on a JEOL ECZ-600R (JEOL Ltd., Japan), and chemical shifts were expressed as parts per million (ppm) downfield of the internal tetramethylsilane standard.

Multiplicity was expressed as follows: s (singlet); d (doublet); t (triplet); q (quartet); m (multiplet); dd (doublet of doublet); ddd (doublet of doublet of doublet); dt (doublet of triplet); td (triplet of doublet); and brs (broad singlet).

Coupling constants were reported in Hz. Routine mass analyses were performed on LC/MS system equipped with a reverse phase column (C-18, 50×2.1 mm, 5 μm) and photodiode array detector using electron spray ionization (ESI) or atmospheric pressure chemical ionization (APCI).

Molecular weight analysis of compounds was performed using high-resolution mass spectrometry (LRMS). LRMS analysis was performed using LCMS-2020 (Shimadzu, Japan).

EXAMPLES

Example 1: Production of Compound 1

Example 1-1: Production of (1-bromo-7-(trifluoromethyl)indolizin-3-yl) (4-(trifluoromethyl)phenyl) methanone (IA-B)

IA-E: IA-E was synthesized as shown in Reaction Scheme 1-1 above. Specifically, dimethylformamide (DMF, 10.0 mL) containing 4-(trifluoromethyl)pyridine (637 μL, 5.50 mmol) and 2-bromo-1-[4-(trifluoromethyl)-phenyl]ethane-1-one (1.54 g, 5.70 mmol) was stirred overnight at 100° C., and then ethyl acrylate (293 μL, 2.75 mmol), copper(II) acetate monohydrate (1.64 g, 8.25 mmol) and sodium acetate (1.35 g, 16.5 mmol) were added thereto, followed by stirring at 100° C. for 16 hours. After completion of the reaction, monitoring by TLC was performed, and then copper acetate was removed by filtration through a celite pad, and the resulting filtrate was concentrated in vacuum. The resulting crude product was washed with water, and the organic phase was extracted three times with DCM. The extracted organic phases were combined, dried over anhydrous $Na_2SO_4$ and concentrated. The concentrated organic phase was purified by silica-gel flash column chromatography (1 to 15% hexane containing EtOAc) to obtain compound IA-E (518 mg, 1.20 mmol, 43.8% yield) as a yellow solid.

[Reaction Scheme 1-1]

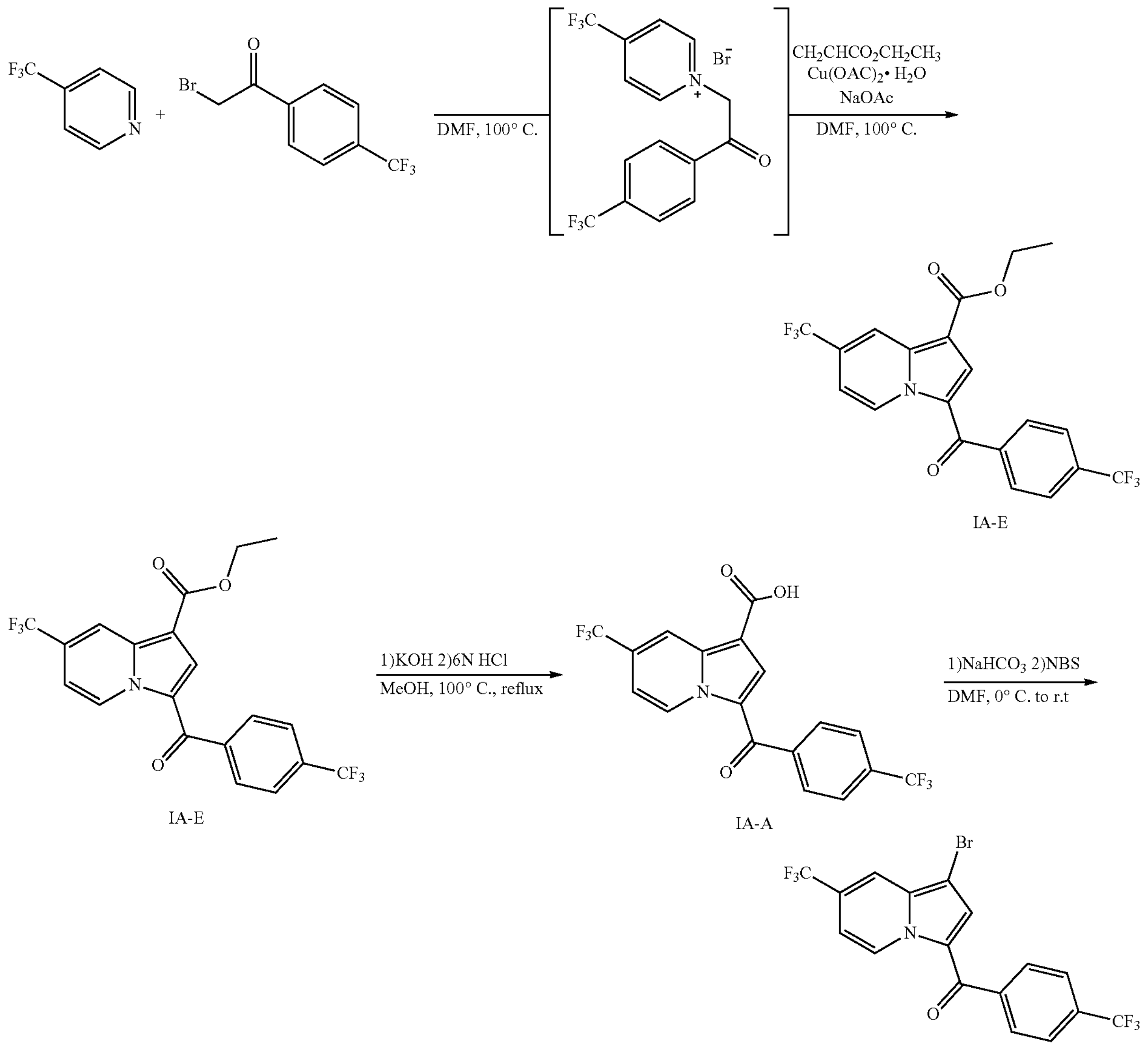

IA-E, IA-E, IA-A, IA-B

The results of NMR analysis are as follows.

$^1$H NMR (400 MHz, $CDCl_3$) δ 10.0 (d, J=7.2 Hz, 1H), 8.70 (s, 1H), 7.91 (d, J=7.6 Hz 2H), 7.82 (s, 1H), 7.79 (d,

J=8.0 Hz, 2H), 7.23 (d, J=7.2 Hz, 1H), 4.40 (q, J=7.2 Hz, 2H), 1.41 (t, J=7.2 Hz, 3H); $^{13}$C NMR (100 MHz, $CDCl_3$), δ 184.0, 162.8, 141.9, 137.7, 133.3, 132.6, 129.3, 128.9, 125.3, 124.7, 124.0, 122.6, 122.0, 121.2, 117.1, 110.9, 108.9, 60.6, 14.4.

IA-B: KOH (5,386 mg, 96.00 mmol) was added to methanol (10 mL) containing IA-E (517.9 mg, 1.206 mmol), followed by stirring overnight at room temperature. The reaction mixture was acidified by adding 6N HCl, and the resulting solid was collected through filtration, washed with water, and dried in a drying oven to obtain compound IA-A as a brown solid.

The obtained compound IA-A was used in the next step without further purification. Sodium bicarbonate (302.4 mg, 3.600 mmol) was added to DMF (10.0 mL) containing IA-A, and NBS (320.3 mg, 1.800 mmol) was added thereto in portions at 0° C. The reaction mixture was stirred at room temperature for 12 hours, and then the resulting crude product was washed with water and the organic phase was extracted three times with DCM. The extracted organic phases were combined, dried over anhydrous $Na_2SO_4$, and then concentrated. The concentrated organic phase was purified by silica-gel flash column chromatography (EA: hexane=1:8-12% ethyl acetate) to obtain compound IA-B (434.1 mg, 0.99 mmol, 82.9% yield) as a yellow solid.

The results of NMR analysis are as follows.

$^1$H NMR (400 MHz, $CDCl_3$) δ 95.5 (d, J=7.2 Hz, 1H), 7.90 (s, 2H), 7.87 (s, 1H), 7.78 (d, J=8.0 Hz, 2H), 7.40 (s, 1H), 7.13 (d, J=7.2 Hz, 1H); $^{13}$C NMR (100 MHz, NNN) δ 183.1, 142.4, 135.0, 133.1, 129.2, 127.6, 126.6, 125.6, 125.5, 124.4, 123.0, 121.7, 115.4, 110.4, 93.0; LRMS (ESI) m/z calculated for $C_{17}H_8BrF_6NO$ [M+Na]$^+$: 435.0, found: 436.3.

Example 1-2: Production of Compound 1

To a solution containing IA-B (50.4 mg, 0.11 mmol) and a 2:1 mixture of DMF and water, 4-triflulorophenyl boronic acid (88.0 mg, 0.46 mmol), tetrakis(triphenyl phosphine) palladium (231 mg, 20.0 mol %) and sodium carbonate (49.0 mg, 0.46 mmol) were added, followed by stirring at 100° C. for 12 hours. After completion of the reaction, monitoring by TLC was performed, and then the reaction solution was washed with water, and the organic phase was extracted three times with DCM. The extracted organic phases were combined, dried over anhydrous $Na_2SO_4$, and then concentrated. The concentrated organic phase was purified by silica-gel flash column chromatography (EA:hexane=1:4-25% ethyl acetate) to obtain Compound 1 (50.0 mg, 0.09 mmol, 86.7% yield) as a yellow solid.

[Compound 1]

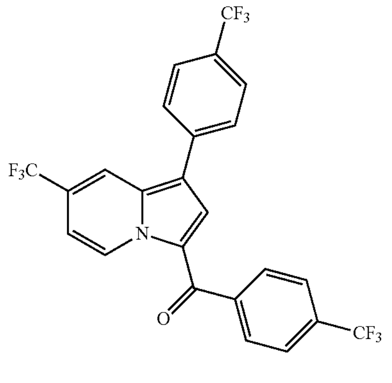

The physical properties of Compound 1 produced in Example 1 are as follows.

$^1$H NMR (400 MHz, $CDCl_3$) δ 10.07 (d, J=7.6 Hz, 1H), 8.11 (s, 1H), 7.95 (d, J=8.8 Hz, 2H), 7.80 (d, J=8.8 Hz, 2H), 7.74 (d, J=8.4 Hz, 2H), 7.66 (s, 1H), 7.64 (s, 1H), 7.52 (s, 1H), 7.18 (dd, J=7.4 Hz, 2 Hz, 1H); $^{13}$C NMR (100 MHz, $CDCl_3$) δ 183.9, 142.9, 137.1, 134.4, 133.4, 133.1, 129.5, 129.2, 128.3, 127.3, 127.0, 126.2, 126.0, 125.6, 125.1, 124.5, 123.2, 122.8, 122.4, 121.8, 119.2, 115.3, 110.4; LRMS (ESI) m/z calculated for $C_{24}H_{13}F_9NO$ [M+H]$^+$: 502.08; found: 502.10.

Example 2: Production of Compound 2

An indolizine derivative compound (48.4 mg, 0.10 mmol, 88.5% yield) was produced in the same manner as in Example 1, except that, in Example 1-2,4-acetylphenyl boronic acid (75.0 mg, 0.46 mmol), tetrakis(triphenylphosphine) palladium (231 mg, 20.0 mol %) and sodium carbonate (49.0 mg, 0.46 mmol) were added to a solution containing IA-B (50.2 mg, 0.11 mmol) and a 2:1 mixture of DMF and water.

[Compound 2]

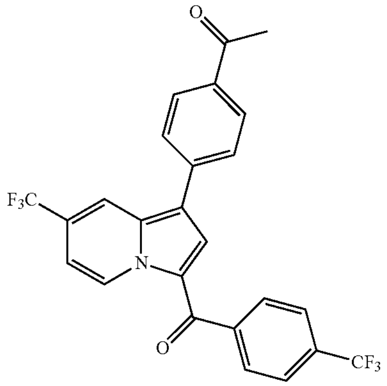

The physical properties of Compound 2 produced in Example 2 are as follows.

$^1$H NMR (400 MHz, $CDCl_3$) δ 10.06 (d, J=7.6 Hz, 1H), 8.15 (s, 1H), 8.07 (d, J=6.8 Hz, 2H), 7.95 (d, J=8.4 Hz, 2H), 7.80 (d, J=8.4 Hz, 2H), 7.64 (d, J=6.8 Hz, 2H), 7.54 (s, 1H), 7.18 (dd, J=7.6 Hz, 2 Hz, 1H), 2.65 (s, 3H); $^{13}$C NMR (100 MHz, $CDCl_3$) δ 197.2, 183.9, 142.9, 138.2, 135.8, 134.4, 133.0, 129.5, 129.3, 129.2, 128.0, 127.3, 126.9, 125.9, 125.6, 124.5, 123.3, 122.4, 121.8, 119.4, 115.5, 115.4, 110.4, 26.9; LRMS (ESI) m/z calculated for $C_{25}H_{16}F_6NO_2$ [M+H]$^+$: 476.10; found: 476.15.

Example 3: Production of Compound 3

An indolizine derivative compound (48.7 mg, 0.11 mmol, 96.0% yield) was produced in the same manner as in Example 1, except that, in Example 1-2, phenyl boronic acid (57.0 mg, 0.46 mmol), tetrakis(triphenylphosphine) palladium (231 mg, 20.0 mol %) and sodium carbonate (49.0 mg, 0.46 mmol) were added to a solution containing IA-B (51.2 mg, 0.11 mmol) and a 2:1 mixture of DMF and water.

[Compound 3]

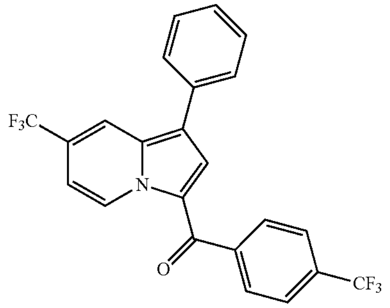

The physical properties of Compound 3 produced in Example 3 are as follows.

$^{1}H$ NMR (400 MHz, $CDCl_3$) δ 10.05 (d, J=7.6 Hz, 1H), 8.14 (s, 1H), 7.95 (d, J=8.0 Hz, 2H), 7.79 (d, J=8.0 Hz, 2H), 7.55 (s, 1H), 7.53 (d, J=3.6 Hz, 2H), 7.49 (d, J=3.2 Hz, 2H), 7.39 (d, J=7.2 Hz, 1H), 7.14 (dd, J=7.4 Hz, 2.4 Hz, 1H); $^{13}C$ NMR (100 MHz, $CDCl_3$) δ 183.7, 143.1, 134.4, 133.3, 133.2, 132.9, 129.3, 129.2, 128.1, 127.5, 126.6, 125.8, 125.5, 125.4, 125.1, 124.7, 122.9, 122.0, 120.9, 115.7, 110.1; HRMS (ESI) m/z calculated for $C_{23}H_{14}F_6NO$ $[M+H]^+$: 434.0980; found: 434.0979.

Example 4: Production of Compound 4

An indolizine derivative compound (51.4 mg, 0.11 mmol, 94.8% yield) was produced in the same manner as in Example 1, except that, in Example 1-2,4-methoxyphenyl boronic acid (71.0 mg, 0.46 mmol), tetrakis(triphenylphosphine)palladium(231 mg, 20.0 mol %) and sodium carbonate (49.0 mg, 0.46 mmol) were added to a solution containing IA-B (51.0 mg, 0.11 mmol) and a 2:1 mixture of DMF and water.

[Compound 4]

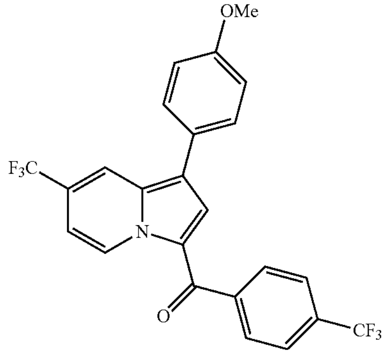

The physical properties of Compound 4 produced in Example 4 are as follows.

$^{1}H$ NMR (400 MHz, $CDCl_3$) δ 10.02 (d, J=6.8 Hz, 1H), 8.08 (s, 1H), 7.94 (d, J=8.0 Hz, 2H), 7.78 (d, J=8.0 Hz, 2H), 7.46 (s, 1H), 7.42 (d, J=5.0 Hz, 2H), 7.10 (dd, J=7.4 Hz, 2.0 Hz, 1H), 7.02 (dd, J=6.8 Hz, 2.0 Hz, 2H), 3.86 (s, 3H); $^{13}C$ NMR (100 MHz, $CDCl_3$) δ 183.5, 159.0, 143.1, 134.4, 133.0, 132.7, 129.2, 127.6, 126.3, 125.9, 125.6, 125.5, 125.4, 125.4, 125.1, 125.6, 122.7, 122.4, 121.9, 120.7, 115.7, 114.6, 114.1, 109.9; LRMS (ESI) m/z calculated $C_{24}H_{16}F_6NO_2$ for $[M+H]^+$: 464.10; found: 464.10.

Example 5: Production of Compound 5

An indolizine derivative compound (51.5 mg, 0.10 mmol, 91.6% yield) was produced in the same manner as in Example 1, except that, in Example 1-2,4-(dimethylamino) phenyl boronic acid (78.0 mg, 0.47 mmol), tetrakis(triphenylphosphine)palladium(231 mg, 20.0 mol %) and sodium carbonate (50.0 mg, 0.47 mmol) were added to a solution containing IA-B (51.4 mg, 0.11 mmol) and a 2:1 mixture of DMF and water.

[Compound 5]

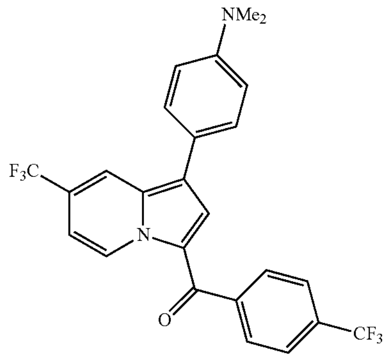

The physical properties of Compound 5 produced in Example 5 are as follows.

$^{1}H$ NMR (400 MHz, $CDCl_3$) δ 10.01 (d, J=7.6 Hz, 1H), 8.12 (s, 1H), 7.94 (d, J=8.0 Hz, 2H), 7.78 (d, J=8.0 Hz, 2H), 7.41 (d, J=5.0 Hz, 2H), 7.40 (s, 1H), 7.09 (d, J=7.6 Hz, 1H), 6.84 (d, J=7.6 Hz, 2H), 3.02 (s, 6H); $^{13}C$ NMR (100 MHz, $CDCl_3$) δ 183.4, 149.8, 143.3, 134.3, 132.9, 132.6, 129.2, 129.1, 128.8, 125.9, 125.7, 125.5, 125.1, 124.7, 122.6, 122.4, 122.0, 121.5, 121.4, 121.0, 116.0, 115.9, 112.9, 109.7, 40.6; LRMS (ESI) m/z calculated for $C_{25}H_{19}F_6N_2O$ $[M+H]^+$: 477.13; found: 477.35.

Example 6: Production of Compound 6

Example 6-1: (1-bromo-7-(trifluoromethyl)indolizin-3-yl) (phenyl)methanone (IC-B)

[Reaction Scheme 1-2]

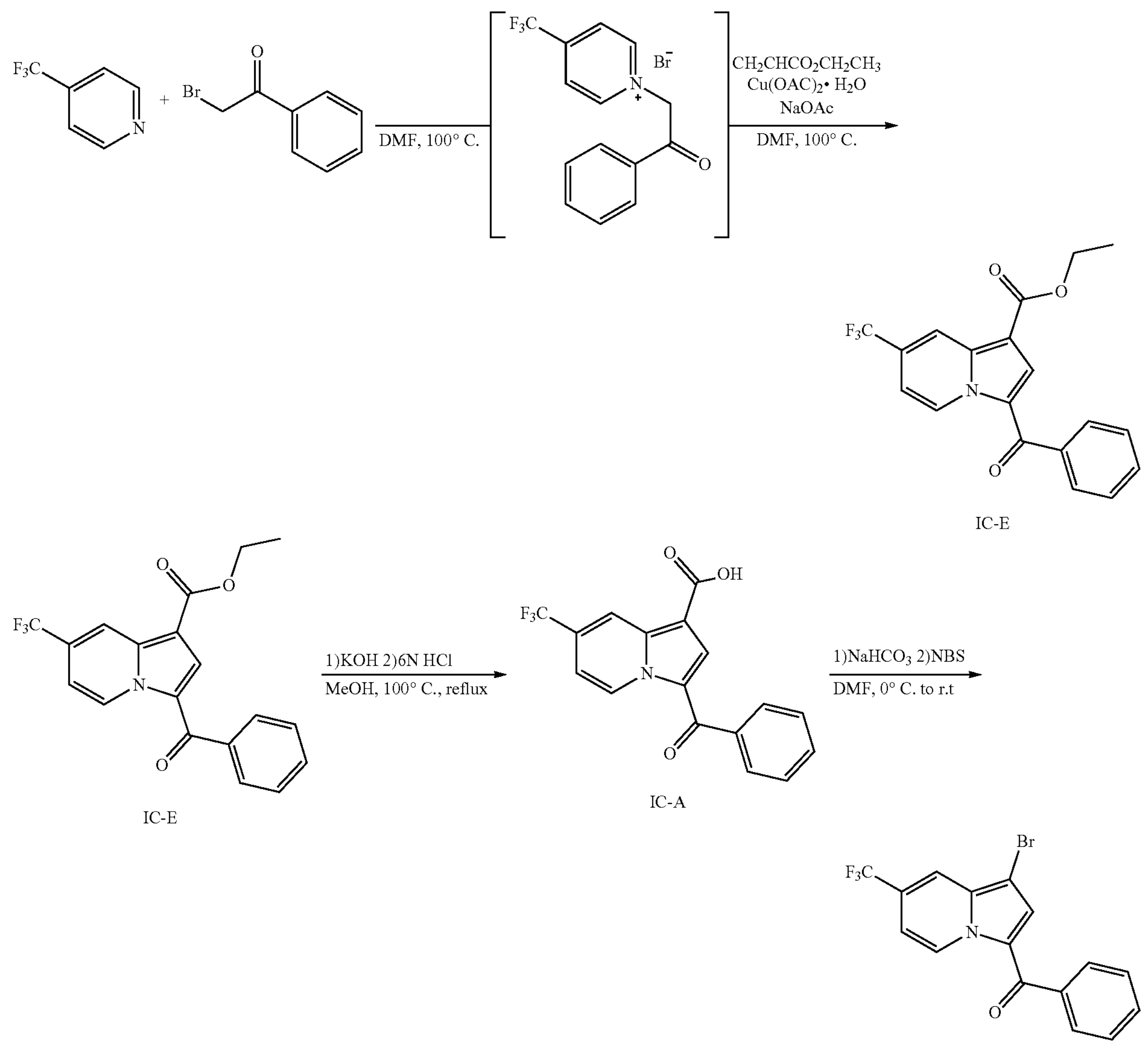

IC-E

IC-E

IC-A

IC-B

IC-E: IC-E was synthesized as shown in Reaction Scheme 1-2 above. Specifically, DMF (7.0 mL) containing 4-(trifluoromethyl)pyridine (348 μL, 3.00 mmol) and 2-bromoacetophenone (627 mg, 3.15 mmol) was stirred overnight at 100° C., and then ethyl acrylate (160 μL, 0.50 mmol), copper (II) acetate monohydrate (898 mg, 1.50 mmol) and sodium acetate (738 mg, 9.00 mmol) were added thereto, followed by stirring at 100° C. for 16 hours. After completion of the reaction, monitoring by TLC was performed, and then copper acetate was removed by filtration through a celite pad, and the resulting filtrate was concentrated in vacuum. The resulting crude product was washed with water, and the organic phase was extracted three times with DCM. The extracted organic phases were combined, dried over anhydrous $Na_2SO_4$ and then concentrated. The concentrated organic phase was purified by silica-gel flash column chromatography (1 to 15% hexane containing EtOAc) to obtain compound IC-E (481.9 mg, 1.3 mmol, 88.9% yield) as a yellow solid.

The results of NMR analysis are as follows.

$^1$H NMR (400 MHz, $CDCl_3$) δ 9.88 (d, J=7.6 Hz, 1H), 8.59 (s, 1H), 7.78 (s, 1H), 7.74 (d, J=6.8 Hz, 2H), 7.53 (t, J=7.4 Hz, 1H), 7.44 (d, J=7.6 Hz, 2H), 7.10 (dd, J=7.4 Hz, 1H), 4.35 (q, J=7.1 Hz, 2H), 1.37 (t, J=7.0 Hz, 3H) [00301] 13C NMR (100 MHz, $CDCl_3$) δ 185.3, 163.0, 138.8, 137.2, 131.7, 129.2, 128.8, 128.5, 128.3, 128.2, 128.0, 124.2, 123.2, 121.5, 117.0, 110.4, 108.5, 60.5, 14.5

LRMS (ESI) m/z calculated for $C_{19}H_{14}F_3NO$ $[M+Na]^+$: 361.1, found: 362.1.

IC-B: KOH (519 mg, 10.0 mmol) was added to methanol (10 mL) containing IC-E (481.9 mg, 1.3 mmol), followed by stirring at room temperature for 4 hours. The reaction mixture was acidified by adding 6N HCl, and the resulting solid was collected through filtration, washed with water, and dried in a drying oven to obtain compound IC-A as a white solid.

The obtained compound IC-A was used in the next step without further purification. Sodium bicarbonate (162.4 mg, 1.9 mmol) was added to DMF (10.0 mL) containing IC-A, and NBS (172.0 mg, 0.9 mmol) was added thereto in portions at 0° C. The reaction mixture was stirred at room temperature for 12 hours, and then the resulting crude product was washed with water and the organic phase was extracted three times with DCM. The extracted organic phases were combined, dried over anhydrous $Na_2SO_4$, and then concentrated. The concentrated organic phase was purified by silica-gel flash column chromatography (EA: hexane=1:8-12% ethyl acetate) to obtain compound IC-B (219.2 mg, 0.595 mmol, 99.2% yield) as a yellow solid.

The results of NMR analysis are as follows.

$^1H$ NMR (400 MHz, $CDCl_3$) δ 9.96 (d, J=7.6 Hz, 1H), 7.90 (s, 1H), 7.79 (d, J=8.0 Hz, 2H), 7.59 (t, J=7.4 Hz, 1H), 7.51 (t, J=7.4 Hz, 1H), 7.46 (s, 1H), 7.09 (d, J=7.6 Hz, 1H)

$^{13}C$ NMR (100 MHz, $CDCl_3$) δ 185.4, 139.1, 134.2, 131.7, 128.9, 128.8, 128.3, 127.4, 126.1, 125.7, 124.4, 123.2, 121.7, 115.1, 109.8, 92.3

LRMS (ESI) m/z calculated for $C_{16}H_9BrF_3NO$ [M+Na]+ 367.0, found: 368.0.

Example 6-2: Production of Compound 6

To a solution containing IC-B (51.2 mg, 0.14 mmol) and a 2:1 mixture of DMF and water, 4-triflulorophenyl boronic acid (106 mg, 0.55 mmol), tetrakis(triphenyl phosphine) palladium (231 mg, 20.0 mol %) and sodium carbonate (59.0 mg, 0.55 mmol) were added, followed by stirring at 100° C. for 5 hours. After completion of the reaction, monitoring by TLC was performed, and then the reaction solution was washed with water, and the organic phase was extracted three times with DCM. The extracted organic phases were combined, dried over anhydrous $Na_2SO_4$, and then concentrated. The concentrated organic phase was purified by silica-gel flash column chromatography (EA:hexane=1:4-25% ethyl acetate) to obtain Compound 6 (54.0 mg, 0.12 mmol, 89.0% yield) as a yellow solid.

[Compound 6]

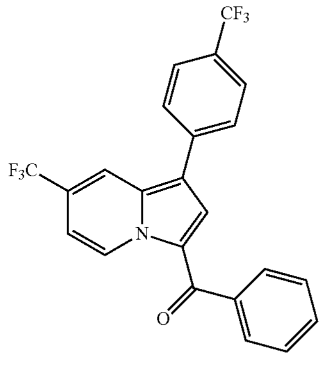

The physical properties of Compound 6 produced in Example 6 are as follows.

$^1H$ NMR (400 MHz, $CDCl_3$) δ 10.05 (d, J=7.6 Hz, 1H), 8.09 (s, 1H), 7.85 (d, J=8.2 Hz, 2H), 7.74 (d, J=8.0 Hz, 2H), 7.66 (d, J=8.0 Hz, 2H), 7.60 (t, J=6.8 Hz, 1H), 7.57 (s, 1H), 7.54 (d, J=7.6 Hz, 2H), 7.14 (dd, J=7.4 Hz, 2.0 Hz, 1H); $^{13}C$ NMR (100 MHz, $CDCl_3$) δ 185.5, 139.8, 137.5, 133.9, 131.8, 129.5, 129.1, 128.6, 128.3, 126.4, 126.2, 126.2, 126.0, 125.8, 123.8, 118.7, 115.3, 110.0, 110.0, 47.1, 34.7; LRMS (ESI) m/z calculated for $C_{23}H_{14}F_6NO$ $[M+H]^+$: 434.09; found: 434.30.

Example 7: Production of Compound 7

An indolizine derivative compound (38.1 mg, 0.09 mmol, 93.5% yield) was produced in the same manner as in Example 6, except that, in Example 6-2,4-acetylphenyl boronic acid (65.6 mg, 0.4 mmol), tetrakis(triphenylphosphine) palladium (231 mg, 20.0 mol %) and sodium carbonate (42.4 mg, 0.4 mmol) were added to a solution containing IC-B (36.9 mg, 0.1 mmol) and a 2:1 mixture of DMF and water, followed by stirring at 100° C. for 6 hours, and the concentrated organic phase was purified by silica-gel flash column chromatography (EA hexane=1:5-20% ethyl acetate).

[Compound 7]

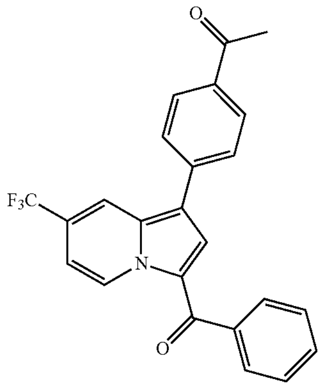

The physical properties of Compound 7 produced in Example 7 are as follows.

$^1H$ NMR (400 MHz, $CDCl_3$) δ 10.03 (d, J=7.2 Hz, 1H), 8.13 (s, 1H), 8.06 (d, J=8.4 Hz, 2H), 7.84 (d, J=8.4 Hz, 2H), 7.64 (d, J=8.0 Hz, 2H), 7.59 (s, 1H), 7.52 (d, J=7.4 Hz, 3H), 7.12 (dd, J=7.2 Hz, 1.6 Hz, 1H), 2.65 (s, 3H); $^{13}C$ NMR (100 MHz, $CDCl_3$) δ 197.5, 185.6, 139.9, 138.8, 135.8, 134.1, 132.0, 129.7, 129.5, 129.3, 128.7, 128.1, 126.8, 126.5, 126.1, 124.9, 123.9, 122.2, 119.1, 115.6, 115.6, 110.1, 110.2, 27.1; LRMS (ESI) m/z calculated for $C_{24}H_{17}F_3NO_2$ $[M+H]^+$: 408.11; found: 408.10.

Example 8: Production of Compound 8

An indolizine derivative compound (79.8 mg, 0.10 mmol, 94.5% yield) was produced in the same manner as in Example 6, except that, in Example 6-2, phenyl boronic acid (53.7 mg, 0.44 mmol), tetrakis(triphenylphosphine) palladium (231 mg, 20.0 mol %) and sodium carbonate (46.6 mg, 0.44 mmol) were added to a solution containing IC-B (40.5 mg, 0.11 mmol) and a 2:1 mixture of DMF and water, followed by stirring at 100° C. for 12 hours.

[Compound 8]

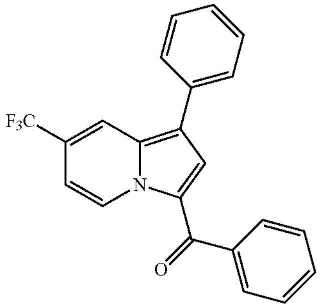

The physical properties of Compound 8 produced in Example 8 are as follows.

$^1$H NMR (400 MHz, $CDCl_3$) δ 10.04 (d, J=7.2 Hz, 1H), 8.12 (s, 1H), 7.86 (d, J=7.2 Hz, 2H), 7.58 (d, J=6.0 Hz, 1H), 7.52 (m, 7H), 7.38 (d, J=7.6 Hz, 1H), 7.10 (dd, J=7.6 Hz, 1.6 Hz, 1H); $^{13}$C NMR (100 MHz, $CDCl_3$) δ 185.3, 140.0, 133.8, 133.7, 131.5, 129.2, 129.1, 129.1, 128.4, 128.1, 127.3, 126.0, 125.8, 125.7, 123.4, 122.1, 120.4, 115.7, 115.6, 109.6, 47.0, 34.6; LRMS (ESI) m/z calculated for $C_{22}H_{15}F_3NO$ $[M+H]^+$: 366.10; found: 366.10.

Example 9: Production of Compound 9

An indolizine derivative compound (57.6 mg, 0.14 mmol, 100% yield) was produced in the same manner as in Example 6, except that, in Example 6-2,4-methoxyphenyl boronic acid (79.0 mg, 0.52 mmol), tetrakis (triphenylphosphine)palladium (231 mg, 20.0 mol %) and sodium carbonate (55.1 mg, 0.52 mmol) were added to a solution containing IC-B (47.9 mg, 0.13 mmol) and a 2:1 mixture of DMF and water, followed by stirring at 100° C. for 8 hours.

[Compound 9]

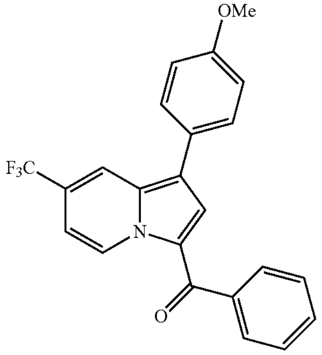

The physical properties of Compound 9 produced in Example 9 are as follows.

$^1$H NMR (400 MHz, $CDCl_3$) δ 10.02 (d, J=7.6 Hz, 1H), 8.07 (s, 1H), 7.85 (d, J=6.8 Hz, 2H), 7.58 (d, J=7.2 Hz, 1H), 7.52 (d, J=8.0 Hz, 2H), 7.48 (s, 1H), 7.46 (d, J=8.8 Hz, 2H), 7.07 (dd, J=7.2 Hz, 1.6 Hz, 1H), 7.02 (d, J=8.8 Hz, 2H), 3.86 (s, 3H); $^{13}$C NMR (100 MHz, $CDCl_3$) δ 185.1, 158.8, 139.9, 133,6, 131.4, 129.2, 129.0(2), 128.3, 125.9, 125.6, 125.5, 125.4, 125.2, 123.1, 120.1, 115.6, 115.5, 114.5, 109.4, 109.3, 55.5; LRMS (ESI) m/z calculated for $C_{23}H_{17}F_3NO_2$ $[M+H]^+$: 396.11; found: 396.10.

Example 10: Production of Compound 10

An indolizine derivative compound (43.5 mg, 0.10 mmol, 99.7% yield) was produced in the same manner as in Example 6, except that, in Example 6-2,4-(dimethylamino) phenyl boronic acid (45.5 mg, 0.43 mmol), tetrakis (triphenylphosphine)palladium (231 mg, 20.0 mol %) and sodium carbonate (108 mg, 1.01 mmol) were added to a solution containing IC-B (39.5 mg, 0.10 mmol) and a 2:1 mixture of DMF and water, followed by stirring at 100° C. for 19 hours.

[Compound 10]

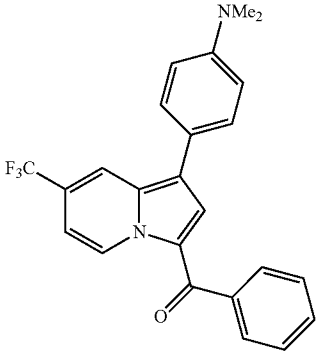

The physical properties of Compound 10 produced in Example 10 are as follows.

$^1$H NMR (400 MHz, $CDCl_3$) δ 10.02 (d, J=7.2 Hz, 1H), 8.11 (s, 1H), 7.87 (d, J=7.2 Hz, 2H), 7.57 (d, J=7.2 Hz, 2H), 7.52 (d, J=7.6 Hz, 1H), 7.48 (s, 1H), 7.43 (d, J=8.8 Hz, 2H), 7.05 (dd, J=7.4 Hz, 2.0 Hz, 1H), 6.87 (d, J=8.0 Hz, 2H), 3.02 (s, 6H); $^{13}$C NMR (100 MHz, $CDCl_3$) δ 185.2, 166.7, 149.8, 140.3, 133.8, 131.5, 129.2, 129.0, 128.4, 127.3, 125.8, 125.4, 125.1, 125.0, 123.2, 122.3, 121.0, 116.1, 116.0, 113.2, 109.4, 47.1, 41.0, 34.7; LRMS (ESI) m/z calculated for $C_{24}H_{20}F_3N_2O$ $[M+H]^+$: 409.14; found: 409.20.

Example 11: Production of Compound 11

Example 11-1: (1-bromo-7-(trifluoromethyl)indolizin-3-yl) (4-methoxyphenyl)methanone (ID-B)

[Reaction Scheme 1-3]

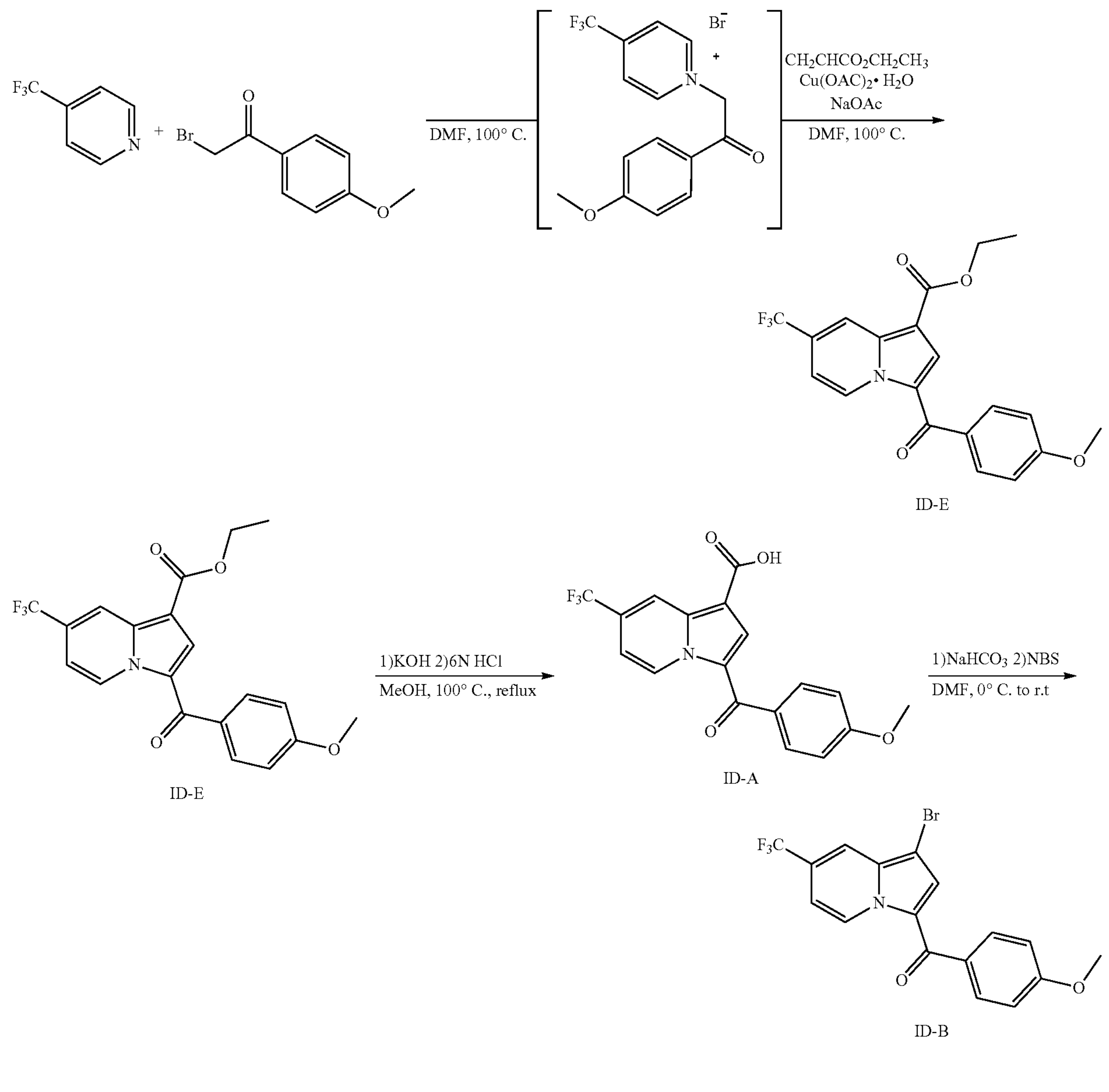

ID-E: ID-E was synthesized as shown in Reaction Scheme 1-3 above. Specifically, DMF (10.0 mL) containing 4-(trifluoromethyl)pyridine (695 μL, 6.00 mmol) and 2-bromo-4-methoxyacetophenone (1.44 g, 6.30 mmol) was stirred overnight at 100° C., and then ethyl acrylate (320 μL, 3.00 mmol), copper(II) acetate monohydrate (1.79 g, 9.00 mmol) and sodium acetate (1.47 g, 18.0 mmol) were added thereto, followed by stirring at 100° C. for 16 hours. After completion of the reaction, monitoring by TLC was performed, and then copper acetate was removed by filtration through a celite pad, and the resulting filtrate was concentrated in vacuum. The resulting crude product was washed with water, and the organic phase was extracted three times with DCM. The extracted organic phases were combined, dried over anhydrous $Na_2SO_4$ and then concentrated. The concentrated organic phase was purified by silica-gel flash column chromatography (1 to 15% hexane containing EtOAc) to obtain compound ID-E (1.02 g, 2.63 mmol, 87.6% yield) as a yellow solid.

The results of NMR analysis are as follows.

$^{1}H$ NMR (400 MHz, $CDCl_3$) δ 9.93 (d, J=7.2 Hz, 1H), 8.69 (s, 1H), 7.89 (s, 1H), 7.86 (d, J=8.8 Hz, 2H), 7.18 (d, J=7.4 Hz, 1H), 7.03 (d, J=8.8 Hz, 2H), 4.41 (d, J=7.2 Hz, 2H), 3.92 (s, 3H), 1.42 (d, J=6.6 Hz, 3H); $^{13}C$ NMR (100 MHz, $CDCl_3$) δ 184.1, 163.2, 162.7, 137.0, 131.3, 131.1, 129.2, 127.9, 127.8, 127.6, 124.3, 123.3, 121.6, 121.3, 116.9, 113.6, 110.1, 108.2, 60.5, 55.4, 14.5; LRMS (ESI) m/z calculated for $C_{20}H_{16}F_3NO_4$ $[M+Na]^+$: 391.1, found: 392.2.

ID-B: KOH (5.91 g, 105 mmol) was added to methanol (18 mL) containing ID-E (1.02 g, 2.62 mmol), followed by stirring at room temperature for 4 hours. The reaction mixture was acidified by adding 6N HCl, and the resulting solid was collected through filtration, washed with water, and dried in a drying oven to obtain compound ID-A as a white solid.

The obtained compound ID-A was used in the next step without further purification. Sodium bicarbonate (660 mg, 7.86 mmol) was added to DMF (10.0 mL) containing ID-A, and NBS (699 mg, 3.93 mmol) was added thereto in portions at 0° C. The reaction mixture was stirred at room temperature for 12 hours, and then the resulting crude product was washed with water and the organic phase was extracted three times with DCM. The extracted organic phases were combined, dried over anhydrous $Na_2SO_4$, and then concentrated. The concentrated organic phase was purified by silica-gel flash column chromatography (EA:hexane=1:8-12% ethyl acetate) to obtain compound ID-B (0.93 g, 2.36 mmol, 90.0% yield) as a yellow solid.

The results of NMR analysis are as follows.

$^1$H NMR (400 MHz, $CDCl_3$) δ 9.88 (d, J=8.0 Hz, 1H), 7.88 (s, 1H), 7.82 (d, J=8.8 Hz, 2H), 7.46 (s, 1H), 7.05 (d, J=7.6 Hz, 1H), 7.01 (d, J=8.8 Hz, 2H), 3.90 (s, 3H); $^{13}$C NMR (100 MHz, $CDCl_3$) δ 183.3, 162.5, 133.8, 131.5, 131.1, 128.8, 126.7, 125.6, 125.3, 124.4, 123.3, 121.7, 121.3, 115.1, 109.4, 62.0, 55.5.

Example 11-2: Production of Compound 11

To a solution containing ID-B(105.7 g, 0.26 mmol) and a 2:1 mixture of DMF and water, 4-triflulorophenyl boronic acid (202 mg, 1.06 mmol), tetrakis(triphenyl phosphine) palladium (231 mg, 20.0 mol %) and sodium carbonate (112 mg, 1.06 mmol) were added, followed by stirring at 100° C. for 5 hours. After completion of the reaction, monitoring by TLC was performed, and then the reaction solution was washed with water, and the organic phase was extracted three times with DCM. The extracted organic phases were combined, dried over anhydrous $Na_2SO_4$, and then concentrated. The concentrated organic phase was purified by silica-gel flash column chromatography (EA:hexane=1:4-25% ethyl acetate) to obtain Compound 11 (90.2 mg, 0.19 mmol, 73.4% yield) as a yellow solid.

[Compound 11]

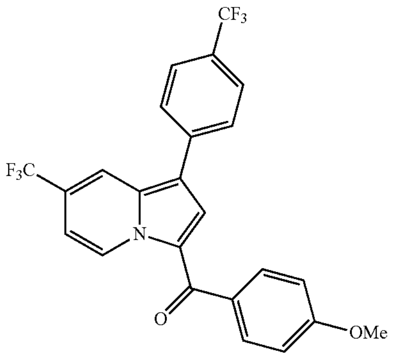

The physical properties of Compound 1 produced in Example 1 are as follows.

$^1$H NMR (400 MHz, $CDCl_3$) δ 9.91 (d, J=7.2 Hz, 1H), 8.05 (s, 1H), 7.65 (s, 1H), 7.51 (m, 6H), 7.37 (t, J=7.2 Hz, 2H), 6.98 (dd, J=7.4 Hz, 1.6 Hz, 1H), 2.63 (s, 3H); $^{13}$C NMR (100 MHz, $CDCl_3$) δ 187.4, 133.6, 132.8, 129.0, 128.8, 127.9, 127.1, 125.2, 124.9, 124.7, 123.4, 122.9, 122.0, 119.9, 115.4, 115.4, 109.3, 109.2, 27.7. HRMS (ESI) m/z calculated for $C_{24}H_{16}F_6NO_2$ $[M+H]^+$: 464.1085; found: 464.1080.

Example 12: Production of Compound 12

An indolizine derivative compound (48.4 mg, 0.10 mmol, 88.5% yield) was produced in the same manner as in Example 11, except that, in Example 11-2,4-acetylphenyl boronic acid (155 mg, 0.94 mmol), tetrakis(triphenylphosphine) palladium (231 mg, 20.0 mol %) and sodium carbonate (100 mg, 0.94 mmol) were added to a solution containing ID-B (94.3 mg, 0.23 mmol) and a 2:1 mixture of DMF and water, followed by stirring at 100° C. for 9 hours, and the concentrated organic phase was purified by silica-gel flash column chromatography (EA hexane=1:5-20% ethyl acetate).

[Compound 12]

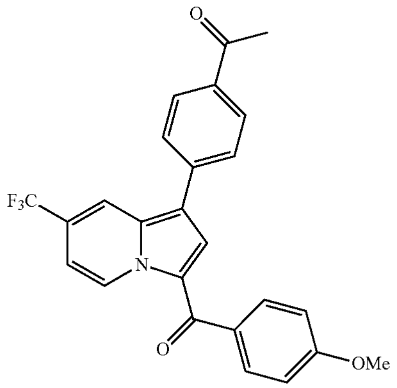

The physical properties of Compound 12 produced in Example 12 are as follows.

$^1$H NMR (400 MHz, $CDCl_3$) δ 9.96 (d, J=7.6 Hz, 1H), 8.12 (s, 1H), 8.07 (t, J=8.2 Hz, 3H), 7.88 (d, J=9.2 Hz, 2H), 7.72 (d, J=8.4 Hz, 1H), 7.66 (d, J=8.4 Hz, 1H), 7.60 (s, 1H), 7.09 (dd, J=7.4 Hz, 2.0 Hz, 1H), 7.03 (d, J=8.8 Hz, 1H), 3.91 (s, 3H), 2.66 (s, 3H); $^{13}$C NMR (100 MHz, $CDCl_3$) 197.0, 183.8, 162.4, 143.8, 138.4, 136.2, 135.2, 133.0, 131.8, 131.1, 129.0, 128.7, 127.5, 127.1, 125.4, 124.9, 124.5, 123.6, 121.8, 118.3, 115.1, 113.5, 109.2, 55.4, 26.6; LRMS (ESI) m/z calculated for $C_{25}H_{19}F_3NO_3$ $[M+H]^+$: 437.12; found: 438.15.

Example 13: Production of Compound 13

An indolizine derivative compound (97.6 mg, 0.24 mmol, 100% yield) was produced in the same manner as in Example 11, except that, in Example 11-2, phenyl boronic acid (115 mg, 0.94 mmol), tetrakis(triphenylphosphine) palladium (231 mg, 20.0 mol %) and sodium carbonate (100 mg, 0.94 mmol) were added to a solution containing ID-B (94.0 mg, 0.23 mmol) and a 2:1 mixture of DMF and water, followed by stirring at 100° C. for 12 hours.

[Compound 13]

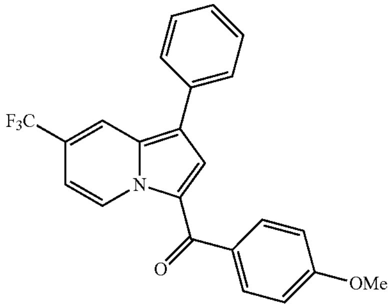

The physical properties of Compound 13 produced in Example 13 are as follows.

$^1H$ NMR (400 MHz, $CDCl_3$) δ 9.95 (d, J=7.6 Hz, 1H), 8.11 (s, 1H), 7.88 (d, J=8.8 Hz, 2H), 7.56 (m, 3H), 7.49 (t, J=7.8 Hz, 2H), 7.38 (m, 1H), 7.06 (dd, J=7.8 Hz, 2.0 Hz, 1H), 7.02 (d, J=8.8 Hz, 2H), 3.91 (s, 3H); $^{13}C$ NMR (100 MHz, $CDCl_3$) δ 184.5, 162.7, 134.1, 133.6, 132.7, 131.6, 129.4, 129.3, 128.4, 127.5, 125.8, 125.5, 125.4, 125.1, 123.7, 122.4, 120.3, 115.9, 115.8, 114.0, 109.6, 109.5, 55.9; LRMS (ESI) m/z calculated for $C_{23}H_{17}F_3NO_2$ $[M+H]^+$: 396.11; found: 396.10.

Example 14: Production of Compound 14

An indolizine derivative compound (125.6 mg, 0.29 mmol, 98.4% yield) was produced in the same manner as in Example 11, except that, in Example 11-2, 4-methoxyphenyl boronic acid (182 mg, 1.20 mmol), tetrakis(triphenylphosphine)palladium (231 mg, 20.0 mol %) and sodium carbonate (127 mg, 1.20 mmol) were added to a solution containing ID-B (120 mg, 0.30 mmol) and a 2:1 mixture of DMF and water, followed by stirring at 100° C. for 8 hours.

[Compound 14]

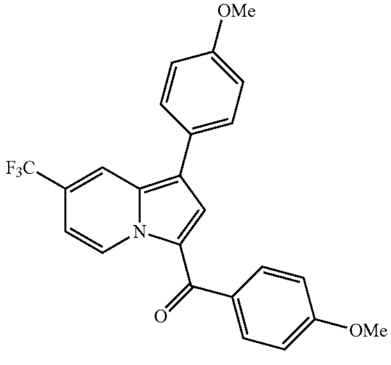

The physical properties of Compound 14 produced in Example 14 are as follows.

$^1H$ NMR (400 MHz, $CDCl_3$) δ 9.93 (d, J=7.6 Hz, 1H), 8.05 (s, 1H), 7.87 (d, J=8.8 Hz, 2H), 7.49 (s, 1H), 7.47 (d, J=8.8 Hz, 2H), 7.03 (d, J=6.4 Hz, 3H), 7.01 (d, J=6.4 Hz, 2H), 3.90 (s, 3H), 3.87 (s, 3H); $^{13}C$ NMR (100 MHz, $CDCl_3$) δ 183.8, 162.2, 158.7, 133.0, 132.2, 131.1, 129.0, 128.8, 126.0, 124.9, 124.8, 124.7, 124.6, 123.1, 122.1, 119.7, 115.4, 115.4, 114.4, 113.5, 108.8, 108.9, 55.4, 55.3; LRMS (ESI) m/z calculated for $C_{24}H_{19}F_3NO_3$ $[M+H]^+$: 426.12; found: 426.15.

Example 15: Production of Compound 15

An indolizine derivative compound (151 mg, 0.34 mmol, 100% yield) was produced in the same manner as in Example 11, except that, in Example 11-2, 4-(dimethylamino)phenyl boronic acid (220 mg, 1.33 mmol), tetrakis(triphenylphosphine)palladium (231 mg, 20.0 mol %) and sodium carbonate (141 mg, 1.33 mmol) were added to a solution containing ID-B (132.8 mg, 0.33 mmol) and a 2:1 mixture of DMF and water, followed by stirring at 100° C. for 9 hours.

[Compound 15]

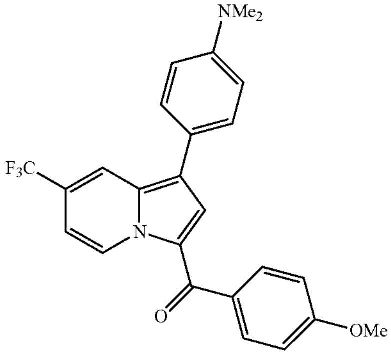

The physical properties of Compound 15 produced in Example 15 are as follows.

$^1H$ NMR (400 MHz, $CDCl_3$) δ 9.92 (d, J=7.6 Hz, 1H), 8.08 (s, 1H), 7.87 (d, J=7.6 Hz, 2H), 7.48 (s, 1H), 7.43 (d, J=8.8 Hz, 2H), 7.01 (d, J=8.8 Hz, 3H), 6.85 (d, J=8.8 Hz, 2H), 3.90 (s, 3H), 3.01 (s, 6H); $^{13}C$ NMR (100 MHz, $CDCl_3$) δ 183.8, 162.1, 149.5, 133.0, 132.4, 131.1, 128.7, 128.6, 127.5, 124.8, 124.5, 124.4, 124.2, 123.8, 123.0, 122.1, 121.4, 120.5, 119.4, 115.7, 113.4, 112.7, 108.7, 55.4, 40.5; LRMS (ESI) m/z calculated for $C_{25}H_{22}F_3N_2O_2[M+H]^+$: 439.16; found: 439.15.

Example 16: Production of Compound 16
Example 16-1: (1-bromo-7-(trifluoromethyl)indolizin-3-yl) (4-(diethylamino)phenyl)methanone (IE-B)
[Reaction Scheme 1-4]
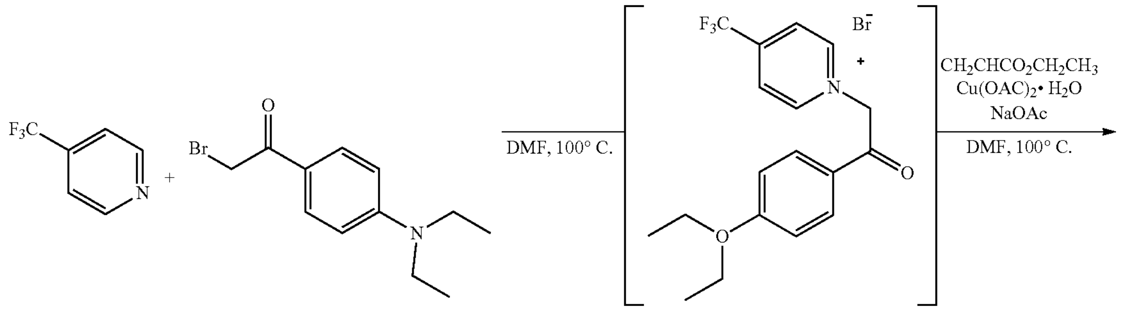
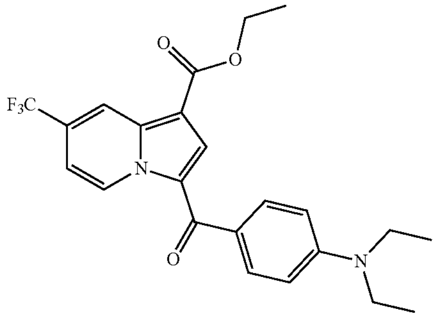
IE-E
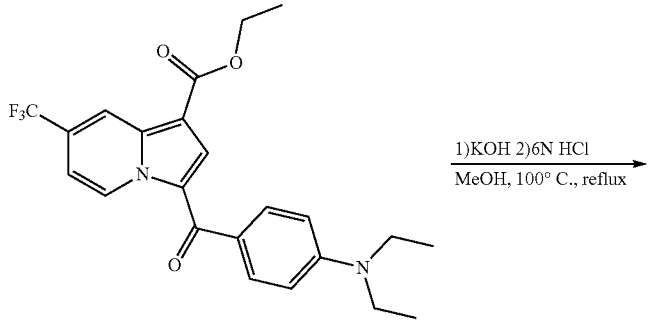
IE-E
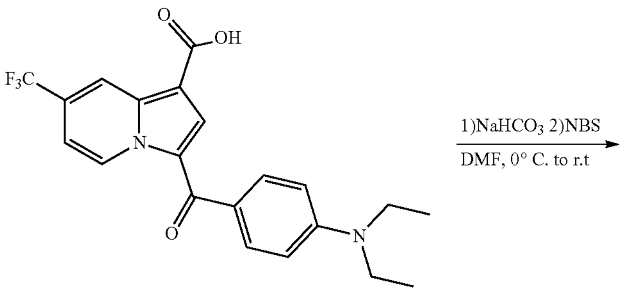
IE-A -continued

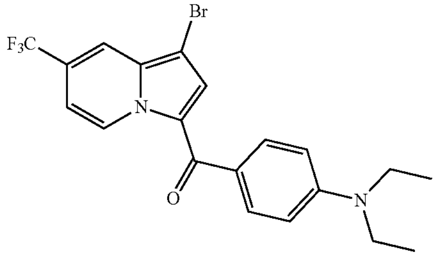

IE-B

IE-E: IE-E was synthesized as shown in Reaction Scheme 1-4 above. Specifically, DMF (6.0 mL) containing 4-(trifluoromethyl)pyridine (695 μL, 6.00 mmol) and 2-bromo-4'-(diethylamino)aceto-phenone (1.70 mL, 6.30 mmol) was stirred overnight at 100° C., and then ethyl acrylate (320 μL, 3.00 mmol), copper(II) acetate monohydrate (1.79 g, 9.00 mmol) and sodium acetate (1.47 g, 18.0 mmol) were added thereto, followed by stirring at 100° C. for 16 hours. After completion of the reaction, monitoring by TLC was performed, and then copper acetate was removed by filtration through a celite pad, and the resulting filtrate was concentrated in vacuum. The resulting crude product was washed with water, and the organic phase was extracted three times with DCM. The extracted organic phases were combined, dried over anhydrous $Na_2SO_4$ and then concentrated. The concentrated organic phase was purified by silica-gel flash column chromatography (1 to 15% hexane containing EtOAc) to obtain compound IE-E (1.12 g, 2.60 mmol, 86.9% yield) as a yellow solid.

The results of NMR analysis are as follows.

$^1$H NMR (400 MHz, $CDCl_3$) δ 9.83 (d, J=8.0 Hz, 1H), 8.66 (s, 1H), 7.91 (s, 1H), 7.84 (d, J=8.8 Hz, 2H), 7.11 (d, J=7.4 Hz, 1H), 6.72 (d, J=5.4 Hz, 2H), 4.41 (q, J=6.9, 2H), 3.46 (q, J=6.6 Hz, 4H), 1.43 (t, J=5.2, 3H), 1.25 (d, J=5.5 Hz, 6H); $^{13}$C NMR (100 MHz, $CDCl_3$) δ 182.8, 163.1, 150.4, 136.1, 131.4, 128.9, 126.7, 126.4, 126.1, 124.6, 124.3, 123.6, 121.6, 116.5(2), 109.8, 109.1, 109.2, 107.4, 60.0, 44.2, 14.3, 12.3; LRMS (ESI) m/z calculated for $C_{23}H_{23}F_3N_2O_3$[M+Na]$^+$: 432.2, found: 433.2.

IE-B: KOH (5.85 g, 104 mmol) was added to methanol (10 mL) containing IE-E (1.12 g, 2.60 mmol), followed by stirring at room temperature for 4 hours. The reaction mixture was acidified by adding 6N HCl, and the resulting solid was collected through filtration, washed with water, and dried in a drying oven to obtain compound IE-A as a white solid.

The obtained compound IE-A was used in the next step without further purification. Sodium bicarbonate (655 mg, 7.80 mmol) was added to DMF (10.0 mL) containing IE-A, and NBS (694 mg, 3.90 mmol) was added thereto in portions at 0° C. The reaction mixture was stirred at room temperature for 12 hours, and then the resulting crude product was washed with water and the organic phase was extracted three times with DCM. The extracted organic phases were combined, dried over anhydrous $Na_2SO_4$, and then concentrated. The concentrated organic phase was purified by silica-gel flash column chromatography (EA:hexane=1:8-12% ethyl acetate) to obtain compound IE-B (829 mg, 1.88 mmol, 72.6% yield) as a yellow solid.

The results of NMR analysis are as follows.

$^1$H NMR (400 MHz, $CDCl_3$), δ 9.83 (d, J=8.0 Hz, 1H), 8.66 (s, 1H), 7.91 (s, 1H), 7.84 (d, J=8.8 Hz, 2H), 7.11 (d, J=7.4 Hz, 1H), 6.72 (d, J=5.4 Hz, 2H), 4.41 (q, J=6.9, 2H), 3.46 (q, J=6.6 Hz, 4H), 1.43 (t, J=5.2, 3H), 1.25 (d, J=5.5 Hz, 6H); $^{13}$C NMR (100 MHz, $CDCl_3$) δ 182.0, 152.9, 135.2, 134.2, 133.9, 129.0, 128.8, 126.9, 126.0, 125.7, 124.6, 123.2, 122.3, 121.9, 120.1, 115.3, 92.5, 46.5, 12.8, 12.7.

Example 16-2: Production of Compound 16

To a solution containing IE-B (54.0 mg, 0.12 mmol) and a 2:1 mixture of DMF and water, 4-triflulorophenyl boronic acid (94.4 mg, 0.49 mmol), tetrakis(triphenyl phosphine) palladium (231 mg, 20.0 mol %) and sodium carbonate (52.7 mg, 0.49 mmol) were added, followed by stirring at 100° C. for 5 hours. After completion of the reaction, monitoring by TLC was performed, and then the reaction solution was washed with water, and the organic phase was extracted three times with DCM. The extracted organic phases were combined, dried over anhydrous $Na_2SO_4$, and then concentrated. The concentrated organic phase was purified by silica-gel flash column chromatography (EA:hexane=1:4-25% ethyl acetate) to obtain Compound 16 (43.1 mg, 0.08 mmol, 68.8% yield) as a yellow solid.

[Compound 16]

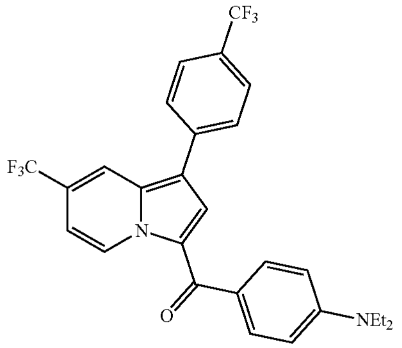

The physical properties of Compound 16 produced in Example 16 are as follows.

$^1$H NMR (400 MHz, $CDCl_3$) δ 9.95 (d, J=7.6 Hz, 1H), 8.07 (s, 1H), 7.83 (d, J=8.6 Hz, 1H), 7.76 (s, 1H), 7.74 (d, J=5.6 Hz, 1H), 7.67 (m, 4H), 7.64 (s, 1H), 7.15 (d, J=8.4 Hz, 1H), 7.09 (dd, J=7.6 Hz, 2.0 Hz, 1H), 3.00 (q, J=6.9 Hz, 4H), 0.98 (t, J=7.0 Hz, 6H); $^{13}$C NMR (100 MHz, $CDCl_3$) δ 184.3, 152.6, 145.1, 137.7, 133.6, 133.5, 133.2, 132.5, 130.1, 129.4, 129.3, 129.0(2), 128.3, 126.3, 126.2(2), 125.7, 125.6, 125.5, 125.1, 124.0, 120.0, 118.4, 46.0, 12.4; LRMS (ESI) m/z calculated for $C_{27}H_{23}F_6N_2O$ [M+H]$^+$: 505.16; found 505.20.

Example 17: Production of Compound 17

An indolizine derivative compound (9.70 mg, 0.02 mmol, 18% yield) was produced in the same manner as in Example 16, except that, in Example 16-2, 4-acetylphenyl boronic acid (74.2 mg, 0.45 mmol), tetrakis (triphenylphosphine) palladium (231 mg, 20.0 mol %) and sodium carbonate (48.0 mg, 0.45 mmol) were added to a solution containing IE-B (49.7 mg, 0.11 mmol) and a 2:1 mixture of DMF and water, followed by stirring at 100° C. for 9 hours, and the concentrated organic phase was purified by silica-gel flash column chromatography (EA hexane=1:5-20% ethyl acetate).

[Compound 17]

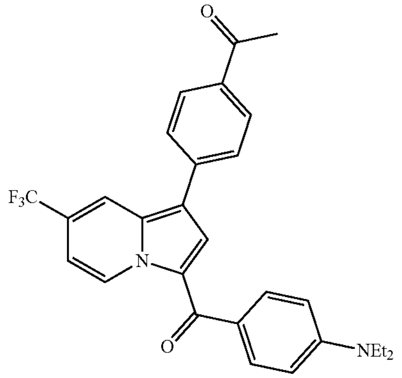

The physical properties of Compound 17 produced in Example 17 are as follows.

$^1$H NMR (400 MHz, $CDCl_3$) δ 9.95 (d, J=7.6 Hz, 1H), 8.12 (s, 1H), 8.08 (d, J=8.4 Hz, 2H), 7.91 (d, J=2.0 Hz, 1H), 7.30 (m, 2H), 7.67 (d, J=8.8 Hz, 2H), 7.63 (s, 1H), 7.00 (m, 2H), 3.29 (q, J=7.0 Hz, 4H), 2.66 (s, 3H), 1.14 (t, J=7.2 Hz, 6H); $^{13}$C NMR (100 MHz, $CDCl_3$) δ 197.2, 183.1, 151.4, 138.6, 135.6, 133.6, 133.3, 132.1, 129.2, 128.7, 128.2, 127.9, 125.2, 121.5, 118.8, 46.1, 29.9, 26.9, 12.7; LRMS (ESI) m/z calculated for $C_{28}H_{26}F_3N_2O_2[M+H]^+$: 479.19; found 479.25.

Example 18: Production of Compound 18

An indolizine derivative compound (39.9 mg, 0.09 mmol, 80.1% yield) was produced in the same manner as in Example 16, except that, in Example 16-2, phenyl boronic acid (55.0 mg, 0.45 mmol), tetrakis(triphenylphosphine) palladium (231 mg, 20.0 mol %) and sodium carbonate (49.0 mg, 0.45 mmol) were added to a solution containing IE-B (50.0 mg, 0.11 mmol) and a 2:1 mixture of DMF and water, followed by stirring at 100° C. for 9 hours.

[Compound 18]

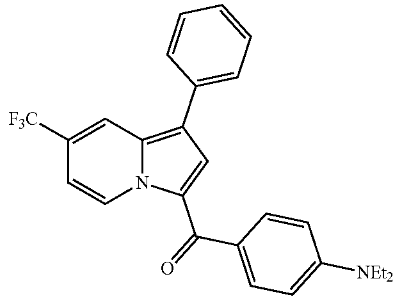

The physical properties of Compound 18 produced in Example 18 are as follows.

$^1$H NMR (400 MHz, $CDCl_3$) δ 9.96 (d, J=7.2 Hz, 1H), 8.11 (s, 1H), 7.81 (s, 1H), 7.66 (s, 1H), 7.59 (t, J=7.6 Hz, 3H), 7.50 (t, J=6.8 Hz, 1H), 7.40 (m, 2H), 7.32 (d, J=6.6 Hz, 1H), 7.13 (d, J=8.4 Hz, 1H), 7.05 (d, J=7.2 Hz, 1H), 3.03 (q, J=6.5 Hz, 4H), 1.01 (t, J=6.6 Hz, 6H); $^{13}$C NMR (100 MHz, $CDCl_3$) δ 184.7, 152.6, 141.7, 135.1, 134.2, 133.6, 133.5, 132.5, 129.7, 129.4, 129.3, 128.8, 128.7, 128.4, 127.4, 127.1, 125.3, 125.2, 124.0, 120.2, 119.8, 115.9, 109.4, 46.1, 12.6; LRMS (ESI) m/z calculated for $C_{26}H_{24}F_3N_2O$ $[M+H]^+$: 437.18; found 437.20.

Example 19: Production of Compound 19

An indolizine derivative compound (44.8 mg, 0.09 mmol, 78.7% yield) was produced in the same manner as in Example 16, except that, in Example 16-2, 4-methoxyphenyl boronic acid (74.0 mg, 0.48 mmol), tetrakis (triphenylphosphine)palladium (231 mg, 20.0 mol %) and sodium carbonate (52.0 mg, 0.48 mmol) were added to a solution containing IE-B (53.7 mg, 0.12 mmol) and a 2:1 mixture of DMF and water, followed by stirring at 100° C. for 10 hours.

[Compound 19]

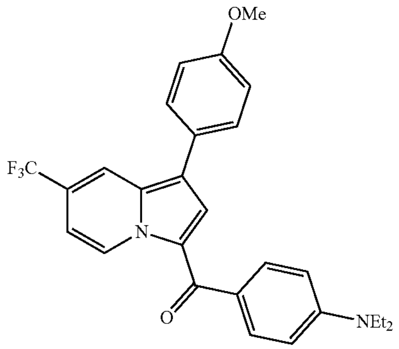

The physical properties of Compound 19 produced in Example 19 are as follows.

$^1$H NMR (400 MHz, $CDCl_3$) δ 9.84 (d, J=7.6 Hz, 1H), 8.02 (s, 1H), 7.86 (d, J=9.2 Hz, 2H), 7.54 (s, 1H), 7.48 (d, J=8.8 Hz, 2H), 7.03 (d, J=8.8 Hz, 2H), 6.96 (dd, J=7.6 Hz, 2.4 Hz, 1H), 6.71 (d, J=9.2 Hz, 2H), 3.87 (s, 3H), 3.45 (q, J=6.9 Hz, 4H), 1.23 (t, J=7.2 Hz, 6H); $^{13}$C NMR (100 MHz, $CDCl_3$) δ 184.0, 152.0, 141.0, 134.4, 133.6, 133.0, 132.8, 131.9, 129.0, 128.7, 128.2, 128.1, 127.8, 126.8, 126.5, 124.9, 124.7, 124.5, 123.3, 121.8, 119.6, 119.1, 115.2, 108.8, 45.4, 29.6, 12.0; LRMS (ESI) m/z calculated for $C_{27}H_{26}F_3N_2O_2[M+H]^+$: 467.19; found: 467.27.

Example 20: Production of Compound 20

An indolizine derivative compound (43.1 mg, 0.08 mmol, 72.4% yield) was produced in the same manner as in Example 16, except that, in Example 16-2, 4-(dimethylamino)phenyl boronic acid (88.0 mg, 0.52 mmol), tetrakis (triphenylphosphine)palladium (231 mg, 20.0 mol %) and sodium carbonate (55.5 mg, 0.52 mmol) were added to a solution containing IE-B (57.5 mg, 0.13 mmol) and a 2:1 mixture of DMF and water, followed by stirring at 100° C. for 12 hours.

[Compound 20]

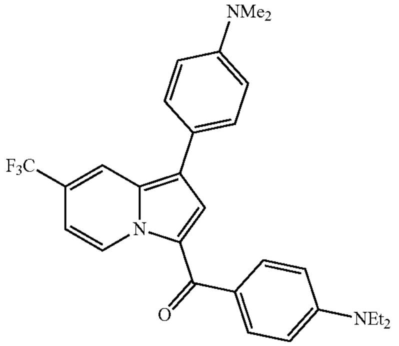

The physical properties of Compound 20 produced in Example 20 are as follows.

$^1H$ NMR (400 MHz, $CDCl_3$) δ 9.95 (d, J=7.2 Hz, 1H), 8.10 (s, 1H), 7.81 (d, J=2.4 Hz, 1H), 7.77 (d, J=8.6 Hz, 1H), 7.61 (s, 1H), 7.52 (d, J=8.8 Hz, 2H), 7.46 (d, J=8.8 Hz, 1H), 7.10 (d, J=8.4 Hz, 1H), 7.00 (dd, J=7.4 Hz, 2.0 Hz, 1H), 6.87 (d, J=8.8 Hz, 1H), 6.79 (d, J=8.8 Hz, 1H), 3.07 (q, J=7.1 Hz, 4H), 3.03 (s, 3H), 3.00 (s, 3H), 1.01 (d, J=7.2 Hz, 6H); $^{13}C$ NMR (100 MHz, $CDCl_3$) δ 184.2, 151.8, 149.3, 149.0, 134.6, 132.7, 132.2, 129.0, 128.8, 128.6, 128.5, 128.1, 124.6, 124.2, 124.1, 123.8, 123.2, 121.9, 121.5, 120.1, 119.2, 115.5, 112.6, 112.1, 108.4, 45.1, 40.4, 11.9; LRMS (ESI) m/z calculated for $C_{28}H_{29}F_3N_3O$ $[M+H]^+$: 480.22; found 480.35.

Example 21: Production of Compound 21

Example 21-1: 1-(1-bromo-3-(4-(trifluoromethyl)benzoyl)indolizin-7-yl)ethanone (IF-B)

[Reaction Scheme 1-5]

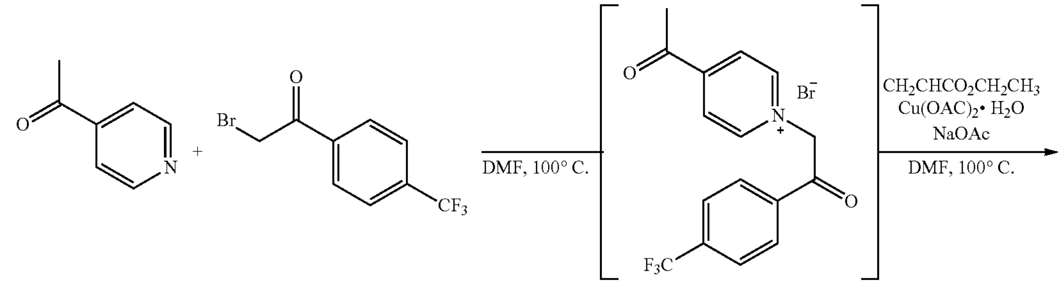

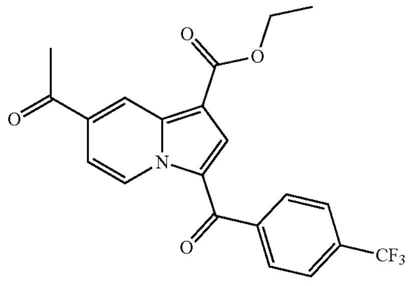

IF-E

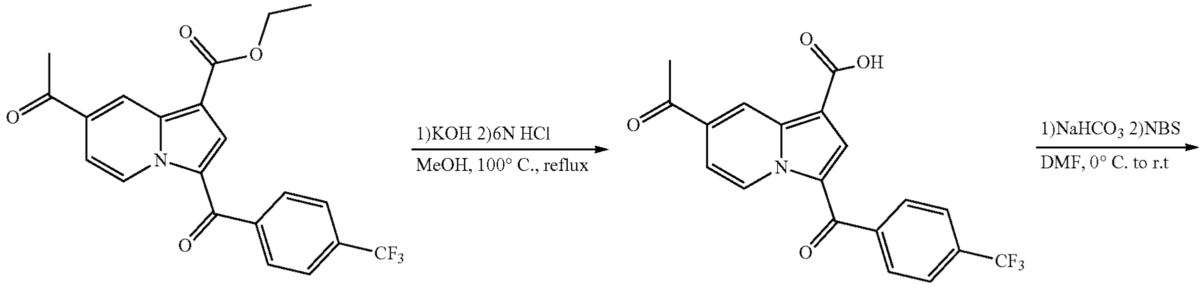

IF-E

IF-A

-continued

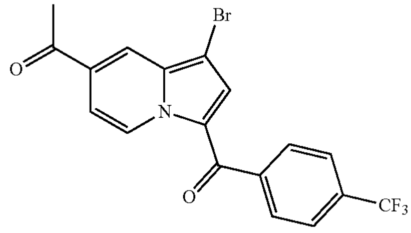

IF-B

IF-E: IF-E was synthesized as shown in Reaction Scheme 1-5 above. Specifically, DMF (12.0 mL) containing 4-acetylpyridine (394.6 μL, 3.567 mmol) and 2-bromo-4'-(trifluoromethyl)acetophenone (1.0 g, 3.8 mmol) was stirred at 80° C. for 4 hours, and then ethyl acrylate (193.6 μl, 1.79 mmol), copper(II) acetate monohydrate (2.14 g, 10.7 mmol) and sodium acetate (1.17 g, 14.3 mmol) were added thereto, followed by stirring at 100° C. for 16 hours. After completion of the reaction, monitoring by TLC was performed, and then copper acetate was removed by filtration through a celite pad, and the resulting filtrate was concentrated in vacuum. The resulting crude product was washed with water, and the organic phase was extracted three times with DCM. The extracted organic phases were combined, dried over anhydrous $Na_2SO_4$ and then concentrated. The concentrated organic phase was purified by silica-gel flash column chromatography (EA:hexane=1:5-40% ethyl acetate) to obtain compound IF-E (556.5 mg, 77.3% yield) as a yellow solid.

The results of NMR analysis are as follows.

$^1H$ NMR (400 MHz, $CDCl_3$), δ 9.87 (dd, J=7.2, 1.2 Hz, 1H), 8.96 (s, 1H), 7.92 (d, J=8.0 Hz, 2H), 7.79 (m, 3H), 7.61 (dd, J=7.4, 2.4 Hz, 1H), 4.40 (q, J=7.2 Hz, 2H), 1.42 (t, J=7.2 Hz, 3H); $^{13}C$ NMR (100 MHz, $CDCl_3$) 195.6, 184.4, 163.5, 142.5, 138.8, 134.8, 133.7, 133.3, 129.4, 129.1, 128.9, 125.8, 125.7 (2), 125.2, 123.4, 122.5, 121.6, 121.1, 113.1, 109.9 60.9, 26.6, 14.9; LRMS (ESI) m/z calculated for $C_{21}H_{16}F_3NO_4$ $[M+Na]^+$: 403.1, found: 404.2.

IF-B: KOH (2.21 g, 55.2 mmol) was added to methanol (5 mL) containing IF-E (556.5 mg, 1.379 mmol), followed by stirring overnight at room temperature. The reaction mixture was acidified by adding 6N HCl, and the resulting solid was collected through filtration, washed with water, and dried in a drying oven to obtain compound IF-A as a brown solid.

The obtained compound IF-A was used in the next step without further purification. Sodium bicarbonate (350.3 mg, 4.170 mmol) was added to DMF (10.0 mL) containing IF-A, and NBS (259.6 mg, 1.459 mmol) was added thereto in portions at 0° C. The reaction mixture was stirred at room temperature for 12 hours, and then the resulting crude product was washed with water and the organic phase was extracted three times with DCM. The extracted organic phases were combined, dried over anhydrous $Na_2SO_4$, and then concentrated. The concentrated organic phase was purified by silica-gel flash column chromatography (EA: hexane=1:5-40% ethyl acetate) to obtain compound IF-B (358.6 mg, 63.4% yield) as a yellow solid.

The results of NMR analysis are as follows.

$^1H$ NMR (400 MHz, $CDCl_3$), δ 9.87 (d, J=7.4 Hz, 1H), 8.18 (s, 1H), 7.90 (d, J=8.0 Hz, 2H), 7.79 (d, J=8.0 Hz, 2H), 7.53 (dd, J=7.4, 2 Hz, 1H), 7.39 (s, 1H), 2.72 (s, 3H); $^{13}C$ NMR (100 MHz, $CDCl_3$) 195.2, 183.3, 142.7, 135.8, 133.5, 133.2, 132.8, 129.3, 128.5, 127.6, 125.7(2), 125.2, 123.5, 122.5, 119.2, 112.5, 94.5, 26.7; LRMS (ESI) m/z calculated for $C_{18}H_{11}BrF_3NO_2$ $[M+Na]^+$: 409.0, found: 410.0.

Example 21-2: Production of Compound 21

To a solution containing IF-B (30.0 mg, 0.063 mmol) and a 10:1 mixture of DMF and water, 4-triflulorophenyl boronic acid (35.9 mg, 0.189 mmol), tetrakis(triphenyl phosphine) palladium (15.0 mg, 0.013 mmol) and sodium carbonate (33.6 mg, 0.315 mmol) were added, followed by stirring at 100° C. for 8 hours. After completion of the reaction, monitoring by TLC was performed, and then the reaction solution was washed with water, and the organic phase was extracted three times with DCM. The extracted organic phases were combined, dried over anhydrous $Na_2SO_4$, and then concentrated. The concentrated organic phase was purified by silica-gel flash column chromatography (EA: hexane=1:5-40% ethyl acetate) to obtain Compound 21 (28.6 mg, 95.4% yield) as a yellow solid.

[Compound 21]

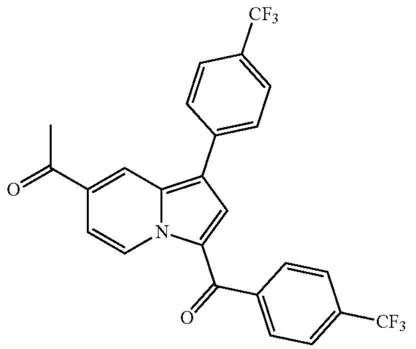

The physical properties of Compound 21 produced in Example 21 are as follows.

$^1H$ NMR (400 MHz, $CDCl_3$) δ 9.97 (d, J=7.4 Hz, 1H), 8.42 (s, 1H), 7.95 (d, J=8.0 Hz, 2H), 7.78 (d, J=8.4 Hz, 2H), 7.75 (d, J=8.0 Hz, 2H), 7.68 (d, J=8.4 Hz, 2H), 7.55 (dd, J=7.2 Hz, 1.6 Hz, 1H), 7.49 (s, 1H), 2.67 (s, 3H); $^{13}C$ NMR (100 MHz, $CDCl_3$) δ 195.3, 183.9, 143.1, 137.4, 135.3, 133.5, 133.1, 129.7, 129.4, 129.3, 128.7, 128.5, 126.3 (2), 125.8, 125.7 (2), 125.2, 123.7, 122.9, 122.5, 120.5, 119.1, 112.6, 26.8; LRMS (APCI) m/z calculated for $C_{25}H_{16}F_6NO_2$ $[M+H]^+$: 476.10; found: 476.59.

Example 22: Production of Compound 22

An indolizine derivative compound (27.3 mg, 96.3% yield) was produced in the same manner as in Example 21, except that, in Example 21-2, 4-acetylphenyl boronic acid (31.0 mg, 0.189 mmol), tetrakis (triphenylphosphine)palladium (15.0 mg, 0.013 mmol) and sodium carbonate (33.6 mg, 0.315 mmol) were added to a solution containing IF-B (30.0 mg, 0.063 mmol) and a 10:1 mixture of DMF and water

[Compound 22]

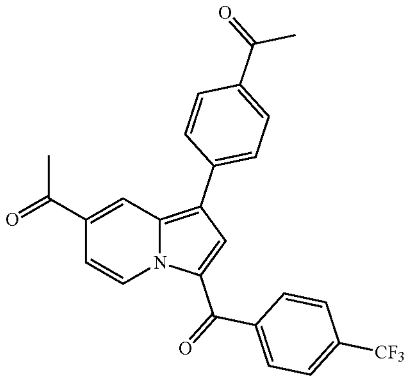

The physical properties of Compound 22 produced in Example 22 are as follows.

$^{1}$H NMR (400 MHz, $CDCl_3$) δ 9.97 (d, J=7.2 Hz, 1H), 8.46 (s, 1H), 8.08 (dd, J=8.4 Hz, 1.6 Hz, 2H), 7.96 (d, J=8.4 Hz, 2H), 7.90 (d, J=8.4 Hz, 1H), 7.80 (d, J=8.4 Hz, 2H), 7.67 (dd, J=6.6 Hz, 2.0 Hz, 2H), 7.55 (dd, J=7.4 Hz, 1.6 Hz, 1H), 7.51 (s, 1H), 6.90 (d, J=8.4 Hz, 1H), 2.67 (dd, J=7.6 Hz, 2.8 Hz, 4H); $^{13}$C NMR (100 MHz, $CDCl_3$) δ 197.4, 196.9, 195.4, 184.0, 160.4, 143.1, 138.6, 135.9, 135.4, 133.5, 133.1, 132.8, 131.1, 130.5, 129.4 (2), 128.8, 128.2, 127.9, 125.9, 125.7 (2), 125.2, 123.8, 122.5, 120.8, 119.8, 119.3, 115.5, 112.6, 36.1, 27.1, 26.8, 26.7. LRMS (APCI) m/z calculated for $C_{26}H_{19}F_3NO_3$ $[M+H]^+$: 450.12; found: 450.63.

Example 23: Production of Compound 23

An indolizine derivative compound (23.6 mg, 91.9% yield) was produced in the same manner as in Example 21, except that, in Example 21-2, 4-acetylphenyl boronic acid (23.0 mg, 0.189 mmol), tetrakis (triphenylphosphine)palladium (15.0 mg, 0.013 mmol) and sodium carbonate (33.6 mg, 0.315 mmol) were added to a solution containing IF-B(30.0 mg, 0.063 mmol) and a 10:1 mixture of DMF and water.

[Compound 23]

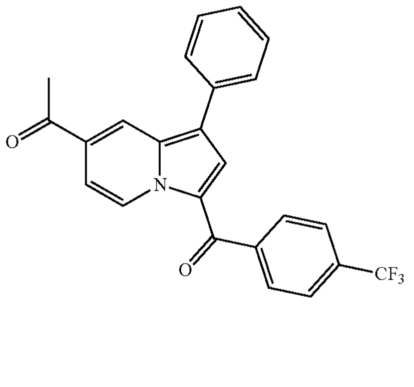

The physical properties of Compound 23 produced in Example 23 are as follows.

$^{1}$H NMR (400 MHz, $CDCl_3$) δ 9.94 (d, J=8.0 Hz, 1H), 8.40 (s, 1H), 7.86 (d, J=7.6 Hz, 2H), 7.75 (d, J=8.4 Hz, 2H), 7.69 (d, J=8.0 Hz, 2H), 7.62 t, J=5.2 Hz, 1H), 7.51 (m, 4H), 2.65 (s, 3H); $^{13}$C NMR (100 MHz, $CDCl_3$) δ 195.4, 185.5, 140.0, 137.8, 134.7, 132.6, 131.8, 129.5, 129.2, 128.6 (2), 128.4, 126.3, 126.2, 125.8, 124.2, 120.1, 119.1, 112.2, 26.7; LRMS (APCI) m/z calculated for $C_{24}H_{17}F_3NO_2$ $[M+H]^+$: 408.11; found: 408.51.

Example 24: Production of Compound 24

An indolizine derivative compound (25.4 mg, 92.2% yield) was produced in the same manner as in Example 21, except that, in Example 21-2, 4-methoxyphenyl boronic acid (28.7 mg, 0.189 mmol), tetrakis (triphenylphosphine)palladium (15.0 mg, 0.013 mmol) and sodium carbonate (33.6 mg, 0.315 mmol) were added to a solution containing IF-B (30.0 mg, 0.063 mmol) and a 10:1 mixture of DMF and water.

[Compound 24]

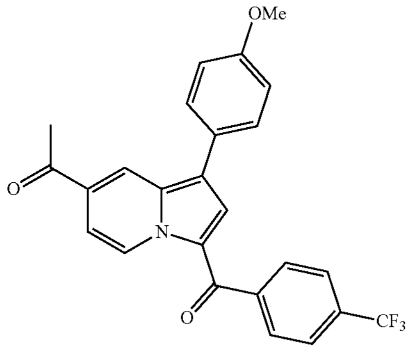

The physical properties of Compound 24 produced in Example 24 are as follows.

$^{1}$H NMR (400 MHz, $CDCl_3$) δ 9.92 (d, J=7.4 Hz, 1H), 8.39 (s, 1H), 7.94 (d, J=8.0 Hz, 2H), 7.78 (d, J=8.4 Hz, 2H), 7.49 (m, 3H), 7.38 (s, 1H), 7.04 (d, J=8.8 Hz, 1H), 6.78 (s, 1H), 3.88 (s, 3H), 2.66 (s, 3H). $^{13}$C NMR (100 MHz, $CDCl_3$) δ 195.5, 183.7, 159.2, 143.4, 135.2, 133.2, 132.9, 132.4, 129.5, 129.4, 128.5, 126.1, 125.6, 125.5, 125.4, 125.3, 123.3, 122.6, 122.3, 119.8, 116.2, 115.0, 114.8, 112.2, 56.1, 55.7, 30.1, 26.7; LRMS (APCI) m/z calculated for $C_{25}H_{19}F_3NO_3$ $[M+H]^+$: 438.12; found: 438.09.

Example 25: Production of Compound 25

An indolizine derivative compound (26.5 mg, 93.5% yield) was produced in the same manner as in Example 21, except that, in Example 21-2, 4-(dimethylamino)phenyl boronic acid (31.2 mg, 0.189 mmol), tetrakis (triphenylphosphine)palladium (15.0 mg, 0.013 mmol) and sodium carbonate (33.6 mg, 0.315 mmol) were added to a solution containing IF-B (30.0 mg, 0.063 mmol) and a 10:1 mixture of DMF and water

[Compound 25]
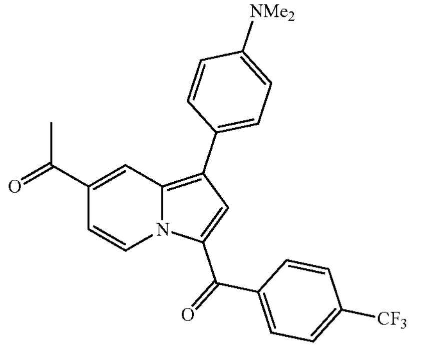
The physical properties of Compound 25 produced in Example 25 are as follows.
$^1$H NMR (400 MHz, $CDCl_3$) δ 9.91 (d, J=7.6 Hz, 1H), 8.43 (s, 1H), 7.95 (d, J=8.0 Hz, 2H), 7.78 (d, J=8.0 Hz, 2H), 7.46 (m, 3H), 7.36 (s, 1H), 6.85 (d, J=8.0 Hz, 2H), 3.03 (s, 6H), 2.65 (s, 3H); $^{13}$C NMR (100 MHz, $CDCl_3$) δ 195.5, 183.6, 150.0, 143.6, 135.2, 133.1, 132.8, 132.1, 129.4, 129.1, 128.4, 125.5 (2), 125.3, 125.0, 123.3, 123.1, 122.6, 121.5, 120.2, 113.1, 112.0, 40.9, 30.1, 26.6; LRMS (APCI) m/z calculated for $C_{26}H_{22}N_2O_2$ $[M+H]^+$: 451.16; found: 451.65.
Example 26: Production of Compound 26
Example 26-1: Production of 1-(3-benzoyl-1-bromoindolizin-7-yl)ethanone (IH-B)
[Reaction Scheme 1-6]
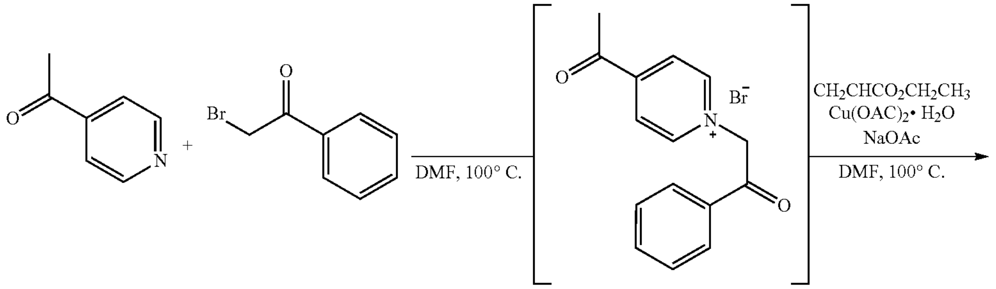
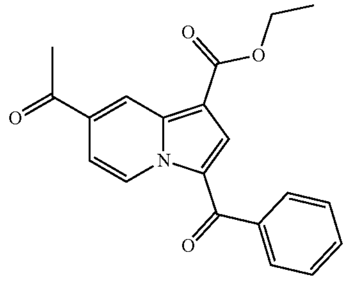
IH-E
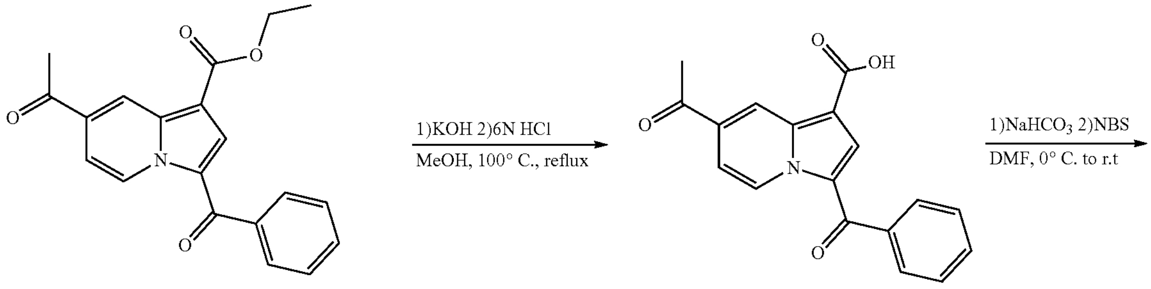
IH-E
IH-A -continued

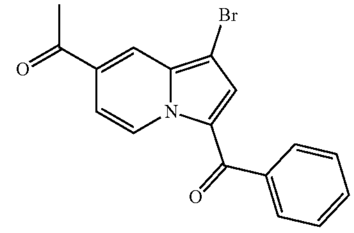

IH-B

IH-E: IH-E was synthesized as shown in Reaction Scheme 1-6 above. Specifically, DMF (4.0 mL) containing 4-acetylpyridine (105.9 μL, 0.957 mmol) and 2-bromoacetophenone (200.0 mg, 1.01 mmol) was stirred at 80° C. for 5 hours, and then ethyl acrylate (51.8 μl, 0.479 mmol), copper(II) acetate monohydrate (573.2 mg, 2.87 mmol) and sodium acetate (314.0 mg, 3.83 mmol) were added thereto, followed by stirring at 100° C. for 5 hours. After completion of the reaction, monitoring by TLC was performed, and then copper acetate was removed by filtration through a celite pad, and the resulting filtrate was concentrated in vacuum. The resulting crude product was washed with water, and the organic phase was extracted three times with DCM. The extracted organic phases were combined, dried over anhydrous $Na_2SO_4$ and then concentrated. The concentrated organic phase was purified by silica-gel flash column chromatography (EA:hexane=1:5-40% ethyl acetate) to obtain compound IH-E (556.5 mg, 77.3% yield) as a yellow solid.

The results of NMR analysis are as follows.

$^1$H NMR (400 MHz, $CDCl_3$) 59.83 (dd, J=7.2, 0.8 Hz, 1H), 8.90 (s, 1H), 7.80 (m, 3H), 7.54 (m, 4H) 4.38 (q, 2H), 2.69 (s, 3H); $^{13}$C NMR (100 MHz, $CDCl_3$) 195.7, 163.7, 139.4, 138.3, 134.3, 132.1, 129.2, 128.9, 128.9, 128.9, 121.1, 60.8, 26.6, 14.9; LRMS (ESI) m/z calculated for $C_{20}H_{17}NO_4$ $[M+Na]^+$: 335.1, found: 336.2.

IH-B: KOH (336.8 mg, 6.0 mmol) was added to methanol (4 mL) containing IH-E (200.0 mg, 0.60 mmol), followed by stirring overnight at room temperature. The reaction mixture was acidified by adding 6N HCl, and the resulting solid was collected through filtration, washed with water, and dried in a drying oven to obtain compound IH-A as a brown solid.

The obtained compound IH-A was used in the next step without further purification. Sodium bicarbonate (131.1 mg, 1.56 mmol) was added to DMF (2.0 mL) containing IH-A, and NBS (97.9 mg, 0.55 mmol) was added thereto in portions at 0° C. The reaction mixture was stirred at room temperature for 12 hours, and then the resulting crude product was washed with water and the organic phase was extracted three times with DCM. The extracted organic phases were combined, dried over anhydrous $Na_2SO_4$, and then concentrated. The concentrated organic phase was purified by silica-gel flash column chromatography (EA: hexane=1:5-40% ethyl acetate) to obtain compound IH-B (135.2 mg, 76.3% yield) as a yellow solid.

The results of NMR analysis are as follows.

$^1$H NMR (400 MHz, $CDCl_3$), δ 9.85 (d, J=7.4 Hz, 1H), 8.17 (s, 1H), 7.8 (d, J=7.6 Hz, 2H), 7.52 (m, 5H), 2.71 (s, 3H); $^{13}$C NMR (100 MHz, $CDCl_3$), δ 195.3, 184.8, 139.5, 135.2, 132.2, 131.9, 129.1, 128.6, 128.3, 127.5, 123.9, 119.2, 112.0, 94.1, 26.7; LRMS (ESI) m/z calculated for $C_{17}H_{12}BrNO_2$ [M+Na]+341.0, found: x.

Example 26-2: Production of Compound 26

To a solution containing IH-B (30.0 mg, 0.088 mmol) and a 10:1 mixture of DMF and water, 4-trifluorophenyl boronic acid (49.95 mg, 0.26 mmol), tetrakis(triphenyl phosphine) palladium (20.28 mg, 0.018 mmol) and sodium carbonate (46.4 mg, 0.44 mmol) were added, followed by stirring at 100° C. for 8 hours. After completion of the reaction, monitoring by TLC was performed, and then the reaction solution was washed with water, and the organic phase was extracted three times with DCM. The extracted organic phases were combined, dried over anhydrous $Na_2SO_4$, and then concentrated. The concentrated organic phase was purified by silica-gel flash column chromatography (EA: hexane=1:4-40% ethyl acetate) to obtain Compound 26 (33.8 mg, 94.3% yield) as a yellow solid.

[Compound 26]

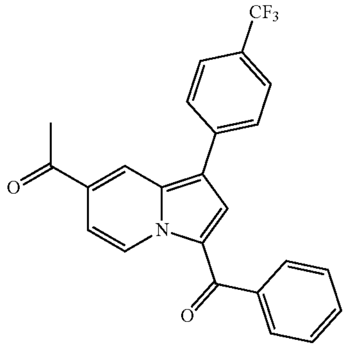

The physical properties of Compound 26 produced in Example 26 are as follows.

$^1$H NMR (400 MHz, $CDCl_3$) δ 9.94 (d, J=7.6 Hz, 1H), 8.40 (s, 1H), 7.85 (dd, J=5.6 Hz, 2.4 Hz, 2H), 7.74 (d, J=8.0 Hz, 2H), 7.66 (d, J=8.0 Hz, 2H), 7.60 (t, J=6.8 Hz, 1H), 7.50 (m, 4H), 2.67 (s, 3H); $^{13}$C NMR (100 MHz, $CDCl_3$) 195.3, 185.5, 140.0, 137.8, 134.7, 132.6, 131.8, 129.2, 128.6, 128.4, 126.3, 126.2(3), 125.8, 124.2, 120.1, 119.1, 112.2, 26.7; LRMS (ESI) m/z calculated for $C_{24}H_{17}F_3NO_2$ $[M+H]^+$: 408.11; found: 408.10.

Example 27: Production of Compound 27

An indolizine derivative compound (32.1 mg, 95.6% yield) was produced in the same manner as in Example 26, except that, in Example 26-2, 4-acetylphenyl boronic acid (343.12 mg, 0.26 mmol), tetrakis (triphenylphosphine)palladium (20.28 mg, 0.018 mmol) and sodium carbonate (46.4 mg, 0.44 mmol) were added to a solution containing IH-B (30.0 mg, 0.088 mmol) and a 10:1 mixture of DMF and water.

[Compound 27]

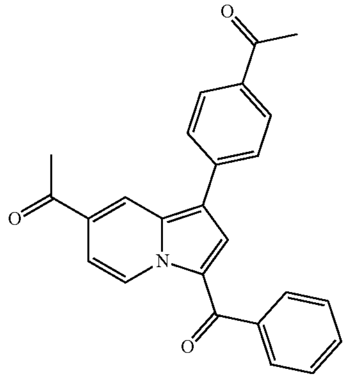

The physical properties of Compound 27 produced in Example 27 are as follows.

$^1$H NMR (400 MHz, $CDCl_3$) δ 9.93 (d, J=7.6 Hz, 1H), 8.44 (s, 1H), 8.07 (d, J=8.0 Hz, 2H), 7.85 (d, J=7.2 Hz, 2H), 7.67 (d, J=12.0 Hz, 2H), 7.54 (m, 5H), 2.66 (s, 3H), 2.65 (s, 3H); $^{13}$C NMR (100 MHz, $CDCl_3$) δ 197.4, 195.4, 185.5, 140.0, 138.9, 135.7, 134.8, 132.6, 131.8, 129.4, 129.2, 128.6, 128.1, 125.8, 124.3, 120.4, 119.3, 112.2, 27.0, 26.7; LRMS (APCI) m/z calculated for $C_{25}H_{20}NO_3$ $[M+H]^+$: 382.14; found: 382.17.

Example 28: Production of Compound 28

An indolizine derivative compound (28.5 mg, 95.4% yield) was produced in the same manner as in Example 26, except that, in Example 26-2, methyl boronic acid (32.07 mg, 0.26 mmol), tetrakis(triphenylphosphine)palladium (20.28 mg, 0.018 mmol) and sodium carbonate (46.4 mg, 0.44 mmol) were added to a solution containing IH-B (30.0 mg, 0.088 mmol) and a 10:1 mixture of DMF and water

[Compound 28]

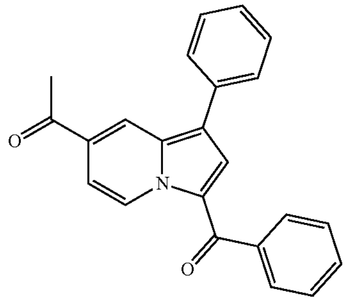

The physical properties of Compound 28 produced in Example 28 are as follows.

$^1$H NMR (400 MHz, $CDCl_3$) δ 9.92 (d, J=7.6 Hz, 1H), 8.42 (s, 1H), 7.84 (dd, J=8.2 Hz, 1.2 Hz, 2H), 7.60 (d, J=4.8 Hz, 3H), 7.50 (m, 6H), 7.38 (t, J=7.2 Hz, 1H), 2.65 (s, 3H); $^{13}$C NMR (100 MHz, $CDCl_3$) δ 195.6, 185.5, 140.2, 134.7, 134.1, 132.1, 131.7, 129.3, 129.2, 128.5, 128.3, 127.4, 125.7, 123.9, 121.9, 119.8, 111.8, 26.7; LRMS (APCI) m/z calculated for $C_{23}H_{18}NO_2$ $[M+H]^+$: 340.13; found: 340.22.

Example 29: Production of Compound 29

An indolizine derivative compound (30.1 mg, 92.7% yield) was produced in the same manner as in Example 26, except that, in Example 26-2, 4-methoxyphenyl boronic acid (39.97 mg, 0.26 mmol), tetrakis (triphenylphosphine)palladium (20.28 mg, 0.018 mmol) and sodium carbonate (46.4 mg, 0.44 mmol) were added to a solution containing IH-B (30.0 mg, 0.088 mmol) and a 10:1 mixture of DMF and water.

[Compound 29]

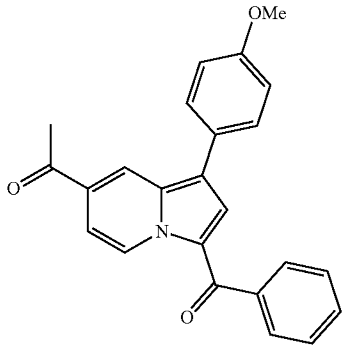

The physical properties of Compound 29 produced in Example 29 are as follows.

$^1$H NMR (400 MHz, $CDCl_3$) δ 9.88 (d, J=7.6 Hz, 1H), 8.36 (s, 1H), 7.84 (dd, J=8.2 Hz, 1.2 Hz, 2H), 7.50 (m, 7H), 7.01 (d, J=4.0 Hz, 2H), 3.86 (s, 3H), 2.65 (s, 3H); $^{13}$C NMR (100 MHz, $CDCl_3$) δ 195.6, 185.4, 159.1, 140.2, 134.6, 131.8, 131.6, 129.5, 129.2, 128.5, 128.3, 126.4, 125.4, 123.8, 121.8, 121.6, 119.9, 114.8, 111.7, 55.7, 26.7; LRMS (ESI) m/z calculated for $C_{24}H_{20}NO_3$ $[M+H]^+$:370.14; found: 370.15.

Example 30: Production of Compound 30

An indolizine derivative compound (32.9 mg, 94.9% yield) was produced in the same manner as in Example 26, except that, in Example 26-2, phenyl (dimethylamino)phenylboronic acid, 43.40 mg, 0.26 mmol), tetrakis(triphenylphosphine)palladium (20.28 mg, 0.018 mmol) and sodium carbonate (46.4 mg, 0.44 mmol) were added to a solution containing IH-B (30.0 mg, 0.088 mmol) and a 10:1 mixture of DMF and water.

[Compound 30]

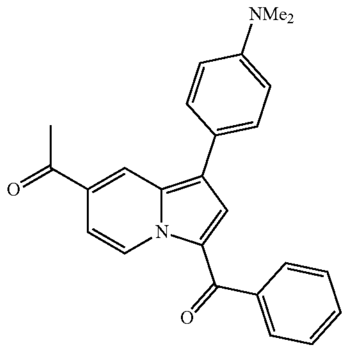

The physical properties of Compound 30 produced in Example 30 are as follows.

$^1$H NMR (400 MHz, $CDCl_3$) δ 9.89 (d, J=7.4 Hz, 1H), 8.42 (s, 1H), 7.86 (dd, J=8.2 Hz, 1.2 Hz, 2H), 7.51 (m, 7H), 6.85 (d=6.8 Hz, 2H), 3.02 (s, 6H), 2.65 (s, 3H); $^{13}$C NMR (100 MHz, $CDCl_3$) δ 195.6, 185.3, 149.9, 140.4, 134.5, 131.5(2), 129.3, 129.1, 128.5, 128.2, 125.0, 123.8, 122.6, 121.9, 120.3, 113.1, 111.5, 53.8, 40.9, 26.6; LRMS (ESI) m/z calculated for $C_{25}H_{23}N_2O_2$ $[M+H]^+$: 383.17; found: 383.20.
Example 31: Production of Compound 31
Example 31-1: Production of 1-(1-bromo-3-(4-methoxybenzoyl)indolizin-7-yl)ethanone (II-B)
[Reaction Scheme 1-7]
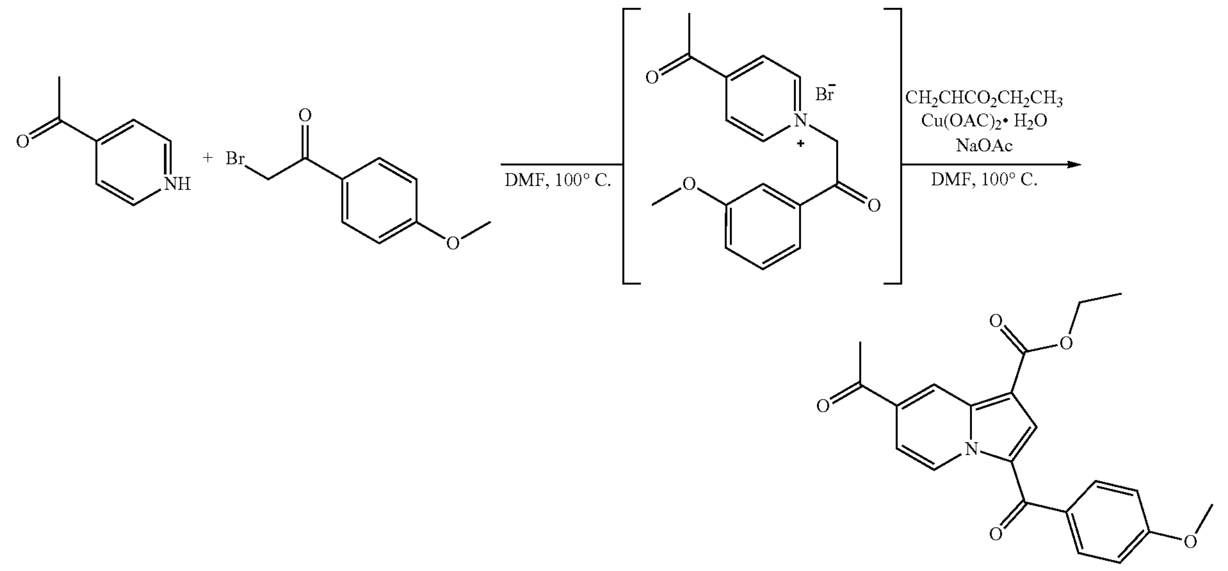
II-E
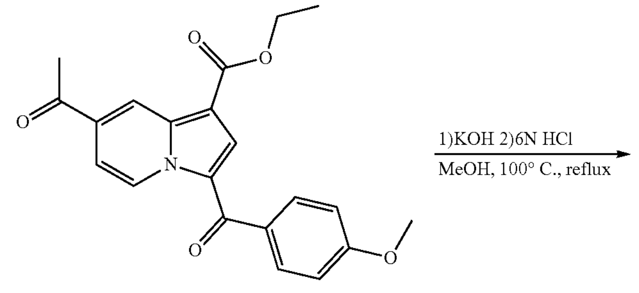
II-E
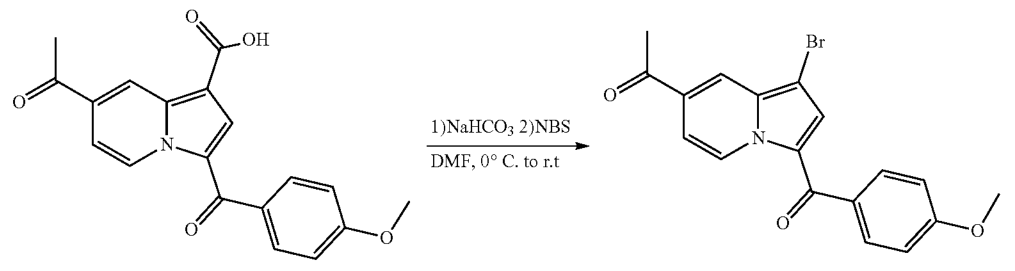
II-A II-B I1-E: II-E was synthesized as shown in Reaction Scheme 1-7 above. Specifically, DMF (17.6 mL) containing 4-acetylpyridine (585.2 μL, 5.29 mmol) and 2-bromoacetophenone (1.5 g, 5.6 mmol) was stirred at 80° C. for 5 hours, and then ethyl acrylate (286.6 μl, 2.65 mmol), copper(II) acetate monohydrate (3.17 g, 15.87 mmol) and sodium acetate (1.74 g, 21.16 mmol) were added thereto, followed by stirring at 100° C. for 5 hours. After completion of the reaction, monitoring by TLC was performed, and then copper acetate was removed by filtration through a celite pad, and the resulting filtrate was concentrated in vacuum. The resulting crude product was washed with water, and the organic phase was extracted three times with DCM. The extracted organic phases were combined, dried over anhydrous $Na_2SO_4$ and then concentrated. The concentrated organic phase was purified by silica-gel flash column chromatography (EA:hexane=1:5-40% ethyl acetate) to obtain compound II-E (709.8 mg, 73.3% yield) as a yellow solid.

The results of NMR analysis are as follows.

$^1$H NMR (400 MHz, $CDCl_3$) 9.62 (dd J=7.4, 0.4 Hz, 1H), 8.76 (s, 1H), 7.74 (dd, J=6.6, 2 Hz, 2H), 7.69 (s, 1H), 7.39 (dd, J=7.4, 2 Hz, 1H), 6.92 (dd, J=6.8, 2 Hz, 2H), 4.33 (q, J=7.2 Hz, 2H), 3.82 (s, 3H), 2.61 (s, 3H), 1.362 (t, J=7.2 Hz, 3H); $^{13}$C NMR (100 MHz, $CDCl_3$) 195.6, 184.3, 163.4, 162.8, 137.6, 133.7, 131.9, 131.4, 128.4, 127.5, 123.2, 120.9, 113.8, 112.5, 109.1, 60.6, 55.6, 26.4, 14.8; LRMS (ESI) m/z calculated for $C_{21}H_{19}NO_4$ $[M+Na]^+$: 365.1, found: 366.2.

I1-B: KOH (3.1 g, 77.6 mmol) was added to methanol (19 mL) containing II-E (709.8 mg, 1.94 mmol), followed by stirring overnight at room temperature. The reaction mixture was acidified by adding 6N HCl, and the resulting solid was collected through filtration, washed with water, and dried in a drying oven to obtain compound II-A as a brown solid.

The obtained compound II-A was used in the next step without further purification. Sodium bicarbonate (478.9 mg, 5.7 mmol) was added to DMF (10.0 mL) containing II-A, and NBS (354.9 mg, 2.0 mmol) was added thereto in portions at 0° C. The reaction mixture was stirred at room temperature for 12 hours, and then the resulting crude product was washed with water and the organic phase was extracted three times with DCM. The extracted organic phases were combined, dried over anhydrous $Na_2SO_4$, and then concentrated. The concentrated organic phase was purified by silica-gel flash column chromatography (EA: hexane=1:5-40% ethyl acetate) to obtain compound II-B (462.0 mg, 72.1% yield) as a yellow solid.

The results of NMR analysis are as follows.

$^1$H NMR (400 MHz, $CDCl_3$) 9.73 (d, J=7.2 Hz, 1H), 8.12 (s, 1H), 7.81 (d, J=8.8 Hz, 2H), 7.42 (m, 1H), 6.99 (d, 2H), 3.88 (s, 3H), 2.68 (s, 3H); $^{13}$C NMR (100 MHz, $CDCl_3$) 195.3, 183.7, 162.8, 134.8, 132.0, 131.9, 131.4, 128.1, 126.9, 124.0, 119.3, 113.9, 111.7, 93.9, 55.8, 26.6; LRMS (ESI) m/z calculated for $C_{18}H_{14}NO_4$ $[M+Na]^+$: 372.2, found: 372.1.

Example 31-2: Production of Compound 31

To a solution (1.1 mL) containing II-B (30.0 mg, 0.081 mmol) and a 10:1 mixture of DMF and water, 4-trifluorophenyl boronic acid (46.2 mg, 0.243 mmol), tetrakis(triphenyl phosphine)palladium (18.7 mg, 0.016 mmol) and sodium carbonate (42.9 mg, 0.405 mmol) were added, followed by stirring at 100° C. for 8 hours. After completion of the reaction, monitoring by TLC was performed, and then the reaction solution was washed with water, and the organic phase was extracted three times with DCM. The extracted organic phases were combined, dried over anhydrous $Na_2SO_4$, and then concentrated. The concentrated organic phase was purified by silica-gel flash column chromatography (EA:hexane=1:4-40% ethyl acetate) to obtain Compound 31 (34.4 mg, 97.2% yield) as a yellow solid.

[Compound 31]

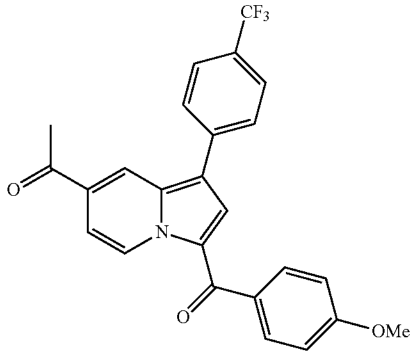

The physical properties of Compound 31 produced in Example 31 are as follows.

$^1$H NMR (400 MHz, $CDCl_3$) δ 9.84 (d, J=7.4 Hz, 1H), 8.39 (s, 1H), 7.88 (dd, J=6.8 Hz, 2.0 Hz, 2H), 7.74 (d, J=8.8 Hz, 2H), 7.69 (d, J=8.8 Hz, 2H), 7.54 (s, 1H), 7.45 (dd, J=7.2 Hz, 2.0 Hz, 1H), 7.02 (d, J=6.8 Hz, 2H), 3.91 (s, 3H), 2.67 (s, 3H); $^{13}$C NMR (100 MHz, $CDCl_3$) δ 195.6, 184.5, 162.8, 137.9, 134.3, 132.4, 132.2, 131.5, 128.4, 126.3, 126.2, 125.3, 124.3, 119.9, 119.3, 114.0, 111.9, 55.9, 26.8; LRMS (ESI) m/z calculated for $C_{25}H_{19}F_3NO_3$ $[M+H]^+$: 438.12; found: 438.15.

Example 32: Production of Compound 32

An indolizine derivative compound (32.5 mg, 97.5% yield) was produced in the same manner as in Example 31, except that, in Example 31-2, 4-acetylphenyl boronic acid (39.8 mg, 0.243 mmol), tetrakis (triphenylphosphine)palladium (18.7 mg, 0.016 mmol) and sodium carbonate (42.9 mg, 0.405 mmol) were added to a solution (1.1 mL) containing II-B (30.0 mg, 0.081 mmol) and a 10:1 mixture of DMF and water

[Compound 32]

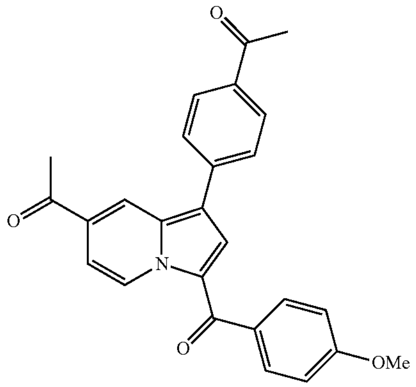

The physical properties of Compound 32 produced in Example 32 are as follows.

$^1H$ NMR (400 MHz, $CDCl_3$) δ 9.84 (d, J=7.2 Hz, 1H), 8.43 (s, 1H), 8.07 (d, J=8.0 Hz, 2H), 7.88 (dd, J=7.0 Hz, 2.0 Hz, 2H), 7.68 (d, J=8.4 Hz, 2H), 7.56 (s, 1H), 7.45 (dd, J=7.4 Hz, 2.0 Hz, 1H), 7.02 (dd, J=6.8 Hz, 1.6 Hz, 2H), 3.90 (s, 3H), 2.65 (s, 6H); $^{13}C$ NMR (100 MHz, $CDCl_3$) 197.4, 195.5, 184.5, 162.8, 139.1, 135.6, 134.3, 132.4, 132.3, 131.5, 129.4, 128.4, 128.1, 125.2, 124.4, 120.1, 119.4, 114.0, 111.9, 55.8, 30.1, 27.0, 26.7; LRMS (ESI) m/z calculated for $C_{26}H_{22}NO_4$ $[M+H]^+$: 412.15; found: 412.15.

Example 33: Production of Compound 33

An indolizine derivative compound (28.9 mg, 96.6% yield) was produced in the same manner as in Example 31, except that, in Example 31-2, benzene boronic acid (29.6 mg, 0.243 mmol), tetrakis(triphenylphosphine)palladium (18.7 mg, 0.016 mmol) and sodium carbonate (42.9 mg, 0.405 mmol) were added to a solution (1.1 mL) containing II-B (30.0 mg, 0.081 mmol) and a 10:1 mixture of DMF and water.

[Compound 33]

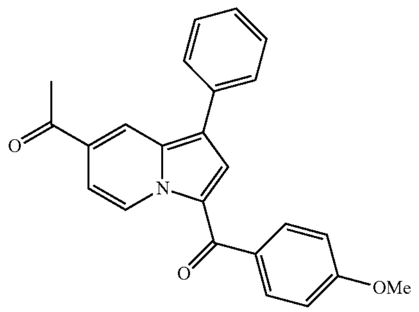

The physical properties of Compound 33 produced in Example 33 are as follows.

$^1H$ NMR (400 MHz, $CDCl_3$) δ 9.84 (d, J=7.2 Hz, 1H), 8.42 (s, 1H), 7.89 (dd, J=6.8 Hz, 1.6 Hz, 2H), 7.60 (dd, J=8.2 Hz, 1.6 Hz, 2H), 7.50 (t, J=8.0 Hz, 3H), 7.43 (dd, J=7.6 Hz, 2.0 Hz, 1H), 7.38 (t, J=7.2 Hz, 1H), 7.01 (dd, J=6.8 Hz, 2.0 Hz, 2H), 3.90 (s, 3H), 2.64 (s, 3H). $^{13}C$ NMR (100 MHz, $CDCl_3$) δ 195.6, 184.4, 162.6, 134.2(2), 132.7, 131.8, 131.5, 129.3, 128.3, 128.2, 127.4, 125.1, 124.1, 121.7, 119.9, 113.9, 111.5, 55.8, 26.7; LRMS (ESI) m/z calculated for $C_{24}H_{20}NO_3$ $[M+H]^+$: 370.14; found: 370.15.

Example 34: Production of Compound 34

An indolizine derivative compound (30.4 mg, 94.0% yield) was produced in the same manner as in Example 31, except that, in Example 31-2, 4-methoxyphenyl boronic acid (36.9 mg, 0.243 mmol), tetrakis (triphenylphosphine)palladium (18.7 mg, 0.016 mmol) and sodium carbonate (42.9 mg, 0.405 mmol) were added to a solution (1.1 mL) containing II-B (30.0 mg, 0.081 mmol) and a 10:1 mixture of DMF and water

[Compound 34]

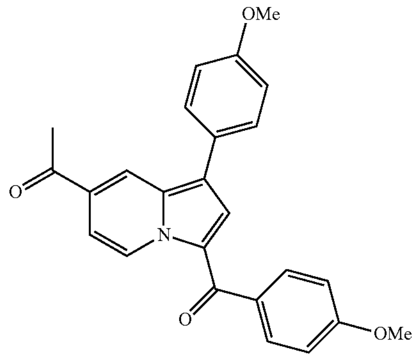

The physical properties of Compound 34 produced in Example 34 are as follows.

$^1H$ NMR (400 MHz, $CDCl_3$) δ 9.81 (d, J=7.2 Hz, 1H), 8.36 (s, 1H), 7.87 (d, J=7.4 Hz, 2.8 Hz, 2H), 7.49 (dd, J=6.6 Hz, 2.0 Hz, 2H), 7.45 (s, 1H), 7.40 (dd, J=7.2 Hz, 2.0 Hz, 1H), 7.02 (m, 4H), 3.90 (s, 3H), 3.87 (s, 3H), 2.63 (s, 3H); $^{13}C$ NMR (100 MHz, $CDCl_3$) δ 195.6, 184.4, 162.6, 159.0, 134.2, 132.7, 131.5, 129.5, 128.1, 126.6, 124.8, 124.0, 121.6, 119.9, 114.8, 113.8, 111.4, 55.8, 55.7, 30.1, 26.6. LRMS (ESI) m/z calculated for $C_{25}H_{22}NO_4$ $[M+H]^+$: 400.15; found: 400.15.

Example 35: Production of Compound 35

An indolizine derivative compound (31.2 mg, 93.3% yield) was produced in the same manner as in Example 31, except that, in Example 31-2, 4-(dimethylamino)phenyl boronic acid (40.0 mg, 0.24 mmol), tetrakis (triphenylphosphine)palladium (18.7 mg, 0.016 mmol) and sodium carbonate (42.9 mg, 0.405 mmol) were added to a solution (1.1 mL) containing II-B (30.0 mg, 0.081 mmol) and a 10:1 mixture of DMF and water

[Compound 35]

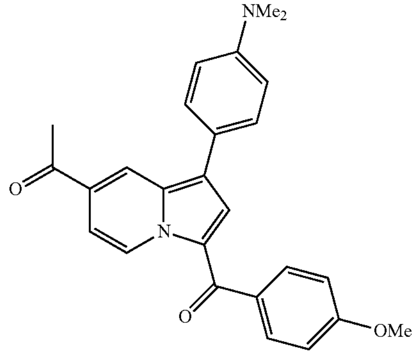

The physical properties of Compound 35 produced in Example 35 are as follows.

$^1H$ NMR (400 MHz, $CDCl_3$) δ 9.80 (d, J=7.2 Hz, 1H), 8.40 (s, 1H), 7.88 (dd, J=6.8 Hz, 2.0 Hz, 2H), 7.46 (m, 3H), 7.40 (dd, J=7.4 Hz, 2.0 Hz, 1H), 7.00 (dd, J=6.6 Hz, 2.0 Hz, 2H), 6.86 (dd, J=6.8 Hz, 2.0 Hz, 2H), 3.90 (s, 3H), 3.02 (s, 6H), 2.63 (s, 3H); $^{13}C$ NMR (100 MHz, $CDCl_3$) δ 195.7, 184.4, 162.5, 149.9, 134.1, 132.9, 131.5, 131.2, 129.1, 128.0, 124.5, 124.0, 122.4, 122.1, 120.4, 113.8, 113.2, 111.2, 55.8, 40.9, 26.6; LRMS (ESI) m/z calculated for $C_{26}H_{25}N_2O_3$ $[M+H]^+$: 413.18; found: 413.20.

Example 36: Production of Compound 36
Example 36-1: Production of 1-(1-bromo-3-(4-(diethylamino)benzoyl)indolizin-7-yl)ethanone (IJ-B)
[Reaction Scheme 1-8]
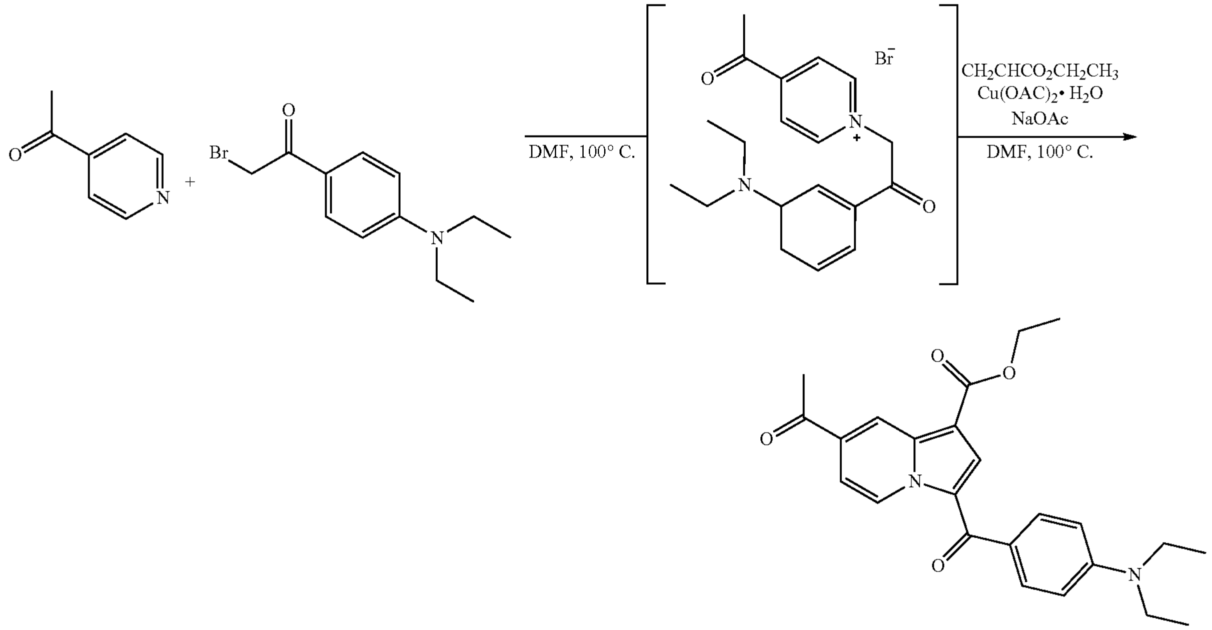
IJ-E
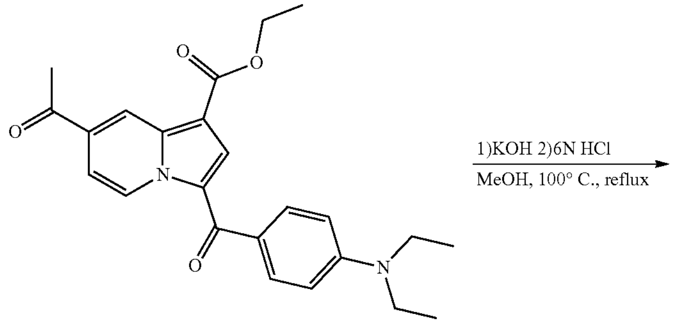
IJ-E
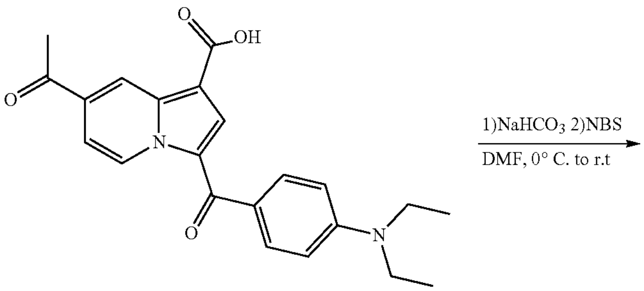
IJ-A -continued

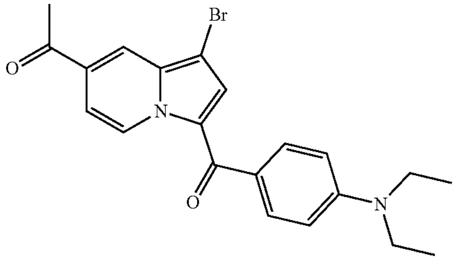

IJ-B

IJ-E: IJ-E was synthesized as shown in Reaction Scheme 1-8 above. Specifically, DMF (6.0 mL) containing 4-acetylpyridine (194.9 μL, 1.76 mm) and 2-bromo-4'-diethylaminoacetophenone (500 mg, 1.85 mmol) was stirred at 80° C. for 5 hours, and then ethyl acrylate (88.1 μl, 0.88 mmol), copper(II) acetate monohydrate (1.05 g, 5.28 mmol) and sodium acetate (577.5 mg, 7.04 mmol) were added thereto, followed by stirring at 100° C. for 5 hours. After completion of the reaction, monitoring by TLC was performed, and then copper acetate was removed by filtration through a celite pad, and the resulting filtrate was concentrated in vacuum. The resulting crude product was washed with water, and the organic phase was extracted three times with DCM. The extracted organic phases were combined, dried over anhydrous $Na_2SO_4$ and then concentrated. The concentrated organic phase was purified by silica-gel flash column chromatography (EA:hexane=1:5-40% ethyl acetate) to obtain compound IJ-E (295.6 mg, 82.7% yield) as a yellow solid.

The results of NMR analysis are as follows.

$^1$H NMR (400 MHz, $CDCl_3$), δ 9.66 (d, J=7.6 Hz, 1H), 8.89 (s, 1H), 7.8 (m, 3H), 7.46 (dd, J=7.6 Hz, 2 Hz, 1H), 6.69 (d, J=7 Hz, 2H), 4.39 (q, J=7.2 Hz, 2H), 3.43 (q, J=7.2 Hz, 4H), 2.68 (s, 3H), 1.42 (t, J=7.2 Hz, 3H), 1.21 (t, J=7.2 Hz, 6H); $^{13}$C NMR (100 MHz, $CDCl_3$), δ 195.9, 183.9, 164.1, 151.0, 137.5, 133.3, 132.3, 132.2, 128.5, 127.1, 125.4, 124.7, 121.6, 121.3, 111.7, 110.5, 108.8, 60.6, 44.9, 26.5, 14.9, 13.0; LRMS (ESI) m/z calculated for $C_{24}H_{26}N_2O_4$ $[M+Na]^+$: 406.2, found: 407.2.

IJ-B: KOH (1.63 g, 29.2 mmol) was added to methanol (16 mL) containing IJ-E (295.6 mg, 0.73 mmol), followed by stirring overnight at room temperature. The reaction mixture was acidified by adding 6N HCl, and the resulting solid was collected through filtration, washed with water, and dried in a drying oven to obtain compound IJ-A as a brown solid.

The obtained compound IJ-A was used in the next step without further purification. Sodium bicarbonate (306.6 mg, 3.65 mmol) was added to DMF (10.0 mL) containing IJ-A, and NBS (136.4 mg, 0.77 mmol) was added thereto in portions at 0° C. The reaction mixture was stirred at room temperature for 12 hours, and then the resulting crude product was washed with water and the organic phase was extracted three times with DCM. The extracted organic phases were combined, dried over anhydrous $Na_2SO_4$, and then concentrated. The concentrated organic phase was purified by silica-gel flash column chromatography (EA: hexane=1:5-40% ethyl acetate) to obtain compound IJ-B (241.0 mg, 80.1% yield) as a yellow solid.

The results of NMR analysis are as follows.

$^1$H NMR (400 MHz, $CDCl_3$), δ 9.61 (d, J=7.2 Hz, 1H), 8.06 (s, 1H), 7.77 (d, J=8.8 Hz, 2H), 7.42 (s, 1H), 7.32 (dd, J=2 Hz, 7.4 Hz), 6.66 (d, J=8.8 Hz, 2H), 3.42 (q, 7.2 Hz, 4H), 2.64 (s, 3H), 1.21 (t, J=7.2 Hz, 6H); $^{13}$C NMR (100 MHz, $CDCl_3$), δ 195.4, 183.1, 150.9, 133.9, 132.1, 131.0, 127.8, 125.9, 125.6, 124.6, 119.4, 111.0, 110.5, 93.4, 77.7, 77.4, 77.1, 44.9, 26.6, 13.0; LRMS (ESI) m/z calculated for $C_{21}H_{21}BrN_2O_2[M+Na]^+$: 412.08, found: x.

Example 36-2: Production of Compound 36

To a solution (1.1 mL) containing IJ-B (20.0 mg, 0.048 mmol) and a 10:1 mixture of DMF and water, 4-trifluloro-phenyl boronic acid (27.3 mg, 0.14 mmol), tetrakis(triphenyl phosphine)palladium (11.1 mg, 0.01 mmol) and sodium carbonate (25.4 mg, 0.24 mmol) were added, followed by stirring at 100° C. for 8 hours. After completion of the reaction, monitoring by TLC was performed, and then the reaction solution was washed with water, and the organic phase was extracted three times with DCM. The extracted organic phases were combined, dried over anhydrous $Na_2SO_4$, and then concentrated. The concentrated organic phase was purified by silica-gel flash column chromatography (EA:hexane=1:4-40% ethyl acetate) to obtain Compound 36 (22.2 mg, 96.6% yield) as a yellow solid.

[Compound 36]

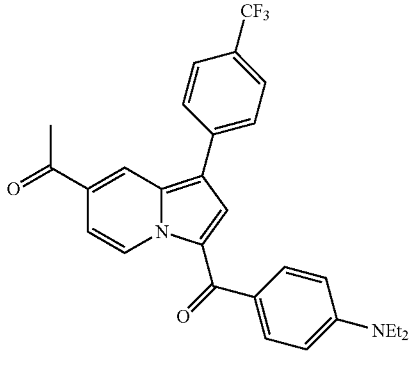

The physical properties of Compound 36 produced in Example 36 are as follows.

$^1$H NMR (400 MHz, $CDCl_3$) δ 9.75 (d, J=7.6 Hz, 1H), 8.39 (s, 1H), 7.87 (d, J=7.2 Hz, 2H), 7.73 (q, J=8.8 Hz, 4H), 7.59 (s, 1H), 7.40 (dd, J=7.6 Hz, 1.6 Hz, 1H), 6.72 (d, J=9.2 Hz, 2H), 3.46 (q, J=7.2 Hz, 4H), 2.65 (s, 3H), 1.24 (t, J=8.0 Hz, 6H); $^{13}$C NMR (100 MHz, $CDCl_3$) δ 195.6, 183.9, 150.9, 138.3, 133.5, 132.2, 131.5, 128.3, 128.2, 126.2, 126.0, 125.0, 124.3, 119.5, 119.4, 111.3, 110.5, 44.9, 26.7, 13.0; LRMS (APCI) m/z calculated for $C_{28}H_{26}F_3N_2O_2[M+H]^+$: 479.19; found: 479.30.

Example 37: Production of Compound 37

An indolizine derivative compound (20.5 mg, 94.5% yield) was produced in the same manner as in Example 36, except that, in Example 36-2, 4-acetylphenyl boronic acid (323.6 mg, 0.14 mmol), tetrakis (triphenylphosphine)palladium (11.1 mg, 0.01 mmol) and sodium carbonate (25.4 mg, 0.24 mmol) were added to a solution (1.1 mL) containing IJ-B (20.0 mg, 0.048 mmol) and a 10:1 mixture of DMF and water

[Compound 37]

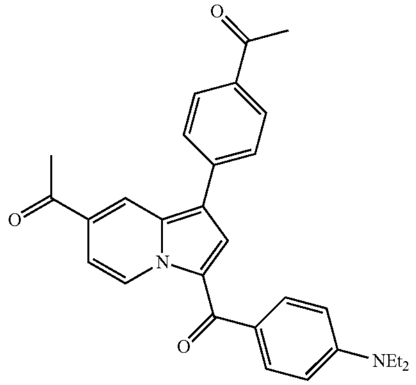

The physical properties of Compound 37 produced in Example 37 are as follows.

$^1$H NMR (400 MHz, $CDCl_3$) δ 9.74 (d, J=7.4 Hz, 1H), 8.43 (s, 1H), 8.08 (dd, J=6.4 Hz, 2.0 Hz, 2H), 7.87 (d, J=8.0 Hz, 2H), 7.70 (dd, J=6.8 Hz, 1.6 Hz, 2H), 7.61 (s, 1H), 7.39 (dd, J=7.8 Hz, 1.6 Hz, 1H), 6.72 (d, J=8.4 Hz, 2H), 3.46 (q, J=7.2 Hz, 4H), 2.67 (s, 3H), 2.65 (s, 3H), 1.24 (t, J=7.2 Hz, 6H); $^{13}$C NMR (100 MHz, $CDCl_3$) δ 197.5, 195.6, 183.9, 150.9, 139.5, 135.4, 133.6, 132.2, 131.5, 129.4, 128.2, 128.0, 126.0, 125.1, 124.3, 119.7, 119.6, 111.3, 110.6, 44.9, 27.0, 26.7, 13.0; LRMS (APCI) m/z calculated for $C_{29}H_{29}N_2O_3$ $[M+H]^+$: 453.21; found: 453.15.

Example 38: Production of Compound 38

An indolizine derivative compound (18.2 mg, 92.2% yield) was produced in the same manner as in Example 36, except that, in Example 36-2, 4-benzene boronic acid (23.8 mg, 0.14 mmol), tetrakis(triphenylphosphine)palladium (11.1 mg, 0.01 mmol) and sodium carbonate (17.6 mg, 0.24 mmol) were added to a solution (1.1 mL) containing IJ-B (20.0 mg, 0.048 mmol) and a 10:1 mixture of DMF and water

[Compound 38]

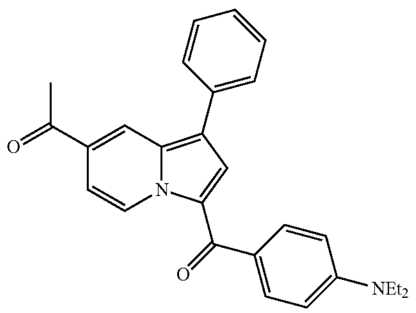

The physical properties of Compound 38 produced in Example 38 are as follows.

$^1$H NMR (400 MHz, $CDCl_3$) δ 9.73 (d, J=7.4 Hz, 1H), 8.41 (s, 1H), 7.88 (d, J=8.0 Hz, 2H), 7.60 (d, J=6.4 Hz, 2H), 7.57 (s, 1H), 7.50 (t, J=6.4 Hz, 2H), 7.37 (d, J=7.2 Hz, 2H), 6.71 (d, J=9.2 Hz, 2H), 3.45 (q, J=6.8 Hz, 4H), 2.63 (s, 3H), 1.24 (t, J=7.2 Hz, 6H); $^{13}$C NMR (100 MHz, $CDCl_3$) δ 195.7, 184.0, 150.8, 134.6, 133.4, 132.1, 131.0 129.2, 128.3, 128.0, 127.1, 126.3, 124.7, 124.3, 121.3, 120.0, 110.9, 110.5, 44.9, 26.6, 13.0; LRMS (APCI) m/z calculated for $C_{27}H_{27}N_2O_2$ $[M+H]^+$: 411.20; found: 411.20.

Example 39: Production of Compound 39

An indolizine derivative compound (19.7 mg, 93.4% yield) was produced in the same manner as in Example 36, except that, in Example 36-2, 4-methoxyphenyl boronic acid (21.9 mg, 0.14 mmol), tetrakis(triphenylphosphine) palladium (11.1 mg, 0.01 mmol) and sodium carbonate (25.4 mg, 0.24 mmol) were added to a solution (1.1 mL) containing IJ-B (20.0 mg, 0.048 mmol) and a 10:1 mixture of DMF and water

[Compound 39]

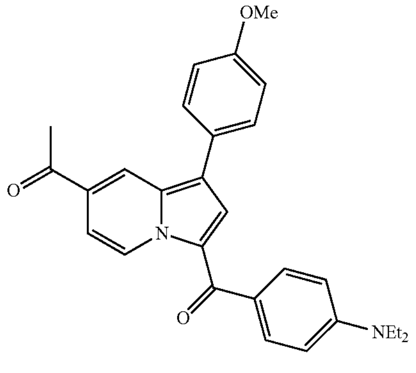

The physical properties of Compound 39 produced in Example 39 are as follows.

$^1$H NMR (400 MHz, $CDCl_3$) δ 9.72 (d, J=7.8 Hz, 1H), 8.36 (s, 1H), 7.87 (dd, J=7.2 Hz, 2.0 Hz, 2H), 7.52 (dd, J=6.6 Hz, 2.4 Hz, 3H), 7.35 (dd, J=7.6 Hz, 1.6 Hz, 1H), 7.04 (dd, J=6.6 Hz, 2.0 Hz, 2H), 6.71 (d, J=8.8 Hz, 2H), 3.88 (s, 3H), 3.45 (q, J=7.2 Hz, 4H), 2.63 (s, 3H), 1.23 (t, J=7.2 Hz, 6H); $^{13}$C NMR (100 MHz, $CDCl_3$) δ 195.7, 183.9, 158.9, 150.7, 133.3, 132.1, 130.7, 129.5, 127.9, 127.0, 126.4, 124.6, 124.0, 121.2, 120.1, 114.7, 110.8, 110.5, 55.7, 44.9, 26.6, 13.0; LRMS (APCI) m/z calculated for $C_{28}H_{29}N_2O_3$ $[M+H]^+$: 441.21; found: 441.15.

Example 40: Production of Compound 40

An indolizine derivative compound (20.2 mg, 93.0% yield) was produced in the same manner as in Example 36, except that, in Example 36-2, 4-(dimethylamino)phenyl boronic acid (23.8 mg, 0.14 mmol), tetrakis (triphenylphosphine)palladium (11.1 mg, 0.01 mmol) and sodium carbonate (25.4 mg, 0.24 mmol) were added to a solution (1.1 mL) containing IJ-B (20.0 mg, 0.048 mmol) and a 10:1 mixture of DMF and water.

[Compound 40]

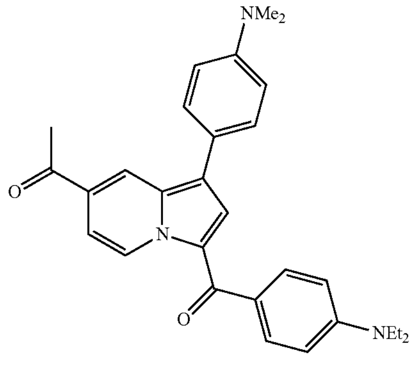

The physical properties of Compound 40 produced in Example 40 are as follows.

$^1H$ NMR (400 MHz, $CDCl_3$) δ 9.70 (d, J=7.2 Hz, 1H), 8.39 (s, 1H), 7.87 (d, J=9.2 Hz, 2H), 7.49 (dd, J=8.6 Hz, 2.0 Hz, 3H), 7.34 (dd, J=7.6 Hz, 2.0 Hz, 1H), 6.87 (d, J=8.8 Hz, 2H), 6.70 (d, J=8.8 Hz, 2H), 3.45 (q, J=7.6 Hz, 4H), 3.03 (s, 6H), 2.62 (s, 3H), 1.24 (t, J=6.8 Hz, 6H); $^{13}C$ NMR (100 MHz, $CDCl_3$) δ 195.8, 184.0, 150.7, 149.8, 133.3, 132.2, 130.4, 129.1, 127.8, 126.4, 124.6, 123.8, 122.5, 122.0, 120.6, 113.2, 110.6, 110.5, 44.9, 41.0, 26.5, 13.0; LRMS (ESI) m/z calculated for $C_{29}H_{32}N_3O_2$ $[M+H]^+$: 454.24; found: 454.23.

Example 41: Production of Compound 41

Example 41-1: Production of (1-bromoindolizin-3-yl) (4-(trifluoromethyl)phenyl)methanone (IK-B)

[Reaction Scheme 1-9]

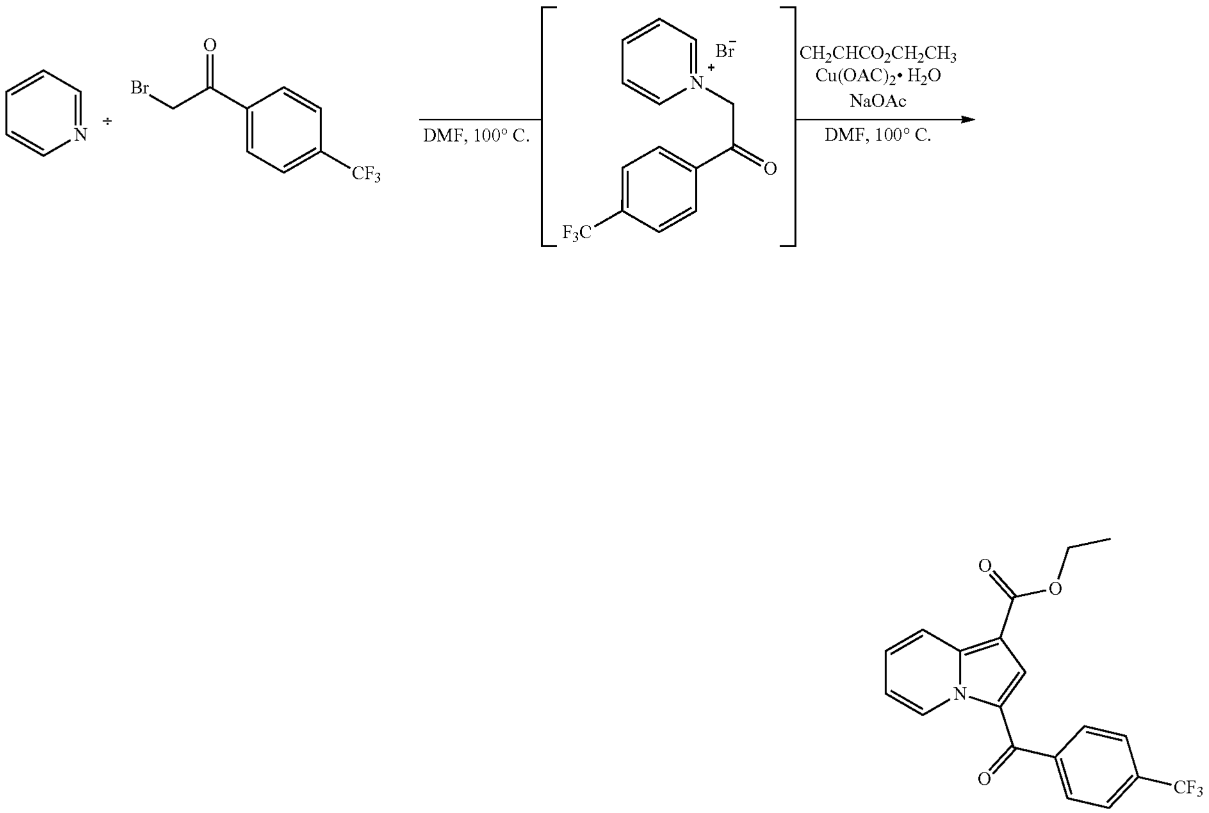

IK-E

-continued

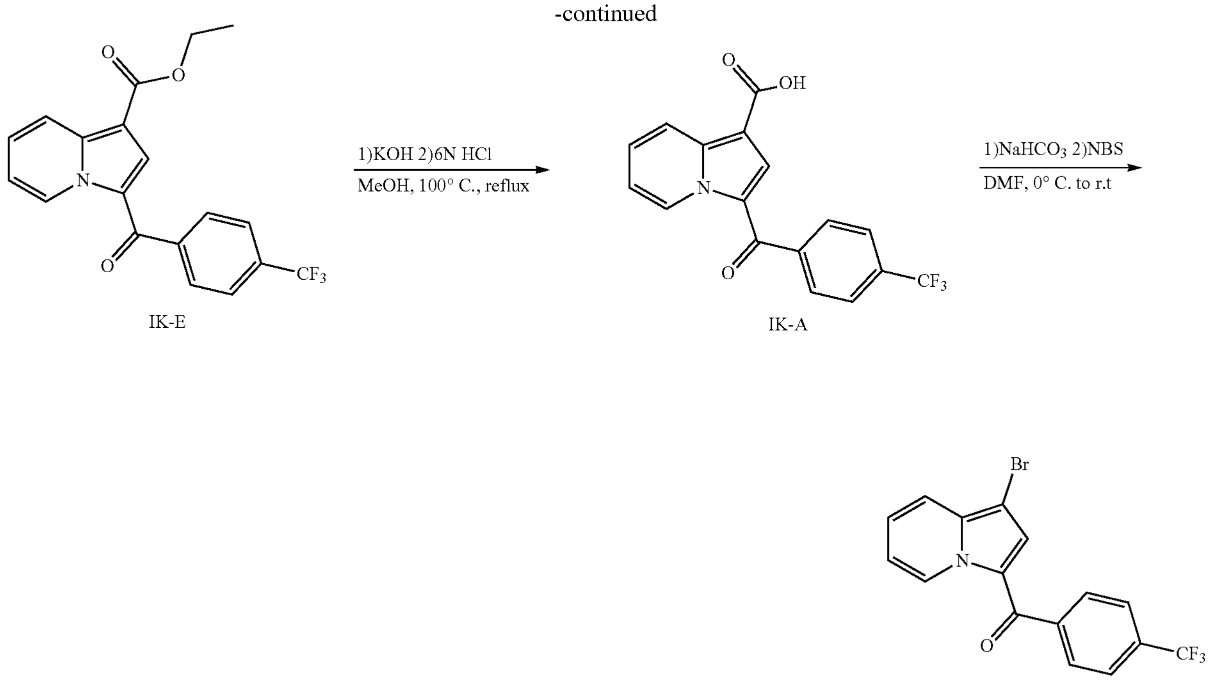

IK-E

IK-A

IK-B

IK-E: IK-E was synthesized as shown in Reaction Scheme 1-9 above. Specifically, DMF (15.0 mL) containing pyridine (564 μL, 7 mmol) and 2-bromo-1-[4-(4 (trifluoromethyl)-phenyl]ethan-1-one (1.96 mL, 7.35 mmol) was stirred overnight at 100° C., and then ethyl acrylate (372 μL, 3.50 mmol), copper(II) acetate monohydrate (2.09 g, 10.5 mmol) and sodium acetate (1.72 g, 21.0 mmol) were added thereto, followed by stirring at 100° C. for 16 hours. After completion of the reaction, monitoring by TLC was performed, and then copper acetate was removed by filtration through a celite pad, and the resulting filtrate was concentrated in vacuum. The resulting crude product was washed with water, and the organic phase was extracted three times with DCM. The extracted organic phases were combined, dried over anhydrous $Na_2SO_4$ and then concentrated. The concentrated organic phase was purified by silica-gel flash column chromatography (1 to 15% hexane containing EtOAc) to obtain compound IK-E (906 mg, 2.50 mmol, 71.6% yield) as a yellow solid.

The results of NMR analysis are as follows.

$^1H$ NMR (400 MHz, $CDCl_3$), δ 9.98 (d, J=6.8 Hz, 1H), 8.42 (d, J=9.2 Hz, 1H), 7.91 (d, J=8.0 Hz, 2H), 7.78 (d, J=8.4 Hz, 2H), 7.76 (s, 1H), 7.50 (t, J=8.0 Hz, 1H), 7.14 (d, J=6.2 Hz, 1H), 4.38 (q, J=7.1 Hz, 2H), 1.40 (t, J=7.1 Hz, 3H); $^{13}C$ NMR (100 MHz, $CDCl_3$) δ 183.6, 163.6, 142.9, 140.0, 132.9, 132.6, 129.1, 129.9, 128.9, 128.1, 125.3(3), 125.0, 122.3, 121.9, 121.4, 119.5, 115.6, 106.8, 60.3, 14.7; LRMS (ESI) m/z calculated for $C_{19}H_{14}F_3NO_3$ $[M+Na]^+$: 361.1, found 362.1.

IK-B: KOH (8.44 g, 150 mmol) was added to methanol (20 mL) containing IK-E (632 mg, 2.50 mmol), followed by stirring at room temperature for 4 hours. The reaction mixture was acidified by adding 6N HCl, and the resulting solid was collected through filtration, washed with water, and dried in a drying oven to obtain compound IK-A as a white solid.

The obtained compound IK-A was used in the next step without further purification. Sodium bicarbonate (630 mg, 7.50 mmol) was added to DMF (10.0 mL) containing IK-A, and NBS (667 mg, 3.75 mmol) was added thereto in portions at 0° C. The reaction mixture was stirred at room temperature for 12 hours, and then the resulting crude product was washed with water and the organic phase was extracted three times with DCM. The extracted organic phases were combined, dried over anhydrous $Na_2SO_4$, and then concentrated. The concentrated organic phase was purified by silica-gel flash column chromatography (EA:hexane=1:8-12% ethyl acetate) to obtain compound IK-B (664 mg, 1.80 mmol, 72.1% yield) as a yellow solid.

The results of NMR analysis are as follows.

$^1H$ NMR (400 MHz, $CDCl_3$), δ 9.96 (d, J=7.2 Hz, 1H), 7.87 (d, J=7.6 Hz, 2H), 7.76 (d, J=8.0 Hz, 2H), 7.64 (d, J=9.2 Hz, 1H), 7.35 (t, J=7.8 Hz, 1H), 7.32 (s, 1H), 7.05 (t, J=7.0 Hz, 1H); $^{13}C$ NMR (100 MHz, $CDCl_3$) δ 181.4, 142.9, 136.6, 132.4, 128.8, 128.3, 126.5, 125.4, 125.0, 124.9, 122.2, 121.3, 116.7, 114.6, 89.9; LRMS (ESI) m/z calculated for $C_{16}H_9BrF_3NO[M+Na]^+$: 367.0, found: 368.0.

Example 41-2: Production of Compound 41

To a solution containing IK-B (59.0 mg, 0.16 mmol) and a 2:1 mixture of DMF and water, 4-trifluorophenyl boronic acid (122 mg, 0.64 mmol), tetrakis(triphenyl phosphine) palladium (231 mg, 20.0 mol %) and sodium carbonate (68.0 mg, 0.64 mmol) were added, followed by stirring at 100° C. for 1 hour. After completion of the reaction, monitoring by TLC was performed, and then the reaction solution was washed with water, and the organic phase was extracted three times with DCM. The extracted organic phases were combined, dried over anhydrous $Na_2SO_4$, and then concentrated. The concentrated organic phase was purified by silica-gel flash column chromatography (EA:hexane=1:4-25% ethyl acetate) to obtain Compound 41 (62.1 mg, 0.14 mmol, 89.5% yield) as a yellow solid.

[Compound 41]

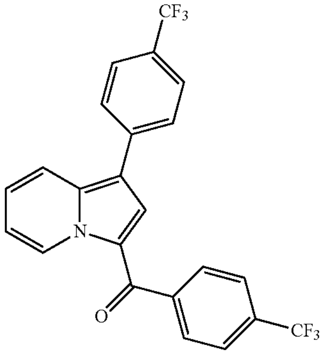

The physical properties of Compound 41 produced in Example 41 are as follows.

$^1H$ NMR (400 MHz, $CDCl_3$) δ 10.05 (d, J=6.8 Hz, 1H), 7.93 (d, J=8.0 Hz, 1H), 7.90 (d, J=8.8 Hz, 1H), 7.78 (d, J=8.4 Hz, 2H), 7.68 (q, J=8.0 Hz, 5H), 7.43 (s, 1H), 7.37 (dt, J=7.9 Hz, 1.2 Hz, 1H), 7.08 (dt, J=6.2 Hz, 1.6 Hz, 1H); $^{13}C$ NMR (100 MHz, $CDCl_3$) δ 182.8, 143.6, 138.0, 136.7, 132.7, 132.4, 129.2, 129.0, 128.7, 128.4, 127.8, 126.2, 125.8, 125.8, 125.5, 125.4, 125.3(2), 122.1, 117.3, 116.4, 114.9; LRMS (ESI) m/z calculated for $C_{23}H_{14}F_6NO$ $[M+H]^+$: 434.35; found: 434.15.

Example 42: Production of Compound 42

An indolizine derivative compound (58.4 mg, 0.14 mmol, 89.5% yield) was produced in the same manner as in Example 41, except that, in Example 41-2, 4-acetylphenyl boronic acid (104 mg, 0.64 mmol), tetrakis(triphenylphosphine) palladium (231 mg, 20.0 mol %) and sodium carbonate (67.5 mg, 0.64 mmol) were added to a solution containing IK-B (58.6 mg, 0.16 mmol) and a 2:1 mixture of DMF and water, followed by stirring at 100° C. for 7 hours, and the concentrated organic phase was purified by silica-gel flash column chromatography (EA hexane=1:5-20% ethyl acetate).

[Compound 42]

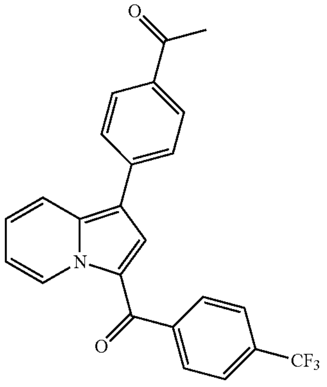

The physical properties of Compound 42 produced in Example 42 are as follows.

$^1H$ NMR (400 MHz, $CDCl_3$) δ 10.03 (d, J=7.2 Hz, 1H), 7.93 (d, J=8.0 Hz, 2H), 7.84 (d, J=9.2 Hz, 1H), 7.77 (d, J=8.0 Hz, 2H), 7.46 (d, J=8.8 Hz, 2H), 7.34 (s, 1H), 7.27 (dt, J=7.8 Hz, 0.8 Hz, 1H), 7.00 (d, J=8.8 Hz, 3H), 3.86 (s, 3H); $^{13}C$ NMR (100 MHz, $CDCl_3$) δ 182.3, 158.5, 144.0, 136.8, 132.4, 132.0, 129.0(2), 126.6, 125.3, 125.2(2), 125.1(2), 124.9, 122.5, 121.5, 118.0, 117.6, 114.5, 114.3, 55.4; LRMS (ESI) m/z calculated for $C_{24}H_{17}F_3NO_2$ $[M+H]^+$: 408.11; found: 408.23.

Example 43: Production of Compound 43

An indolizine derivative compound (53.1 mg, 0.14 mmol, 100% yield) was produced in the same manner as in Example 41, except that, in Example 41-2, phenyl boronic acid (71.2 mg, 0.57 mmol), tetrakis (triphenylphosphine) palladium (231 mg, 20.0 mol %) and sodium carbonate (61.0 mg, 0.57 mmol) were added to a solution containing IK-B (53.0 mg, 0.14 mmol) and a 2:1 mixture of DMF and water, followed by stirring at 100° C. for 9 hours.

[Compound 43]

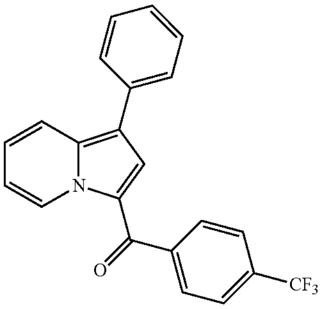

The physical properties of Compound 43 produced in Example 43 are as follows.

$^1H$ NMR (400 MHz, $CDCl_3$) δ 10.04 (d, J=6.8 Hz, 1H), 7.92 (t, J=8.0 Hz, 2H), 7.76 (d, J=8.0 Hz, 2H), 7.55 (d, J=7.6 Hz, 3H), 7.45 (t, J=7.8 Hz, 2H), 7.39 (s, 1H), 7.32 (m, 2H), 7.04 (dt, J=6.9 Hz, 1.2 Hz, 1H); $^{13}C$ NMR (100 MHz, $CDCl_3$) δ 182.5, 143.9, 136.8, 134.2, 132.5, 132.1, 129.1, 129.0, 128.9, 127.8, 126.7, 125.6, 125.3, 125.2, 122.5, 121.7, 118.2, 117.6, 114.6; LRMS (ESI) m/z calculated for $C_{22}H_{15}F_3NO$ $[M+H]^+$: 366.10; found: 366.24.

Example 44: Production of Compound 44

An indolizine derivative compound (65.9 mg, 0.16 mmol, 100% yield) was produced in the same manner as in Example 41, except that, in Example 41-2, 4-methoxyphenyl boronic acid (92.8 mg, 0.61 mmol), tetrakis (triphenylphosphine)palladium (231 mg, 20.0 mol %) and sodium carbonate (64.7 mg, 0.61 mmol) were added to a solution containing IK-B (56.2 mg, 0.15 mmol) and a 2:1 mixture of DMF and water, followed by stirring at 100° C. for 10 hours.

[Compound 44]

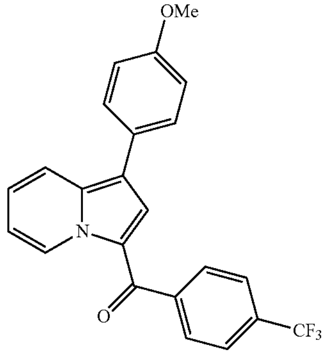

The physical properties of Compound 44 produced in Example 44 are as follows.

$^1H$ NMR (400 MHz, $CDCl_3$) δ 9.99 (d, J=7.2 Hz, 1H), 7.99 (d, J=8.4 Hz, 2H), 7.88 (d, J=8.4 Hz, 2H), 7.73 (d, J=8.4 Hz, 2H), 7.66 (d, J=8.4 Hz, 1H), 7.60 (d, J=8.0 Hz, 2H), 7.42 (s, 1H), 7.32 (t, J=8.0 Hz, 1H), 7.01 (t, J=6.8 Hz, 1H), 2.60 (s, 3H); $^{13}C$ NMR (100 MHz, $CDCl_3$) δ 197.1, 182.6, 144.0, 143.5, 139.1, 136.7, 136.3, 135.0, 132.6, 132.2, 129.1, 128.9, 128.8, 127.4, 127.2, 126.2, 125.2, 122.4, 122.1, 117.4, 116.6, 114.9, 26.7; LRMS (ESI) m/z calculated for $C_{23}H_{17}F_3NO_2$ $[M+H]^+$: 396.11; found: 395.98.

Example 45: Production of Compound 45

An indolizine derivative compound (59.5 mg, 0.14 mmol, 91% yield) was produced in the same manner as in Example 41, except that, in Example 41-2, 4-(dimethylamino)phenyl boronic acid (108.6 mg, 0.66 mmol), tetrakis (triphenylphosphine)palladium (231 mg, 20.0 mol %) and sodium carbonate (69.7 mg, 0.66 mmol) were added to a solution containing IK-B (60.6 mg, 0.16 mmol) and a 2:1 mixture of DMF and water, followed by stirring at 100° C. for 11 hours.

[Compound 45]

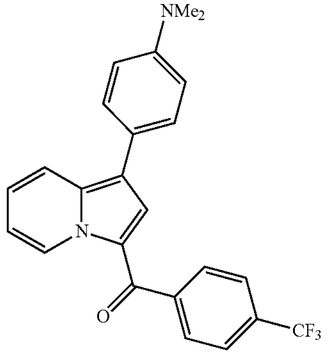

The physical properties of Compound 45 produced in Example 45 are as follows.

$^1H$ NMR (400 MHz, $CDCl_3$) δ 10.03 (d, J=6.8 Hz, 1H), 7.92 (d, J=8.0 Hz, 2H), 7.87 (d, J=8.4 Hz, 1H), 7.75 (d, J=8.0 Hz, 2H), 7.42 (d, J=8.8 Hz, 2H), 7.31 (s, 1H), 7.27 (t, J=7.2 Hz, 1H), 7.00 (dt, J=6.9 Hz, 1.6 Hz, 1H), 6.82 (d, J=8.8 Hz, 2H), 2.98 (s, 6H); $^{13}C$ NMR (100 MHz, $CDCl_3$) δ 181.7, 149.1, 143.8, 136.5, 131.9, 131.6, 128.8, 128.6, 128.3, 124.9, 124.8, 124.7, 124.3, 122.2, 121.8, 121.1, 118.4, 117.5, 114.1, 112.5, 40.3; LRMS (ESI) m/z calculated for $C_{24}H_{20}F_3N_2O$ $[M+H]^+$: 409.14; found: 409.15.

Example 46: Production of Compound 46

Example 46-1: Production of (1-bromoindolizin-3-yl) (phenyl)methanone (IM-B)

[Reaction Scheme 1-10]

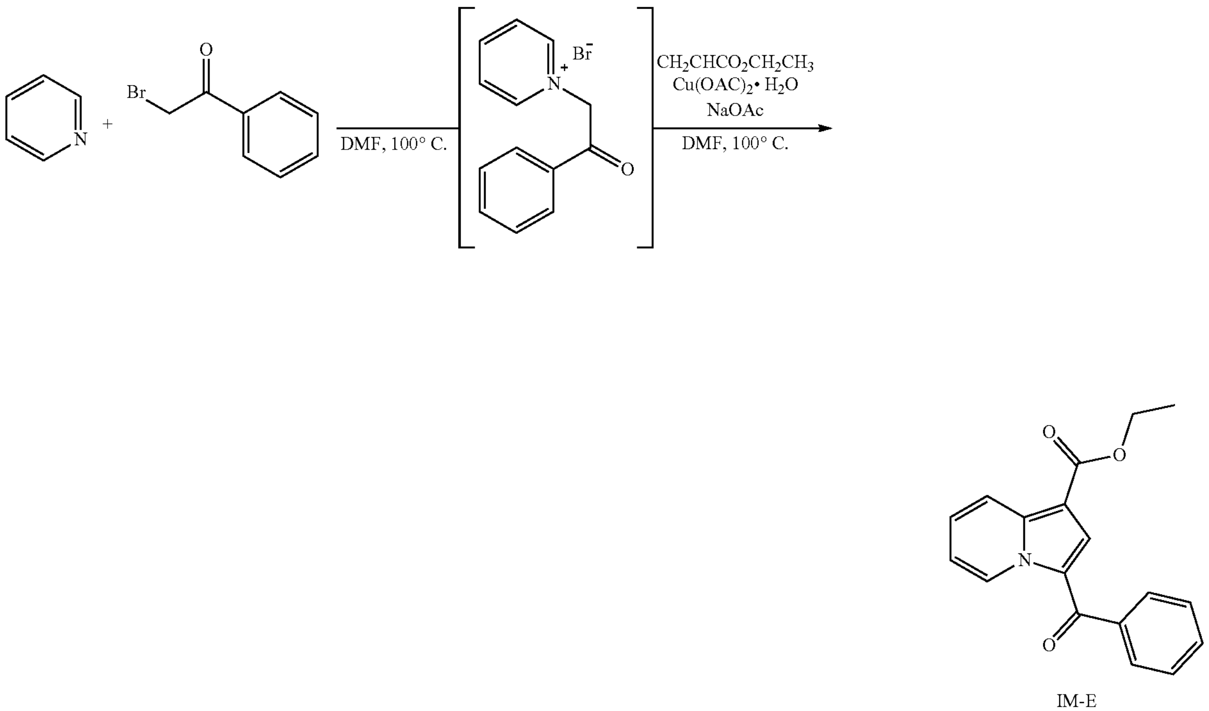

IM-E

-continued

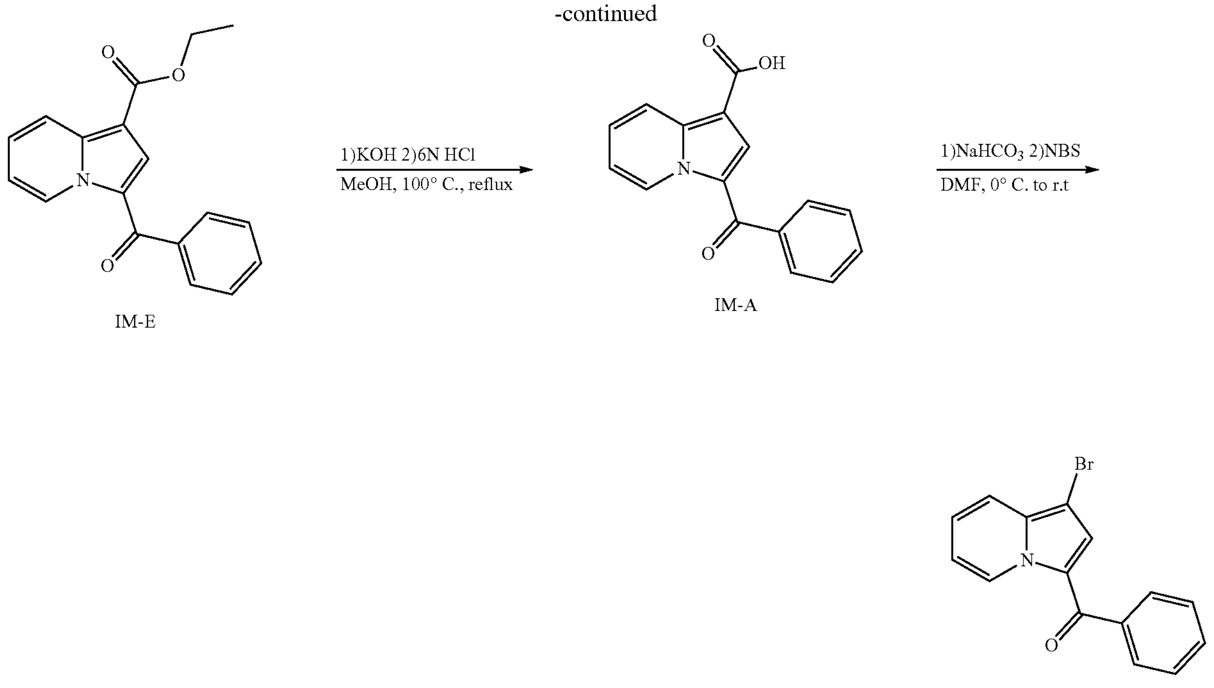

IM-E

IM-A

IM-B

IM-E: IM-E was synthesized as shown in Reaction Scheme 1-10 above. Specifically, DMF (15.0 mL) containing pyridine (564 μL, 7.00 mmol) and bromoacetophenone (1.46 g, 7.35 mmol) was stirred overnight at 100° C., and then ethyl acrylate (373 μL, 3.50 mmol), copper(II) acetate monohydrate (2.09 g, 10.5 mmol) and sodium acetate (1.72 g, 21.0 mmol) were added thereto, followed by stirring at 100° C. for 16 hours. After completion of the reaction, monitoring by TLC was performed, and then copper acetate was removed by filtration through a celite pad, and the resulting filtrate was concentrated in vacuum. The resulting crude product was washed with water, and the organic phase was extracted three times with DCM. The extracted organic phases were combined, dried over anhydrous $Na_2SO_4$ and then concentrated. The concentrated organic phase was purified by silica-gel flash column chromatography (1 to 15% hexane containing EtOAc) to obtain compound IM-E (616 mg, 2.10 mmol, 60% yield) as a yellow solid.

The results of NMR analysis are as follows.

$^1$H NMR (400 MHz, $CDCl_3$), δ 9.83 (d, J=7.2 Hz, 1H), 8.25 (d, J=9.0 Hz, 1H), 7.73 (d, J=7.2 Hz, 2H), 7.71 (s, 1H), 7.46 (d, J=7.2 Hz, 1H), 7.40 (t, J=7.2 Hz, 2H), 7.29 (t, J=8.0 Hz, 1H), 6.93 (t, J=7.0 Hz, 1H), 4.29 (q, J=7.0 Hz, 2H), 1.31 (t, J=7.0 Hz, 3H); $^{13}$C NMR (100 MHz, $CDCl_3$) δ 184.8, 163.4, 139.5, 139.3, 131.1, 128.7, 128.6, 128.4, 128.0, 127.2, 122.1, 121.2, 119.0, 114.9, 105.9, 59.9, 14.5; LRMS (ESI) m/z calculated for $C_{18}H_{15}NO_3$ $[M+Na]^+$: 293.1, found: 294.2.

IM-B: KOH (7.06 g, 126 mmol) was added to methanol (20 mL) containing IM-E (616 mg, 2.10 mmol), followed by stirring at room temperature for 4 hours. The reaction mixture was acidified by adding 6N HCl, and the resulting solid was collected through filtration, washed with water, and dried in a drying oven to obtain compound IM-A as a white solid.

The obtained compound IM-A was used in the next step without further purification. Sodium bicarbonate (529 mg, 6.30 mmol) was added to DMF (10.0 mL) containing IM-A, and NBS (561 mg, 3.15 mmol) was added thereto in portions at 0° C. The reaction mixture was stirred at room temperature for 12 hours, and then the resulting crude product was washed with water and the organic phase was extracted three times with DCM. The extracted organic phases were combined, dried over anhydrous $Na_2SO_4$, and then concentrated. The concentrated organic phase was purified by silica-gel flash column chromatography (EA:hexane=1:8-12% ethyl acetate) to obtain compound IM-B (590 mg, 1.96 mmol, 93.6% yield) as a yellow solid.

The results of NMR analysis are as follows.

$^1$H NMR (400 MHz, $CDCl_3$), δ 10.04 (d, J=6.8 Hz, 1H), 7.78 (d, J=6.4 Hz, 2H), 7.61 (d, J=8.8 Hz, 1H), 7.54 (d, J=7.6 Hz, 1H), 7.50 (d, J=7.6 Hz, 2H), 7.37 (s, 1H), 7.30 (m, 1H), 6.98 (t, J=7.0 Hz, 1H); $^{13}$C NMR (100 MHz, $CDCl_3$) δ 184.0, 140.3, 136.9, 131.3, 129.0, 128.8, 128.5, 127.2, 125.4, 122.3, 117.3, 114.8, 89.9, 47.1, 34.8; LRMS (ESI) m/z calculated for $C_{15}H_{10}BrNO$ $[M+Na]^+$: 299.0, found: 300.0.

Example 46-2: Production of Compound 46

To a solution containing IM-B (59.4 mg, 0.19 mmol) and a 2:1 mixture of DMF and water, 4-trifluloropheny1 boronic acid (150 mg, 0.79 mmol), tetrakis(triphenyl phosphine) palladium (231 mg, 20.0 mol %) and sodium carbonate (84.0 mg, 0.79 mmol) were added, followed by stirring at 100° C. for 9 hours. After completion of the reaction, monitoring by TLC was performed, and then the reaction solution was washed with water, and the organic phase was extracted three times with DCM. The extracted organic phases were combined, dried over anhydrous $Na_2SO_4$, and then concentrated. The concentrated organic phase was purified by silica-gel flash column chromatography (EA:hexane=1:4-25% ethyl acetate) to obtain Compound 46 (33.9 mg, 0.09 mmol, 46.8% yield) as a yellow solid.

[Compound 46]

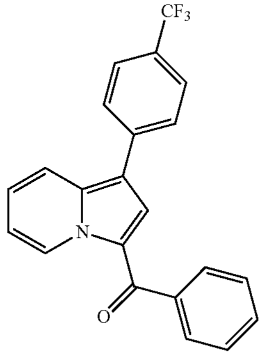

The physical properties of Compound 46 produced in Example 46 are as follows.

$^1$H NMR (400 MHz, $CDCl_3$) δ 10.04 (d, J=6.8 Hz, 1H), 7.88 (d, J=8.8 Hz, 1H), 7.84 (m, J=6.8 Hz, 2H), 7.67 (m, J=2.4 Hz, 4H), 7.56 (d, J=7.2 Hz, 1H), 7.52 (d, J=7.2 Hz, 2H), 7.49 (s, 1H), 7.31 (dt, J=7.9 Hz, 1.2 Hz, 1H), 7.03 (dt, J=6.9 Hz, 1.6 Hz, 1H); $^{13}$C NMR (100 MHz, $CDCl_3$) δ 184.5, 140.4, 138.3, 136.1, 131.0, 129.0, 128.8, 128.7, 128.4, 128.2, 128.0, 127.7, 125.7, 125.7, 125.7, 125.6, 125.4, 122.9, 122.4, 117.1, 115.8, 114.4; LRMS (ESI) m/z calculated for $C_{22}H_{15}F_3NO$ $[M+H]^+$: 366.10; found: 366.10.

Example 47: Production of Compound 47

An indolizine derivative compound (50.0 mg, 0.14 mmol, 79.2% yield) was produced in the same manner as in Example 46, except that, in Example 46-2, 4-acetylphenyl boronic acid (121 mg, 0.74 mmol), tetrakis (triphenylphosphine)palladium (231 mg, 20.0 mol %) and sodium carbonate (78.7 mg, 0.74 mmol) were added to a solution containing IM-B(55.5 mg, 0.18 mmol) and a 2:1 mixture of DMF and water, followed by stirring at 100° C. for 12 hours, and the concentrated organic phase was purified by silica-gel flash column chromatography (EA:hexane=1:2.5-40% ethyl acetate).

[Compound 47]

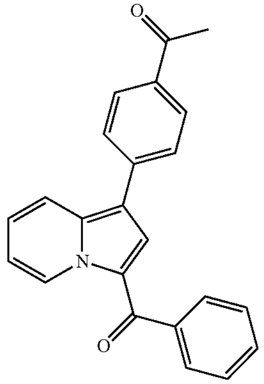

The physical properties of Compound 47 produced in Example 47 are as follows.

$^1$H NMR (400 MHz, $CDCl_3$) δ 10.02 (d, J=6.8 Hz, 1H), 8.02 (d, J=7.2 Hz, 2H), 7.89 (d, J=8.8 Hz, 1H), 7.84 (d, J=6.8 Hz, 2H), 7.69 (d, J=7.6 Hz, 1H), 7.63 (d, J=7.6 Hz, 2H), 7.56 (d, J=7.2 Hz, 1H), 7.53 (s, 1H), 7.51 (s, 1H), 7.29 (t, J=7.0 Hz, 1H), 7.00 (t, J=6.6 Hz, 1H), 2.63 (s, 3H); $^{13}$C NMR (100 MHz, $CDCl_3$) δ 197.0, 184.3, 143.9, 140.3, 139.4, 136.2, 136.1, 134.6, 130.9, 128.9, 128.8, 128.7, 128.1, 127.2, 127.1, 125.6, 125.3, 122.4, 117.2, 115.9, 114.4, 26.7, 26.6; LRMS (ESI) m/z calculated for $C_{23}H_{18}NO_2$ $[M+H]^+$: 340.13; found: 340.27.

Example 48: Production of Compound 48

An indolizine derivative compound (56.2 mg, 0.18 mmol, 89.9% yield) was produced in the same manner as in Example 46, except that, in Example 46-2, phenyl boronic acid (100 mg, 0.82 mmol), tetrakis (triphenylphosphine) palladium (231 mg, 20.0 mol %) and sodium carbonate (87.0 mg, 0.82 mmol) were added to a solution containing IM-B (61.5 mg, 0.21 mmol) and a 2:1 mixture of DMF and water.

[Compound 48]

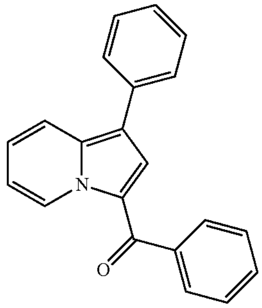

The physical properties of Compound 48 produced in Example 48 are as follows.

$^1$H NMR (400 MHz, $CDCl_3$) δ 10.04 (d, J=6.8 Hz, 1H), 7.89 (d, J=9.2 Hz, 1H), 7.84 (d, J=6.8 Hz, 2H), 7.19 (m, 7H), 7.31 (t, J=7.4 Hz, 1H), 7.27 (d, J=6.6 Hz, 1H), 7.25 (d, J=6.6 Hz, 1H), 6.99 (t, J=6.6 Hz, 1H); $^{13}$C NMR (100 MHz, $CDCl_3$) δ 183.9, 140.3, 135.9, 134.2, 130.4, 128.5, 128.4, 127.8, 127.5, 126.1, 125.0, 124.6, 121.8, 117.2, 117.1, 113.8; LRMS (ESI) m/z calculated for $C_{21}H_{16}NO$ $[M+H]^+$: 298.12; found: 298.10.

Example 49: Production of Compound 49

An indolizine derivative compound (51.4 mg, 0.15 mmol, 74.7% yield) was produced in the same manner as in Example 46, except that, in Example 46-2, 4-methoxyphenyl boronic acid (129 mg, 0.83 mmol), tetrakis (triphenylphosphine)palladium (231 mg, 20.0 mol %) and sodium carbonate (88.0 mg, 0.83 mmol) were added to a solution containing IM-B (62.0 mg, 0.21 mmol) and a 2:1 mixture of DMF and water.

[Compound 49]

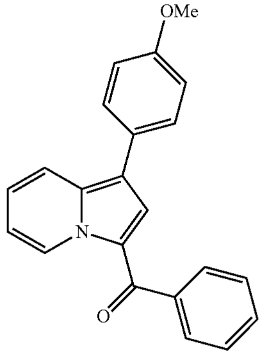

The physical properties of Compound 49 produced in Example 49 are as follows.

$^1$H NMR (400 MHz, $CDCl_3$) δ 10.03 (d, J=6.8 Hz, 1H), 7.84 (s, 1H), 7.82 (m, 2H), 7.53 (d, J=6.8 Hz, 1H), 7.50 (s, 1H), 7.48 (m, 4H), 7.40 (s, 1H), 7.23 (m, 1H), 6.99 (d, J=8.8 Hz, 2H), 3.85 (s, 3H); $^{13}$C NMR (100 MHz, $CDCl_3$) δ 184.1, 158.3, 140.7, 136.2, 130.7, 128.9, 128.8, 128.8, 128.1, 127.0, 125.0, 124.7, 121.9, 121.3, 117.5, 117.4, 114.2, 114.0, 55.4; LRMS (ESI) m/z calculated for $C_{22}H_{18}NO_2$ $[M+H]^+$: 328.13; found: 328.10.

Example 50: Production of Compound 50

An indolizine derivative compound (67.0 mg, 0.19 mmol, 87% yield) was produced in the same manner as in Example 46, except that, in Example 46-2, 4-(dimethylamino)phenyl boronic acid (149 mg, 0.90 mmol), tetrakis (triphenylphosphine)palladium (231 mg, 20.0 mol %) and sodium carbonate (95.7 mg, 0.90 mmol) were added to a solution containing IM-B(27.5 mg, 0.11 mmol) and a 2:1 mixture of DMF and water, followed by stirring at 100° C. for 11 hours.

[Compound 50]

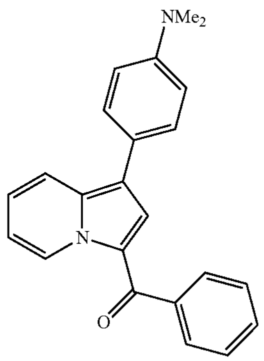

The physical properties of Compound 50 produced in Example 50 are as follows.

$^1$H NMR (400 MHz, $CDCl_3$) δ 10.02 (d, J=7.6 Hz, 1H), 7.87 (s, 1H), 7.84 (d, J=6.4 Hz, 2H), 7.53 (d, J=7.6 Hz, 1H), 7.49 (d, J=7.6 Hz, 2H), 7.43 (d, J=8.8 Hz, 2H), 7.39 (s, 1H), 7.21 (dt, J=7.8 Hz, 1.2 Hz, 1H), 6.95 (dt, J=7.0 Hz, 1.2 Hz, 1H), 6.82 (d, J=8.8 Hz, 2H), 2.99 (s, 6H); $^{13}$C NMR (100 MHz, $CDCl_3$) δ 183.9, 149.3, 140.9, 136.2, 130.6, 128.8, 128.7, 128.6, 128.0, 124.7, 124.3, 122.5, 121.8, 121.3, 118.1, 117.7, 113.9, 112.8, 40.7; LRMS (ESI) m/z calculated for $C_{23}H_{21}N_2O$ $[M+H]^+$: 341.16; found: 341.15.

Example 51: Production of Compound 51

Example 51-1: Production of (1-bromoindolizin-3-yl) (4-methoxyphenyl)methanone (IN-B)

[Reaction Scheme 1-11]

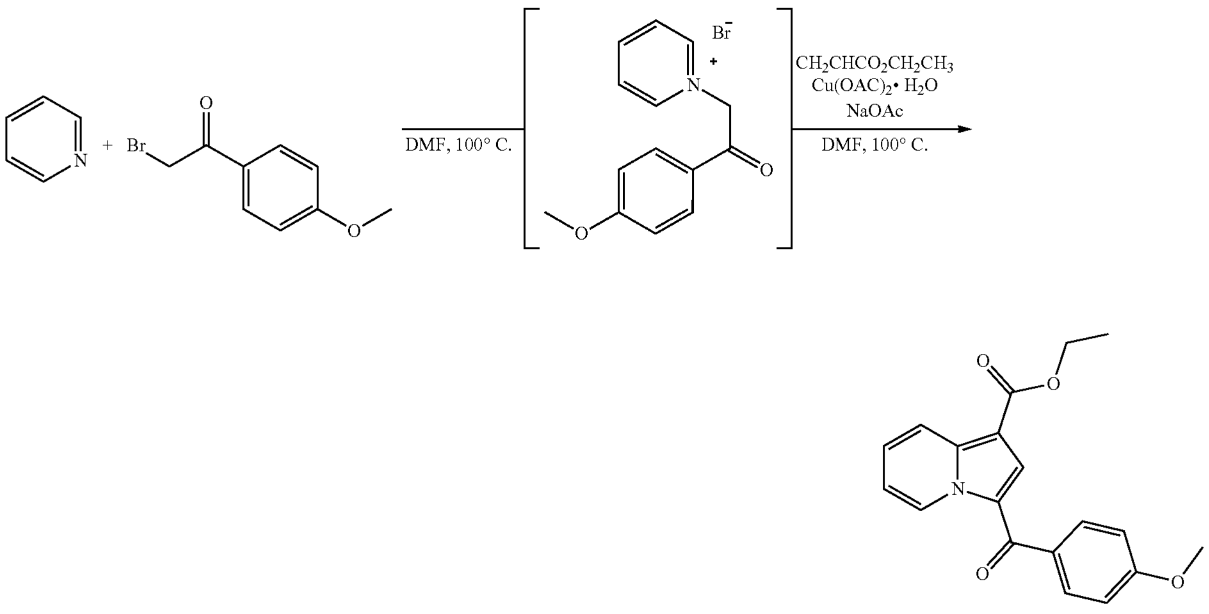

IN-E

-continued

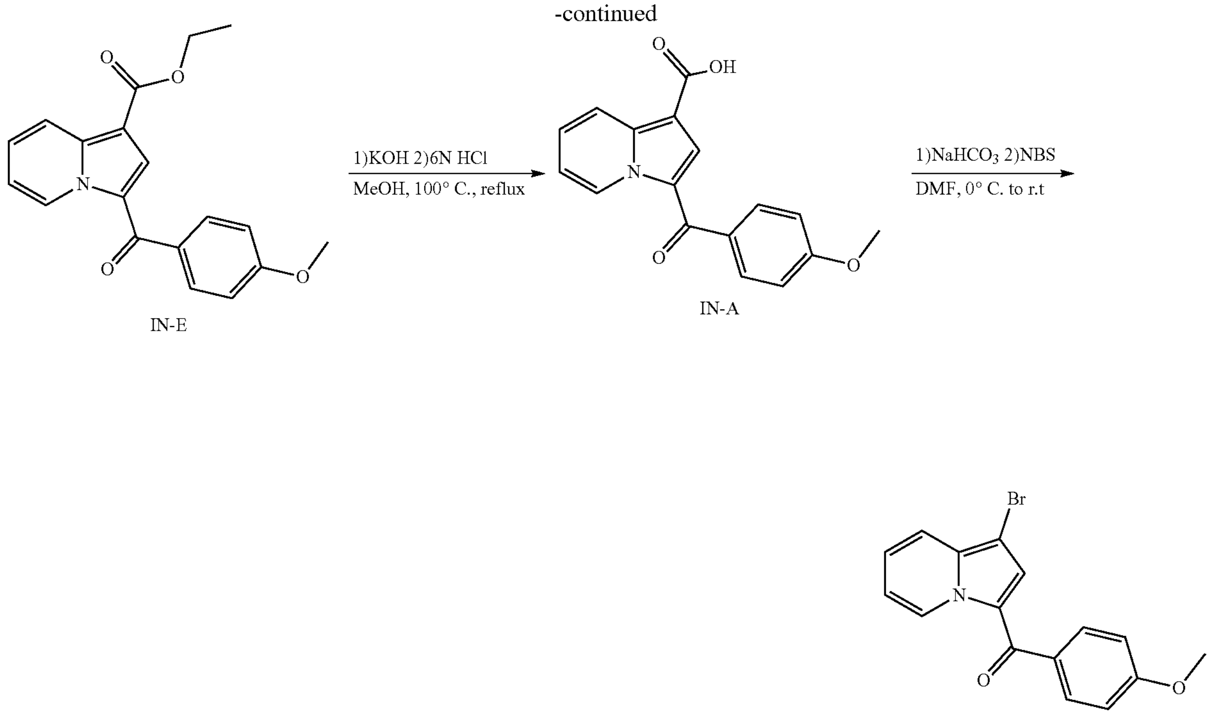

IN-E IN-A IN-B

IN-E: IN-E was synthesized as shown in Reaction Scheme 1-11 above. Specifically, DMF (10.0 mL) containing pyridine (483 μL, 6.00 mmol) and 2-bromo-4-methoxyacetophenone (1.44 g, 6.30 mmol) was stirred overnight at 100° C., and then ethyl acrylate (320 μL, 3.00 mmol), copper(II) acetate monohydrate (1.79 g, 9.00 mmol) and sodium acetate (1.47 g, 18.0 mmol) were added thereto, followed by stirring at 100° C. for 16 hours. After completion of the reaction, monitoring by TLC was performed, and then copper acetate was removed by filtration through a celite pad, and the resulting filtrate was concentrated in vacuum. The resulting crude product was washed with water, and the organic phase was extracted three times with DCM. The extracted organic phases were combined, dried over anhydrous $Na_2SO_4$ and then concentrated. The concentrated organic phase was purified by silica-gel flash column chromatography (1 to 15% hexane containing EtOAc) to obtain compound IN-E (467 mg, 1.44 mmol, 48.2% yield) as a yellow solid.

The results of NMR analysis are as follows.

$^1H$ NMR (400 MHz, $CDCl_3$), δ 9.90 (d, J=6.8 Hz, 1H), 8.38 (d, J=8.8 Hz, 1H), 7.85 (s, 1H), 7.83 (d, J=3.2 Hz, 2H), 7.42 (q, J=9.0 Hz, 1H), 6.97 (t, J=7.0 Hz, 1H), 7.01 (d, J=8.8 Hz, 2H), 4.38 (q, J=7.1 Hz, 2H), 3.90 (s, 3H), 1.40 (t, J=7.0 Hz, 3H); $^{13}C$ NMR (100 MHz, $CDCl_3$) δ 183.6, 163.6, 162.2, 139.2, 132.1, 131.0, 128.7, 127.6, 127.0, 122.3, 121.6, 119.0, 114.7, 113.5, 105.7, 60.0, 55.4, 14.7; LRMS (ESI) m/z calculated for $C_{19}H_{17}NO_4$ $[M+Na]^+$: 323.1, found: 324.2.

IN-B: KOH (4.84 g, 86.4 mmol) was added to methanol (10 mL) containing IN-E (467 mg, 1.44 mmol), followed by stirring at room temperature for 14 hours. The reaction mixture was acidified by adding 6N HCl, and the resulting solid was collected through filtration, washed with water, and dried in a drying oven to obtain compound IN-A as a white solid.

The obtained compound IN-A was used in the next step without further purification. Sodium bicarbonate (363 mg, 4.32 mmol) was added to DMF (5.0 mL) containing IN-A, and NBS (384 mg, 2.16 mmol) was added thereto in portions at 0° C. The reaction mixture was stirred at room temperature for 12 hours, and then the resulting crude product was washed with water and the organic phase was extracted three times with DCM. The extracted organic phases were combined, dried over anhydrous $Na_2SO_4$, and then concentrated. The concentrated organic phase was purified by silica-gel flash column chromatography (EA:hexane=1:8-12% ethyl acetate) to obtain compound IN-B (350 mg, 1.06 mmol, 73.6% yield) as a yellow solid.

The results of NMR analysis are as follows.

$^1H$ NMR (400 MHz, $CDCl_3$), δ 9.83 (d, J=6.8 Hz, 1H), 7.77 (d, J=8.8 Hz, 2H), 7.51 (d, J=8.8 Hz, 1H), 7.34 (s, 1H), 7.18 (q, J=8.8 Hz, 1H), 6.95 (d, J=8.8 Hz, 2H), 6.89 (t, J=6.8 Hz, 1H), 3.84 (s, 3H); $^{13}C$ NMR (100 MHz, $CDCl_3$) δ 184.0, 164.1, 162.2, 139.3, 132.0, 130.9, 128.7, 127.9, 127.1, 122.3, 119.1, 114.8, 113.4, 105.3, 55.4, 51.2.

Example 51-2: Production of Compound 51

To a solution containing IN-B (50.2 mg, 0.15 mmol) and a 2:1 mixture of DMF and water, 4-trifluorophenyl boronic acid (115 mg, 0.60 mmol), tetrakis(triphenyl phosphine) palladium (231 mg, 20.0 mol %) and sodium carbonate (64.4 mg, 0.60 mmol) were added, followed by stirring at 100° C. for 12 hours. After completion of the reaction, monitoring by TLC was performed, and then the reaction solution was washed with water, and the organic phase was extracted three times with DCM. The extracted organic phases were combined, dried over anhydrous $Na_2SO_4$, and then concentrated. The concentrated organic phase was purified by silica-gel flash column chromatography (EA:hexane=1:4-25% ethyl acetate) to obtain Compound 51 (48.2 mg, 0.12 mmol, 80.2% yield).

[Compound 51]

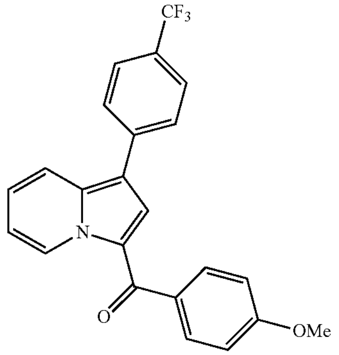

The physical properties of Compound 51 produced in Example 51 are as follows.

$^{1}H$ NMR (400 MHz, $CDCl_3$) δ 9.96 (d, J=6.8 Hz, 1H), 7.85 (dd, J=7.0 Hz, 1.6 Hz, 3H), 7.67 (d, J=2.0 Hz, 3H), 7.51 (s, 1H), 7.28 (t, J=7.6 Hz, 1H), 7.01 (d, J=8.8 Hz, 2H), 6.98 (d, J=6.8 Hz, 1H), 6.93 (d, J=8.4 Hz, 1H); $^{13}C$ NMR (100 MHz, $CDCl_3$) δ 183.8, 162.1, 138.4, 136.1, 132.8, 131.1, 129.0, 128.4, 128.1, 127.8, 126.9, 125.8(2), 125.6, 125.4, 125.1, 122.6, 117.2, 115.7, 115.6, 114.4, 113.6, 55.6; LRMS (ESI) m/z calculated for $C_{23}H_{17}F_3NO_2$ $[M+H]^+$: 396.11; found: 396.10.

Example 52: Production of Compound 52

An indolizine derivative compound (22.6 mg, 0.06 mmol, 97.1% yield) was produced in the same manner as in Example 51, except that, in Example 51-2, 4-acetylphenyl boronic acid (42 mg, 0.25 mmol), tetrakis(triphenylphosphine)palladium (231 mg, 20.0 mol %) and sodium carbonate (27 mg, 0.25 mmol) were added to a solution containing IN-B (21 mg, 0.06 mmol) and a 2:1 mixture of DMF and water, and the concentrated organic phase was purified by silica-gel flash column chromatography (EA hexane=1:5-20% ethyl acetate).

[Compound 52]

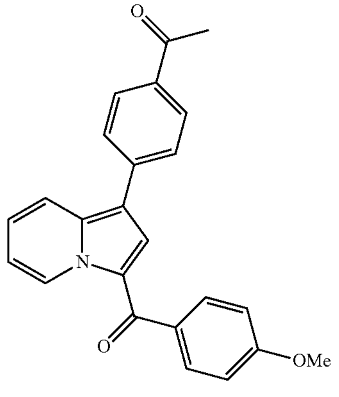

The physical properties of Compound 52 produced in Example 52 are as follows.

$^{1}H$ NMR (400 MHz, $CDCl_3$) δ 9.96 (d, J=7.2 Hz, 1H), 8.03 (d, J=8.4 Hz, 2H), 7.90 (d, J=9.2 Hz, 2H), 7.86 (d, J=8.4 Hz, 2H), 7.66 (d, J=8.0 Hz, 2H), 7.54 (s, 1H), 7.28 (t, J=7.8 Hz, 1H), 7.02 (d, J=8.4 Hz, 2H), 3.90 (s, 3H), 2.64 (s, 3H); $^{13}C$ NMR (100 MHz, $CDCl_3$) δ 197.1, 183.4, 161.8, 139.4, 135.7, 134.4, 132.5, 130.7, 128.7, 127.1, 125.1, 124.7, 122.4, 177.0, 115.5, 114.0, 113.3, 55.3, 26.4; LRMS (ESI) m/z calculated for $C_{24}H_{20}NO_3$ $[M+H]^+$: 370.14; found: 370.15.

Example 53: Production of Compound 53

An indolizine derivative compound (21.8 mg, 0.06 mmol, 100% yield) was produced in the same manner as in Example 51, except that, in Example 51-2, phenyl boronic acid (29.0 mg, 0.24 mmol), tetrakis (triphenylphosphine) palladium (231 mg, 20.0 mol %) and sodium carbonate (26.0 mg, 0.24 mmol) were added to a solution containing IN-B (20.0 mg, 0.06 mmol) and a 2:1 mixture of DMF and water, followed by stirring at 100° C. for 13 hours.

[Compound 53]

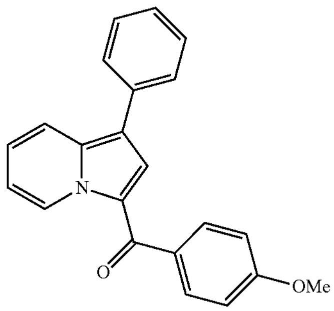

The physical properties of Compound 53 produced in Example 53 are as follows.

$^{1}H$ NMR (400 MHz, $CDCl_3$) δ 9.97 (d, J=6.8 Hz, 1H), 7.87 (d, J=6.4 Hz, 2H), 7.57 (d, J=8.0 Hz, 2H), 7.49 (s, 1H), 7.44 (d, J=7.6 Hz, 2H), 7.31 (t, J=7.4 Hz, 1H), 7.21 (t, J=7.6 Hz, 1H), 7.0 (d, J=8.4 Hz, 2H), 6.92 (t, J=6.9 Hz, 1H), 6.89 (t, J=6.8 Hz, 1H), 3.89 (s, 3H); $^{13}C$ NMR (100 MHz, $CDCl_3$) δ 183.5, 161.9, 136.0, 134.7, 133.2, 131.0, 128.8, 127.9, 126.4, 126.6, 124.9, 124.6, 123.9, 122.2, 118.6, 117.5, 117.3, 115.4, 114.0, 113.5, 102.3, 55.6; LRMS (ESI) m/z calculated for $C_{22}H_{18}NO_2$ $[M+H]^+$: 328.13; found: 328.15.

Example 54: Production of Compound 54

An indolizine derivative compound (22.6 mg, 0.06 mmol, 100% yield) was produced in the same manner as in Example 51, except that, in Example 51-2, 4-methoxyphenyl boronic acid (38.0 mg, 0.25 mmol), tetrakis (triphenylphosphine)palladium (231 mg, 20.0 mol %) and sodium carbonate (26.7 mg, 0.25 mmol) were added to a solution containing IN-B (20.8 mg, 0.06 mmol) and a 2:1 mixture of DMF and water, followed by stirring at 100° C. for 13 hours.

[Compound 54]

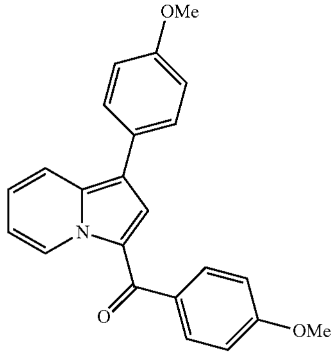

The physical properties of Compound 54 produced in Example 54 are as follows.

$^1$H NMR (400 MHz, $CDCl_3$) δ 9.96 (d, J=7.2 Hz, 1H), 7.86 (d, J=8.8 Hz, 2H), 7.81 (d, J=7.6 Hz, 1H), 7.48 (d, J=8.8 Hz, 2H), 7.42 (s, 1H), 7.19 (dt, J=7.7 Hz, 1.2 Hz, 1H), 7.00 (d, J=2.4 Hz, 2H), 6.98 (d, J=2.4 Hz, 2H), 6.94 (dt, J=6.4 Hz, 1.2 Hz, 1H), 3.89 (s, 3H), 3.85 (s, 3H); $^{13}$C NMR (100 MHz, $CDCl_3$) δ 183.7, 162.1, 158.6, 136.2, 133.6, 131.3, 129.3, 129.1, 127.5, 124.9, 124.7, 122.4, 117.8, 117.4, 114.6, 114.2, 113.8, 55.9, 55.8; LRMS (ESI) m/z calculated for $C_{23}H_{20}NO_3$ [M+H]$^+$: 358.14; found: 358.10.

Example 55: Production of Compound 55

An indolizine derivative compound (23.8 mg, 0.06 mmol, 100% yield) was produced in the same manner as in Example 51, except that, in Example 51-2, 4-(dimethylamino)phenyl boronic acid (40.0 mg, 0.24 mmol), tetrakis (triphenylphosphine)palladium (231 mg, 20.0 mol %) and sodium carbonate (26.0 mg, 0.24 mmol) were added to a solution containing IN-B (20.0 mg, 0.06 mmol) and a 2:1 mixture of DMF and water, followed by stirring at 100° C. for 13 hours.

[Compound 55]

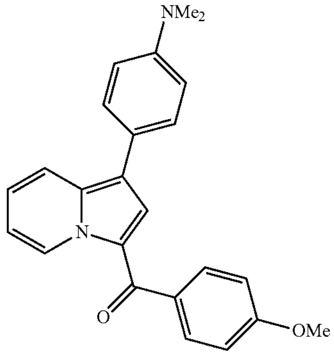

The physical properties of Compound 55 produced in Example 55 are as follows.

$^1$H NMR (400 MHz, $CDCl_3$) δ 9.96 (d, J=7.2 Hz, 1H), 7.86 (d, J=8.8 Hz, 3H), 7.44 (d, J=6.8 Hz, 2H), 7.41 (s, 1H), 7.17 (dt, J=8.8 Hz, 1.2 Hz, 1H), 6.99 (d, J=8.8 Hz, 2H), 6.92 (dt, J=6.9 Hz, 1.6 Hz, 1H), 6.83 (d, J=8.8 Hz, 2H), 3.89 (s, 3H), 2.99 (s, 6H); $^{13}$C NMR (100 MHz, $CDCl_3$) δ 183.3, 161.8, 149.3, 136.0, 133.5, 131.1, 128.7(2), 124.4, 124.0, 122.9, 117.8, 113.8, 113.5, 113.0, 55.6, 40.9; LRMS (ESI) m/z calculated for $C_{24}H_{23}N_2O_2$ [M+H]$^+$: 371.17; found: 371.15.

Example 56: Production of Compound 56

Example 56-1: Production of (1-bromoindolizin-3-yl) (4-(diethylamino)phenyl)methanone (IO-B)

[Reaction Scheme 1-12]

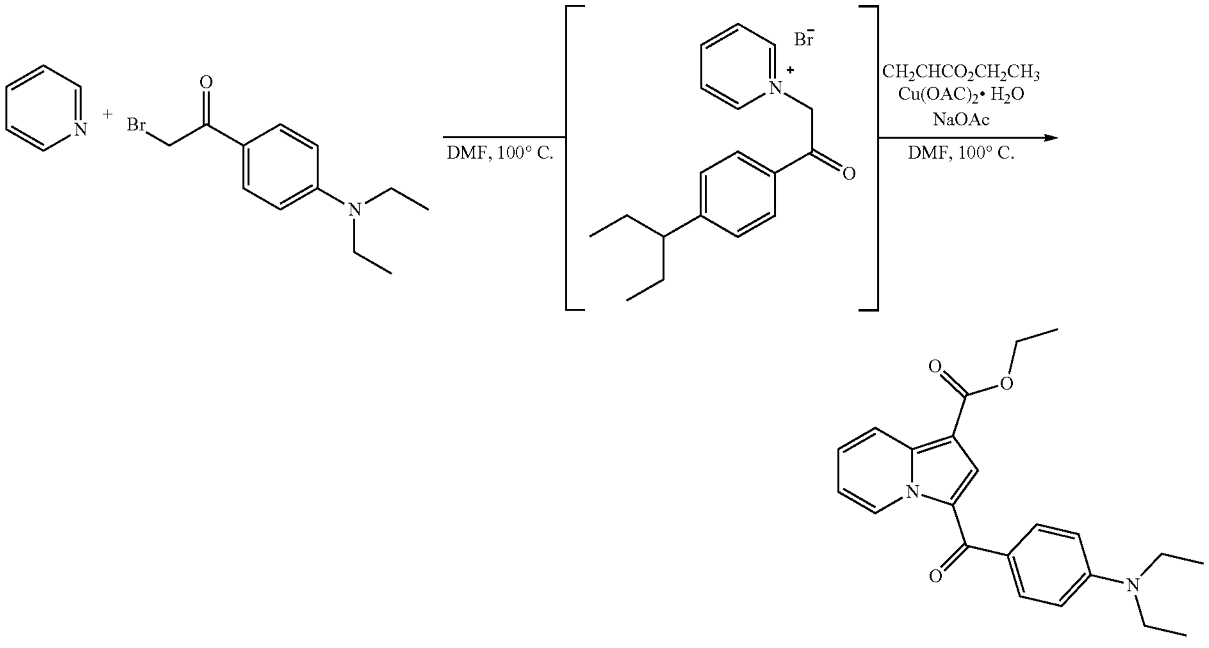

IO-E

-continued

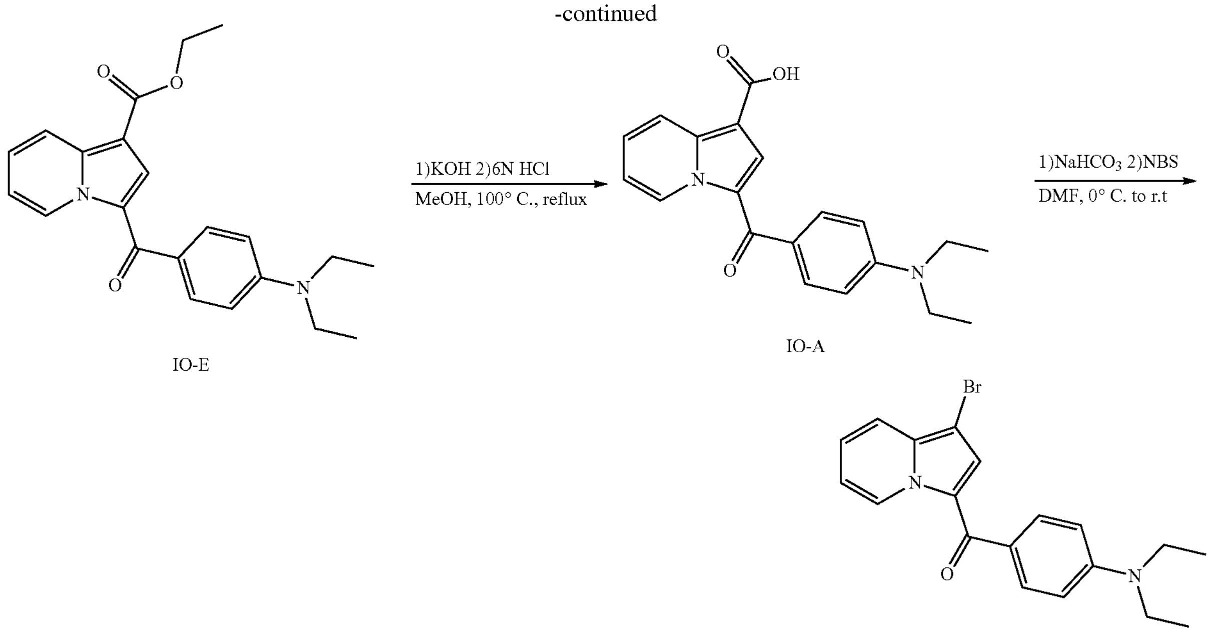

IO-E

IO-A

IO-B

IO-E: IO-E was synthesized as shown in Reaction Scheme 1-12 above. Specifically, DMF (10.0 mL) containing pyridine (695 μL, 6.00 mmol) and 2-bromo-4'-(diethylamino) acetophenone (1.70 mL, 6.3 mmol) was stirred overnight at 100° C., and then ethyl acrylate (320 μL, 3.00 mmol), copper(II) acetate monohydrate (1.79 g, 9.00 mmol) and sodium acetate (1.47 g, 18.0 mmol) were added thereto, followed by stirring at 100° C. for 16 hours. After completion of the reaction, monitoring by TLC was performed, and then copper acetate was removed by filtration through a celite pad, and the resulting filtrate was concentrated in vacuum. The resulting crude product was washed with water, and the organic phase was extracted three times with DCM. The extracted organic phases were combined, dried over anhydrous $Na_2SO_4$ and then concentrated. The concentrated organic phase was purified by silica-gel flash column chromatography (1 to 15% hexane containing EtOAc) to obtain compound IO-E (273 mg, 0.75 mmol, 25.0% yield) as a yellow solid.

The results of NMR analysis are as follows.

$^1H$ NMR (400 MHz, $CDCl_3$), δ 9.94 (d, J=8.0 Hz, 1H), 8.35 (d, J=8.0 Hz, 1H), 7.89 (d, J=6.0 Hz, 1H), 7.86 (s, 2H), 7.34 (m, 1H), 6.98 (t, J=7.6 Hz, 1H), 6.72 (d, J=9.2 Hz, 2H), 4.41 (q, J=7.2 Hz, 2H), 3.43 (q, J=7.1 Hz, 4H), 1.43 (t, J=7.2 Hz, 3H), 1.22 (t, J=7.2 Hz, 6H).; $^{13}C$ NMR (100 MHz, $CDCl_3$) δ 186.8, 156.2, 136.0, 134.4, 129.4, 128.8, 127.8, 126.5, 124.8, 124.4, 124.1, 123.0, 122.1, 120.0, 118.5, 117.5, 117.4, 115.4, 114.3, 113.9, 102.5, 27.1, 27.9; LRMS (ESI) m/z calculated for $C_{22}H_{24}N_2O_3$ $[M+Na]^+$: 364.2, found: 365.2.

IO-B: KOH (4.20 g, 74.9 mmol) was added to methanol (10 mL) containing IO-E (273 mg, 0.74 mmol), followed by stirring overnight at room temperature. The reaction mixture was acidified by adding 6N HCl, and the resulting solid was collected through filtration, washed with water, and dried in a drying oven to obtain compound IO-A as a white solid.

The obtained compound IO-A was used in the next step without further purification. Sodium bicarbonate (189 mg, 2.24 mmol) was added to DMF (5.0 mL) containing IO-A, and NBS (200 mg, 1.12 mmol) was added thereto in portions at 0° C. The reaction mixture was stirred at room temperature for 12 hours, and then the resulting crude product was washed with water and the organic phase was extracted three times with DCM. The extracted organic phases were combined, dried over anhydrous $Na_2SO_4$, and then concentrated. The concentrated organic phase was purified by silica-gel flash column chromatography (EA:hexane=1:8-12% ethyl acetate) to obtain compound IO-B (187 mg, 0.50 mmol, 67.3% yield) as a yellow solid.

The results of NMR analysis are as follows.

$^1H$ NMR (400 MHz, $CDCl_3$), δ 9.88 (d, J=7.2 Hz, 1H), 8.03 (s, 1H), 7.83 (s, 1H), 7.69 (dd, J=8.2 Hz, 1H), 7.60 (d, J=8.8 Hz, 1H), 7.41 (s, 1H), 7.28 (m, 1H), 7.12 (d, J=8.4 Hz, 1H), 6.98 (t, J=7.0 Hz, 1H), 3.25 (q, J=6.9 Hz, 4H), 1.10 (t, J=7.0 Hz, 6H); $^{13}C$ NMR (100 MHz, $CDCl_3$) δ 181.4, 152.2, 136.6, 135.2, 134.9, 128.6, 126.5, 125.1, 122.6, 122.0, 121.9, 120.5, 117.2, 114.6, 89.7, 46.6, 46.43, 12.8, 12.7.

Example 56-2: Production of Compound 56

To a solution containing IO-B (24 mg, 0.06 mmol) and a 2:1 mixture of DMF and water, 4-trifluorophenyl boronic acid (49.0 mg, 0.25 mmol), tetrakis(triphenyl phosphine) palladium (231 mg, 20.0 mol %) and sodium carbonate (27.0 mg, 0.25 mmol) were added, followed by stirring at 100° C. for 12 hours. After completion of the reaction, monitoring by TLC was performed, and then the reaction solution was washed with water, and the organic phase was extracted three times with DCM. The extracted organic phases were combined, dried over anhydrous $Na_2SO_4$, and then concentrated. The concentrated organic phase was purified by silica-gel flash column chromatography (EA:hexane=1:4-25% ethyl acetate) to obtain Compound 56 (19.0 mg, 0.04 mmol, 72.5% yield) as a yellow solid.

[Compound 56]

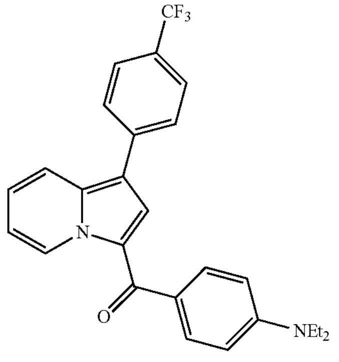

The physical properties of Compound 56 produced in Example 56 are as follows.

$^1H$ NMR (400 MHz, $CDCl_3$) δ 9.97 (d, J=7.2 Hz, 1H), 7.86 (d, J=8.0 Hz, 1H), 7.81 (d, J=8.4 Hz, 1H), 7.70 (m, 6H), 7.58 (s, 1H), 7.26 (m, 1H), 7.15 (d, J=8.4 Hz, 1H), 6.98 (dt, J=6.9 Hz, 1.2 Hz, 1H), 2.99 (q, J=7.0 Hz, 4H), 0.98 (t, J=7.2 Hz, 6H); $^{13}C$ NMR (100 MHz, $CDCl_3$) δ 183.9, 152.2, 136.3, 134.0, 133.7, 133.1, 130.1, 129.3(2), 129.2, 128.2(2), 126.1(2), 125.7, 125.6(2), 123.0, 120.3, 117.5, 115.9, 114.6, 46.2, 30.2, 12.5; LRMS (ESI) m/z calculated for $C_{26}H_{24}F_3N_2O$ $[M+H]^+$: 437.18; found: 437.20.

Example 57: Production of Compound 57

An indolizine derivative compound (18.9 mg, 0.04 mmol, 57.5% yield) was produced in the same manner as in Example 56, except that, in Example 56-2, 4-acetylphenyl boronic acid (53.0 mg, 0.32 mmol), tetrakis (triphenylphosphine)palladium (231 mg, 20.0 mol %) and sodium carbonate (34.0 mg, 0.32 mmol) were added to a solution containing IO-B (30.0 mg, 0.08 mmol) and a 2:1 mixture of DMF and water, and the concentrated organic phase was purified by silica-gel flash column chromatography (EA:hexane=1: 5-20% ethyl acetate).

[Compound 57]

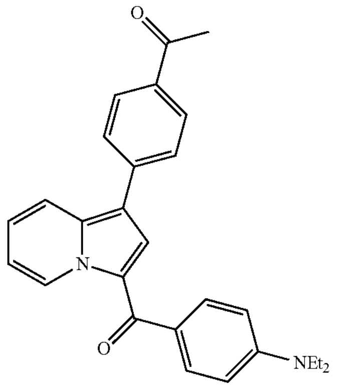

The physical properties of Compound 57 produced in Example 57 are as follows.

$^1H$ NMR (400 MHz, $CDCl_3$) δ 9.95 (d, J=6.8 Hz, 1H), 8.05 (d, J=7.2 Hz, 3H), 7.90 (s, 1H), 7.71 (d, J=8.4 Hz, 3H), 7.67 (d, J=8.4 Hz, 1H), 7.56 (s, 1H), 7.30 (dt, J=7.4 Hz, 1.2 Hz, 1H), 7.12 (d, J=8.0 Hz, 1H), 7.00 (m, 1H), 3.27 (q, J=7.0 Hz, 4H), 2.65 (s, 3H), 1.13 (t, J=7.0 Hz, 6H); $^{13}C$ NMR (100 MHz, $CDCl_3$) δ 197.1, 182.1, 150.4, 143.9, 139.3, 136.1, 135.9, 134.5, 134.1, 131.5, 128.7, 128.6, 128.4, 127.7, 127.1, 125.3, 124.6, 122.1, 121.4, 117.1, 115.7, 114.1, 45.8, 29.6, 26.6, 12.3; LRMS (ESI) m/z calculated for $C_{27}H_{27}N_2O_2$ $[M+H]^+$: 411.20; found: 411.38.

Example 58: Production of Compound 58

An indolizine derivative compound (22.2 mg, 0.06 mmol, 75.3% yield) was produced in the same manner as in Example 56, except that, in Example 56-2, phenyl boronic acid (39.4 mg, 0.32 mmol), tetrakis (triphenylphosphine) palladium (231 mg, 20.0 mol %) and sodium carbonate (34.0 mg, 0.32 mmol) were added to a solution containing IO-B (30.0 mg, 0.08 mmol) and a 2:1 mixture of DMF and water, followed by stirring at 100° C. for 13 hours.

[Compound 58]

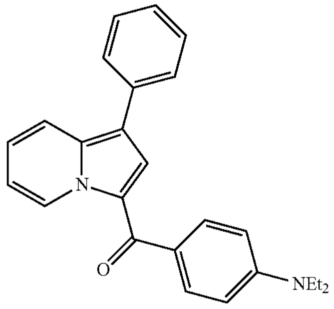

The physical properties of Compound 58 produced in Example 58 are as follows.

$^1H$ NMR (400 MHz, $CDCl_3$) δ 9.98 (d, J=7.2 Hz, 1H), 7.87 (d, J=9.2 Hz, 1H), 7.80 (d, J=7.6 Hz, 1H), 7.59 (t, J=7.4 Hz, 3H), 7.45 (t, J=7.6 Hz, 2H), 7.39 (t, J=7.6 Hz, 2H), 7.30 (d, J=7.6 Hz, 1H), 7.20 (dt, J=7.8 Hz, 1.2 Hz, 1H), 7.12 (dd, J=8.2 Hz, 2.4 Hz, 1H), 6.94 (dt, J=6.9 Hz, 1.2 Hz, 1H), 3.01 (q, J=4.4 Hz, 4H), 0.97 (t, J=7.0 Hz, 6H); $^{13}C$ NMR (100 MHz, $CDCl_3$) δ 183.5, 151.4, 141.1, 135.6, 134.6, 133.0, 132.7, 128.8, 128.5, 128.3, 128.0, 127.6, 126.4, 126.1, 124.5, 124.1, 122.1, 121.1, 119.3, 117.2, 116.8, 113.6, 45.9, 45.5, 12.0; LRMS (ESI) m/z calculated for $C_{25}H_{25}N_2O$ $[M+H]^+$: 369.19; found: 369.36.

Example 59: Production of Compound 59

An indolizine derivative compound (42.5 mg, 0.10 mmol, 100% yield) was produced in the same manner as in Example 56, except that, in Example 56-2, 4-methoxyphenyl boronic acid (65.0 mg, 0.42 mmol), tetrakis(triphenylphosphine) palladium (231 mg, 20.0 mol %) and sodium carbonate (45.0 mg, 0.42 mmol) were added to a solution containing IO-B (39.5 mg, 0.10 mmol) and a 2:1 mixture of DMF and water, followed by stirring at 100° C. for 13 hours.

[Compound 59]

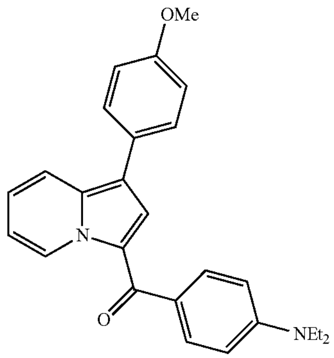

The physical properties of Compound 59 produced in Example 59 are as follows.

$^1$H NMR (400 MHz, $CDCl_3$) δ 9.95 (d, J=6.8 Hz, 1H), 7.89 (s, 1H), 7.82 (d, J=8.8 Hz, 1H), 7.70 (dd, J=8.2 Hz, 2.0 Hz, 1H), 7.49 (d, J=8.8 Hz, 2H), 7.44 (s, 1H), 7.22 (t, J=7.9 Hz, 1H), 7.11 (d, J=8.0 Hz, 1H), 7.00 (d, J=6.8 Hz, 2H), 6.95 (dt, J=7.2 Hz, 1.2 Hz, 2H), 3.86 (s, 3H), 3.26 (q, J=7.1 Hz, 4H), 0.96 (t, J=7.2 Hz, 6H); $^{13}$C NMR (100 MHz, $CDCl_3$) δ 182.2, 158.4, 150.4, 136.3, 135.0, 131.8, 129.7, 129.1, 128.9, 128.0, 127.1, 124.7, 124.6, 121.8(2), 117.6, 117.4, 114.4, 114.1, 113.7, 55.5, 46.7, 45.7, 29.9, 12.6; LRMS (ESI) m/z calculated for $C_{26}H_{27}N_2O_2$ $[M+H]^+$: 399.20; found: 399.35.

Example 60: Production of Compound 60

An indolizine derivative compound (257.8 mg, 0.14 mmol, 84.6% yield) was produced in the same manner as in Example 56, except that, in Example 56-2, 4-(dimethyl-amino)phenyl boronic acid (109 mg, 0.66 mmol), tetrakis (triphenylphosphine)palladium (231 mg, 20.0 mol %) and sodium carbonate (70.0 mg, 0.66 mmol) were added to a solution containing IO-B (73.0 mg, 0.16 mmol) and a 2:1 mixture of DMF and water.

[Compound 60]

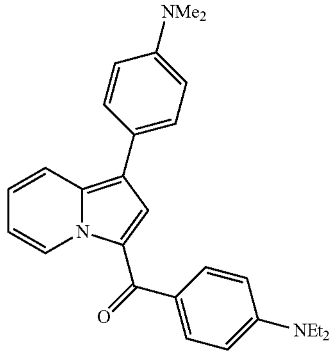

The physical properties of Compound 60 produced in Example 60 are as follows.

$^1$H NMR (400 MHz, $CDCl_3$) δ 9.95 (d, J=6.8 Hz, 1H), 7.89 (d, J=2.4 Hz, 1H), 7.84 (d, J=8.0 Hz, 1H), 7.70 (d, J=8.4 Hz, 1H), 7.50 (d, J=8.8 Hz, 1H), 7.45 (d, J=8.8 Hz, 2H), 7.43 (s, 1H), 7.20 (dt, J=7.9 Hz, 1.2 Hz, 1H), 7.11 (d, J=8.4 Hz, 1H), 6.93 (dt, J=6.8 Hz, 1.2 Hz, 1H), 6.84 (d, J=6.8 Hz, 2H), 3.26 (q, J=7.1 Hz, 4H), 3.00 (s, 6H), 1.12 (t, J=7.0 Hz, 6H); $^{13}$C NMR (100 MHz, $CDCl_3$) δ 197.5, 197.2, 183.5, 151.8, 146.4, 139.7, 135.9, 135.4, 134.7, 133.6, 133.1, 132.7, 129.7, 129.0, 128.9, 128.7, 128.5, 127.4, 125.3, 124.7, 122.7, 119.8, 117.3, 115.7, 114.2, 45.8, 26.8, 12.2; LRMS (ESI) m/z calculated for $C_{27}H_{30}N_3O$ $[M+H]^+$: 412.23; found: 412.25.

Example 61: Production of Compound 61

Example 61-1: Production of 1-(3-benzoyl-1-bromoindolizin-7-yl)ethanone (IH-B)

1-(3-benzoyl-1-bromoindolizin-7-yl)ethanone, a compound represented by IH-B, was produced in the same manner as in Example 26-1.

Example 61-2: Production of Compound 61

To a solution containing IH-B (20.0 mg, 0.06 mmol) and a 2:1 mixture of DMF and water, 4-pyridyl boronic acid (8.9 mg, 0.02 mmol), tetrakis(triphenyl phosphine)palladium (9.0 mg, 0.3 mol %) and sodium carbonate (11.0 mg, 0.10 mmol) were added, followed by stirring at 100° C. for 10 hours. After completion of the reaction, monitoring by TLC was performed, and then the reaction solution was washed with water, and the organic phase was extracted three times with DCM. The extracted organic phases were combined, dried over anhydrous $Na_2SO_4$, and then concentrated. The concentrated organic phase was purified by silica-gel flash column chromatography (EA:hexane=1:1-50% ethyl acetate 50%) to obtain Compound 61 (1.5 mg, 16.9% yield) as a yellow solid.

[Compound 61]

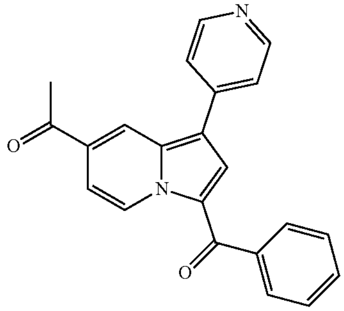

The physical properties of Compound 61 produced in Example 61 are as follows.

$^1$H NMR (600 MHz, $CDCl_3$) δ 9.88 (d, J=7.5 Hz, 1H), 8.19 (s, 1H), 7.83 (d, J=7.6 Hz, 2H), 7.71 (dd, J=12.7, 5.9 Hz, 2H), 7.58 (t, J=7.4 Hz, 1H), 7.51 (t, J=7.6 Hz, 2H), 7.45 (dd, J=7.3, 1.5 Hz, 1H), 7.42 (dd, J=10.9, 5.9 Hz, 2H), 7.39 (d, J=7.6 Hz, 2H), 6.81 (d, J=4.6 Hz, 1H), 2.67 (s, 3H); $^{13}$C NMR (100 MHz, $CDCl_3$) δ 195.1, 185.5, 140.3, 131.8, 131.6, 131.3m 129.2, 128.5, 128.3, 125.6, 120.1, 118.5, 114.5, 111.6 105.4, 102.0, 26.4, 17.3, 16.6; LRMS (ESI) m/z calculated for $C_{22}H_{17}N_2O_2$ $[M+H]^+$: 341.12; found: 341.2650.

Example 62: Production of Compound 62

Compound 62 (11.6 mg, 52.5% yield) was obtained as a yellow solid in the same manner as in Example 61, except that 3-amino-4-methylphenyl boronic acid (27.0 mg, 0.18 mmol), tetrakis (triphenylphosphine)palladium (21.0 mg, 0.3 mol %) and sodium carbonate (19.0 mg, 0.18 mmol)

were added to a solution containing IH-B (20.7 mg, 0.06 mmol) and a 2:1 mixture of DMF and water, followed by stirring at 100° C. for 19 hours, and the concentrated organic phase was purified by silica-gel flash column chromatography (EA:hexane=1:4-20% ethyl acetate).

[Compound 62]

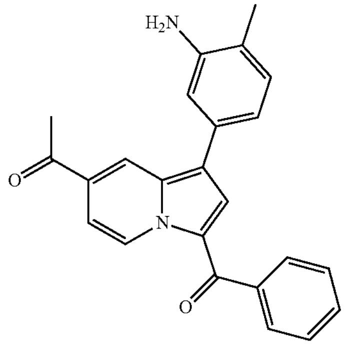

The physical properties of Compound 62 produced in Example 62 are as follows.

$^1$H NMR (600 MHz, $CDCl_3$) δ 9.90 (d, J=7.5 Hz, 1H), 8.44 (s, 1H), 7.85 (m, 2H), 7.58 (m, 1H), 7.51 (t, J=7.6 Hz, 2H), 7.46 (dd, J=7.0, 2.4 Hz, 2H), 7.17 (d, J=7.6 Hz, 1H), 6.89 (m, 2H), 6.18 (m, 1H), 2.64 (s, 3H), 2.24 (s, 3H); $^{13}$C NMR (100 MHz, $CDCl_3$) δ 195.1, 185.5, 140.3, 131.8, 131.6, 131.3m 129.2, 128.5, 128.3, 125.6, 120.1, 118.5, 114.5, 111.6 105.4, 102.0, 26.4, 17.3, 16.6; LRMS (ESI) m/z calculated for $C_{24}H_{21}N_2O_2$ $[M+H]^+$: 369.15; found: 369.3428.

Example 63: Production of Compound 63

Compound 63 (14.1 mg, 82.9% yield) was obtained as a yellow solid in the same manner as in Example 61, except that 4-aminobenzeneboronic acid (25.0 mg, 0.14 mmol), tetrakis (triphenylphosphine)palladium (19.5 mg, 0.3 mol %) and sodium carbonate (19.4 mg, 0.14 mmol) were added to a solution containing IH-B (17.4 mg, 0.04 mmol) and a 2:1 mixture of DMF and water, followed by stirring at 100° C. for 1 hour.

[Compound 63]

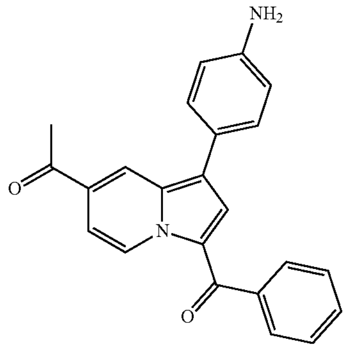

The physical properties of Compound 63 produced in Example 63 are as follows.

$^1$H NMR (600 MHz, $CDCl_3$) δ 9.89 (d, J=7.5 Hz, 1H), 8.38 (s, 1H), 7.85 (d, J=7.8 Hz, 2H), 7.56 (m, 1H), 7.51 (t, J=7.5 Hz, 2H), 7.43 (m, 1H), 7.42 (s, 1H), 7.36 (d, J=8.2 Hz, 2H), 6.80 (d, J=8.2 Hz, 2H), 3.80 (s, 2H), 2.63 (s, 3H); $^{13}$C NMR (100 MHz, $CDCl_3$) δ 195.7, 185.5, 146.0, 140.3, 134.5, 131.6, 131.5, 129.3, 129.2, 128.4, 128.2, 125.1, 124.1, 123.7, 122.4, 120.0, 115.7, 111.5, 26.3; LRMS (ESI) m/z calculated for $C_{23}H_{19}N_2O_2$ $[M+H]^+$: 355.14; found: 355.2327.

Example 64: Production of Compound 64

Compound 64 (10.7 mg, 74.5% yield) was obtained as a yellow solid in the same manner as in Example 61, except that 4-(diethylamino)benzeneboronic acid (6.8 mg, 0.03 mmol), tetrakis(triphenylphosphine)palladium (12.0 mg, 0.3 mol %) and sodium carbonate (11.2 mg, 0.10 mmol) were added to a solution containing IH-B (10.1 mg, 0.03 mmol) and a 2:1 mixture of DMF and water, followed by stirring at 100° C. for 3 hours, and the concentrated organic phase was purified by silica-gel flash column chromatography (EA: hexane=1:3-25% ethyl acetate).

[Compound 64]

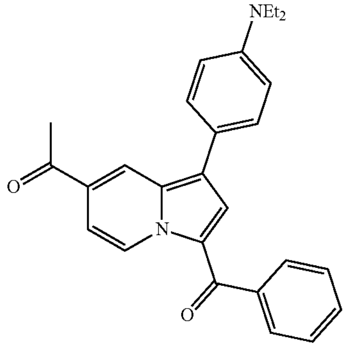

The physical properties of Compound 64 produced in Example 64 are as follows.

$^1$H NMR (600 MHz, $CDCl_3$) δ 9.89 (d, J=7.6 Hz, 1H), 8.43 (s, 1H), 7.86 (d, J=7.1 Hz, 2H), 7.57 (m, 1H), 7.51 (t, J=7.6 Hz, 2H), 7.43 (m, 4H), 6.80 (d, J=8.6 Hz, 2H), 3.42 (q, J=7.1 Hz, 4H), 2.64 (s, 3H), 1.22 (t, J=7.1 Hz, 6H); $^{13}$C NMR (100 MHz, $CDCl_3$) δ 195.8, 185.4, 140.4, 134.5, 131.4, 129.3, 129.2, 128.4, 128.2, 124.9, 122.8, 120.4, 112.3, 111.4, 44.6, 26.3, 12.7; LRMS (ESI) m/z calculated for $C_{27}H_{27}N_2O_2$ $[M+H]^+$: 411.20; found: 411.3622.

Example 65: Production of Compound 65

Compound 65 (6.1 mg, 92.8% yield) was obtained as a yellow solid in the same manner as in Example 61, except that 4-(dipropylamino)phenylboronic acid (11.9 mg, 0.05 mmol), tetrakis (triphenylphosphine)palladium (19.0 mg, 0.3 mol %) and sodium carbonate (17.0 mg, 0.16 mmol) were added to a solution containing IH-B (5.3 mg, 0.01 mmol) and a 1:1 mixture of DMF and water, followed by stirring at 100° C. for 3 hours, and the concentrated organic phase was purified by silica-gel flash column chromatography (EA:hexane=1:2-33% ethyl acetate).

[Compound 65]

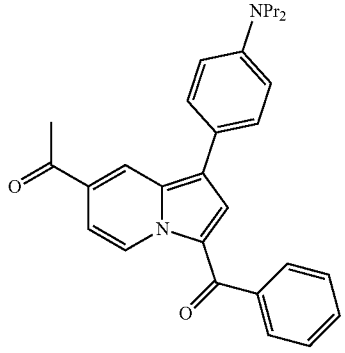

The physical properties of Compound 65 produced in Example 65 are as follows.

$^1$H NMR (600 MHz, $CDCl_3$) δ 9.88 (d, J=7.4 Hz, 1H), 8.43 (s, 1H), 7.85 (d, J=7.1 Hz, 2H), 7.57 (dd, J=10.4, 4.2 Hz, 1H), 7.50 (t, J=7.6 Hz, 2H), 7.44 (dd, J=7.3, 1.8 Hz, 1H), 7.41 (t, J=4.3 Hz, 3H), 6.75 (d, J=8.8 Hz, 2H), 3.30 (m, 4H), 2.64 (s, 3H), 1.66 (dd, J=15.1, 7.5 Hz, 4H), 0.96 (t, J=7.3 Hz, 6H); $^{13}$C NMR (100 MHz, $CDCl_3$) δ 195.8, 147.6, 140.4, 131.4, 129.2(2), 128.4, 128.2, 124.9, 122.8, 120.4, 112.2, 111.4, 54.1, 53.0, 51.9, 47.6, 29.8, 26.3, 20.5, 11.6; LRMS (ESI) m/z calculated for $C_{29}H_{31}N_2O_2$ $[M+H]^+$: 439.23; found: 439.3939.

Example 66: Production of Compound 67

Example 66-1: Production of (1-bromoindolizin-3-yl) (phenyl)methanone (IM-B)

(1-bromoindolizin-3-yl) (phenyl)methanone, a compound represented by IM-B, was produced in the same manner as in Example 46-1.

Example 66-2: Production of Compound 67

To a solution containing IM-B (21.6 mg, 0.07 mmol) and a 2:1 mixture of DMF and water, 4-pyridyl boronic acid (26.5 mg, 0.21 mmol), tetrakis(triphenyl phosphine)palladium (25.0 mg, 0.3 mol %) and sodium carbonate (22.8 mg, 0.21 mmol) were added, followed by stirring at 100° C. for 12 hours. After completion of the reaction, monitoring by TLC was performed, and then the reaction solution was washed with water, and the organic phase was extracted three times with DCM. The extracted organic phases were combined, dried over anhydrous $Na_2SO_4$, and then concentrated. The concentrated organic phase was purified by silica-gel flash column chromatography (EA:hexane=1:1-50% ethyl acetate 50%) to obtain Compound 67 (5.1 mg, 23.7% yield) as a yellow solid.

[Compound 67]

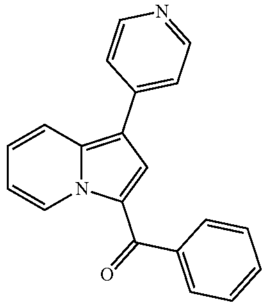

The physical properties of Compound 67 produced are as follows.

$^1$H NMR (600 MHz, $CDCl_3$) δ 9.98 (d, J=7.1 Hz, 1H), 7.79 (m, 3H), 7.53 (m, 6H), 7.36 (m, 1H), 7.19 (m, 1H), 6.94 (t, J=6.8 Hz, 1H), 6.53 (d, J=4.6 Hz, 1H); $^{13}$C NMR (100 MHz, $CDCl_3$) δ 185.1, 149.6, 140.4, 136.6, 132.2, 132.1, 131.4, 129.5, 129.0, 128.5(2), 126.4, 125.7, 122.1, 117.3, 114.9; LRMS (ESI) m/z calculated for $C_{20}H_{15}N_2O$ $[M+H]^+$: 299.11; found: 299.1516.

Example 67: Production of Compound 68

Compound 68 (20.4 mg, 81.2% yield) was obtained as a yellow solid in the same manner as in Example 66, except that 3-amino-4-methylphenyl boronic acid (46.7 mg, 0.30 mmol), tetrakis (triphenylphosphine)palladium (33.0 mg, 0.3 mol %) and sodium carbonate (33.0 mg, 0.3 mmol) were added to a solution containing IM-B (23.2 mg, 0.07 mmol) and a 2:1 mixture of DMF and water, followed by stirring at 100° C. for 6 hours, and the concentrated organic phase was purified by silica-gel flash column chromatography (EA: hexane=1:2-33% ethyl acetate).

[Compound 68]

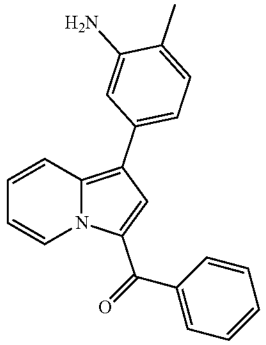

The physical properties of Compound 68 produced are as follows.

$^1$H NMR (600 MHz, $(CD_3)_2SO$) δ 9.92 (d, J=7.0 Hz, 1H), 8.00 (d, J=9.0 Hz, 1H), 7.81 (dd, J=7.9, 0.9 Hz, 2H), 7.62 (t, J=7.4 Hz, 1H), 7.56 (t, J=7.6 Hz, 2H), 7.42 (m, 1H), 7.36 (s, 1H), 7.18 (t, J=6.9 Hz, 1H), 7.00 (d, J=7.6 Hz, 1H), 6.90 (s, 1H), 6.74 (d, J=7.6 Hz, 1H), 4.92 (s, 2H), 2.08 (s, 3H); $^{13}$C NMR (100 MHz, $(CD_3)_2SO$) δ 183.3, 140.2, 135.4, 131.9, 131.0, 130.4, 128.6, 128.3, 128.0, 125.4, 124.1, 121.1, 118.0, 117.6, 114.7, 54.9, 17.1; LRMS (ESI) m/z calculated for $C_{22}H_{19}N_2O$ $[M+H]^+$: 327.14; found: 327.3095.

Example 68: Production of Compound 69

Compound 69 (13.6 mg, 90.7% yield) was obtained as a yellow solid in the same manner as in Example 66, except that 4-aminobenzeneboronic acid (25.1 mg, 0.14 mmol), tetrakis (triphenylphosphine)palladium (17.0 mg, 0.3 mol %) and sodium carbonate (15.0 mg, 0.14 mmol) were added to a solution containing IM-B (15.0 mg, 0.04 mmol) and a 2:1 mixture of DMF and water, followed by stirring at 100° C. for 3 hour, and the concentrated organic phase was purified by silica-gel flash column chromatography (EA: hexane=1:3-25% ethyl acetate).

[Compound 69]

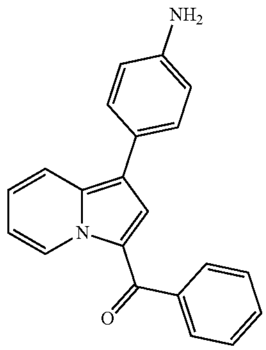

The physical properties of Compound 69 produced are as follows.

$^1H$ NMR (600 MHz, $CDCl_3$) δ 10.01 (dt, J=7.2, 1.0 Hz, 1H), 7.82 (dt, J=3.4, 1.4 Hz, 3H), 7.53 (m, 1H), 7.47 (m, 2H), 7.37 (s, 1H), 7.34 (m, 2H), 7.21 (ddd, J=8.8, 6.7, 1.0 Hz, 1H), 6.95 (td, J=6.9, 1.2 Hz, 1H), 6.76 (m, 2H), 3.74 (s, 2H).; $^{13}C$ NMR (100 MHz, $CDCl_3$) δ 184.5, 145.3, 141.1, 136.5, 130.9, 129.1(5), 128.3(2), 125.0(2), 124.7, 122.0, 118.1, 117.9, 115.6, 114.2, 29.8; LRMS (ESI) m/z calculated for $C_{21}H_{17}N_2O$ $[M+H]^+$: 313.13; found: 313.2500.

Example 69: Production of Compound 70

Compound 70 (17.3 mg, 90.3% yield) was obtained as a yellow solid in the same manner as in Example 66, except that 4-(diethylamino)phenylboronic acid (30.5 mg, 0.15 mmol), tetrakis (triphenylphosphine)palladium (18.0 mg, 0.3 mol %) and sodium carbonate (17.0 mg, 0.15 mmol) were added to a solution containing IM-B (16.0 mg, 0.05 mmol) and a 2:1 mixture of DMF and water, followed by stirring at 100° C. for 2 hours, and the concentrated organic phase was purified by silica-gel flash column chromatography (EA:hexane=1:2-33% ethyl acetate).

[Compound 70]

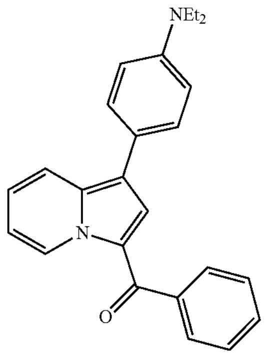

The physical properties of Compound 70 produced are as follows.

$^1H$ NMR (600 MHz, $CDCl_3$) δ 10.03 (dt, J=7.0, 1.0 Hz, 1H), 7.87 (dt, J=8.9, 1.2 Hz, 1H), 7.84 (m, 2H), 7.54 (m, 1H), 7.49 (m, 2H), 7.41 (m, 2H), 7.39 (s, 1H), 7.21 (ddd, J=8.9, 6.7, 1.1 Hz, 1H), 6.96 (td, J=6.9, 1.3 Hz, 1H), 6.77 (m, 2H), 3.40 (q, J=7.1 Hz, 4H), 1.20 (t, J=7.1 Hz, 6H); $^{13}C$ NMR (100 MHz, $CDCl_3$) δ 184.3, 146.7, 141.2, 136.5, 130.8, 129.1(2), 128.2, 124.9, 124.5, 122.0, 121.5, 118.5, 118.0, 114.1, 112.2, 44.5, 12.7; LRMS (ESI) m/z calculated for $C_{25}H_{25}N_2O$ $[M+H]^+$: 369.19; found: 369.3269.

Example 70: Production of Compound 71

Compound 71 (10.0 mg, 50.4% yield) was obtained as a yellow solid in the same manner as in Example 66, except that 4-(dipropylamino)phenylboronic acid (10.0 mg, 0.05 mmol), tetrakis(triphenylphosphine)palladium (16.0 mg, 0.03 mol %) and sodium carbonate (14.0 mg, 0.13 mmol) were added to a solution containing IM-B (13.0 mg, 0.05 mmol) and a 2:1 mixture of DMF and water, followed by stirring at 100° C. for 3 hours, and the concentrated organic phase was purified by silica-gel flash column chromatography (EA:hexane=1:2-33% ethyl acetate).

[Compound 71]

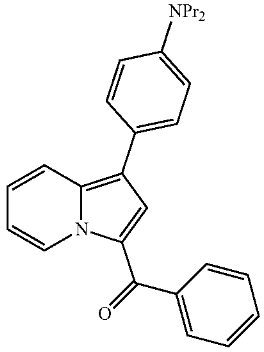

The physical properties of Compound 71 produced are as follows.

$^1H$ NMR (600 MHz, $CDCl_3$) δ 10.01 (dt, J=7.1, 1.1 Hz, 1 Hz), 7.85 (dt, J=8.9, 1.2 Hz, 1H), 7.82 (m, 2H), 7.52 (m, 1H), 7.48 (m, 3H), 7.38 (m, 2H), 7.37 (s, 1H), 7.20 (ddd, J=8.9, 6.7, 1.1 Hz, 1H), 6.94 (td, J=6.9, 1.3 Hz, 1H), 6.71 (m, 1H), 3.26 (m, 4H), 1.63 (dd, J=15.2, 7.5 Hz, 4H), 0.94 (t, J=7.4 Hz, 6H); $^{13}C$ NMR (100 MHz, $CDCl_3$) δ 184.3, 147.1, 141.2, 136.5, 130.8, 129.1, 129.0, 128.2, 124.9, 124.5, 122.0, 121.3, 118.5, 118.0, 114.1, 112.0, 53.0, 20.5, 11.6; LRMS (ESI) m/z calculated for $C_{27}H_{29}N_2O$ $[M+H]^+$: 397.22; found: 397.3389.

Example 71: Production of Compound 73

Example 71-1: Production of 1-(1-bromo-7-(trifluoromethyl)indolizin-3-yl)ethanone (IB-B)

[Reaction Scheme 1-13]

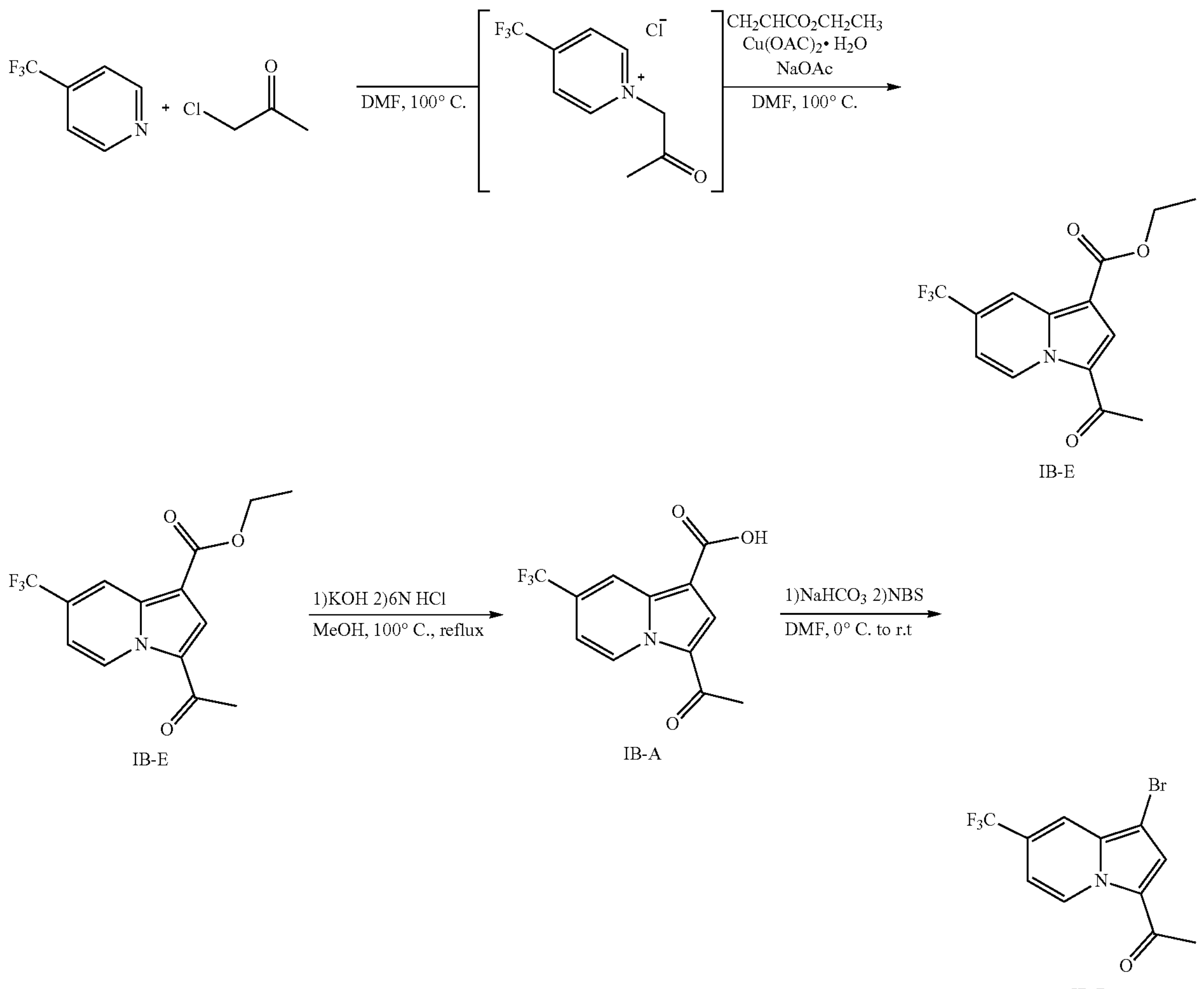

IB-E

IB-E IB-A

IB-B

IB-E: IB-E was synthesized as shown in Reaction Scheme 1-13 above. Specifically, DMF (10.0 mL) containing 4-(trifluoromethyl)pyridine (695 μL, 6.00 mmol) and chloroacetone (501 μL, 6.30 mmol) was stirred overnight at 100° C., and then ethyl acrylate (320 μL, 3 mmol), copper(II) acetate monohydrate (1.79 g, 9.00 mmol) and sodium acetate (1,476.5 mg, 18 mmol) were added thereto, followed by stirring at 100° C. for 16 hours. After completion of the reaction, monitoring by TLC was performed, and then copper acetate was removed by filtration through a celite pad, and the resulting filtrate was concentrated in vacuum. The resulting crude product was washed with water, and the organic phase was extracted three times with DCM. The extracted organic phases were combined, dried over anhydrous $Na_2SO_4$ and then concentrated. The concentrated organic phase was purified by silica-gel flash column chromatography (1 to 15% hexane containing EtOAc) to obtain compound IB-E (659.5 mg, 2.2 mmol, 73.4% yield) as a yellow solid.

The results of NMR analysis are as follows.

$^1H$ NMR (400 MHz, $CDCl_3$), δ 9.96 (d, J=7.2 Hz, 1H), 8.66 (t, J=1.2 Hz, 1H), 8.06 (s, 1H), 7.15 (dd, J=2 Hz, 1H), 4.43 (q, J=7.2 Hz, 2H), 2.63 (s, 3H), 1.45 (t, J=7.0 Hz, 3H); $^{13}C$ NMR (400 MHz, $CDCl_3$) δ 188.0, 163.1, 136.7, 129.1, 128.3, 128.0, 127.6, 127.3, 126.9, 126.0, 124.2, 123.4, 121.5, 118.8, 116.9, 116.8, 110.5, 110.4, 108.1, 60.6, 27.5, 14.5; LRMS (ESI) m/z calculated for $C_{14}H_{12}F_3NO_3$ $[M+Na]^+$: 299.1, found: 300.1.

IB-B: KOH (5,386 mg, 96.00 mmol) was added to methanol (10 mL) containing IB-E (0.66 g, 2.20 mmol), followed by stirring at room temperature for 4 hours. The reaction mixture was acidified by adding 6N HCl, and the resulting solid was collected through filtration, washed with water, and dried in a drying oven to obtain compound IB-A as a brown solid.

The obtained compound IB-A was used in the next step without further purification. Sodium bicarbonate (554 mg, 6.60 mmol) was added to DMF (10.0 mL) containing IB-A, and NBS (587 mg, 3.30 mmol) was added thereto in portions at 0° C. The reaction mixture was stirred at room temperature for 12 hours, and then the resulting crude product was washed with water and the organic phase was extracted three times with DCM. The extracted organic phases were combined, dried over anhydrous $Na_2SO_4$, and then concentrated. The concentrated organic phase was purified by silica-gel flash column chromatography (EA:hexane=1:8-12% ethyl acetate) to obtain compound IB-B (588 mg, 1.92 mmol, 100% yield) as a yellow solid.

The results of NMR analysis are as follows.

$^1$H NMR (400 MHz, $CDCl_3$) δ 9.88 (d, J=7.2 Hz, 1H), 7.85 (s, 1H), 7.60 (s, 1H), 7.02 (d, J=7.6 Hz, 1H), 2.59 (s, 1H); $^{13}$C NMR (100 MHz, $CDCl_3$) δ 204.4, 186.9, 133.6, 128.7, 124.9, 123.5, 121.7, 115.2, 109.7, 92.0, 27.5.

Example 71-2: Production of Compound 73

To a solution containing IB-B (74.6 mg, 0.24 mmol) and a 2:1 mixture of DMF and water, 4-triflulorophenyl boronic acid (103 mg, 0.97 mmol), tetrakis(triphenyl phosphine) palladium (231 mg, 20.0 mol %) and sodium carbonate (49.0 mg, 0.46 mmol) were added, followed by stirring at 100° C. for 8 hours. After completion of the reaction, monitoring by TLC was performed, and then the reaction solution was washed with water, and the organic phase was extracted three times with DCM. The extracted organic phases were combined, dried over anhydrous $Na_2SO_4$, and then concentrated. The concentrated organic phase was purified by silica-gel flash column chromatography (EA:hexane=1:4-25% ethyl acetate) to obtain Compound 73 (75.9 mg, 0.2 mmol, 85% yield) as a yellow solid.

[Compound 73]

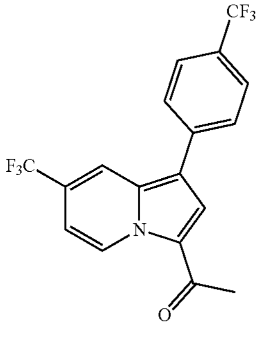

The physical properties of Compound 73 produced are as follows.

$^1$H NMR (400 MHz, $CDCl_3$) δ 9.95 (d, J=7.2 Hz, 1H), 8.03 (s, 1H), 7.75 (d, J=8.4 Hz, 2H), 7.71 (s, 1H), 7.67 (d, J=8.0 Hz, 2H), 7.03 (dd, J=7.4 Hz, 2.0 Hz, 1H), 2.65 (s, 3H); $^{13}$C NMR (100 MHz, $CDCl_3$) δ 187.6, 137.4, 133.0, 129.2, 129.0, 128.1, 126.1, 125.7, 125.5, 124.6, 123.8, 123.1, 122.8, 121.9, 118.2, 115.1, 109.7, 27.8; LRMS (ESI) m/z calculated for $C_{18}H_{12}F_6NO$ $[M+H]^+$: 372.07; found: 372.05.

Example 72: Production of Compound 74

An indolizine derivative compound (56.4 mg, 0.16 mmol, 74.2% yield) was produced in the same manner as in Example 71, except that, in Example 71-2, 4-acetylphenyl boronic acid (144 mg, 0.88 mmol), tetrakis (triphenylphosphine)palladium (231 mg, 20.0 mol %) and sodium carbonate (93.0 mg, 0.88 mmol) were added to a solution containing IB-B (52.4 mg, 0.22 mmol) and a 2:1 mixture of DMF and water, followed by stirring at 100° C. for 17 hours, and the concentrated organic phase was purified by silica-gel flash column chromatography (EA:hexane=1:5-20% ethyl acetate).

[Compound 74]

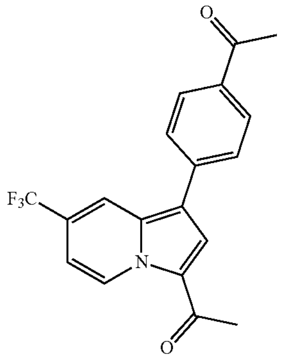

The physical properties of Compound 74 produced are as follows.

$^1$H NMR (400 MHz, $CDCl_3$) δ 9.91 (d, J=7.2 Hz, 1H), 8.06 (d, J=8.4 Hz, 2H), 8.01 (d, J=8.0 Hz, 1H), 7.72 (s, 1H), 7.67 (d, J=8.8 Hz, 1H), 7.63 (d, J=8.0 Hz, 1H), 7.01 (d, J=7.2 Hz, 1H), 2.63 (s, 3H), 2.61 (s, 3H); $^{13}$C NMR (100 MHz, $CDCl_3$) δ 197.4, 187.9, 144.4, 138.8, 136.7, 135.8, 133.3, 129.5, 128.0, 127.6, 124.9, 124.1, 123.4, 122.1, 118.7, 115.5, 109.9, 28.1, 27.1; LRMS (ESI) m/z calculated for $C_{19}H_{15}F_3NO_2$ $[M+H]^+$: 346.10; found: 346.10.

Example 73: Production of Compound 75

An indolizine derivative compound (79.8 mg, 0.26 mmol, 100% yield) was produced in the same manner as in Example 71, except that, in Example 71-2, phenyl boronic acid (117 mg, 0.96 mmol), tetrakis(triphenylphosphine) palladium (231 mg, 20.0 mol %) and sodium carbonate (102 mg, 0.96 mmol) were added to a solution containing IB-B (73.8 mg, 0.24 mmol) and a 2:1 mixture of DMF and water.

[Compound 75]

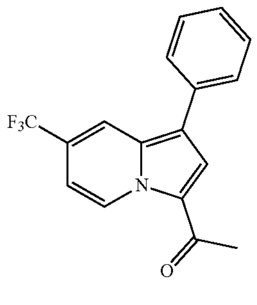

The physical properties of Compound 75 produced are as follows.

$^1$H NMR (400 MHz, $CDCl_3$) δ 9.94 (d, J=7.6 Hz, 1H), 8.07 (s, 1H), 7.86 (d, J=8.8 Hz, 2H), 7.73 (d, J=8.4 Hz, 1H), 7.66 (d, J=8.0 Hz, 1H), 7.57 (s, 1H), 7.07 (dd, J=7.2 Hz, 2.0 Hz, 1H), 7.01 (d, J=8.8 Hz, 1H), 3.90 (s, 3H); $^{13}$C NMR (100 MHz, $CDCl_3$) δ 184.2, 162.6, 137.5, 133.3, 132.1, 131.2, 129.2, 128.1, 126.1, 126.0, 125.8, 125.1, 123.7, 118.2, 113.7, 109.5, 55.6. HRMS (ESI) m/z calculated for $C_{17}H_{13}F_3NO$ $[M+H]^+$: 304.0949; found: 304.0944.

Example 74: Production of Compound 76

An indolizine derivative compound (547.2 mg, 0.14 mmol, 64% yield) was produced in the same manner as in Example 71, except that, in Example 71-2, 4-methoxyphenyl boronic acid (133 mg, 0.87 mmol), tetrakis(triphenylphosphine)palladium (231 mg, 20.0 mol %) and sodium carbonate (92.7 mg, 0.87 mmol) were added to a solution containing IB-B (52.1 mg, 0.22 mmol) and a 2:1 mixture of DMF and water.

[Compound 76]

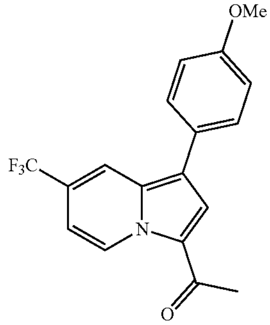

The physical properties of Compound 76 produced are as follows.

$^1H$ NMR (400 MHz, $CDCl_3$) δ 9.89 (d, J=7.2 Hz, 1H), 7.99 (s, 1H), 7.60 (s, 1H), 7.45 (d, J=8.8 Hz, 2H), 7.03 (d, J=8.8 Hz, 2H), 6.96 (dd, J=7.4 Hz, 1.6 Hz, 1H), 3.87 (s, 3H), 2.62 (s, 3H); $^{13}C$ NMR (100 MHz, $CDCl_3$) δ 187.4, 158.8, 132.8, 129.1, 128.8, 126.0, 125.0, 124.8, 124.6, 123.3, 122.7, 122.1, 119.8, 115.5, 114.5, 109.2, 55.5, 27.7; LRMS (ESI) m/z calculated for $C_{18}H_{15}F_3NO_2$ $[M+H]^+$: 334.10; found: 334.15.

Example 75: Production of Compound 77

An indolizine derivative compound (85.3 mg, 0.25 mmol, 100% yield) was produced in the same manner as in Example 71, except that, in Example 71-2, 4-(dimethylamino)phenyl boronic acid (167 mg, 1.01 mmol), tetrakis (triphenylphosphine)palladium (231 mg, 20.0 mol %) and sodium carbonate (108 mg, 1.01 mmol) were added to a solution containing IB-B (77.8 mg, 0.25 mmol) and a 2:1 mixture of DMF and water, followed by stirring at 100° C. for 12 hours.

[Compound 77]

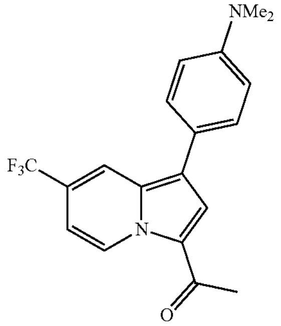

The physical properties of Compound 77 produced are as follows.

$^1H$ NMR (400 MHz, $CDCl_3$) δ 9.88 (d, J=8.0 Hz, 1H), 8.03 (s, 1H), 7.57 (s, 1H), 7.41 (d, J=8.8 Hz, 2H), 6.94 (dd, J=7.6 Hz, 2.0 Hz, 1H), 6.83 (d, J=8.8 Hz, 2H), 3.01 (s, 6H), 2.62 (s, 3H); $^{13}C$ NMR (100 MHz, $CDCl_3$) δ 186.9, 149.3, 132.4, 128.3, 124.5, 124.1, 123.8, 122.9, 121.9, 121.8, 121.1, 121.0, 120.1, 115.4, 112.5, 108.6, 40.2, 27.3; LRMS (ESI) m/z calculated for $C_{19}H_{18}F_3N_2O$ $[M+H]^+$: 347.13; found: 347.15.

Example 76: Production of Compound 78

Example 76-1: Production of 1,1'-(1-bromoindolizine-3,7-diyl)diethanone (IG-B)

[Reaction Scheme 1-14]

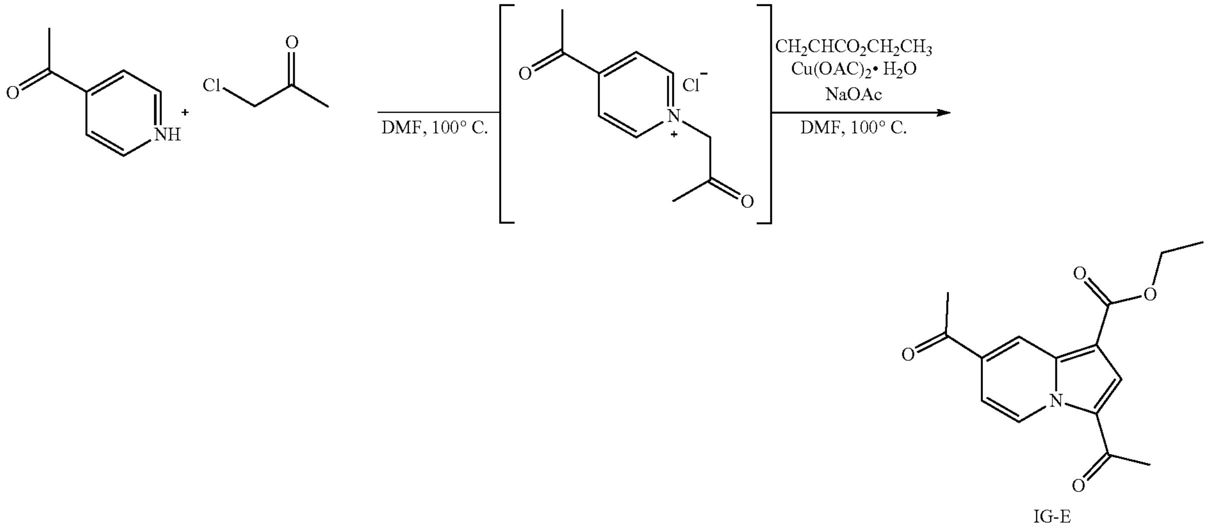

IG-E

-continued

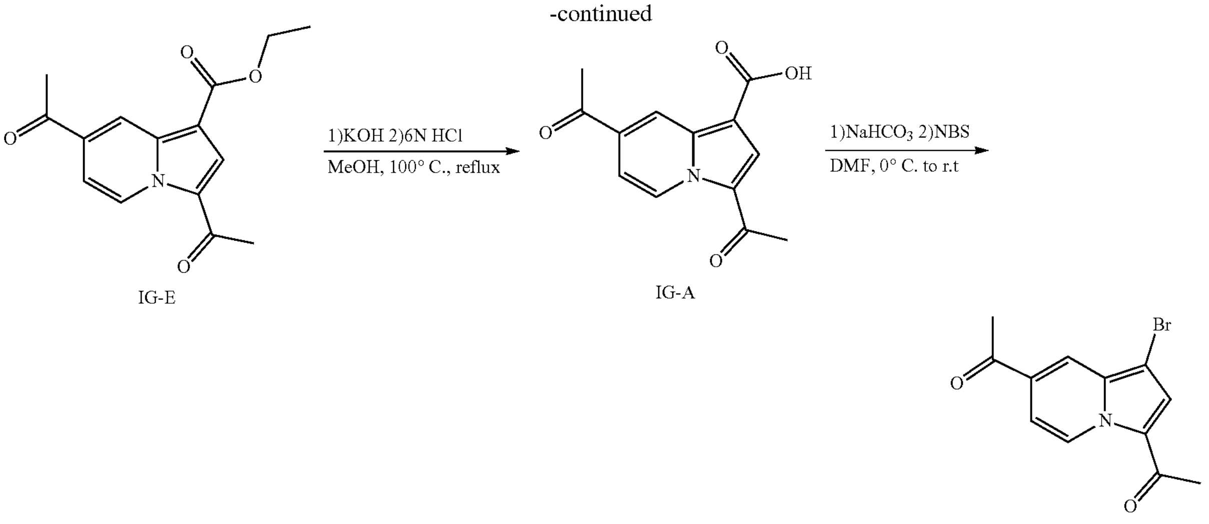

IG-E IG-A IG-B

IG-E: IG-E was synthesized as shown in Reaction Scheme 1-14 above. Specifically, DMF (12.0 mL) containing 4-acetylpyridine (158.1 μL, 1.431 mmol) and 2-chloroacetone (120.7 μL, 1.5 mmol) was stirred for 4 hours at 80° C., and then ethyl acrylate (77.5 μl, 0.715 mmol), copper(II) acetate monohydrate (856.5 mg, 4.29 mmol) and sodium acetate (469.2 mg, 5.72 mmol) were added thereto, followed by stirring at 100° C. for 5 hours. After completion of the reaction, monitoring by TLC was performed, and then copper acetate was removed by filtration through a celite pad, and the resulting filtrate was concentrated in vacuum. The resulting crude product was washed with water, and the organic phase was extracted three times with DCM. The extracted organic phases were combined, dried over anhydrous $Na_2SO_4$ and then concentrated. The concentrated organic phase was purified by silica-gel flash column chromatography (EA:hexane=1:5-40% ethyl acetate) to obtain compound IG-E (166.7 mg, 85.3% yield) as a yellow solid.

The results of NMR analysis are as follows.

$^1$H NMR (400 MHz, $CDCl_3$), δ 9.85 (d, J=6.8 Hz, 1H), 8.80 (s, 1H), 7.44 (d, J=7.4 Hz, 1H), 4.39 (q, J=14.2 Hz, 2H), 2.62 (s, 3H), 2.58 (s, 3H), 1.43 (t, J=7.6 Hz, 3H); $^{13}$C NMR (100 MHz, $CDCl_3$), δ 185.4, 159.1, 140.2, 134.6, 131.8, 131.6, 129.5, 129.2, 128.5, 128.3, 126.4, 125.4, 123.8, 121.8, 121.6, 119.9, 114.8, 111.7, 55.7, 26.7% LRMS (ESI) m/z calculated for $C_{15}H_{15}NO_4$ $[M+Na]^+$: 273.3, found: 274.1.

IG-B: KOH (1.37 g, 24.4 mmol) was added to methanol (5 mL) containing IG-E (166.7 mg, 0.610 mmol), followed by stirring overnight at room temperature. The reaction mixture was acidified by adding 6N HCl, and the resulting solid was collected through filtration, washed with water, and dried in a drying oven to obtain compound IG-A as a brown solid.

The obtained compound IG-A was used in the next step without further purification. Sodium bicarbonate (51.2 mg, 1.83 mmol) was added to DMF (10.0 mL) containing IG-A, and NBS (108.5 mg, 0.64 mmol) was added thereto in portions at 0° C. The reaction mixture was stirred at room temperature for 12 hours, and then the resulting crude product was washed with water and the organic phase was extracted three times with DCM. The extracted organic phases were combined, dried over anhydrous $Na_2SO_4$, and then concentrated. The concentrated organic phase was purified by silica-gel flash column chromatography (EA: hexane=1:5-40% ethyl acetate) to obtain compound IG-B (135.5 mg, 79.3% yield) as a yellow solid.

The results of NMR analysis are as follows.

$^1$H NMR (400 MHz, $CDCl_3$), δ 9.65 (d, J=7.4 Hz, 1H), 8.00 (s, 1H), 7.49 (s, 1H), 7.32 (d, 7.4 Hz), 2.63 (s, 3H), 2.53 (s, 3H); $^{13}$C NMR (100 MHz, $CDCl_3$), δ 195.2, 187.1, 134.4, 131.7, 128.0, 124.8, 124.1, 119.1, 111.8, 93.6, 27.9, 26.6; LRMS (ESI) m/z calculated for $C_{12}H_{10}BrNO_2$ $[M+Na]^+$: 280.1, found: 280.0.

Example 76-2: Production of Compound 78

To a solution containing IG-B (25.0 mg, 0.089 mmol) and a 10:1 mixture of DMF and water, 4-triflulorophenyl boronic acid (50.71 mg, 0.27 mmol), tetrakis(triphenyl phosphine) palladium (20.58 mg, 0.018 mmol) and sodium carbonate (47.13 mg, 0.45 mmol) were added, followed by stirring at 100° C. for 8 hours. After completion of the reaction, monitoring by TLC was performed, and then the reaction solution was washed with water, and the organic phase was extracted three times with DCM. The extracted organic phases were combined, dried over anhydrous $Na_2SO_4$, and then concentrated. The concentrated organic phase was purified by silica-gel flash column chromatography (EA: hexane=1:5-40% ethyl acetate) to obtain Compound 78 (29.9 mg, 97.2% yield) as a yellow solid.

[Compound 78]

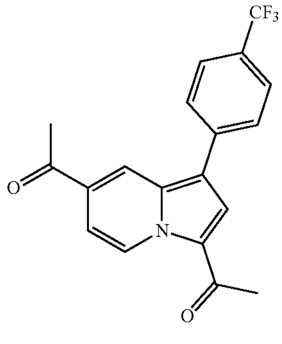

The physical properties of Compound 78 produced are as follows.

$^1H$ NMR (400 MHz, $CDCl_3$) δ 9.86 (d, J=7.6 Hz, 1H), 8.36 (s, 1H), 7.77 (d, J=8.4 Hz, 2H), 7.70 (d. J=12.0 Hz, 3H), 7.42 (dd, J=8.0 Hz, 2.0 Hz, 1H), 2.66 (s, 3H), 2.64 (s, 3H); $^{13}C$ NMR (100 MHz, $CDCl_3$) δ 195.5, 187.9, 156.9, 137.8, 134.0, 132.1, 129.5, 129.1, 128.4, 126.3 (2), 125.7, 124.4, 123.1, 123.0, 119.8, 119.1, 112.1, 28.1, 26.7; LRMS (ESI) m/z calculated for $C_{19}H_{15}F_3NO_2$ $[M+H]^+$: 346.10; found: 346.10.

Example 77: Production of Compound 79

An indolizine derivative compound (27.6 mg, 97.2% yield) was produced in the same manner as in Example 76, except that, in Example 76-2, 4-acetylphenyl boronic acid (43.78 mg, 0.27 mmol), tetrakis (triphenylphosphine)palladium (20.58 mg, 0.018 mmol) and sodium carbonate (47.13 mg, 0.45 mmol) were added to a solution containing IG-B (25.0 mg, 0.089 mmol) and a 10:1 mixture of DMF and water.

[Compound 79]

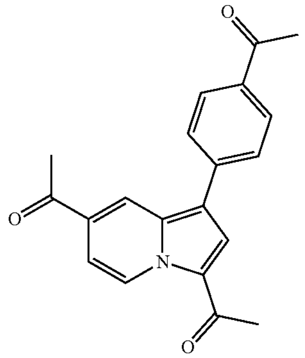

The physical properties of Compound 79 produced are as follows.

$^1H$ NMR (400 MHz, $CDCl_3$) δ 9.86 (d, J=7.4 Hz, 1H), 8.39 (s, 1H), 8.10 (dd, J=6.6 Hz, 1.6 Hz, 2H), 7.70 (d, J=4.0 Hz, 2H), 7.69 (s, 1H), 7.42 (dd, J=7.2 Hz, 2.0 Hz, 1H), 2.67 (s, 3H), 2.66 (s, 3H), 2.64 (s, 3H); $^{13}C$ NMR (100 MHz, $CDCl_3$) δ 197.5, 195.5, 187.9, 139.0, 135.7, 134.1, 132.1, 129.4, 128.5, 128.1, 124.4, 123.1, 120.1, 119.3, 112.1, 28.1, 27.1, 26.7; LRMS (ESI) m/z calculated for $C_{20}H_{18}NO_3$ $[M+H]^+$: 320.12; found: 320.10.

Example 78: Production of Compound 80

An indolizine derivative compound (23.5 mg, 95.4% yield) was produced in the same manner as in Example 76, except that, in Example 76-2, phenyl boronic acid (32.56 mg, 0.27 mmol), tetrakis(triphenylphosphine)palladium (20.58 mg, 0.018 mmol) and sodium carbonate (47.13 mg, 0.45 mmol) were added to a solution containing IG-B (25.0 mg, 0.089 mmol) and a 10:1 mixture of DMF and water.

[Compound 80]

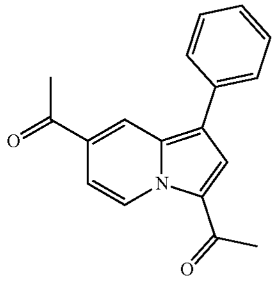

The physical properties of Compound 80 produced are as follows.

$^1H$ NMR (400 MHz, $CDCl_3$) δ 9.82 (d, J=7.4 Hz, 1H), 8.37 (s, 1H), 7.64 (s, 1H), 7.59 (dd, J=6.8 Hz, 1.6 Hz, 2H), 7.51 (dt, J=7.2 Hz, 2.4 Hz 2H), 7.40 (t, J=7.2 Hz, 2H), 2.64 (s, 3H), 2.61 (s, 3H); $^{13}C$ NMR (100 MHz, $CDCl_3$) δ 195.6, 187.8, 134.1, 133.9, 131.6, 129.3, 128.3, 128.2, 127.4, 124.1, 122.9, 121.7, 119.8, 111.7, 28.1, 26.7; HRMS (ESI) m/z calculated for $C_{18}H_{16}NO_2$ $[M+H]^+$: 278.1181; found: 278.1176.

Example 79: Production of Compound 81

An indolizine derivative compound (26.5 mg, 96.9% yield) was produced in the same manner as in Example 76, except that, in Example 76-2, 4-methoxyphenyl boronic acid (40.57 mg, 0.27 mmol), tetrakis (triphenylphosphine)palladium (20.58 mg, 0.018 mmol) and sodium carbonate (47.13 mg, 0.45 mmol) were added to a solution containing IG-B (25.0 mg, 0.089 mmol) and a 10:1 mixture of DMF and water.

[Compound 81]

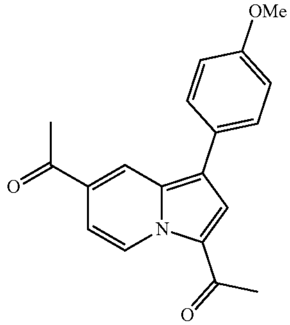

The physical properties of Compound 81 produced are as follows.

$^1H$ NMR (400 MHz, $CDCl_3$) δ 9.78 (d, J=7.4 Hz, 1H), 8.31 (s, 1H), 7.57 (s, 1H), 7.49 (dd, J=7.4 Hz, 1.6 Hz, 2H), 7.35 (dd, J=7.4 Hz, 1.6 Hz, 1H), 7.04 (d, J=8.8 Hz, 2H), 3.88 (s, 3H), 2.62 (s, 3H), 2.60 (s, 3H); $^{13}C$ NMR (100 MHz, $CDCl_3$) δ 195.6, 187.7, 159.1, 133.8, 131.3, 129.4, 128.1, 126.5, 124.0, 122.6, 121.6, 119.9, 114.8, 111.5, 55.7, 28.0, 26.6; LRMS (ESI) m/z calculated for $C_{19}H_{18}NO_3$ $[M+H]^+$: 308.12; found: 308.10.

Example 80: Production of Compound 82

An indolizine derivative compound (26.9 mg, 94.8% yield) was produced in the same manner as in Example 76, except that, in Example 76-2, 4-(dimethylamino)phenyl boronic acid (44.06 mg, 0.27 mmol), tetrakis (triphenylphosphine)palladium (20.58 mg, 0.018 mmol) and sodium carbonate (47.13 mg, 0.45 mmol) were added to a solution containing IG-B (25.0 mg, 0.089 mmol) and a 10:1 mixture of DMF and water.

[Compound 82]

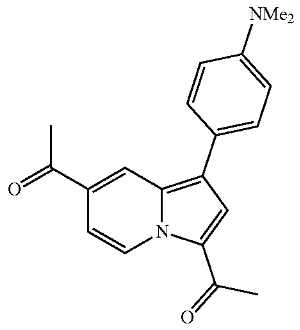

The physical properties of Compound 82 produced are as follows.

$^1H$ NMR (400 MHz, $CDCl_3$) δ 9.78 (d, J=7.2 Hz, 1H), 8.36 (s, 1H), 7.56 (s, 1H), 7.47 (dd, J=9.2 Hz, 2.4 Hz, 2H), 7.36 (dd, J=7.8 Hz, 2.4 Hz, 1H), 6.87 (d, J=8.8 Hz, 2H), 3.03 (s, 6H), 2.64 (s, 3H), 2.60 (s, 3H); $^{13}C$ NMR (100 MHz, $CDCl_3$) δ 195.7, 187.7, 149.9, 133.8, 131.0, 129.1, 128.0, 124.0, 122.4, 122.3, 122.0, 121.6(2), 120.3, 113.2, 111.4, 111.2, 40.9, 28.1, 26.6; LRMS (ESI) m/z calculated for $C_{20}H_{21}N_2O_2$ $[M+H]^+$: 321.15; found: 321.15.

Example 81: Production of Compound 83

Example 81-1: Production of 1-(1-bromoindolizin-3-yl)ethanone (IL-B)

[Reaction Scheme 1-15]

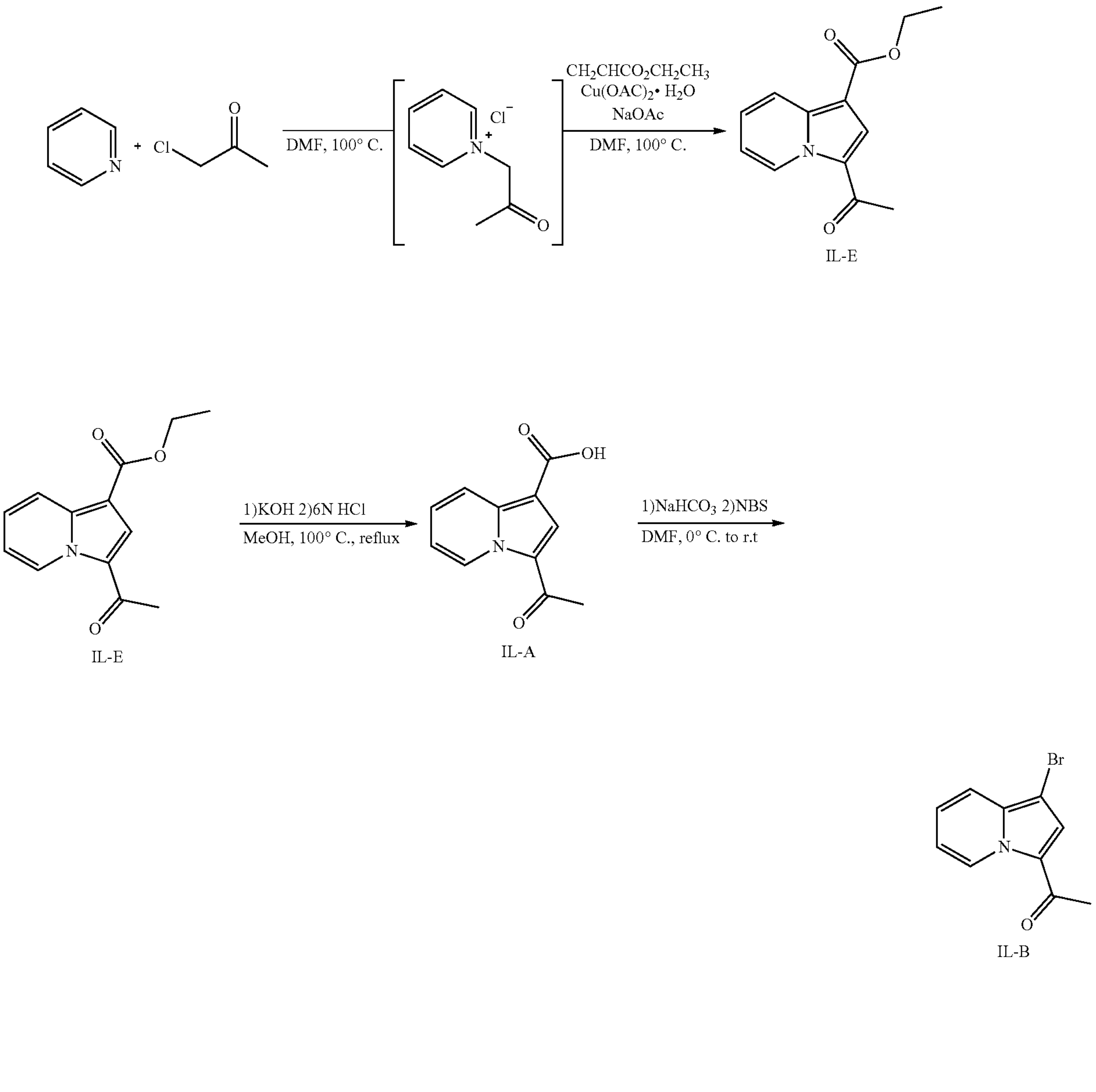

IL-E: IL-E was synthesized as shown in Reaction Scheme 1-15 above. Specifically, DMF (15.0 mL) containing pyridine (564 μL, 7.00 mmol) and chloroacetone (585 μL, 7.35 mmol) was stirred overnight at 100° C., and then ethyl acrylate (373 μL, 3.50 mmol), copper(II) acetate monohydrate (2.09 g, 10.5 mmol) and sodium acetate (1.72 g, 21.0 mmol) were added thereto, followed by stirring at 100° C. for 16 hours. After completion of the reaction, monitoring by TLC was performed, and then copper acetate was removed by filtration through a celite pad, and the resulting filtrate was concentrated in vacuum. The resulting crude product was washed with water, and the organic phase was extracted three times with DCM. The extracted organic phases were combined, dried over anhydrous $Na_2SO_4$ and then concentrated. The concentrated organic phase was purified by silica-gel flash column chromatography (1 to 15% hexane containing EtOAc) to obtain compound IL-E (633 mg, 2.73 mmol, 85.0% yield) as a yellow solid.

The results of NMR analysis are as follows.

$^1H$ NMR (400 MHz, $CDCl_3$), δ 9.88 (d, J=6.4 Hz, 1H), 8.34 (d, J=5.0 Hz, 1H), 7.99 (s, 1H), 7.38 (q, J=9.3 Hz, 1H), 6.95 (t, J=7.0 Hz, 1H), 4.39 (q, J=7.1 Hz, 2H), 2.60 (s, 3H), 1.43 (t, J=7.2 Hz, 3H); $^{13}C$ NMR (100 MHz, $CDCl_3$) δ 187.6, 164.0, 139.2, 129.1, 127.2, 126.2, 122.7, 119.4, 115.2, 105.8, 60.3, 27.6, 14.9; LRMS (ESI) m/z calculated for $C_{13}H_{13}NO_3$ $[M+Na]^+$: 231.1, found: 232.1.

IL-B: KOH (6.14 g, 109 mmol) was added to methanol (20 mL) containing IL-E (633 mg, 2.73 mmol), followed by stirring at room temperature for 4 hours. The reaction mixture was acidified by adding 6N HCl, and the resulting solid was collected through filtration, washed with water, and dried in a drying oven to obtain compound IL-A as a white solid.

The obtained compound IL-A was used in the next step without further purification. Sodium bicarbonate (688 mg, 8.19 mmol) was added to DMF (10.0 mL) containing IL-A, and NBS (2.18 g, 12.3 mmol) was added thereto in portions at 0° C. The reaction mixture was stirred at room temperature for 12 hours, and then the resulting crude product was washed with water and the organic phase was extracted three times with DCM. The extracted organic phases were combined, dried over anhydrous $Na_2SO_4$, and then concentrated. The concentrated organic phase was purified by silica-gel flash column chromatography (EA:hexane=1:8-12% ethyl acetate) to obtain compound IL-B(477 mg, 2.0 mmol, 73.4% yield) as a yellow solid.

The results of NMR analysis are as follows.

$^1H$ NMR (400 MHz, $CDCl_3$), δ 9.83 (d, J=6.8 Hz, 1H), 7.56 (d, J=9.2 Hz, 1H), 7.51 (s, 1H), 7.22 (q, J=7.8 Hz, 1H), 6.91 (t, J=6.4 Hz, 1H), 2.54 (s, 3H); $^{13}C$ NMR (100 MHz, $CDCl_3$) δ 185.5, 135.4, 127.9, 124.0, 123.8, 121.9, 116.5, 113.9, 88.5, 27.1; LRMS (ESI) m/z calculated for $C_{10}H_8BrNO$ $[M+Na]^+$: 237.0, found: 238.0.

Example 81-2: Production of Compound 83

To a solution containing IL-B (21.7 mg, 0.09 mmol) and a 2:1 mixture of DMF and water, 4-triflulorophenyl boronic acid (69.0 mg, 0.36 mmol), tetrakis(triphenyl phosphine) palladium (231 mg, 20.0 mol %) and sodium carbonate (39.0 mg, 0.36 mmol) were added, followed by stirring at 100° C. for 10 hours. After completion of the reaction, monitoring by TLC was performed, and then the reaction solution was washed with water, and the organic phase was extracted three times with DCM. The extracted organic phases were combined, dried over anhydrous $Na_2SO_4$, and then concentrated. The concentrated organic phase was purified by silica-gel flash column chromatography (EA:hexane=1:4-25% ethyl acetate) to obtain Compound 83 (24.4 mg, 0.08 mmol, 89.3% yield) as a yellow solid.

[Compound 83]

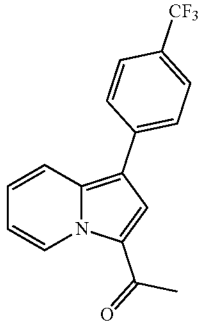

The physical properties of Compound 83 produced are as follows.

$^1H$ NMR (400 MHz, $CDCl_3$) δ 9.93 (d, J=7.6 Hz, 1H), 7.82 (d, J=9.2 Hz, 2H), 7.69 (d, J=4.4 Hz, 2H), 7.65 (s, 1H), 7.49 (d, J=8.6 Hz, 1H), 7.24 (d, J=10.0 Hz, 1H), 6.95 (dt, J=6.9 Hz, 1.2 Hz, 1H), 2.62 (s, 3H); $^{13}C$ NMR (100 MHz, $CDCl_3$) δ 186.8, 138.4, 135.7, 129.0, 128.1, 127.8, 125.8, 125.8, 125.6, 125.1, 122.8, 122.6, 117.1, 115.5(2), 114.4, 27.5; LRMS (ESI) m/z calculated for $C_{17}H_{13}F_3NO$ $[M+H]^+$: 304.09; found: 304.05.

Example 82: Production of Compound 84

An indolizine derivative compound (19.0 mg, 0.06 mmol, 63.4% yield) was produced in the same manner as in Example 81, except that, in Example 81-2, 4-acetylphenyl boronic acid (71.0 mg, 0.43 mmol), tetrakis(triphenylphosphine)palladium (231 mg, 20.0 mol %) and sodium carbonate (46.0 mg, 0.43 mmol) were added to a solution containing IL-B (25.8 mg, 0.10 mmol) and a 2:1 mixture of DMF and water, followed by stirring at 100° C. for 12 hours, and the concentrated organic phase was purified by silica-gel flash column chromatography (EA:hexane=1:5-20% ethyl acetate).

[Compound 84]

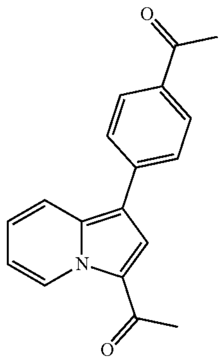

The physical properties of Compound 84 produced are as follows.

$^1H$ NMR (400 MHz, $CDCl_3$) δ 9.91 (d, J=6.8 Hz, 1H), 8.04 (d, J=8.4 Hz, 2H), 7.85 (d, J=8.8 Hz, 1H), 7.68 (s, 1H), 7.66 (d, J=3.6 Hz, 2H), 7.23 (dt, J=7.8 Hz, 1.2 Hz, 1H), 6.93 (dt, J=6.9 Hz, 1.2 Hz, 1H), 2.63 (s, 3H), 2.61 (s, 3H); $^{13}C$

NMR (100 MHz, $CDCl_3$) δ 197.5, 186.9, 139.9, 135.7, 134.9, 129.1, 127.6, 127.5, 125.3, 122.9, 122.8, 117.5, 115.7, 114.5, 27.7, 27.0; LRMS (ESI) m/z calculated for $C_{18}H_{16}NO_2$ $[M+H]^+$: 278.11; found: 278.14.

Example 83: Production of Compound 85

An indolizine derivative compound (66.8 mg, 0.28 mmol, 100% yield) was produced in the same manner as in Example 81, except that, in Example 81-2, phenyl boronic acid (111 mg, 0.91 mmol), tetrakis(triphenylphosphine) palladium (231 mg, 20.0 mol %) and sodium carbonate (97.0 mg, 0.91 mmol) were added to a solution containing IL-B (54.4 mg, 0.23 mmol) and a 2:1 mixture of DMF and water, followed by stirring at 100° C. for 9 hours.

[Compound 85]

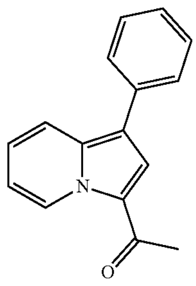

The physical properties of Compound 85 produced are as follows.

$^1H$ NMR (400 MHz, $CDCl_3$) δ 9.91 (d, J=7.2 Hz, 1H), 7.83 (d, J=8.8 Hz, 1H), 7.61 (s, 1H), 7.58 (d, J=7.2 Hz, 2H), 7.46 (t, J=7.6 Hz, 2H), 7.32 (t, J=7.4 Hz, 1H), 7.17 (dt, J=4.4 Hz, 1.2 Hz, 1H), 6.90 (t, J=6.8 Hz, 1H), 2.60 (s, 3H); $^{13}C$ NMR (100 MHz, $CDCl_3$) δ 186.2, 135.2, 134.4, 128.5, 128.4, 127.6, 126.2, 124.0, 122.2, 122.0, 117.2, 116.7, 113.7, 27.2; LRMS (ESI) m/z calculated for $C_{16}H_{14}NO$ $[M+H]^+$: 236.10; found: 236.10.

Example 84: Production of Compound 86

An indolizine derivative compound (13.3 mg, 0.05 mmol, 62.6% yield) was produced in the same manner as in Example 81, except that, in Example 81-2, 4-methoxyphenyl boronic acid (52.0 mg, 0.34 mmol), tetrakis(triphenylphosphine)palladium (231 mg, 20.0 mol %) and sodium carbonate (36.0 mg, 0.34 mmol) were added to a solution containing IL-B (20.3 mg, 0.08 mmol) and a 2:1 mixture of DMF and water, followed by stirring at 100° C. for 13 hours.

[Compound 86]

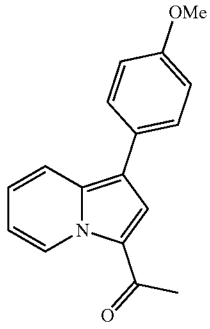

The physical properties of Compound 86 produced are as follows.

$^1H$ NMR (400 MHz, $CDCl_3$) δ 9.90 (d, J=6.8 Hz, 1H), 7.77 (d, J=6.8 Hz, 1H), 7.55 (s, 1H), 7.49 (d, J=8.8 Hz, 2H), 7.16 (dt, J=7.7 Hz, 1.2 Hz, 1H), 7.01 (t, J=6.8 Hz, 2H), 6.89 (dt, J=6.9 Hz, 1.2 Hz, 1H), 3.87 (s, 3H), 2.60 (s, 3H); $^{13}C$ NMR (100 MHz, $CDCl_3$) δ 186.4, 158.3, 135.5, 129.0, 128.7, 127.2, 124.0, 122.2, 117.5, 116.8, 114.3, 113.9, 55.5, 27.5; LRMS (ESI) m/z calculated for $C_{17}H_{16}NO_2$ $[M+H]^+$: 266.11; found: 266.10.

Example 85: Production of Compound 87

An indolizine derivative compound (12.5 mg, 0.04 mmol, 40.8% yield) was produced in the same manner as in Example 81, except that, in Example 81-2, 4-(dimethylamino)phenyl boronic acid (76.0 mg, 0.46 mmol), tetrakis (triphenylphosphine)palladium (231 mg, 20.0 mol %) and sodium carbonate (49.0 mg, 0.46 mmol) were added to a solution containing IL-B (27.5 mg, 0.11 mmol) and a 2:1 mixture of DMF and water, followed by stirring at 100° C. for 11 hours.

[Compound 87]

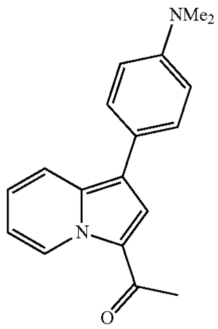

The physical properties of Compound 87 produced are as follows.

$^1H$ NMR (400 MHz, $CDCl_3$) δ 9.89 (d, J=6.4 Hz, 1H), 7.80 (d, J=8.8 Hz, 1H), 7.53 (s, 1H), 7.46 (d, J=7.2 Hz, 2H), 7.13 (t, J=7.8 Hz, 1H), 6.84 (d, J=6.8 Hz, 3H), 3.00 (s, 6H), 2.59 (s, 3H); $^{13}C$ NMR (100 MHz, $CDCl_3$) δ 186.2, 149.3, 135.5, 128.7, 123.7, 122.8, 122.0, 121.9, 117.7, 117.5, 113.8, 113.0, 40.8, 27.5; LRMS (ESI) m/z calculated for $C_{18}H_{19}N_2O$ $[M+H]^+$: 279.14; found: 279.15.

Experimental Methods

Cell Culture and Reagents

Human monocytic THP-1 wild-type (WT) and STING knockout (KO) cell lines were obtained from InvivoGen. Cells were cultured in 1×RPMI 1640 medium containing 10% fetal bovine serum (FBS, Hyclone), 2.05 mM L-glutamine (Hyclone) and 1% penicillin (Corning) in a humidified incubator at 37° C. under 5% $CO_2$.

Luciferase Reporter Assay

To confirm immune responses, THP-1 cells were placed in 384-well plates (Grenier), and treated with each compound and cGAMP (1 μg/ml), and after 24 hours, ISRE activity was analyzed. QUANTI-Luc assay (InvivoGen) was performed using the cell culture supernatant to confirm the luciferase reporter gene signal. Fluorescent signals were measured using a TECAN micro plate reader SPARK, and the results were normalized to DMSO control.

Cell Viability Assay

Cells were analyzed using CellTiter Clo (CTG, Promega). Absorbance was measured using a TECAN micro plate reader SPARK. Results were normalized to DMSO control.

ELISA

Cytokine levels were determined by ELISA analysis. THP-1 cells were placed in a 96-well U bottom plate and tested after 24 hours of treatment with each compound and cGAMP (1 μg/ml). After culturing, cell supernatants were collected and human IFN-β and IP-10 levels were determined by ELISA analysis.

Gene Expression Analysis by Real-Time Quantitative PCR

To confirm gene expression, THP-1 cells were placed in a 24-well plate (SPL) and treated with the compound of the present invention and cGAMP (1 μg/ml) for 6 hours. After culturing, RNA was extracted from the cells using NucleoSpin RNA Plus (MN). mRNA expression levels of IFNB, CXCL10, IFIT3, ISG15, IRF7 and OAS1 were measured by real-time qPCR (CFX96 Real-Time PCR Detection System, Bio-Rad) using IQ SYBR Green Supermix (Bio-Rad). GAPDH was used as a housekeeping gene to normalize cytokine mRNA levels.

Western Blot Analysis

Cells were cultured and lysed in RIPA buffer containing a protease and phosphatase inhibitor cocktail (Thermo Fisher Scientific) and benzonase nuclease (Sigma). After centrifugation, the supernatant was collected, and the amount of protein was measured using a BCA protein assay kit (Thermo Fisher Scientific). Cell lysates were analyzed by SDS-PAGE using an acrylamide gel. After SDS-PAGE, proteins were transferred to a PVDF membrane, blocked with 5% BSA, and then washed with TBST. The membrane was incubated with primary antibodies (anti-STING, anti-pSTING, anti-TBK, anti-pTBK, anti-IRF3, anti-pIRF3, anti-STAT1, anti-pSTAT1, and anti-actin) overnight at 4° C. After washing with TBST, the membrane was treated with HRP-conjugated secondary antibodies at room temperature for 1 hour. The membrane was washed with TBST and treated with ECL solution (Thermo Fisher Scientific). Chemical fluorescence images were taken with ChemiDOC (Bio-Rad).

Anticancer Activity of Compound 42 In Vivo

Eight-week-old female BALB/c mice (DBL) were used for experiments and inoculated subcutaneously with $0.5\times10^6$ 4T1 tumor cells using PBS as the vehicle on the right flank. Following tumor implantation, mice were randomized into treatment groups, each consisting of N=4 (vehicle N=1). On day 5 after tumor cell injection, when the tumor volume reached about 100 $mm^3$, Compound 42 or vehicle was administrated by intravenous injection (20 mg/kg) or vehicle (5% DMSO, 5% Tween 80 in PBS). 2'3'-cGAMP (InvivoGen) was injected by intratumoral injection (2 μg in PBS). Compound 42 was injected once daily, and cGAMP was injected once every 4 days. Tumor and body weight measurements were performed using digital calipers and a weigh scale, respectively. Tumor volume was estimated using the following Equation 1:

$$\text{Tumor volume}=(\text{length}\times\text{width}^2)/2 \qquad \text{[Equation 1]}$$

Mice were euthanized when the tumor volume reached about 2,000 $mm^3$.

Analysis of PK Profiles of Compound 42 after IV and PO Administrations to BALB/c Mice The pharmacokinetics and oral bioavailability of Compound 42 were investigated in mice following single intravenous (IV) injection and oral administration (PO). As shown in FIG. 8, blood was collected at 6 time points (4 hours, 8 hours, 12 hours, 16 hours, 20 hours, 24 hours) for each route of administration, and the amount of the compound in the blood was analyzed by LC/MS.

Experimental Results and Analysis

Results of Evaluation of Indolizine Derivatives

THP-1 cells were co-treated with each of 86 indolizine derivatives and a very small amount of cGAMP (1 μg/ml), the immune response of the THP-1 cells was examined by ISRE reporter assay, and the cytotoxicity of co-treatment was also evaluated (Table 1). All results were compared by normalization to the reporter assay results obtained by treatment with cGAMP alone. As a result, it was confirmed that the indolizine derivative Compound 42 exhibited the highest efficacy while having no cytotoxicity when co-administered with cGAMP. Thus, Compound 42 was used in subsequent experiments.

TABLE 1

| Compound | Normalized RU[(a)] | Normalized cell viability[(b)] |
|---|---|---|
| Compound 1 | 1.46 | 1.10 |
| Compound 2 | 1.42 | 1.03 |
| Compound 3 | 1.40 | 1.04 |
| Compound 4 | 1.33 | 1.05 |
| Compound 5 | 1.58 | 1.05 |
| Compound 6 | 1.38 | 1.19 |
| Compound 7 | 1.54 | 1.20 |
| Compound 8 | 1.18 | 1.06 |
| Compound 9 | 1.21 | 1.03 |
| Compound 10 | 1.67 | 1.21 |
| Compound 11 | 2.02 | 1.16 |
| Compound 12 | 1.31 | 1.25 |
| Compound 13 | 1.62 | 1.14 |
| Compound 14 | 1.48 | 1.30 |
| Compound 15 | 1.18 | 1.17 |
| Compound 16 | 1.66 | 1.22 |
| Compound 17 | 1.45 | 1.29 |
| Compound 18 | 1.85 | 1.17 |
| Compound 19 | 1.58 | 1.29 |
| Compound 20 | 1.46 | 1.05 |
| Compound 21 | 1.86 | 1.19 |
| Compound 22 | 1.31 | 1.09 |
| Compound 23 | 1.23 | 1.11 |
| Compound 24 | 1.33 | 1.21 |
| Compound 25 | 1.75 | 1.12 |
| Compound 26 | 1.60 | 1.21 |
| Compound 27 | 1.18 | 1.17 |
| Compound 28 | 1.69 | 1.13 |
| Compound 29 | 1.00 | 1.20 |
| Compound 30 | 1.33 | 1.26 |
| Compound 31 | 3.42 | 1.33 |
| Compound 32 | 2.91 | 1.11 |
| Compound 33 | 2.18 | 1.22 |
| Compound 34 | 1.52 | 1.26 |
| Compound 35 | 2.22 | 1.26 |
| Compound 36 | 3.37 | 1.27 |
| Compound 37 | 1.62 | 1.25 |
| Compound 38 | 1.77 | 1.34 |
| Compound 39 | 1.47 | 1.18 |
| Compound 40 | 1.09 | 1.17 |
| Compound 41 | 3.85 | 1.25 |
| Compound 44 | 0.89 | 1.24 |
| Compound 43 | 1.08 | 1.13 |
| Compound 42 | 9.32 | 1.20 |
| Compound 45 | 1.28 | 1.22 |
| Compound 46 | 1.08 | 1.25 |
| Compound 47 | 1.15 | 1.12 |
| Compound 48 | 1.37 | 1.18 |
| Compound 49 | 1.17 | 1.21 |
| Compound 50 | 1.18 | 1.30 |
| Compound 51 | 6.08 | 1.32 |
| Compound 52 | 1.61 | 1.15 |
| Compound 53 | 1.30 | 1.18 |
| Compound 54 | 1.51 | 1.16 |

TABLE 1-continued

| Compound | Normalized RU[(a)] | Normalized cell viability[(b)] |
|---|---|---|
| Compound 55 | 1.65 | 1.24 |
| Compound 56 | 1.40 | 1.23 |
| Compound 57 | 0.93 | 1.40 |
| Compound 58 | 0.66 | 1.01 |
| Compound 59 | 1.27 | 1.09 |
| Compound 60 | 1.25 | 1.28 |
| Compound 61 | 1.98 | 1.11 |
| Compound 62 | 2.86 | 1.23 |
| Compound 63 | 2.08 | 0.98 |
| Compound 64 | 1.13 | 1.24 |
| Compound 65 | 1.13 | 1.25 |
| Compound 66 | 1.16 | 1.32 |
| Compound 67 | 2.03 | 1.34 |
| Compound 68 | 3.16 | 1.17 |
| Compound 69 | 2.47 | 1.19 |
| Compound 70 | 1.21 | 1.19 |
| Compound 71 | 0.96 | 1.01 |
| Compound 73 | 1.54 | 0.78 |
| Compound 74 | 2.06 | 0.75 |
| Compound 75 | 1.76 | 1.25 |
| Compound 76 | 2.02 | 1.14 |
| Compound 77 | 1.24 | 1.28 |
| Compound 78 | 2.43 | 0.46 |
| Compound 79 | 3.80 | 1.19 |
| Compound 80 | 1.98 | 1.22 |
| Compound 81 | 2.27 | 1.17 |
| Compound 82 | 2.57 | 1.16 |
| Compound 83 | 0.98 | 1.22 |
| Compound 84 | 2.37 | 1.10 |
| Compound 85 | 2.90 | 1.22 |
| Compound 86 | 2.46 | 1.22 |
| Compound 87 | 2.59 | 1.30 |

[(a)]Relative unit of ISRE reporter signal. Normalized response using DMSO as a control.
[(b)]Normalized THP-1 cell viability. RU and cell viability were measured by treatment with 20 μM of each compound Confirmation of STING-Dependence As shown in FIG. 1, it was confirmed that co-treatment with Compound 42 and cGAMP exhibited an increased effect in the WT cell line, but exhibited no effect in the STING KO cell line, and that this effect was concentration-dependent.

Therefore, it was demonstrated that Compound 42 acts on STING in a concentration-dependent and STING-dependent manner, thereby very effectively enhancing ISRE signaling by cGAMP.

Meanwhile, as shown in FIG. 2, it was confirmed that co-treatment with Compound 42 and cGAMP did not cause toxicity to the cells.

Confirmation of Cytokine Expression Caused by Co-Treatment

As shown in FIG. 3, as a result of measuring the amount of pro-inflammatory cytokines (such as IFN-β or IP-10) secreted by cGAMP using ELISA as well as ISRE reporter gene assay, it was confirmed that co-treatment with Compound 42 and cGAMP increased cytokine secretion very effectively in a concentration-dependent manner compared to treatment with cGAMP alone, and that treatment with Compound 42 alone induced no immune response.

Confirmation of Expression of Type I IFN Signaling-Related Genes

As shown in FIG. 4, it was confirmed that cGAMP-induced expression of various interferon-stimulated genes (ISGs), including IFN-beta, IP-10, ISG15, IRF7, IFIT3, and OAS1, was significantly increased by treatment with Compound 42, indicating that Compound 42 effectively promotes the type I IFN immune response induced by cGAMP.

Evaluation of Activities of TBK, IRF3, and STAT1 (Western Blotting)

As shown in FIG. 5, it was confirmed that Compound 42 increased phosphorylation of IRF3 and phosphorylation of STAT1, which are downstream signaling pathways of STING and TBK induced by cGAMP, indicating that co-administration of Compound 42 and cGAMP exhibited efficacy.

Activity Comparison with STING Pathway-Activating Therapeutic Agent

As shown in FIG. 6, as a result of comparing the degree of STING-dependent immune response activation between the ENPP inhibitor MV658 compound, which is known as a STING pathway-activating therapeutic agent, and Compound 42, it was confirmed that Compound 42 exhibited better activity.

Evaluation of In Vivo Anticancer Activity

As shown in FIG. 7, it was confirmed that co-administration of Compound 42 and cGAMP effectively reduced the tumor volume compared to the administration of cGAMP alone, proving that the co-administration exhibited in vivo anticancer activity.

Analysis of PK Profiles

As shown in FIG. 8 and Tables 2 and 3 below, it was demonstrated that IV administration and PO administration of Compound 42 are possible. Specifically, after IV administration of 5 mg/kg (mpk) of Compound 42, the half-life of Compound 42 was about 7.76 hours, the $C_{max}$ thereof was 2,747 ng/ml, and the $AUC_\infty$ thereof was 3,704 ng/ml. In particular, after IV administration of Compound 42, the mean volume of distribution at steady state (Vss) was 10.15 L/kg, and the mean blood clearance was 22.66 mL/min/kg. Meanwhile, after PO administration of 20 mpk of Compound 42, the half-life of Compound 42 was 11.6 hours, the $C_{max}$ thereof was 224 ng/ml, the $AUC_\infty$ was 3031 ng/ml, and the oral bioavailability thereof was about 18%. This suggests that it is possible to administer Compound 42 intravenously and orally.

TABLE 2

| Compound 42(ng/ml) | | | | | | |
|---|---|---|---|---|---|---|
| IV | | | | | | |
| IV Time (h) | 101 | 102 | 103 | Mean IV | SD | CV (%) |
| 0.083 | 2592.660 | 2724.650 | 2922.650 | 2746.65± | 166.09 | 6.05 |
| 0.25 | 1522.940 | 1228.390 | 1506.240 | 1419.19± | 165.45 | 11.66 |
| 0.50 | 802.916 | 741.777 | 916.427 | 820.37± | 88.62 | 10.80 |
| 1.00 | 378.601 | 319.272 | 350.728 | 349.53± | 29.68 | 8.49 |
| 4.00 | 97.936 | 129.441 | 94.754 | 107.38± | 19.17 | 17.86 |
| 24.00 | 29.232 | 45.260 | 30.044 | 34.85± | 9.03 | 25.91 |

TABLE 2-continued

| Compound 42(ng/ml) | | | | | | |
|---|---|---|---|---|---|---|
| | PO | | | | | |
| PO Time (h) | 201 | 202 | 203 | Mean PO | SD | CV (%) |
| 0.25 | 75.287 | 114.648 | 79.841 | 89.93± | 21.53 | 23.94 |
| 0.50 | 139.403 | 164.520 | 165.563 | 156.50± | 14.81 | 9.46 |
| 1.00 | 211.100 | 232.437 | 230.000 | 224.51± | 11.68 | 5.20 |
| 3.00 | 149.437 | 155.307 | 179.295 | 161.35± | 15.82 | 9.80 |
| 6.00 | 98.657 | 123.919 | 111.651 | 111.41± | 12.63 | 11.34 |
| 24.00 | 38.995 | 37.325 | 50.885 | 42.40± | 7.39 | 17.44 |

* ND = Not determined (Parameters not determined due to inadequately defined terminal elimination phase)

BQL = Below the lower limit of quantitation (LLOQ)

If the adjusted rsq (linear regression coefficient of the concentration value on the terminal phase) is less than 0.9, $T_{1/2}$ might not be accurately estimated.

If the % $AUC_{Extra}$ > 20%, $AUC_{0-inf}$, Cl, $MRT_{0-inf}$ and $Vd_{ss}$ might not be accurately estimated.

If the % $AUMC_{Extra}$ > 20%, $MRT_{0-inf}$ and $V_{dss}$ might not be accurately estimated.

The adjusted linear regression coefficient of the concentration value on the terminal phase is less than 0.9, $T_{1/2}$ might not be accurately estimated.

a: Bioavailability (%) was calculated using $AUC_{0-inf}$ (% $AUC_{Extra}$ < 20%) or $AUC_{0-last}$ (% $AUC_{Extra}$ > 20%) with nominal dose

TABLE 3

| G1 Animal No. | Adminis-tration Route | Dose Level mg/kg | HL_Lambda_z (h) $T_{1/2}$ h | Tmax (h) $T_{max}$ h | Cmax (ng/mL) $C_{max}$ ng/mL | AUClast (h*ng/mL) $AUC_{(0-t)}$ h*ng/mL | AUCINF_obs (h*ng/mL) $AUC_{(0-\infty)}$ h*ng/mL | MRTlast (h) $MRT_{(0-t)}$ h |
|---|---|---|---|---|---|---|---|---|
| 101 | IV | 5.0 | 6.03 | 0.083 | 2592.66 | 3164.01 | 3418.31 | 3.93 |
| 102 | IV | 5.0 | 9.47 | 0.083 | 2724.65 | 3542.76 | 4161.11 | 4.97 |
| 103 | IV | 5.0 | 7.79 | 0.083 | 2922.65 | 3195.55 | 3533.38 | 3.90 |
| n | | 3 | 3 | 3 | 3 | 3 | 3 | 3 |
| GI-Mean | | 5.0 | 7.76 | 0.083 | 2746.65 | 3300.77 | 3704.27 | 4.27 |
| GI-SD | | 0.0 | 1.72 | 0.00 | 166.09 | 210.16 | 399.80 | 0.61 |

| G1 Animal No. | Adminis-tration Route | Dose Level mg/kg | MRTINF_obs (h) $MRT_{(0-\infty)}$ h | C0 (ng/mL) $C_0$ ng/mL | Vss_obs (mL/kg) $V_{ss}$ mL/kg | Vz_obs (mL/kg) $V_z$ mL/kg | Cl_obs (mL/h/kg) Cl mL/h/kg |
|---|---|---|---|---|---|---|---|
| 101 | IV | 5.0 | 6.07 | 3377.42 | 8881.45 | 12724.81 | 1462.71 |
| 102 | IV | 5.0 | 9.83 | 4048.20 | 11809.18 | 16416.27 | 1201.60 |
| 103 | IV | 5.0 | 6.90 | 4063.09 | 9760.09 | 15912.00 | 1415.08 |
| n | | 3 | 3 | 3 | 3 | 3 | 3 |
| GI-Mean | | 5.0 | 7.60 | 3830 | 10150.24 | 15017.70 | 1359.80 |
| GI-SD | | 0.0 | 1.97 | 391.64 | 1502.35 | 2001.64 | 139.05 |

| G2 Animal No. | Administration Route | Dose Level mg/kg | $T_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | F % |
|---|---|---|---|---|---|---|---|---|---|---|
| 201 | PO | 20.0 | 11.62 | 1.000 | 211.10 | 2095.42 | 2749.20 | 7.66 | 15.53 | 15.87 |
| 202 | PO | 20.0 | 10.27 | 1.000 | 232.44 | 2406.25 | 2959.50 | 7.22 | 13.12 | 18.22 |
| 203 | PO | 20.0 | 12.77 | 1.000 | 230.00 | 2448.08 | 3385.50 | 8.04 | 17.56 | 18.54 |
| n | | 3 | 3 | 3 | 3 | 3 | 3 | 3 | 3 | 3 |
| G2-Mean | | 20.0 | 11.55 | 1.000 | 224.51 | 2316.58 | 3031.40 | 7.64 | 15.41 | 17.55 |
| G2-SD | | 0.0 | 1.25 | 0.00 | 11.68 | 192.67 | 324.19 | 0.41 | 2.22 | 1.46 |

CONCLUSION

Based on the above results, it was confirmed that the compound of the present invention very effectively increases the type I IFN-related innate immune response of STING induced by cGAMP, and that the compound of the present invention is a very effective co-administration drug candidate for inducing innate immune responses by STING activity. In addition, it was confirmed through a separate experiment that, when the compound of the present invention was administered alone, it exhibited no significant effect, indicating that the compound of the present invention has few side effects. In addition, it was confirmed that the compound of the present invention exhibited anticancer activity in vivo more effectively when co-administered with cGAMP. These results demonstrated that the compound of the present invention may be co-administered with a STING agonist to treat cancer cells that evaded the immune surveillance system.

So far, the present invention has been described with reference to the embodiments. Those of ordinary skill in the art to which the present invention pertains will appreciate that the present disclosure may be embodied in modified forms without departing from the essential characteristics of the present invention. Therefore, the disclosed embodiments should be considered from an illustrative point of view, not from a restrictive point of view. The scope of the present invention is defined by the claims rather than the foregoing description, and all differences within the scope equivalent thereto should be construed as being included in the present disclosure.

What is claimed is:

1. A method for stimulating interferon gene comprising administering an effective amount of an indolizine derivative compound represented by the following Formula 1; and a cyclic-di-nucleotide:

[Formula 1]

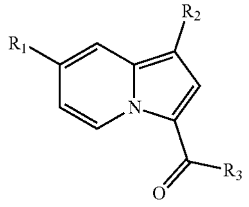

wherein $R_1$ is hydrogen, a $C_1$-$C_8$ straight or branched chain alkyl group, a halogen-substituted $C_1$-$C_8$ straight or branched chain alkyl group, a $C_2$-$C_8$ alkenyl group, a $C_2$-$C_8$ alkynyl group, a halogen group, a nitrile group, a hydroxyl group, a $C_1$-$C_6$ alkoxy group, —$COY_1$ (wherein $Y_1$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), —$CO_2Y_2$ (wherein $Y_2$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), or —$NY_3Y_4$ (wherein $Y_3$ and $Y_4$ are each independently hydrogen, a $C_1$-$C_{10}$ alkyl group, a $C_6$-$C_{20}$ aryl group, or a $C_4$-$C_{20}$ heteroaryl group);

$R_2$ is

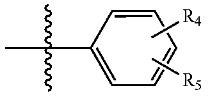

or a pyridinyl group, wherein $R_4$ and $R_5$ are each independently hydrogen, a $C_1$-$C_8$ straight or branched chain alkyl group, a halogen-substituted $C_1$-$C_8$ straight or branched chain alkyl group, a $C_2$-$C_8$ alkenyl group, a $C_2$-$C_8$ alkynyl group, a $C_3$-$C_8$ cycloalkyl group, a $C_5$-$C_{20}$ heterocycloalkyl group, a $C_6$-$C_{20}$ aryl group, a $C_6$-$C_{20}$ heteroaryl group, a halogen group, a nitrile group, a nitro group, a hydroxyl group, a carboxyl group, a $C_1$-$C_6$ alkoxy group, —$COY_5$ (wherein $Y_5$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), —$CO_2Y_6$ (wherein $Y_6$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, a $C_6$-$C_{20}$ aryl group), or —$NY_7Y_8$ (wherein $Y_7$ and $Y_5$ are each independently hydrogen, a $C_1$-$C_{10}$ alkyl group, a $C_6$-$C_{20}$ aryl group, or a $C_4$-$C_{20}$ heteroaryl group); and $R_3$ is a $C_1$-$C_8$ straight or branched chain alkyl group, or

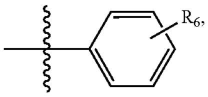

wherein $R_6$ is hydrogen, a $C_1$-$C_8$ straight or branched chain alkyl group, a halogen-substituted $C_1$-$C_8$ straight or branched chain alkyl group, a $C_2$-$C_8$ alkenyl group, a $C_2$-$C_5$ alkynyl group, a $C_3$-$C_8$ cycloalkyl group, a $C_5$-$C_{20}$ heterocycloalkyl group, a $C_6$-$C_{20}$ aryl group, a $C_6$-$C_{20}$ heteroaryl group, a halogen group, a nitrile group, a nitro group, a hydroxyl group, a $C_1$-$C_6$ alkoxy group, —$COY_9$ (wherein $Y_9$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), —$CO_2Y_{10}$ (wherein $Y_{10}$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), or —$NY_{11}Y_{12}$ (wherein $Y_{11}$ and $Y_{12}$ are each independently hydrogen, a $C_1$-$C_{10}$ alkyl group, a $C_6$-$C_{20}$ aryl group, or a $C_4$-$C_{20}$ heteroaryl group), wherein the cyclic-di-nucleotide is any one of the following compounds:

[Compound 2-1]

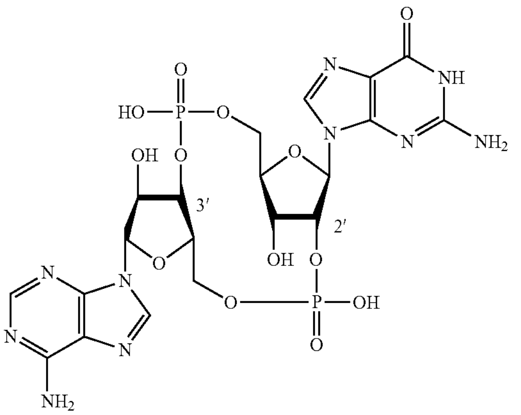

[Compound 2-2]

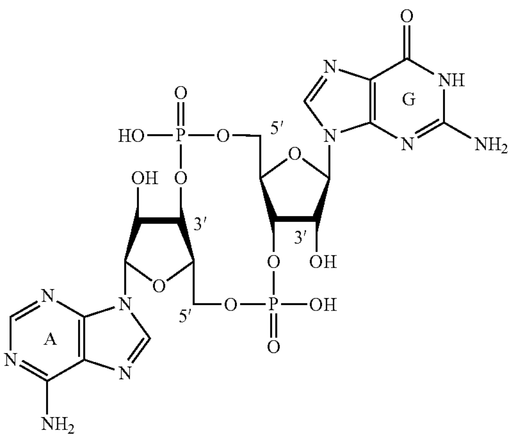

-continued
[Compound 2-3]
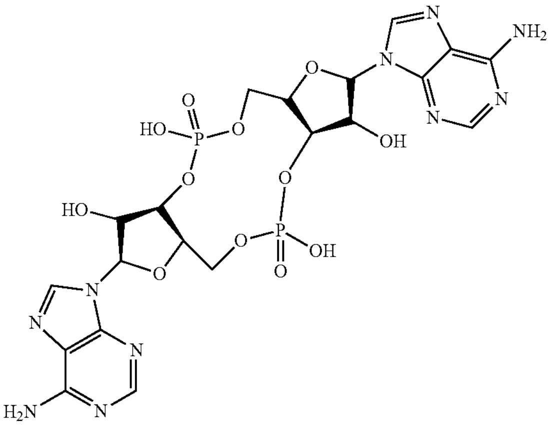
[Compound 2-4]
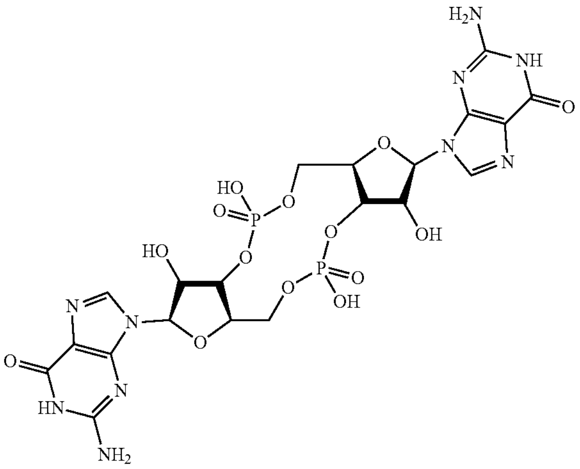
[Compound 2-5]
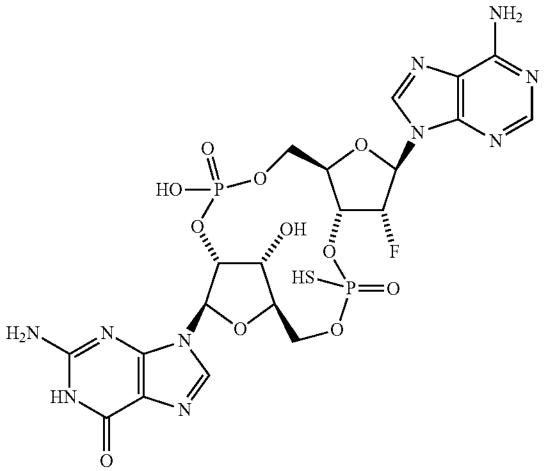
-continued
[Compound 2-6]
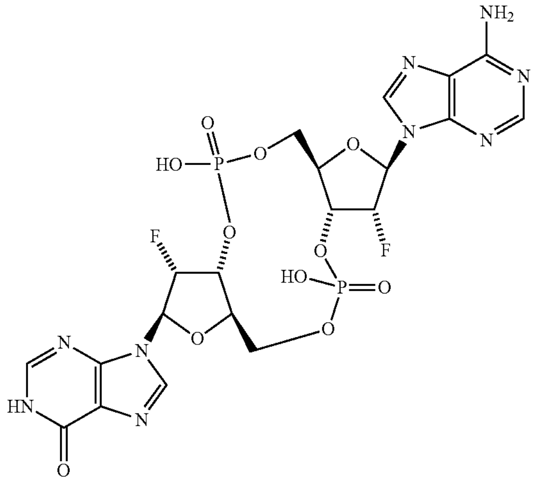
[Compound 2-7]
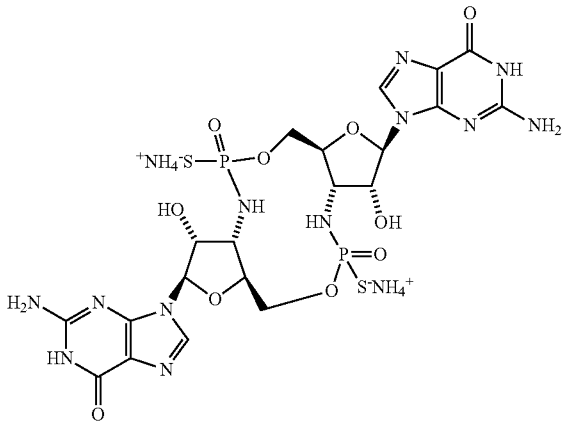
[Compound 2-8]
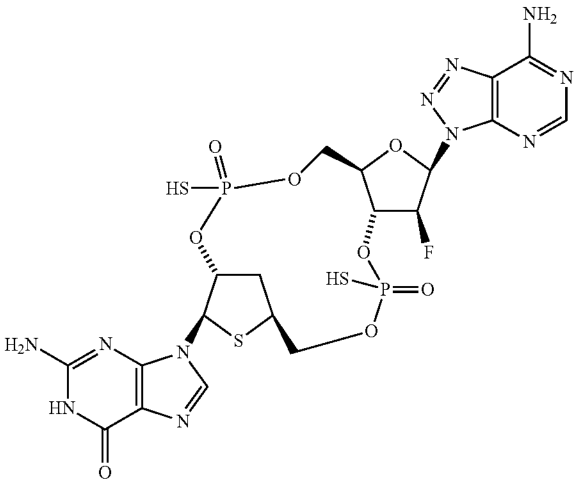

-continued

[Compound 2-9]

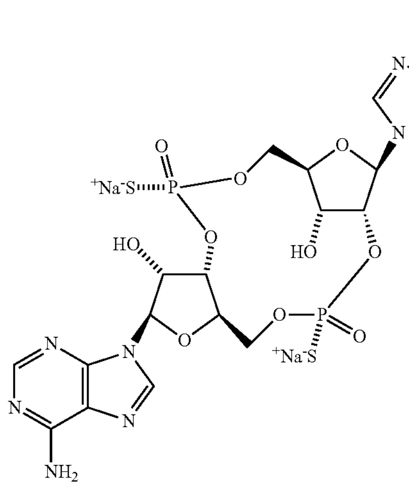

2. The method for stimulating interferon gene of claim 1, wherein the indolizine derivative compound represented by Formula 1 is a compound represented by the following Formula 1-1 or a compound represented by the following Formula 1-2:

[Formula 1-1]

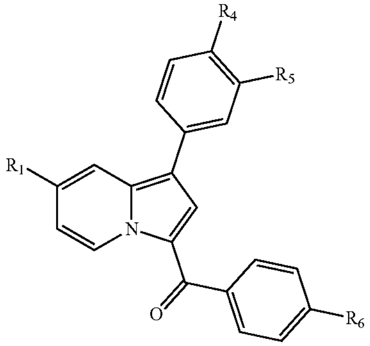

[Formula 1-2]

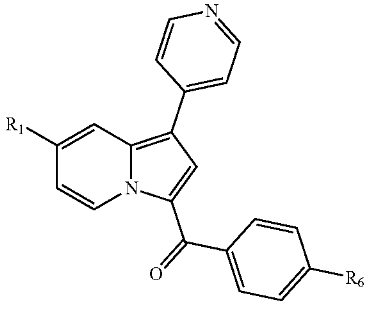

wherein $R_1$ is hydrogen, a $C_1$-$C_8$ straight or branched chain alkyl group, a halogen-substituted $C_1$-$C_8$ straight or branched chain alkyl group, a $C_2$-$C_8$ alkenyl group, a $C_2$-$C_8$ alkynyl group, a halogen group, a nitrile group, a hydroxyl group, a $C_1$-$C_6$ alkoxy group, —$COY_1$ (wherein $Y_1$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), —$CO_2Y_2$ (wherein $Y_2$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), or —$NY_3Y_4$ (wherein $Y_3$ and $Y_4$ are each independently hydrogen, a $C_1$-$C_{10}$ alkyl group, a $C_6$-$C_{20}$ aryl group, or a $C_4$-$C_{20}$ heteroaryl group);

$R_4$ and $R_5$ are each independently hydrogen, a $C_1$-$C_8$ straight or branched chain alkyl group, a halogen-substituted $C_1$-$C_8$ straight or branched chain alkyl group, a $C_2$-$C_8$ alkenyl group, a $C_2$-$C_8$ alkynyl group, a $C_3$-$C_8$ cycloalkyl group, a $C_5$-$C_{20}$ heterocycloalkyl group, a $C_6$-$C_{20}$ aryl group, a $C_6$-$C_{20}$ heteroaryl group, a halogen group, a nitrile group, a nitro group, a hydroxyl group, a carboxyl group, a $C_1$-$C_6$ alkoxy group, —$COY_5$ (wherein $Y_5$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), —$CO_2Y_6$ (wherein $Y_6$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, a $C_6$-$C_{20}$ aryl group), or —$NY_7Y_8$ (wherein $Y_7$ and $Y_5$ are each independently hydrogen, a $C_1$-$C_{10}$ alkyl group, a $C_6$-$C_{20}$ aryl group, or a $C_4$-$C_{20}$ heteroaryl group); and $R_6$ is hydrogen, a $C_1$-$C_8$ straight or branched chain alkyl group, a halogen-substituted $C_1$-$C_8$ straight or branched chain alkyl group, a $C_2$-$C_8$ alkenyl group, a $C_2$-$C_8$ alkynyl group, a $C_3$-$C_8$ cycloalkyl group, a $C_5$-$C_{20}$ heterocycloalkyl group, a $C_6$-$C_{20}$ aryl group, a $C_6$-$C_{20}$ heteroaryl group, a halogen group, a nitrile group, a nitro group, a hydroxyl group, a $C_1$-$C_6$ alkoxy group, —$COY_9$ (wherein $Y_9$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), —$CO_2Y_{10}$ (wherein $Y_{10}$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), or —$NY_{11}Y_{12}$ (wherein $Y_{11}$ and $Y_{12}$ are each independently hydrogen, a $C_1$-$C_{10}$ alkyl group, a $C_6$-$C_{20}$ aryl group, or a $C_4$-$C_{20}$ heteroaryl group).

3. The method for stimulating interferon gene of claim 1, wherein the indolizine derivative compound represented by Formula 1 is a compound represented by the following Formula 1-3:

[Formula 1-3]

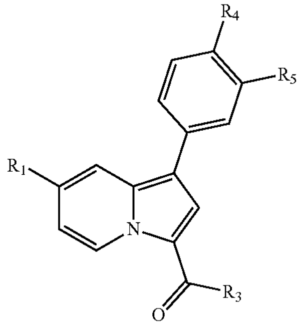

wherein $R_1$ is hydrogen, a $C_1$-$C_8$ straight or branched chain alkyl group, a halogen-substituted $C_1$-$C_8$ straight or branched chain alkyl group, a $C_2$-$C_8$ alkenyl group, a $C_2$-$C_8$ alkynyl group, a halogen group, a nitrile group, a hydroxyl group, a $C_1$-$C_6$ alkoxy group, —$COY_1$ (wherein $Y_1$ is hydrogen, a $C_1$-$C_8$ straight or branched chain alkyl group, a $C_2$-$C_5$ alkenyl group, a $C_2$-$C_5$ alkynyl group, a $C_3$-$C_8$ cycloalkyl group, or a $C_6$-$C_{20}$ aryl group), —$CO_2Y_2$ (wherein $Y_2$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), or —$NY_3Y_4$ (wherein $Y_3$ and $Y_4$ are each independently hydrogen, a $C_1$-$C_{10}$ alkyl group, a $C_6$-$C_{20}$ aryl group, or a $C_4$-$C_{20}$ heteroaryl group);

$R_4$ and $R_5$ are each independently hydrogen, a $C_1$-$C_8$ straight or branched chain alkyl group, a halogen-substituted $C_1$-$C_8$ straight or branched chain alkyl group, a $C_2$-$C_8$ alkenyl group, a $C_2$-$C_8$ alkynyl group, a $C_3$-$C_8$ cycloalkyl group, a $C_5$-$C_{20}$ heterocycloalkyl group, a $C_6$-$C_{20}$ aryl group, a $C_6$-$C_{20}$ heteroaryl group, a halogen group, a nitrile group, a nitro group, a hydroxyl group, a carboxyl group, a $C_1$-$C_6$ alkoxy group, —$COY_5$ (wherein $Y_5$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, or a $C_6$-$C_{20}$ aryl group), —$CO_2Y_6$ (wherein $Y_6$ is hydrogen, a $C_1$-$C_8$ straight or branched chain alkyl group, a $C_2$-$C_8$ alkenyl group, a $C_2$-$C_8$ alkynyl group, a $C_3$-$C_8$ cycloalkyl group, a $C_6$-$C_{20}$ aryl group), or —$NY_7Y_8$ (wherein $Y_7$ and $Y_5$ are each independently hydrogen, a $C_1$-$C_{10}$ alkyl group, a $C_6$-$C_{20}$ aryl group, or a $C_4$-$C_{20}$ heteroaryl group); and $R_3$ is a $C_1$-$C_8$ straight or branched chain alkyl group.

4. The method for stimulating interferon gene of claim 1, wherein the indolizine derivative compound represented by Formula 1 is any one of the following Compounds 1 to 72:

[Compound 1]

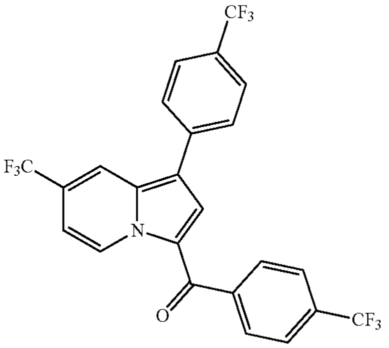

[Compound 2]

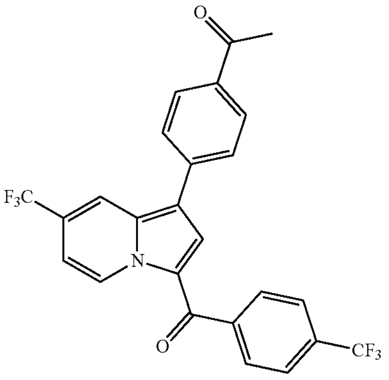

-continued

[Compound 3]

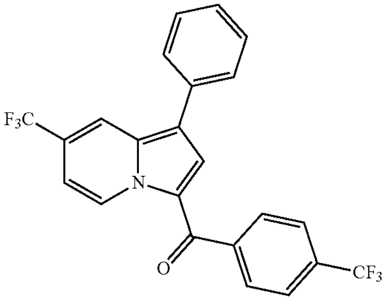

[Compound 4]

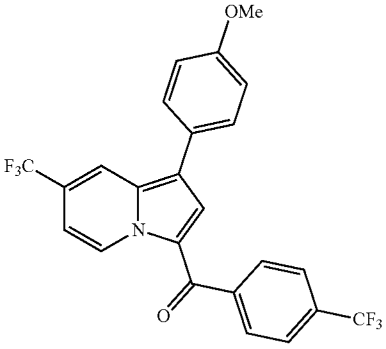

[Compound 5]

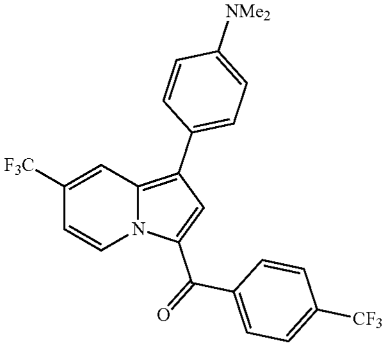

[Compound 6]

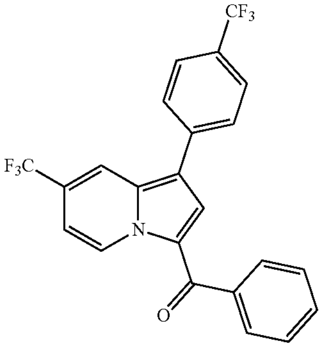

[Compound 7]
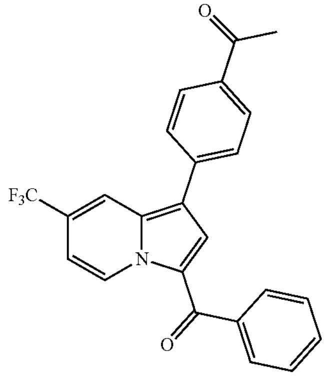
[Compound 8]
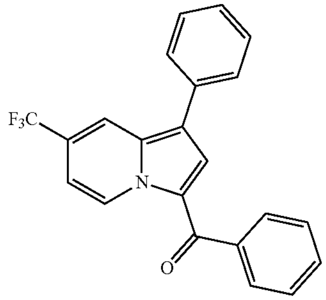
[Compound 9]
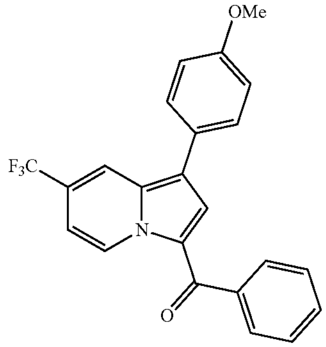
[Compound 10]
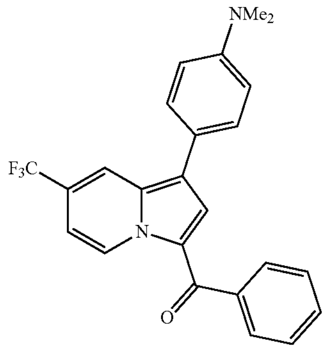
[Compound 11]
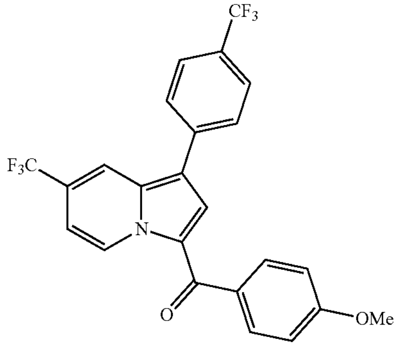
[Compound 12]
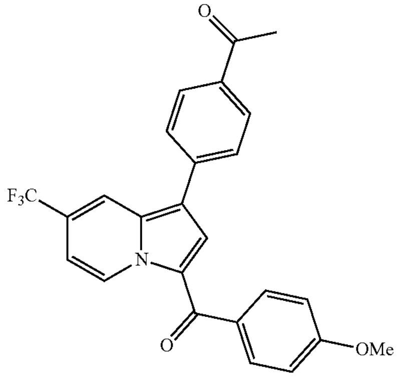
[Compound 13]
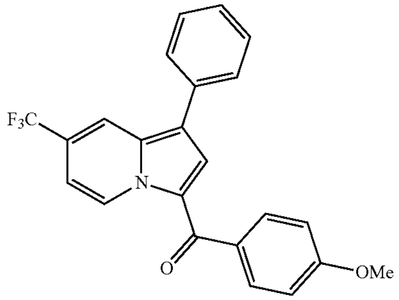
[Compound 14]
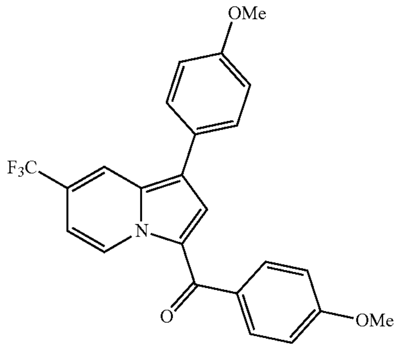

-continued
[Compound 15]
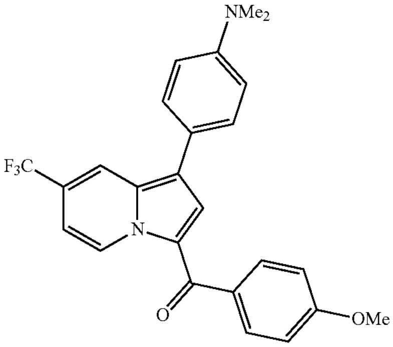
[Compound 16]
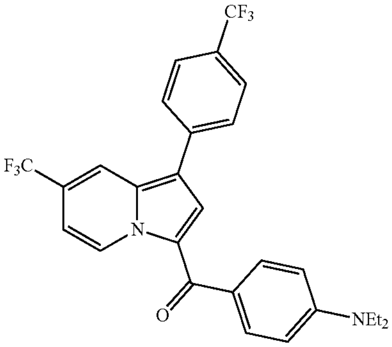
[Compound 17]
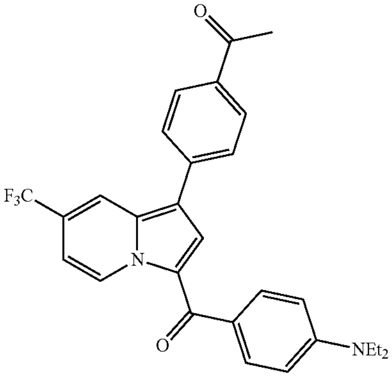
[Compound 18]
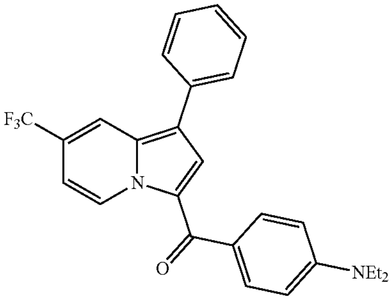
-continued
[Compound 19]
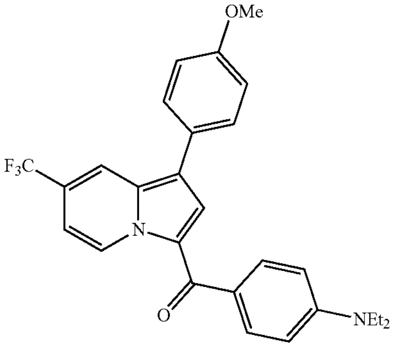
[Compound 20]
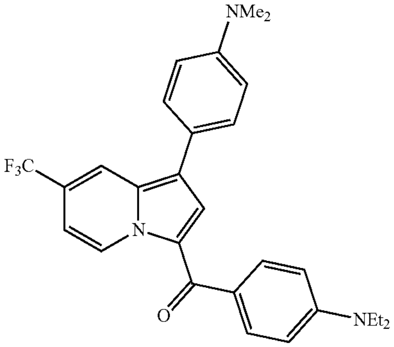
[Compound 21]
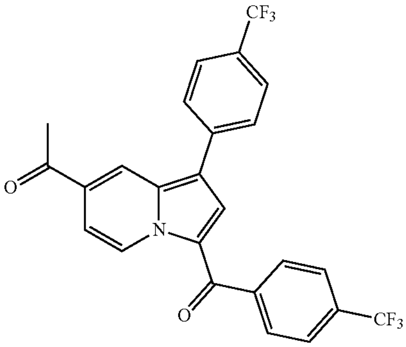
[Compound 22]
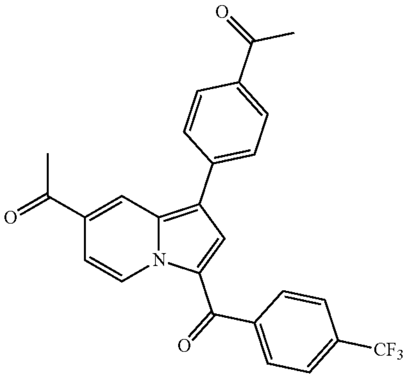

-continued
[Compound 23]
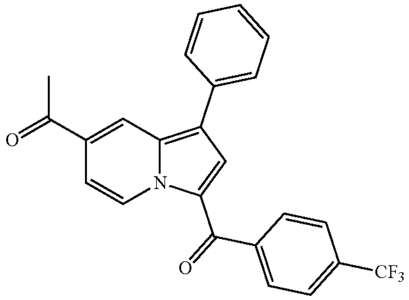
[Compound 24]
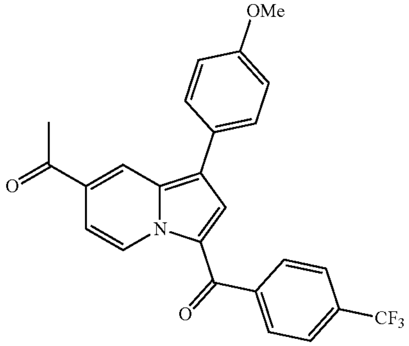
[Compound 25]
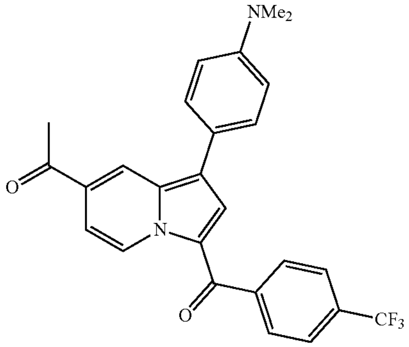
[Compound 26]
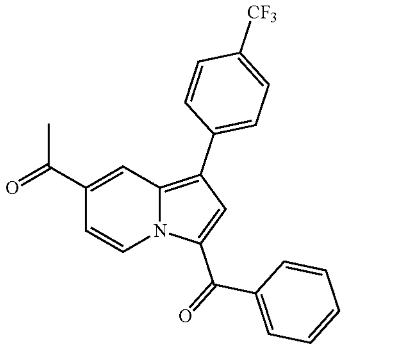
-continued
[Compound 27]
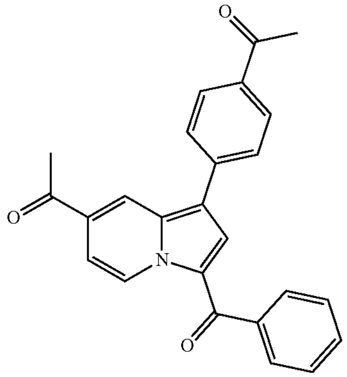
[Compound 28]
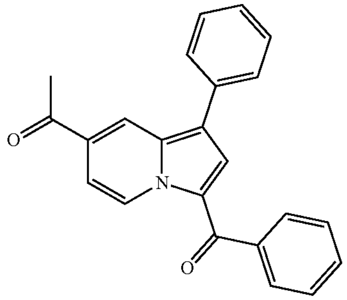
[Compound 29]
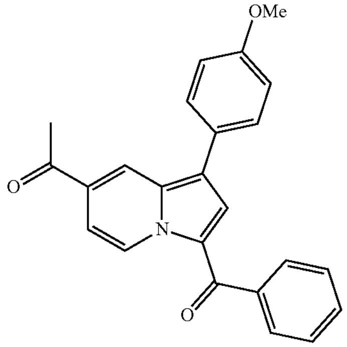
[Compound 30]
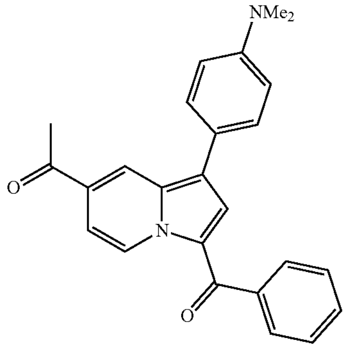

-continued
[Compound 31]
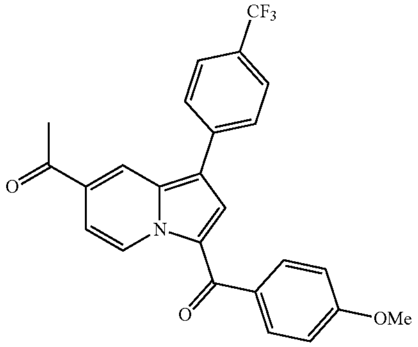
[Compound 32]
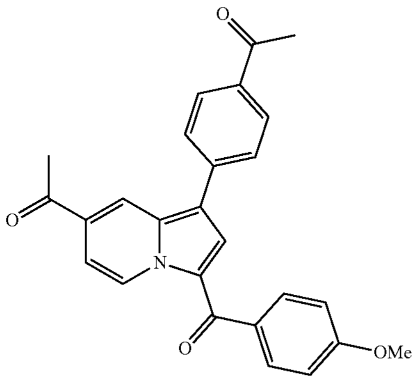
[Compound 33]
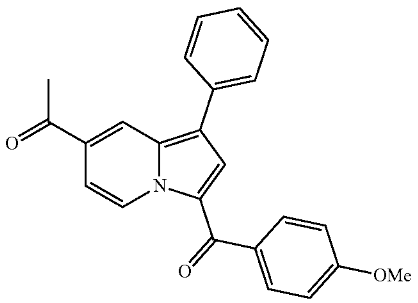
[Compound 34]
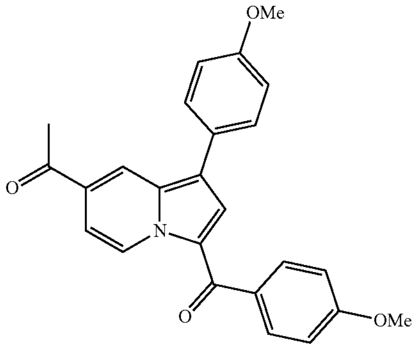
-continued
[Compound 35]
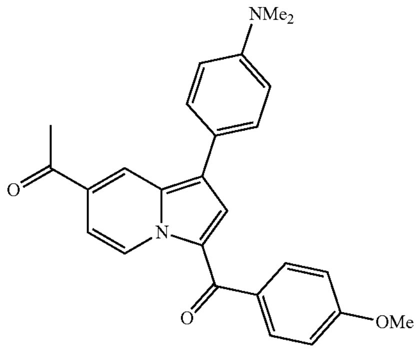
[Compound 36]
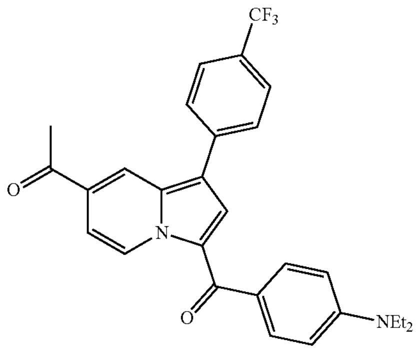
[Compound 37]
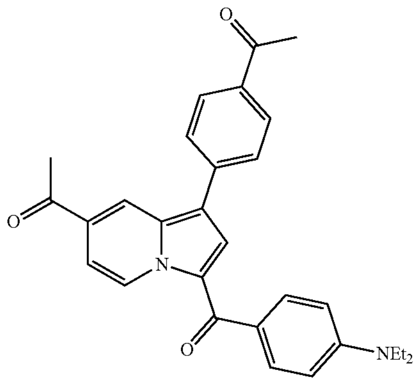
[Compound 38]
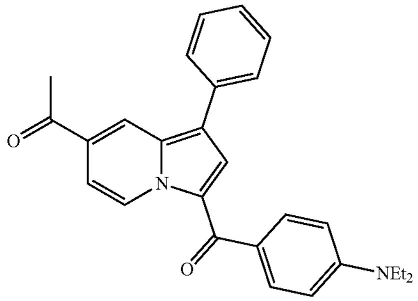

-continued
[Compound 39]
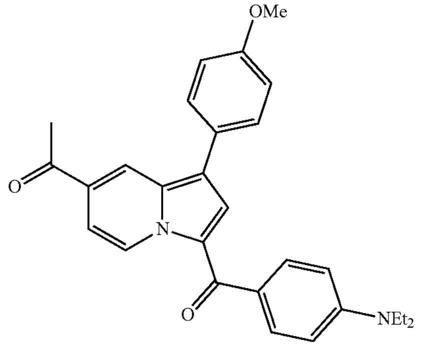
[Compound 40]
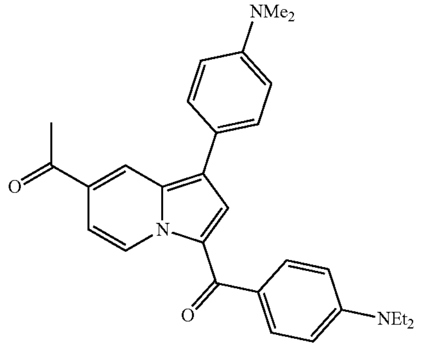
[Compound 41]
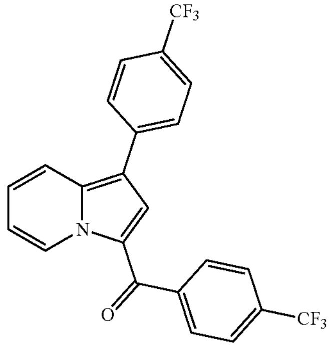
[Compound 42]
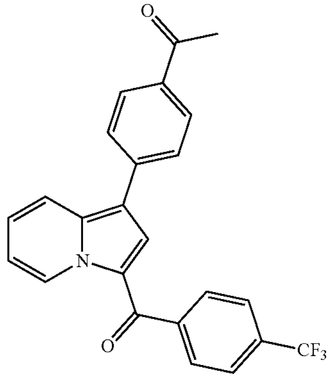
-continued
[Compound 43]
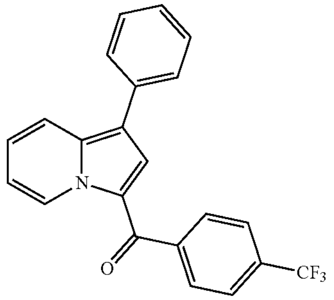
[Compound 44]
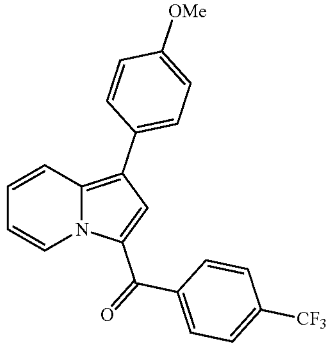
[Compound 45]
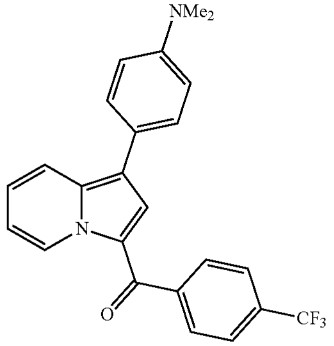
[Compound 46]
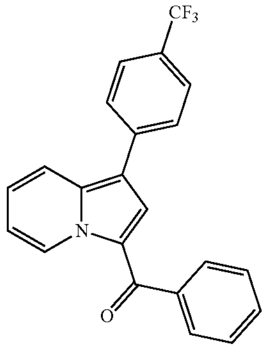

-continued
[Compound 47]
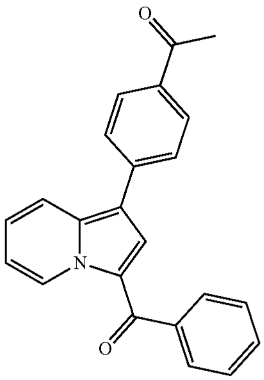
[Compound 48]
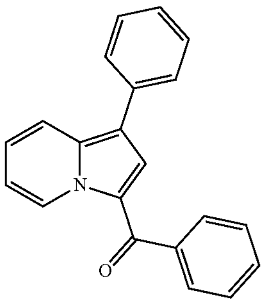
[Compound 49]
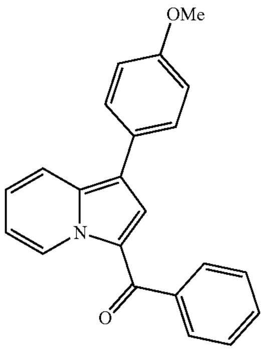
[Compound 50]
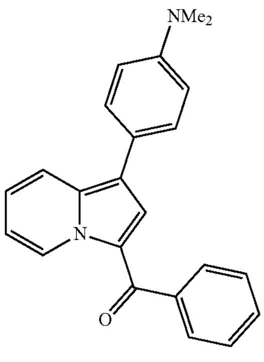
-continued
[Compound 51]
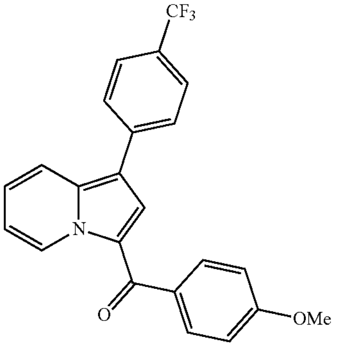
[Compound 52]
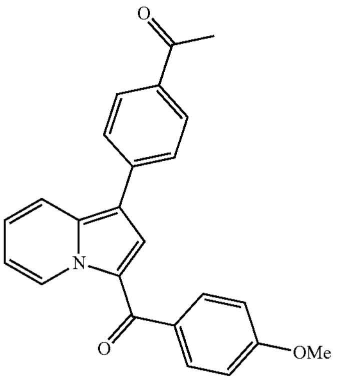
[Compound 53]
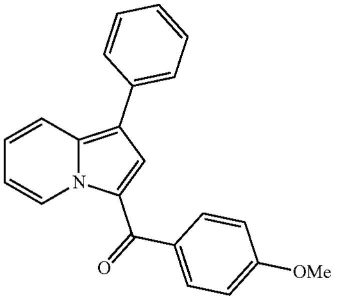
[Compound 54]
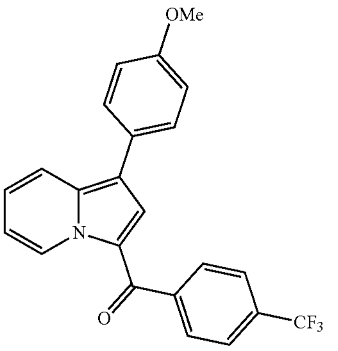

-continued
[Compound 55]
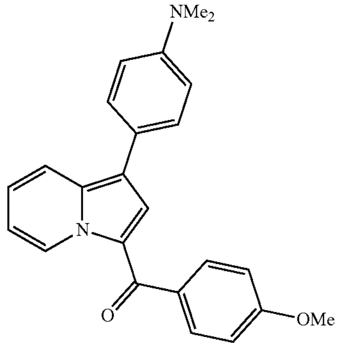
[Compound 56]
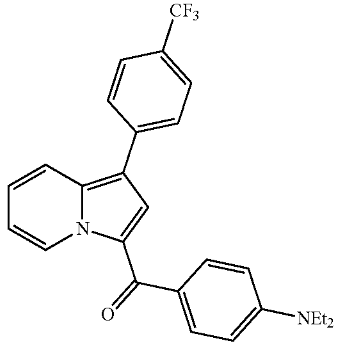
[Compound 57]
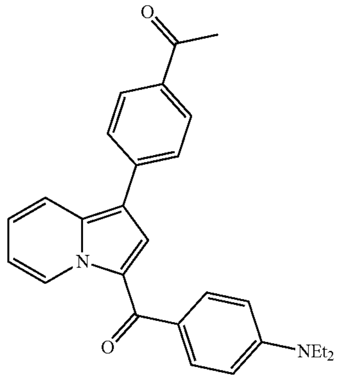
[Compound 58]
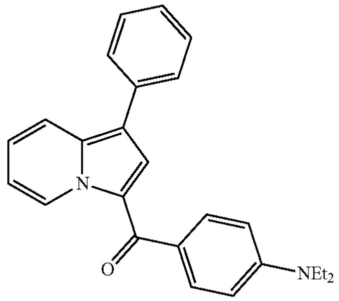
-continued
[Compound 59]
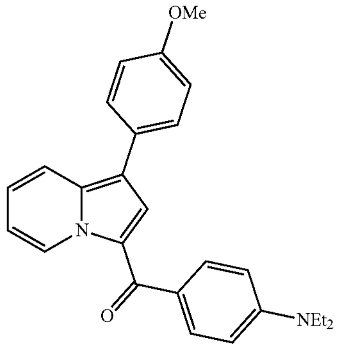
[Compound 60]
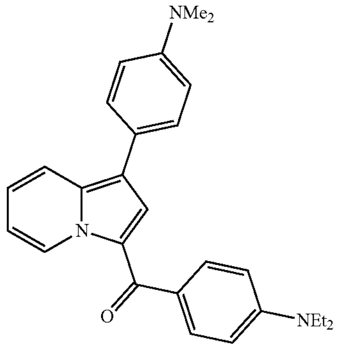
[Compound 61]
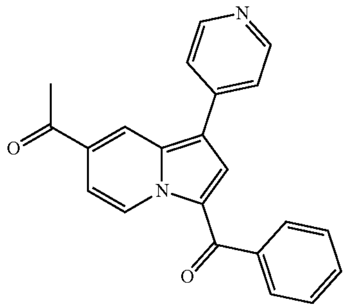
[Compound 62]
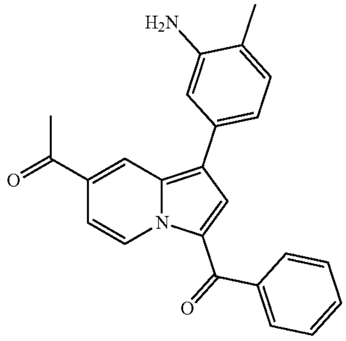

-continued
[Compound 63]
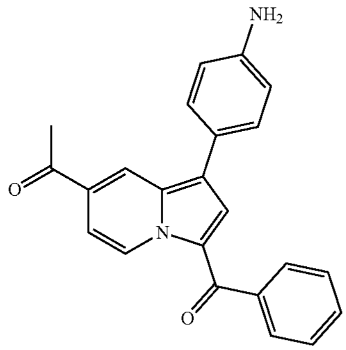
[Compound 64]
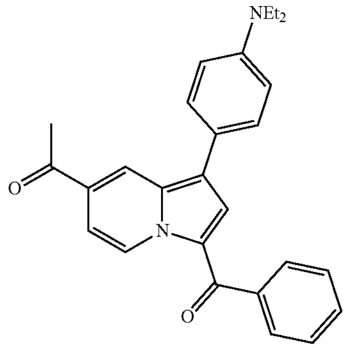
[Compound 65]
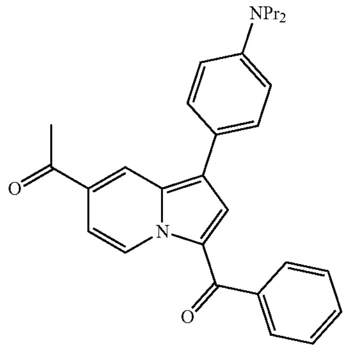
[Compound 66]
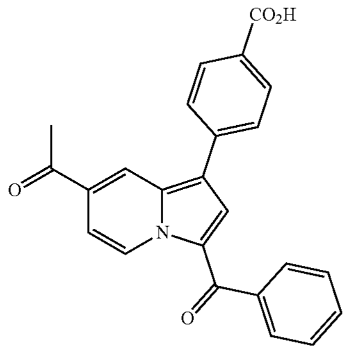
-continued
[Compound 67]
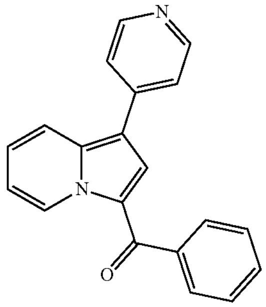
[Compound 68]
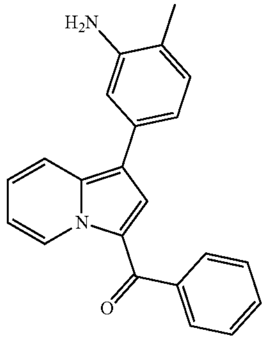
[Compound 69]
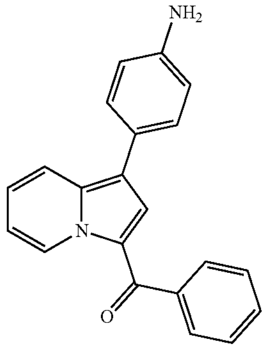
[Compound 70]
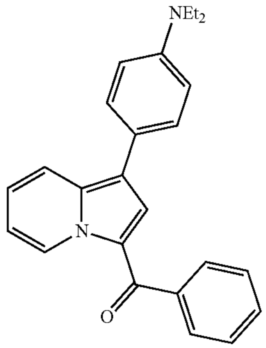

-continued
[Compound 71]
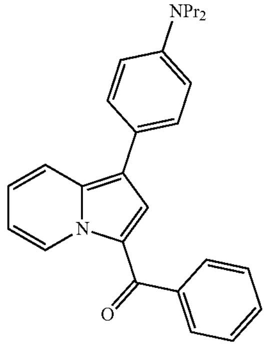
[Compound 72]
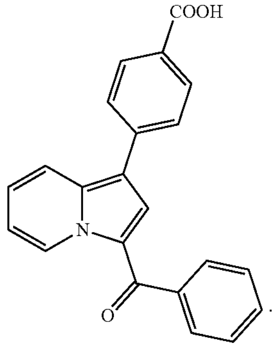
5. The method for stimulating interferon gene of claim 1, wherein the indolizine derivative compound represented by Formula 1 is any one of the following compounds 73 to 87:
[Compound 73]
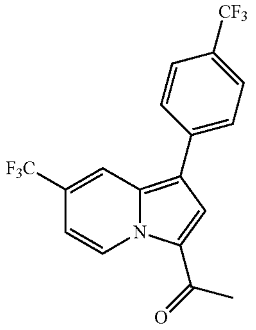
[Compound 74]
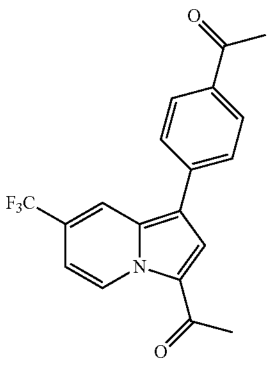
-continued
[Compound 75]
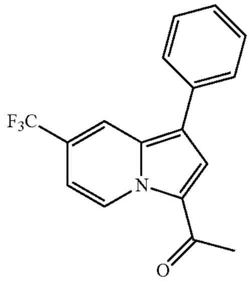
[Compound 76]
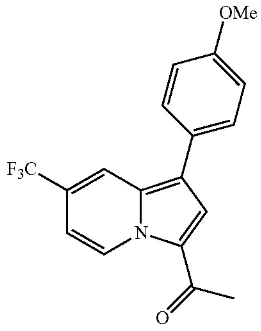
[Compound 77]
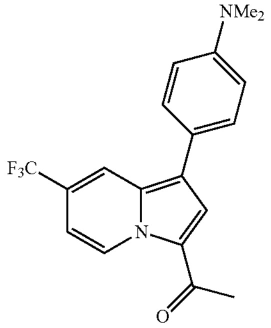
[Compound 78]
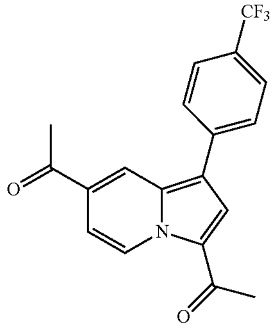
[Compound 79]
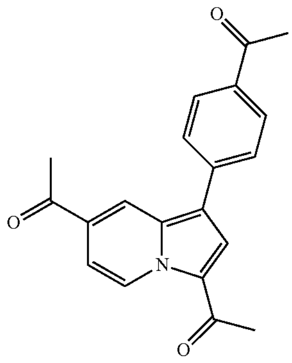

-continued

[Compound 80]

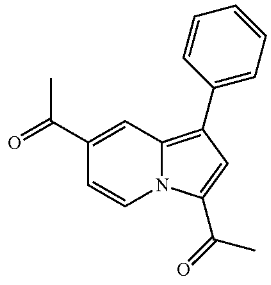

[Compound 81]

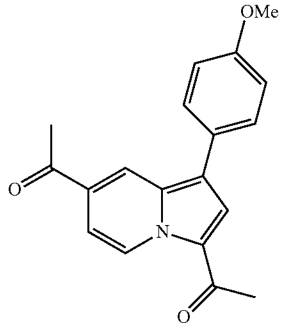

[Compound 82]

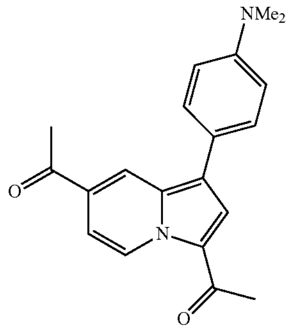

[Compound 83]

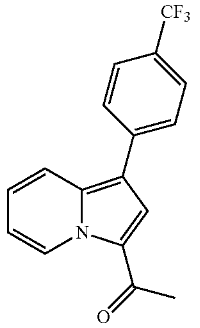

[Compound 84]

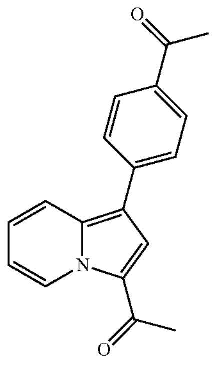

-continued

[Compound 85]

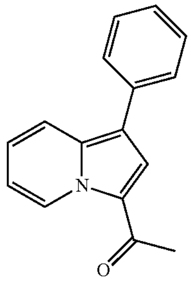

[Compound 86]

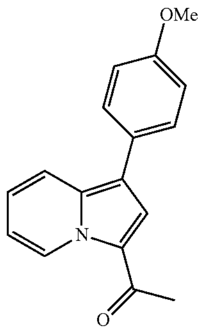

[Compound 87]

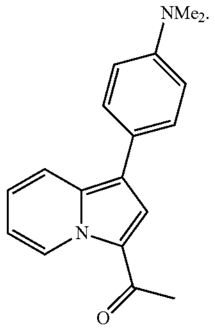

6. The method for stimulating interferon gene of claim 1, wherein the cyclic-di-nucleotide is substituted with fluorine at any one or more of 2'- and 3'-positions.

7. The method for stimulating interferon gene of claim 1, which is for treatment of any one autoimmune disease selected from among cancer, solid cancer, non-T cell invasive cancer, cancer having low responsiveness to immune checkpoint inhibitors, and STING-associated vasculopathy with onset in fancy (SAVI).

* * * * *